United States Patent [19]
Facciotti et al.

[11] Patent Number: 6,140,486
[45] Date of Patent: Oct. 31, 2000

[54] PRODUCTION OF POLYUNSATURATED FATTY ACIDS BY EXPRESSION OF POLYKETIDE-LIKE SYNTHESIS GENES IN PLANTS

[75] Inventors: Daniel Facciotti; James George Metz; Michael Lassner, all of Davis, Calif.

[73] Assignee: Calgene LLC, Davis, Calif.

[21] Appl. No.: 09/090,793

[22] Filed: Jun. 4, 1998

Related U.S. Application Data

[60] Provisional application No. 60/048,650, Jun. 4, 1997.
[51] Int. Cl.⁷ .................................................. C07H 21/04
[52] U.S. Cl. ......................................... 536/23.2; 435/69.1
[58] Field of Search ........................... 536/23.2; 435/69.1

[56] References Cited

U.S. PATENT DOCUMENTS

| | | | |
|---|---|---|---|
| 5,246,841 | 9/1993 | Yazawa | 435/134 |
| 5,639,790 | 6/1997 | Voelker | 514/552 |
| 5,672,491 | 9/1997 | Khosla | 435/148 |
| 5,683,898 | 11/1997 | Yazawa | 435/136 |

FOREIGN PATENT DOCUMENTS

| | | |
|---|---|---|
| 0 594 868 | 4/1994 | European Pat. Off. . |
| WO93/23545 | 11/1993 | WIPO . |
| WO96/21735 | 7/1996 | WIPO . |

OTHER PUBLICATIONS

Kyle et al., "Long–chain Omega–3 Polyunsaturated Fatty Acids: Prospects for Introduction into Horticultural Food Plants," *HortScience.* vol. 25, Dec. 1990 pp. 1523–1526.
Nakahara, Toro, "Physiological activity of docosahexaenoic acid (DHA) and its production by microbial culture," *Yukagaku* (1995) 44(10) pp. 821–827.
Nasu et al., "Efficient Transformation of *Marchantia polymorpha* That is Haploid and Has Very Small Genome DNA," *Journal of Fermentation and Bioengineering* vol. 84, No. 6, 519–523 1997.
Somerville, Chris, "Future prospects for genetic modification of the composition of edible oils from higher plants," *Am. J. Clin. Nutr.* (1993) 58 pp. 270s–275s.
DeLong & Yayanos, (1986) *Appl. Environ. Microbiol.* 51(4):730–737.
Hopwood & Sherman, (1990) *Annu. Rev. Genet.* 24:37–66.
Hutchinson, (1995) *Annu. Rev. Microbiol.* 49:201–238.
Katz & Donadio, (1993) *Annu. Rev. Microbiol.* 47:875–912.
Watanabe et al., (1997) *J. Biochem.* 122:467–473.
Yazawa, (1996) *Lipids* 31(supplement):S–297–S–300.

*Primary Examiner*—Elizabeth F. McElwain
*Attorney, Agent, or Firm*—Barbara Rae-Venter; Jennifer Wahlsten; Rae-Venter Law Group, P.C.

[57] ABSTRACT

The present invention relates to compositions and methods for preparing poly-unsaturated long chain fatty acids in plants, plant parts and plant cells, such as leaves, roots, fruits and seeds. Nucleic acid sequences and constructs encoding PKS-like genes required for the poly-unsaturated long chain fatty acid production, including the genes responsible for eicosapentenoic acid production of *Shewanella putrefaciens* and novel genes associated with the production of docosahexenoic acid in *Vibrio marinus* are used to generate transgenic plants, plant parts and cells which contain and express one or more transgenes encoding one or more of the PKS-like genes associated with such long chain polyunsaturated fatty acid production. Expression of the PKS-like genes in the plant system permits the large scale production of poly-unsaturated long chain fatty acids such as eicosapentenoic acid and docosahexenoic acid for modification of the fatty acid profile of plants, plant parts and tissues. Manipulation of the fatty acid profiles allows for the production of commercial quantities of novel plant oils and products.

3 Claims, 123 Drawing Sheets

Orf6    8.3 KB  -  293 kD
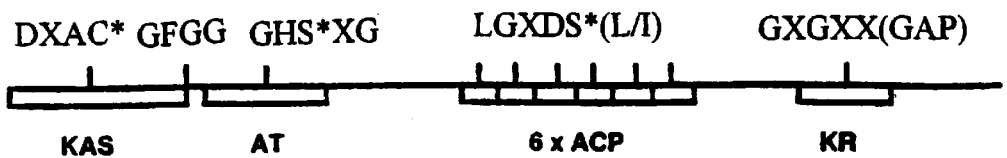
Acetate-like        FIG. 2A
Orf7    2.3 KB  -  84 kD
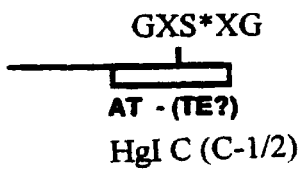
HgI C (C-1/2)
FIG. 2B
Orf3    0.8 KB  -  30 kD
☐
Het I- pantetheine transferase
FIG. 2E
Orf8    6.0 KB  -  217 kD
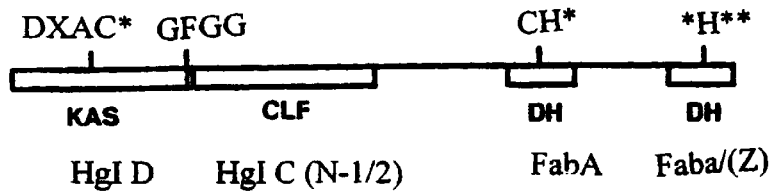
HgI D    HgI C (N-1/2)    FabA    Faba/(Z)
FIG. 2C
Orf9    1.6 KB  -  59 kD
☐
Anabeana - Orf552 homolog
FIG. 2D

```
GATCTCTTAC AAAGAAACTA TCTCAATGTG AATTTAACCT TAATTCCGTT TAATTACGGC    60
CTGATAGAGC ATCACCCAAT CAGCCATAAA ACTGTAAAGT GGTACTCAA  AGGTGGCTGG   120
GCGATTCTTC TCAAATACAA AGTGCCCAAC CCAAGCAAAT CCATATCCGA TAACAGGTAA   180
AAGTAGCAAT AAACCCCAGC GCTGAGTTAG TAATACATAA GCGAATAATA GGATCACTAA   240
ACTACTGCCG AAATAGTGTA ATATTCGACA GTTTCTATGC TGATGTTGAG ATAAATAAAA   300
AGGGTAAAAT TCAGCAAAAG AACGATAGCG CTTACTCATT ACTCACACCT CGTAAAAAAA   360
GCAACTCGCC ATTAACTTGG CCAATCGTCA GTTGTTCTAT CGTCTCAAAG TTATGCCGAC   420
TAAATAACTC TATATGTGCA TTATGATTAG CAAAAACTCC GATACCATCA AGATGAAGTT   480
GTTCATCACA CCAACTCAAA ACTGCGTCGA TAAGCTTACT GCCATAGCCC TTGCCTTGCT   540
CCACATTTGC GATAGCAATA AACTGTAAAA TGCCACATTG GCCACTTGGT AAGCTCTCTA   600
TAATCTGATT TTCTTTGTTA ATAAGTGCCT GAGTTGAATA CCAACCAGTA CTTAACAACA   660
TCTTTAAACG CCAATGCCAA AAACGCGCTT CACCTAAGGG AACCTGCTGA GTCACTATGC   720
AGGCTACGCC TATCAATCTA CGCGAAGCTT ACATACCAAT AAGTGCTTGC TCCTGTTGCC   780
AGAGCTCATT GAGTTCTTCT CGAATAGCCC TTGCTCATAC TGCGCTTGAT   840
CACCACTAAA AAGTGTTTCG GATCATCATG ATAGGCGTTA TAGAGAATAG   900
AGGCTGCTAT GCGTAAATCT TCTGCCGTGA ATAAAAAAGG TCCATGGCTT   960
GATCTTCCAT TGTTATTGTC CTTGACCTTG ATCACACAAC ACCAATGTAA CAAGACTGTA  1020
```

FIG. 4A-1

```
TAGAAGTGCA ATTAATAATC AATTCGTGCA TTAAGCAGGT CAGCATTTCT TTGCTAAACA 1080
AGCTTTATTG GCTTTGACAA AACTTTGCCT AGACTTTAAC GATAGAAATC ATAATGAAAG 1140
AGAAAAGCTA CAACCTAGAG GGGAATAATC AAACAACTGC TAAGATCTAG ATAATGTAAT 1200
AAACACCGAG TTTATCGACC ATACTTAGAT AGAGTCATAG CAACGAGAAT AGTTATGGAT 1260
ACAACGCCGC AAGATCTATC ACACCTGTTT TTACAGCTAG GATTAGCAAA TGATCAACCC 1320
GCAATTGAAC AGTTTATCAA TGACCATCAA TTAGCGGACA ATATATTGCT ACATCAAGCA 1380
AGCTTTTGGA GCCCATCGCA AAAGCACTTC TTAATTGAGT CATTTAATGA AGATGCCCAG 1440
TGGACCGAAG TCATCGACCA CTTAGACACC CCCACCCCA TTATTAAGAA CAACAGCGTT GTTGCTTATG 1500
CAACTTTAAA TTTTGCCGTA AGCCATCTCC TTTAGTCGTT TTACCATCAC CATGGGTACG TTGAGTGCGA 1620
ACCACTGGAG TACATTCGTC TTTATCGGCC TGAATATAGG CTTCGTTAAA ATCAGCTGTT 1680
TAAAAAGCA CATAAACTTC TTTATCGGCC TGAATATAGG CTTCGTTAAA ATCAGCTGTT 1680
CCCATTAAAG TAACCACTTG CTCTTTACTC ATGCCTAGAG ATATCTTTGT CAAATTGTCA 1740
CGGTTTTTAT CTTGAGTTTT CTCCCAAGCA CCGTGATTAT CCCAGTCAGA TTCCCCATCA 1800
CCAACATTGA CCACACAGCC CGTTAGCCCT AAGCTTGCAA TCCCAAAACA TGCTAAACCT 1860
AATAATTTAT TTTTCATTTT AACTTCCTGT TATGACATTA TTTTTGCTTA GAAGAAAAGC 1920
AACTTACATG CCAAAACACA AGCTGTTGTT TTAAATGACT TTATTTATTA TTAGCCTTTT 1980
AGGATATGCC TAGAGCAATA ATAATTACCA ATGTTTAAGG AATTTGACTA ACTATGAGTC 2040
```

FIG. 4A-2

```
CGATTGAGCA AGTGCTAACA GCTGCTAAAA AAATCAATGA ACAAGGTAGA GAACCAACAT 2100
TAGCATTGAT TAAAACCAAA CTTGGTAATA GCATCCCAAT GCGCGAGTTA ATCCAAGGTT 2160
TGCAACAGTT TAAGTCTATG AGTGCAGAAG AAAGACAAGC AATACCTAGC AGCTTAGCAA 2220
CAGCAAAAGA AACTCAATAT GGTCAATCAA GCTTATCTCA ATCTGAACAA GCTGATAGGA 2280
TCCTCCAGCT AGAAAACGCC CTCAATGAAT TAAGAAACGA ATTTAATGGG CTAAAAAGTC 2340
AATTTGATAA CTTACAACAA AACCTGATGA ATAAAGAGCC TGACACCAAA TGCATGTAAT 2400
TGAACTACGA TTTGAATGTT TTGATAACAC CACGATTACT GCAGCAGAAA AAGCCATTAA 2460
TGGTTTGCTT GAAGCTTATC GAGCCAATGG CCAGGTTCTA GGTCGTGAAT TTGCCGTTGC 2520
ATTTAACGAT GGTGAGTTTA AAGCACGCAT GTTAACCCCA GAAAAAAGCA GCTTATCTAA 2580
ACGCTTTAAT AGTCCCTGGG TAAATAGTGC ACTCGAAGAG CTAACCGAAG CCAAATTGCT 2640
TGCGCCACGT GAAAAGTATA TTGGCCAAGA TATTAATTCT GAAGCATCTA GCCAAGACAC 2700
ACCAAGTTGG CAGCCTATTC ACACAAGTTA TGTGCACATG TGCTCACCAC TAAGAAATGG 2760
CGACACCTTG CAGCCTATTC CACTTGAAGA AATTCCAGCA ACTGCCAACG GCGATCATAA 2820
ACGAATGATC CGTTGGCAAA CAGAATGGCA AGCTTGTGAT GAATTGCAAA TGGCCGCAGC 2880
TACTAAAGCT GAATTTGCCG CACTTGAAGA GCTAACCAGT ATACTTGACG CATCAGAGTG ATCTATTTAG 2940
GCGTGGTTGG GACTTACGTG GCAGAGTCGA ATACTTGACG AAAATTCCGA CCTATTACTA 3000
TTTATACCGT GTTGGCGGTG AAAGCTTAGC AGTAGAAAAG CAGCGCTCTT GTCCTAAGTG 3060
```

FIG. 4A-3

```
TGGCAGTCAA GAATGGCTGC TCGATAAACC ATTATTGGAT ATGTTCCATT TTCGCTGTGA 3120
CACCTGCCGC ATCGTATCTA ATATCTCTTG GGACCATTTA TAACTCTTCC GAGTCTTATC 3180
ACACTAGAGT TTAGTCAGCA TAAAAATGGC GCTTATATTT CAATTAAAAG AAATATAAGC 3240
GCCATTTTCA TCGATACTAT ATATCAGCAG ACTATTTTCC GCGTAAATTA GCCCACATTA 3300
ATTTCATTCT TTGCCAGATC CCTGGATGAT CTAGTTGTGG CATCGACTCT TCAATAGGTT 3360
TAACCGCAGG TGTAACCCTT GGAGTCAATT CGTTTATAAA CTCGTTTAAA CTGTCACTTA 3420
ATTTAACGCT TTGTACTTCA CCTGGAATTT CAATCCATAC GCTGCCATCA CTATTATTAA 3480
CCGTCAACAT TTTATCTTCA TCATCAAGAA TACCAATAAA TGTTTTGTTG CCAAGTCGGC TCTTGCTTAA 3540
GCTTTCTCTT CATCATTAAA TGACCAATGA TGTTTTGTTG CCCATTGTGA TAAGTATTCA AAATCAGTTT 3600
GATCCCACAC TTGGATTAGC TCACCTTGGC CCCATTGTGA CTGCAGATAA AGCGGGTGCAG 3660
AAAAATGACT GCCAAAAAAT GGATTAATTT CTGCAGATAA TGTCATTTCA AGTGCTGTTT 3720
CAACATTAGC AAATTCACCA GGTTGTTGAC GTACAACCGA TTGCCAAAAC ACTGCGCCAT 3780
CGGAGCCCCGC TTCGGCGACA ACACACTCAG ACTTTTGTCC TTGCGCATAA TATCTTGGCT 3840
GTTCACCAAG CTTATCCATG TAGGCTTGTT GATATTTAGA TAAAAAAAGA TCTAAAGCAG 3900
GTAAAGAAGA CACTTAAGCC AGTTCCAAAA TCAGTTATAA TAGGGGTCTA TTTTGACATG 3960
GAAACCGTAT TGATGACACA ACATCATGAT CCCTACAGTA ACGCCCCCGA ACTTTCTGAA 4020
TTAACTTTAG GAAAGTCGAC CGGTTATCAA GAGCAGTATG ATGCATCTTT ACTACAAGCG 4080
```

```
TGCCGCGTAA ATTAAACCGT GATGCTATCG GTCTAACCAA TGAGCTACCT TTTCATGGCT 4140
GTGATATTTG GACTGGCTAC GAACTGTCTT GGCTAAATGC TAAAGGCAAG CCAATGATTG 4200
CTATTGCAGA CTTTAACCTA AGTTTTGATA GTAAAAATCT GATCGAGTCT AAGTCGTTTA 4260
AGCTGTATTT AAACAGCTAT AACCAAACAC GATTTGATAG CGTTCAAGCG GTTCAAGAAC 4320
GTTTAACTGA AGACTTAAGC GCCTGTGCCC AAGGCACAGT TACGGTAAAA GTGATTGAAC 4380
CTAAGCAATT TAACCACCTG AGAGTGGTTG ATATGCCAGG TACCTGCATT GACGATTTAG 4440
ATATTGAAGT TGATGACTAT AGCTTTAACT CTGACTATCT CACCGACAGT GTTGATGACA 4500
AAGTCATGGT TGCTGAAACG CTAACGTCAA ACTTATTGAA ATCAAACTGC CTAATCACTT 4560
CTCAGCCTGA CTGGGGTACA GTGATGATCC GTTATCAAGG GCCTAAGATA GACCGTGAAA 4620
AGCTACTTAG ATATCTGATT TCATTTAGAC AGCACAATGA ATTTCATGAG CAGTGTGTTG 4680
AGCGTATATT TGTTGATTTA AAGCACTATT GCCAATGTGC CAAACTTACT GTCTATGCAC 4740
GTTATACCCG CCGTGGTGGT TTAGATATCA ACCCATATCG TAGCGACTTT GAAAACCCTG 4800
CAGAAAATCA GCGCCTAGCG AGACAGTAAT TGATTGCAGT ACCTACAAAA AACAATGCCT 4860
ATAAGCCAAG CTTATGGGCA TTTTTATATT ATCAACTTGT CATCAAACCT CAGCCGCCAA 4920
GCCTTTTAGT TTTATCGCTA AATTAAGCCG CTCTCTCAGC CAAATATTTG CAGGATTTTG 4980
CTGTAATTTA TGGCTCCACA CCATGAAATA CTCTATCGGC TCTACCGCAA AAGGTAAGTC 5040
AAATACCTGT AAGCCAAACA GCTTGGCATA TTCGTCAGTG TGGGCTTTTG ACGGATAGC 5100
```

FIG. 4A-5

```
TAACGCATCA CTTTTTGAGG CAACCGACAT CATACTTAAT ATTGATGATT GCTCGCTGTG  5160
CATTTGCCTT GCCGGTAACA CCTGTTTAGT CAGCAAGTCG GCAACACTTA AATTGTAGCG  5220
GCGCATCTTA AAAATAATAT GCTTTTCATT AAAGTATTGC TCTTGCGTCA ACCCACCTTG  5280
GATCCCTTGGG TGAGCATTTC GTGCCACACA AACTAATTTA TCCTGCATTA CTTTTTGACT  5340
CTTAAATGCC GCAGATTCTG GCAGCCAAAT ATCTAAGGCT AAATCCACCT TTTCTAGTTG  5400
TAGGTCCATC TGCAACTCTT CTTCAATGAG CGGCGGCTCA CGAAATACAA TATTAATTGC  5460
AGTGCCCTGT AACACTTGCT CAATTTGATC TTGCAAGAGT TGTATTGCCG ACTCGCTGGC  5520
ATACACATAA AAAGTTCGCT CACTTGAAGT GGGGTCAAAT GCTTCAAAGC TAGTCGCAAC  5580
TTGCTCAATT GTTGACATAG CGCCCGCGAG CTGTTGATAA AGCGTCATCG CACTTGCGGT  5640
AGGTTTAACT CCCCTACCCA CTCGAGTAAA CAACTCTTCT CCAACAATAC TTTTTAGCCT  5700
CGAAATCGCA TTACTAACCG ACGACTGAGT CAAATCCAGC TCTTCTGCCG CCCGGCTAAA  5760
AGATGAGGTG CGATACACCG CAGTAAAAAC GCGAAATAAA TTAAGATCAA AAGCTTTTTG  5820
CTGCGACATA AATCAGCTAT CTCCTTATCC TTATCCTTAT CCTTATATAAAA AGTTAGCTCC  5880
AGAGCACTCT AGCTCAAAAA CAACTCAGCG TATTAAGCCA ATATTTGGG AACTCAATTA  5940
ATATTCATAA TAAAAGTATT CATAATATAA ATACCAAGTC ATAATTTAGC CCTAATTATT  6000
AATCAATTCA AGTTACCTAT ACTGGCCTCA ATTAAGCAAA TGTCTCATCA GTCTCCCTGC  6060
AACTAAAATGC AATATTGAGA CATAAAGCTT TGAACTGATT CAATCTTACG AGGGTAACTT  6120
```

FIG. 4A-6

```
ATGAAACAGA CTCTAATGGC TATCTCAATC ATGTCGCTTT TTTCATTCAA TGCGCTAGCA 6180
GCGCAACATG AACATGACCA CATCACTGTT GATTACGAAG GGAAAGCCGC AACAGAACAC 6240
ACCATAGCTC ACAACCAAGC TGTAGCTAAA ACACTTAACT TTGCCGACAC GCGTGCATTT 6300
GAGCAATCGT CTAAAAATCT AGTCGCCAAG TTTGATAAAG CAACTGCCGA TATATTACGT 6360
GCCGAATTTG CTTTTATTAG CGATGAAATC CCTGACTCGG TTAACCCGTC TCTCTACCGT 6420
CAGGCTCAGC TTAATATGGT GCCTAATGGT CTGTATAAAG TGAGCGATGG CATTTACCAG 6480
GTCCGCGGTA CCGACTTATC TAACCTTACA CTTATCCGCA GTGATAACGG TTGGATAGCA 6540
TACGATGTTT TGTTAACCAA AGAAGCAGCA AAAGCCTCAC TACAATTTGC GTTAAAGAAT 6600
CTACCTAAAG ATGGCGATTT ACCCGTTGTT GCGATGATTT ACTCCCATAG CCATGCGGAC 6660
CACTTTGGCG GAGCTCGCGG TGTTCAAGAG ATGTTCCCTG ATGTCAAAGT CTACGGCTCA 6720
GATAACATCA CTAAAGAAAT TGTCGATGAG AACGTACTTG CCGGTAACGC CATGAGCCGC 6780
CGGCAGCTT ATCAATACGG CGCAACACTG GGCAAACATG ACCACGGTAT TGTTGATGCT 6840
GCGCTAGGTA AAGGTCTATC AAAAGGTGAA ATCACTTACG TCGCCCCAGA CTACACCTTA 6900
AACAGTGAAG GCAAATGGGA AACGCTGACG ATTGATGGTC TAGAGATGGT GTTTATGGAT 6960
GCCTCGGGCA CCGAAGCTGA GTCAGAAATG ATCACTTATA TTCCCTCTAA AAAAGCGCTC 7020
TGGACGGCGG AGCTTACCTA TCAAGGTATG CACAACATTT ATACGCTGCG CGGCGCTAAA 7080
GTACGTGATG CGCTCAAGTG GTCAAAAGAT ATCAACGAAA TGATCAATGC CTTTGGTCAA 7140
```

FIG. 4A-7

```
GATGTCGAAG TGCTGTTTGC CTCGCACTCT GCGCCAGTGT GGGGTAACCA AGCGATCAAC 7200
GATTTCTTAC GCCTACAGCG TGATAACTAC GGCCTAGTGC ACAATCAAAC CTTGAGACTT 7260
GCCAACGATG GTGTCGGTAT ACAAGATATT GGCGATGCGA TTCAAGACAC GATTCCAGAG 7320
TCTATCTACA AGACGTGGCA TACCACGGCA CTTATAGCCA TAACGCTAAA 7380
GCGGTTTATA ACAAGTATCT AGGCTACTTC GATATGAACC CAGCCAACCT TAATCCGCTG 7440
CCAACCAAGC AAGAATCTGC CAAGTTTGTC GAATACATGG GCGGGCGCAGA TGCCGCAATT 7500
AAGCGCGCTA AAGATGATTA CGCTCAAGGT GAATACCGCT TTGTTGCAAC GGCATTAAAT 7560
AAGGTGGTGA TGGCCGAGCC AGAAAATGAC TCCGCTCGTC AATTGCTAGC CGATACCTAT 7620
GAGCAACTTG GTTATCAAGC AGAAGGGGCT GGCTGGAGAA ACATTTACTT AACTGGCGCA 7680
CAAGAGCTAC GAGTAGGTAT TCAAGCTGGC GCGCCTAAAA CCGCATCGGC AGATGTCATC 7740
AGTGAAATGG ACATGCCGAC TCTATTTGAC TTCCTCGCGG TGAAGATTGA TAGTCAACAG 7800
GCGGCTAAGC ACGGCTTAGT TAAGATGAAT GTTATCACCC CTGATACTAA AGATATTCTC 7860
TATATTGAGC TAAGCAACGG TAACTTAAGC AACGCAGTGG TCGACAAAGA GCAAGCAGCT 7920
GACGCAAACC TTATGGTTAA TAAAGCTGAC GTTAACCGCA TCTTACTTGG CCAAGTAACC 7980
CTAAAAGCGT TATTAGCCAG CGGCGATGCC AAGCTCACTG GTGATAAAAC GGCATTTAGT 8040
AAAATAGCCG ATAGCATGGT CGAGTTTACA CCTGACTTCG AAATCGTACC AACGCCTGTT 8100
AAATGAGGCA TTAATCTCAA CAAGTGCAAG CTAGACATAA AAATGGGGCG ATTAGACGCC 8160
```

FIG. 4A-8

| | | | | | |
|---|---|---|---|---|---|
| CCATTTTTTA | TGCAATTTTG | AACTAGCTAG | TCTTAGCTGA | AGCTCGAACA | ACAGCTTTAA 8220 |
| AATTCACTTC | TTCTGCTGCA | ATACTTATTT | GCTGACACTG | ACCAATACTC | AGTGCAAAAC 8280 |
| GATAACTATC | ATCAAGATGG | CCCAGTAAAC | AATGCCAATT | ATCAGCAGCG | TTCATTTGCT 8340 |
| GTTCTTTAGC | CTCAATCAAA | CCTAAACCAG | ACTTTTGTGG | CTCAGCGTTA | GGCTTATTAG 8400 |
| AACTCGACTC | TAGTAAAGCA | AGACCAATAT | CTTGTTTTAA | CAAAACCTGT | CGCTGATTAA 8460 |
| GTTGATGCTC | AACCTTGTGA | TCCGCAATAG | CATCGGAAAT | ATCAACACAA | TGGCTCAAGC 8520 |
| TTTAGGTGC | ATTAACTCCA | AGAAAAGTTT | CGCTCAGTGC | AGAGAAGTCA | AACGCAAAAG 8580 |
| ATTTTAGCGA | TAATGCCAGC | CCAAGTCCCT | TCGCTTTAAT | GTAAGACTCC | TTGAGCGCCC 8640 |
| ACAAATCAAA | AAAGCGGTCT | CGCTGCAAGG | CCTCTGGTAA | CGCTAACAAG | GCTCGCTTTT 8700 |
| CTGATTCAGA | GAAATAATGA | CTAAGAATAG | AGTGGATATT | GGTGCTGTTA | CGGCAACGCT 8760 |
| CAATGTCGAC | GCCAAACTCA | ATACTAGCAG | AGTCAGTTTC | CTCCTTGCTT | GCCTGACTGG 8820 |
| CGCCTTTATT | ATCAGCAGTG | CAAATGCCTA | CTAATAGCCA | ATCTCCACTA | TGACTCACAT 8880 |
| TAAAGTGGAC | CCCGGTTTGA | GCAAATTGCG | CATCACTCAA | TCTAGGCTTA | CCTTTGTCGC 8940 |
| CATATTCAAA | GCGCCATTCA | TTGGGGCGTA | TTTCACTATG | TTGTGACAAT | AAAGCGGCA 9000 |
| AATAGCCTCT | TACCATTAAA | CCTTGAGTTT | TAGCTTCTTG | TTTAATGTAG | CGATTAACCT 9060 |
| TAATTAACTC | ATCTTCAGGC | AGCCATGACT | TAACCAACTC | TGTAGTCTGG | TTATCGCACT 9120 |
| CTTGTATTGT | TAACGGACAG | AAGTATAAGG | AAATCAATCG | AGAAGTTAGC | AATTTTTCAG 9180 |

FIG. 4A-9

```
GACACTCTTT AAAGCAACAA ACATAACCCC TATTTTTACC AATTTAAGAT CAAAACTAAA 9240
GCCAAAACTA ATTGAGAATA GTGTCAAACT AGCTTTAAAG GAAAAAAATA TAAAAAGAAC 9300
ATTATACTTG TATAAATTAT TTTACACACC AAAGCCATGA TCTTCACAAA ATTAGCTCCC 9360
TCTCCCTAAA ACAAGATTGA ATAAAAAAAT AAACCTTAAC TTTCATATAG ATAAAACAAA 9420
CCAATGGGAT AAAGTATATT GAATTCATTT TTAAGGAAAA ATTCAAATTG AATTCAAGCT 9480
CTTCAGTAAA AGCATATTTT GCCGTTAGTG TGAAAAAAAA CAAATTTAAA AACCAACATA 9540
GAACAAATAA GCAGACAATA AAACCAAGGC GCAACACAAA CAACGCGCTT ACAATTTTCA 9600
CAAAAAAGCA ACAAGAGTAA CGTTTAGTAT TTGGATATGG TTATTGTAAT TGAGAATTTT 9660
ATAACAATTA TATTAAGGGA ATGAGTATGT TTTTAAATTC AAAACTTTCG CGCTCAGTCA 9720
AACTTGCCAT ATCCGCAGGC TTAACAGCCT CGCTAGCTAT GCCTGTTTTT GCAGAAGAAA 9780
CTGCTGCTGA AGAACAAATA GAAAGAGTCG CAGTGACCGG ATCGCGAATC GCTAAAGCAG 9840
AGCTAACTCA ACCAGCTCCA GTCGTCAGCC TTTCAGCCCA AGAACTGACA AAATTTGGTA 9900
ATCAAGATTT AGGTAGCGTA CTAGCAGAAT TACCTGCTAT TGGTGCAACC AACACTATTA 9960
TTGGTAATAA CAATAGCAAC TCAAGCGCAG GTGTTAGCTC AGCAGACTTG CGTCGTCTAG 10020
GTGCTAACAG AACCTTAGTA TTAGTCAACG GTAAGCGCTA CGTTGCCGGC CAACCGGGCT 10080
CAGCTGAGGT AGATTTGTCA ACTATACCAA CTAGCATGAT CTCGCGAGTT GAGATTGTAA 10140
CCGGCGGTGC TTCAGCAATT TATGGTTCGG ACGCTGTATC AGGTGTTATC AACGTTATCC 10200
```

FIG. 4A-10

```
TTAAAGAAGA CTTTGAAGGC TTTGAGTTTA ACGCACGTAC TAGCGGTTCT ACTGAAAGTG 10260
TAGGCACTCA AGAGCACTCT TTTGACATTT TGGGTGGTGC AAACGTTGCA GATGGACGTG 10320
GTAATGTAAC CTTCTACGCA GGTTATGAAC GTACAAAAGA AGTCATGGCT ACCGACATTC 10380
GCCAATTCGA TGCTTGGGGA ACAATTAAAA ACGAAGCCGA TGGTGGTGAA GATGATGGTA 10440
TTCCAGACAG ACTACGTGTA CCACGAGTTT ATTCTGAAAT GATTAATGCT ACCGGTGTTA 10500
TCAATGCATT TGGTGGTGGA ATTGGTCGCT CAACCTTTGA CAGTAACGGC AATCCTATTG 10560
CACAACAAGA ACGTGATGGG ACTAACAGCT TTGCATTTGG TTCATTCCCT AATGGCTGTG 10620
ACACATGTTT CAACACTGAA GCATACGAAA ACTATATTCC AGGGGTAGAA AGAATAAACG 10680
TTGGCTCATC ATTCAACTTT GATTTTACCG ATAACATTCA ATTTTACACT GACTTCAGAT 10740
ATGTAAAGTC AGATATTCAG CAACAATTTC AGCCTTCATT CCGTTTTTGGT AACATTAATA 10800
TCAATGTTGA AGATAACGCC TTTTTGAATG ACGACTTGCG TCAGCAAATG CTCGATGCGG 10860
GTCAAACCAA TGCTAGTTTT GCCAAGTTTT TTGATGAATT AGGAAATCGC TCAGCAGAAA 10920
ATAAACGCGA ACTTTTCCGT TACGTAGGTG GCTTTAAAGG TGGCTTTGAT ATTAGCGAAA 10980
CCATATATTGA TTACGACCTT TACTATGTTT ATGGCGAGAC TAATAACCGT CGTAAAACCC 11040
TTAATGACCT AATTCCTGAT AACTTTGTCG CAGCTGTCGA CTCTGTTATT GATCCTGATA 11100
CTGGCTTAGC AGCGTGTCGC TCACAAGTAG CAAGCGCTCA AGGCGATGAC TATACAGATC 11160
CCGCGTCTGT AAATGGTAGC GACTGTGTTG CTTATAACCC ATTGGCATG GGTCAAGCTT 11220
```

FIG. 4A-11

```
CAGCAGAAGC CCGGCGACTGG GTTTCTGCTG ATGTGACTCG TGAAGACAAA ATAACTCAAC 11280
AAGTGATTGG TGGTACTCTC GGTACCGATT CTGAAGAACT ATTTGAGCTT CAAGGTGGTG 11340
CAATCGCTAT GGTTGTTGGT TTTGAATACC GTGAAGAAAC GTCTGGTTCA ACAACCGATG 11400
AATTTACTAA AGCAGGTTTC TTGACAAGCG CTGCAACGCC AGATTCTTAT GGCGAATACG 11460
ACGTGACTGA GTATTTTGTT GAGGTGAACA TCCCAGTACT AAAAGAATTA CCTTTTGCAC 11520
ATGAGTTGAG CTTTGACGGT GCATACCGTA ATGCTGATTA CTCACATGCC GGTAAGACTG 11580
AAGCATGGAA AGCTGGTATG TTCTACTCAC CATTAGAGCA ACTTGCATTA CGTGGTACGG 11640
TAGGTGAAGC AGTACGAGCA CCAAACATTG CAGAAGCCTT TAGTCCACGC TCTCCTGGTT 11700
TTGGCCGCGT TTCAGATCCA TGTGATGCAG ATCCCTCCAG TAGTCCAAGT TGACGATCCG 11760
CAAACTGTGC AGCATTGGGG ATCCCTCCAG AACCTGAAAC ATCAACATCC TTTACAGGTG 11820
ATACCCTTATC TGGTGGTAAC CCAGATCTAA AACCTGAAAC ATCAACATCC TTTACAGGTG 11820
```

```
CTGATGAGAT TAATGATGAA AAAGGCGAAG TAGGTGATCC AGAGCTGCAG TTCCGCCTAG 12300
GCATCGATTA CCGTCTAGAT GATCTAAGTG TTAGCTGGAA CACGCGTTAT ATTGATAGCG 12360
TAGTAACTTA TGATGTCTCT GAAAATGGTG GCTCTCCTGA AGATTATAT CCAGGCCACA 12420
TAGGCTCAAT GACAACTCAT GACTTGAGCG CTACATACTA CATCAATGAG AACTTCATGA 12480
TTAACGGTGG TGTACGTAAC CTATTTGACG CACTTCCACC TGGATACACT AACGATGCGC 12540
TATATGATCT AGTTGGTCGC CGTGCATTCC TAGGTATTAA GGTAATGATG TAATTAATTA 12600
TTACGCCTCT AACTAATAAA AATGCAATCT CTTCGTAGAG ATTGCATTT TTTATGAAAT 12660
CCAATCTTAA ACTGGTTCTC CGAGCATCTT ACGCCTTAAA AACCCCGCCC CTCAATGTAA 12720
CGCCAAAGTT AATTGCTTAC ACGCACTTAC ACAAACGAAC AATTTCATTA ACACGAGACA 12780
CAGCTCACGC TTTTTATTT ACCCTTGATT TTACTACATA AAATTGCGTT TTAGCGCACA 12840
AGTGTTCTCC CAAGCTGGTC GTATCTGTAA TTATTCAGTC CCAGGTGATT GTATTGACCC 12900
ATAAGCTCAG GTAGTCTGCT CTGCCATTAG CTAAACAATA TTGACAAAAT GGCGATAAAA 12960
TGTGGCTTAG CGCTAAGTTC ACCGTAAGTT TTATCGGCAT TAAGTCCCAA CAGATTATTA 13020
ACGGAAACCC GCTAAACTGA TGGCAAAAAT AAATAGTGAA CACTTGGATG AAGCTACTAT 13080
TACTTCGAAT AAGTGTACGC AAACAGAGAC TGAGGCTCGG CATAGAAATG CCACTACAAC 13140
ACCTGAGATG CGCCGATTCA TACAAGAGTC GGATCTCAGT GTTAGCCAAC TGTCTAAAAT 13200
ATTAAATATC AGTGAAGCTA CCGTACGTAA GTGGCGCAAG CGTGACTCTG TCGAAAACTG 13260
```

FIG. 4A-13

```
TCCTAATACC  CCGCACCATC  TCAATACCAC  GCTAACCCCT  TTGCAAGAAT  ATGTGGTTGT  13320
GGGCCTGCGT  TATCAATTGA  AAATGCCATT  AGACAGATTG  CTCAAAGCAA  CCCAAGAGTT  13380
TATCAATCCA  AACGTGTCGC  GCTCAGGTTT  AGCAAGATGT  TTGAAGCGTT  ATGGCGTTTC  13440
ACGGGTGAGT  GATATCCAAA  GCCCACACGT  ACCAATGCGC  TACTTTAATC  AAATTCCAGT  13500
CACTCAAGGC  AGCGATGTGC  AAACCTACAC  CCTGCACTAT  GAAACGCTGG  CAAAAACCTT  13560
AGCCTTACCT  AGTACCGATG  GTGACAATGT  GGTGCAAGTG  GTGTCTCTCA  CCATTCCACC  13620
AAAGTTAACC  GAAGAAGCAC  CCAGTTCAAT  TACACAAGCC  ATTGATCCTC  ATAGCGACTG  13680
GATCTATCTC  GACATATACC  AAGATGGCAA  AAAGTTACTC  ACGAATAGAT  ATATGGCTTA  13740
TGTGCTAAAA  CACGGGCCAT  TCCATTTACG  TCGCCGCCCC  GTGCGTAACT  ATCACACCTT  13800
TTTACAGCGC  TTTCCTGGAG  CGACGCAAAA  CAGTGGAGAC  TCTAAAGATA  TGCCTGAAAC  13860
AATCAACAAG  ACGCCTGAAA  CACAGGCACC  CAGTGGAGAC  TCATAATGAG  CCAGACCTCT  13920
AAACCTACAA  ACTCAGCAAC  TGAGCAAGCA  CAAGACTCAC  AAGCTGACTC  TCGTTTAAAT  13980
AAAAGACTAA  AAGATATGCC  AATTGCTATT  GTTGGCATGG  CGAGTATTTT  TGCAAACTCT  14040
CGCTATTTGA  ATAAGTTTTG  GGACTTAATC  AGCGAAAAAA  TTGATGCGAT  TACTGAATTA  14100
CCATCAACTC  ACTGGCAGCC  TGAAGAATAT  TACGACGCAG  ATAAAACCGC  AGCAGACAAA  14160
AGCTACTGTA  AACGTGGTGG  CTTTTTGCCA  GATGTAGACT  TCAACCCAAT  GGAGTTTGGC  14220
CTGCCGCCAA  ACATTTTGGA  ACTGACCGAT  TCATCGCAAC  TATTATCACT  CATCGTTGCT  14280
```

FIG. 4A-14

```
AAAGAAGTGT  TGGCTGATGC  TAACTTACCT  GAGAATTACG  ACCGCGATAA  AATTGGTATC  14340
ACCTTAGGTG  TCGGCGGTGG  TCAAAAAATT  AGCCACAGCC  TAACAGCGCG  TCTGCAATAC  14400
CCAGTATTGA  AGAAAGTATT  CGCCAATAGC  GGCATTAGTG  ACACCGACAG  CGAAATGCTT  14460
ATCAAGAAAT  TCCAAGACCA  ATATGTACAC  TGGGAAGAAA  ACTCGTTCCC  AGTTCACTT   14520
GGTAACGTTA  TTGCGGGCCG  TATCGCCAAC  CGCTTCGATT  TTGGCGGGCAT GAACTGTGTG  14580
GTTGATGCTG  CCTGTGCTGG  ATCACTTGCT  GCTATGCGTA  TGGCGCTAAC  AGAGCTAACT  14640
GAAGGTCGCT  CTGAAATGAT  GATCACCGGT  GGTGTGTGTA  CTGATAACTC  ACCCTCTATG  14700
TATATGAGCT  TTTCAAAAAC  GCCCGCCTTT  ACCACTAACG  AAACCATTCA  GCCATTTGAT  14760
ATCGACTCAA  AAGGCATGAT  GATTGGTGAA  GGTATTGGCA  TGGTGGCGCT  AAAGCGTCTT  14820
GAAGATGCAG  AGCGCGATGG  CGACCGCATT  TACTCTGTAA  CCTCGCCCAT  GGGTGCATCA  14880
TCTGACGGTA  AGTTTAAATC  AATCTATGCC  CCTCGCCCAT  CAGGCCAAGC  TAAAGCACTT  14940
AACCGTGCCT  ATGATGACGC  AGGTTTTGCG  CCGCATACCT  TAGGTCTAAT  TGAAGCTCAC  15000
GGAACAGGTA  CTGCAGCAGG  TGACGCGGCA  GAGTTTGCCG  GCCTTTGCTC  AGTATTTGCT  15060
GAAGGCAACG  ATACCAAGCA  ACACATTGCG  CTAGGTTCAG  TTAAATCACA  AATTGGTCAT  15120
ACTAAATCAA  CTGCAGGTAC  AGCAGGTTTA  ATTAAAGCTG  CTCTTGCTTT  GCATCACAAG  15180
GTACTGCCGC  CGACCATTAA  CGTTAGTCAG  CCAAGCCCTA  AACTTGATAT  CGAAAACTCA  15240
CCGTTTTATC  TAAACACTGA  GACTCGTCCA  TGGTTACCAC  GTGTTGATGG  TACGCCGCGC  15300
```

FIG. 4A-15

```
CGCGCGGGTA TTAGCTCATT TGGTTTTGGT GGCACTAACT TCCATTTGT ACTAGAAGAG 15360
TACAACCAAG AACACAGCCG TACTGATAGC GAAAAAGCTA AGTATCGTCA AGCCAAGTG  15420
GCGCAAAGCT TCCTTGTTAG CGCAAGCGAT AAAGCATCGC TAATTAACGA GTTAAACGTA 15480
CTAGCAGCAT CTGCAAGCCA AGCTGAGTTT ATCCTCAAAG ATGCAGCAGC AAACTATGGC 15540
GTACGTGAGC TTGATAAAAA TGCACCACGG ATCGGTTTAG TTGCAAACAC AGCTGAAGAG 15600
TTAGCAGGCC TAATTAAGCA AGCACTTGCC AAACTAGCAG CTAGCGATGA TAACGCATGG 15660
CAGCTACCTG GTGGCACTAG CTACCCGCGCC GCTGCAGTAG AAGGTAAAGT TGCCGCACTG 15720
TTTGCTGGCC AAGGTTCACA ATATCTCAAT ATGGGCCGTG ACCTTACTTG TTATTACCCA 15780
GAGATGCGTC AGCAATTTGT AACTGCAGAT AAAGTATTTG CCGCAAATGA TAAAACGCCG 15840
TTATCGCAAA CTCTGTATCC AAAGCCTGTA TTTAATAAAG ATGAATTAAA GGCTCAAGAA 15900
GCCATTTTGA CCAATACCGC CAATGCCCAA AGCGCAATTG GTGCGATTTC AATGGGTCAA 15960
TACGATTTGT TTACTGCGGC TGGCTTTAAT GCCGACATGG TTGCAGGCCA TAGCTTTGGT 16020
GAGCTAAGTG CACTGTGTGC TGCAGGTGTT ATTTCAGCTG ATGACTACTA CAAGCTGGCT 16080
TTTGCTCGTG GTGAGGCTAT GGCAACAAAA GCACCGGCTA AAGACGGCGT TGAAGCAGAT 16140
GCAGGAGCAA TGTTTGCAAT CATAACCAAG AGTGCTGCAG ACCTTGAAAC CGTTGAAGCC 16200
ACCATCGCTA AATTTGATGG GGTGAAAGTC GCTAACTATA ACGCGCCAAC GCAATCAGTA 16260
ATTGCAGGCC CAACAGCAAC TACCGCTGAT GCGGCTAAAG CGCTAACTGA GCTTGGTTAC 16320
```

FIG. 4A-16

```
AAAGCGATTA  ACCTGCCAGT  ATCAGGTGCA  TTCCACACTG  AACTTGTTGG  TCACGCTCAA  16380
GCGCCATTTG  CTAAAGCGAT  TGACGCAGCC  AAATTTACTA  AAACAAGCCG  AGCACTTTAC  16440
TCAAATGCAA  CTGGCGGACT  TTATGAAAGC  ACTGCTGCAA  AGATTAAAGC  CTCGTTTAAG  16500
AAACATATGC  TTCAATCAGT  GCGCTTTACT  AGCCAGCTAG  AAGCCATGTA  CAACGACGGC  16560
GCCCGTGTAT  TTGTTGAATT  TGGTCCAAAG  AACATCTTAC  AAAAATTAGT  TCAAGGCACG  16620
CTTGTCAACA  CTGAAAATGA  AGTTTGCACT  ATCTCTATCA  ACCCTAATCC  TAAAGTTGAT  16680
AGTGATCTGC  AGCTTAAGCA  AGCAGCAATG  CAGCTAGCGG  TTACTGGTGT  GGTACTCAGT  16740
GAAATTGACC  CATACCAAGC  CGATATTGCC  GCACCAGCGA  AAAAGTCGCC  AATGAGCATT  16800
TCGCTTAATG  CTGCTAACCA  TATCAGCAAA  GCAACTCGCG  CTAAGATGGC  CAAGTCTTTA  16860
GAGACAGGTA  TCGTCACCTC  GCAAATAGAA  CATGTTATTG  AAGAAAAAAT  CGTTGAAGTT  16920
GAGAAACTGG  TTGAAGTCGA  AAAGATCGTC  GAAAAGTGG   TTGAAGTAGA  GAAAGTTGTT  16980
GAGGTTGAAG  CTCCTGTTAA  TTCAGTGCAA  GCCAATGCAA  TTCAAACCCG  TTCAGTTGTC  17040
GCTCCAGTAA  TAGAGAACCA  AGTCGTGTCT  AAAAACAGTA  AGCCAGCAGT  CCAGAGCATT  17100
AGTGGTGATG  CACTCAGCAA  CTTTTTTGCT  GCACAGCAGC  AAACCGCACA  GTTGCATCAG  17160
CAGTTCTTAG  CTATTCCGCA  GCAATATGGT  GAGACGTTCA  CTACGCTGAT  GACCGAGCAA  17220
GCTAAACTGG  CAAGTTCTGG  TGTTGCAATT  CCAGAGAGTC  TGCAACGCTC  AATGGAGCAA  17280
TTCCACCAAC  TACAAGCGCA  AACACTACAA  AGCCACACCC  AGTTCCTTGA  GATGCAAGCG  17340
```

FIG. 4A-17

```
GGTAGCAACA TTGCAGCGTT AAACCTACTC AATAGCAGCC AAGCAACTTA CGCTCCAGCC 17400
ATTCACAATG AAGCGATTCA AAGCCAAGTG GTTCAAAGCC AAACTGCAGT CCAGCCAGTA 17460
ATTTCAACAC AAGTTAACCA TGTGTCAGAG CAGCCAACTC AAGCTCCAGC TCCAAAAGCG 17520
CAGCCAGCAC CTGTGACAAC TGCAGTTCAA ACTGCTCCGG CACAAGTTGT TCGTCAAGCC 17580
GCACCAGTTC AAGCCGCTAT TGAACCGATT AATACAAGTG TTGCGACTAC AACGCCTTCA 17640
GCCTTCAGCG CCGAAACAGC CCTGAGCGCA ACAAAAGTCC AAGCCACTAT GCTTGAAGTG 17700
GTTGCTGAGA AAACCGGTTA CCCAACTGAA ATGCTAGAGC TTGAAATGGA TATGGAAGCC 17760
GATTAGGCA TCGATTCTAT CAAGCGTGTA GAAATTCTTG GCACAGTACA AGATGAGCTA 17820
CCGGGTCTAC CTGAGCTTAG CCCTGAAGAT CTAGCTGAGT GTCGAACGCT AGGCGAAATC 17880
GTTGACTATA TGGGCAGTAA ACTGCCGGCT GAAGGCTCTA TGAATTCTCA GCTGTCTACA 17940
GGTTCCGCAG CTGCGACTCC TGCAGCGAAT GGTCTTTCTG CGGAGAAAGT TCAAGCGACT 18000
ATGATGTCTG TGGTTGCCGA AAAGACTGGC TACCCAACTG AAATGCTAGA GCTTGAAATG 18060
GATATGGAAG CCGATTTAGG CATAGATTCT ATCAAGCGCG TTGAAATTCT TGGCACAGTA 18120
CAAGATGAGC TACCGGGTCT ACCTGAGCTT AGCCCTGAAG ATCTAGCTGA GTGTCGTACT 18180
CTAGGCGAAA TCGTTGACTA TATGAACTCT AAACTCGCTG ACGGCTCTAA GCTGCCGGCT 18240
GAAGGCTCTA TGAATTCTCA GCTGTCTACA AGTGCCGCAG CTGCGACTCC TGCAGCGAAT 18300
GGTCTCTCTG CGGAGAAAGT TCAAGCGACT ATGATGTCTG TGGTTGCCGA AAAGACTGGC 18360
```

FIG. 4A-18

```
TACCCAACTG AAATGCTAGA ACTTGAAATG GATATGGAAG CTGACCTTGG CATCGATTCA 18420
ATCAAGCGCG TTGAAATTCT TGGCACAGTA CAAGATGAGC TACCGGGTTT ACCTGAGCTA 18480
AATCCAGAAG ATTTGGCAGA GTGTCGTACT CTTGGCGAAA TCGTGACTTA TATGAACTCT 18540
AAACTCGCTG ACGGCTCTAA GCTGCCAGCT GAAGGCTCTA TGCACTATCA GCTGTCTACA 18600
AGTACCGCTG CTGCGACTCC TGTAGCGAAT GGTCTCTCTG CAGAAAAAGT TCAAGCGACC 18660
ATGATGTCTG TAGTTGCAGA TAAAACTGGC TACCCAACTG AAATGCTTGA ACTTGAAATG 18720
GATATGGAAG CCGATTTAGG TATCGATTCT TTGAAATTCT TGGCACAGTA 18780
CAAGATGAGC TACCGGGTTT ACCTGAGCTA ATCAAGCGCG GTGTCGCACC 18840
CTAGGCGAAA TCGTGACTTA TATGGGCAGT AAACTGCCGG CTCAAGGCTC TGCTAATACA 18900
AGTGCCGCTG CGTCTCTTAA TGTTAGTGCC GTTGCGGCGC CTCAAGCTGC TGCGACTCCT 18960
GTATCGAACG GTCTCTCTGC AGAGAAAGTG CAAAGCACTA TGATGTCAGT AGTTGCAGAA 19020
AAGACCGGCT ACCCAACTGA AATGCTAGAA CTTGGCATGG ATATGGAAGC CGATTTAGGT 19080
ATCGACTCAA TTAAACGCGT TGAGATTCTT GGCACAGTAC AAGATGAGCT ACCGGGTCTA 19140
CCAGAGCTTA ATCCTGAAGA TTTAGCTGAG TGCCGTACGC TGGGCGAAAT CGTTGACTAT 19200
ATGAACTCTA AGCTGGCTGA CGGCTCTAAG CTTCCAGCTG AAGGCTCTGC TAATACAAGT 19260
GCCACTGCTG CGACTCCTGC AGTGAATGGT CTTTCTGCTG ACAAGGTACA GGCGACTATG 19320
ATGTCTGTAG TTGCTGAAAA GACCGGCTAC CCAACTGAAA TGCTAGAACT TGGCATGGAT 19380
```

FIG. 4A-19

```
ATGGAAGCAG ACCTTGGTAT TGATTCTATT AAGCGCGTTG AAATTCTTGG CACAGTACAA 19440
GATGAGCTCC CAGGTTTACC TGAGCTTAAT CCTGAAGATC TCGCTGAGTG CCGCACGCTT 19500
GGCGAAATCG TTAGCTATAT GAACTCTCAA CTGGCTGATG GCTCTAAACT TTCTACAAGT 19560
GCGGCTGAAG GCTCTGCTGA TACAAGTGCT GCAAATGCTG CAAAGCCGGC AGCAATTTCG 19620
GCAGAACCAA GTGTTGAGCT TCCTCCTCAT AGCGAGGTAG CGCTAAAAAA GCTTAATGCG 19680
GCGAACAAGC TAGAAAATTG TTTCGCCGCA GACGCAAGTG TTGTGATTAA CGATGATGGT 19740
CACAACGCAG GCGTTTTAGC TGAGAAACTT ATTAAACAAG GCCTAAAAGT AGCCGTTGTG 19800
CGTTTACCGA AAGGTCAGCC TCAATCGCCA CTTTCAAGCG ATGTTGCTAG CTTTGAGCTT 19860
GCCTCAAGCC AAGAATCTGA GCTTGAAGCC AGTATCACTG CAGTTATCGC GCAGATTGAA 19920
ACTCAGGTTG GCGCTATTGG TGGCTTTATT CACTTGCAAC CAGAAGCGAA TACAGAAGAG 19980
CAAACGGCAG TAAACCTAGA TGCGCAAAGT TTTACTCACG TTAGCAATGC GTTCTTGTGG 20040
GCCAAATTAT TGCAACCAAA GCTCGTTGCT GGAGCAGATG CTAAATACTG TTTTGTAACA 20100
GTAAGCCCGTA TCGACGGTGG CTTTGGTTAC AAAAACCTTAA ACGCCCTAAA AGATGCTGAG 20160
CTAAACCAAG CAGCATTAGC TGGTTTAACT TGCAACAGAT GTTGATGCAA GCCACAAGTG 20220
TTCTGTGCCG CGCTAGATAT CCAAGCTCAG CCCATCTTGC TGATGCAATC 20280
ACCAGTGAAC TATTTGATAG CCAAGCTCAG CTACCTGAAG TGGGCTTAAG CTTAATTGAT 20340
GGCAAAGTTA ACCGCGTAAC TCTAGTTGCT GCTGAAGCTG CAGATAAAAC AGCAAAAGCA 20400
```

FIG. 4A-20

```
GAGCTTAACA GCACAGATAA AATCTTAGTG ACTGGTGGGG CAAAAGGGGT GACATTTGAA 20460
TGTGCACTGG CATTAGCATC TCGCAGCCAG TCTCACTTTA TCTTAGCTGG GCGCAGTGAA 20520
TTACAAGCTT TACCAAGCTG GGCTGAGGGT AAGCAAACTA GCGAGCTAAA ATCAGCTGCA 20580
ATCGCACATA TTATTTCTAC TGGTCAAAAG CCAACGCCTA AGCAAGTTGA AGCCGCTGTG 20640
TGGCCAGTGC AAAGCAGCAT TGAAATTAAT GCCGCCCTAG CCGCCTTTAA CAAAGTTGGC 20700
GCCTCAGCTG AATACGTCAG ACCGATAGCG CCGCAATCAC AGCAGCACTT 20760
AATGGTCGCT CAAATGAGAT CACCGGTCTT ATTCATGGCG CAGGTGTACT AGCCGACAAG 20820
CATATTCAAG ACAAGACTCT TGCTGAACTT ATGGCACTAA AGTCAACGGC 20880
CTAAAAGCGC TGCTCGCGGC ACTTGAGCCA AGCAAAAATTA AATTACTTGC TATGTTCTCA 20940
TCTGCAGCAG CAGCGCTGCA GTTCACCGCT CAAAGCGATT ACGCGATGTC GAACGATATT 21000
CTTAACAAGG GTTTTTACGG TAATATCGGC CAAACCCAC AAGCTAAAGT CATGAGCTTT 21060
AACTGGGGTC CTTGGGATGG CGGCATGGT TTAAAAAGAT GTTTACCGAG 21120
CGTGGTGTGT ACGTTATTCC ACTAAAAGCA GGTGCAGAGC TATTTGCCAC TCAGCTATTG 21180
GCTGAAACTG GCGTGCAGTT GCTCATTGGT ACGTCAATGC AAGGTGGCAG CGACACTAAA 21240
GCAACTGAGA CTGCTTCTGT AAAAAAGCTT AATGCGGGTG AGGTGCTAAG TGCATCGCAT 21300
CCGCGTGCTG GTGCACAAAA AACACCACTA CAAGCTGTCA CTGCAACGCG TCTGTTAACC 21360
CCAAGTGCCA TGGTCTTCAT TGAAGATCAC CGCATTGGCG GTAACAGTGT GTTGCCAACG 21420
```

FIG. 4A-21

```
GTATGCGCCA TCGACTGGAT GCGTGAAGCG GCAAGCGACA TGCTTGGGCG TCAAGTTAAG 21480
GTACTTGATT ACAAGCTATT AAAAGGCATT GTATTTGAGA CTGATGAGCC GCAAGAGTTA 21540
ACACTTGAGC TAACGCCAGA CGATTCAGAC GAAGCTACGC TACAAGCATT AATCAGCTGT 21600
AATGGGCGTC CGCAATACAA GGCGACGCTT ATCAGTGATA ATGCCGATAT TAAGCAACTT 21660
AACAAGCAGT TTGATTTAAG CGCTAAGGCG ATTACCACAG CAAAAGAGCT TTATAGCAAC 21720
GGCACCTTGT TCCACGGTCC GCGTCTACAA GGGATCCAAT CTGTAGTGCA GTTCGATGAT 21780
CAAGGCTTAA TTGCTAAAGT CGCTCTGCCT AAGGTTGAAC TTAGCGATTG TGGTGAGTTC 21840
TTGCCGCAAA CCCACATGGG TGGCAGTCAA CCTTTTGCTG AGGACTTGCT ATTACAAGCT 21900
ATGCTGGTTT GGGCTCGCCT TAAAACTGGC TCGGCAAGTT TGCCATCAAG CATTGGTGAG 21960
TTTACCTCAT ACCAACCAAT GGCCTTTGGT GAAGCGAAT GTTGCGCTAT TGAAGTGATT 22020
AAGCACAACA AACGCTCACT TGAAGCTCACT ATTAGCAAAA GCTTAAATTC CGGCGAGTTA 22080
AGTGCCATGT TTAAGTCAGC TAAAATCACC ATTAGCAAAA GCTTAAATTC AGCATTTTTA 22140
CCTGCTGTCT TAGCAAACGA CAGTGAGGCG AATTAGTGGA ACAAACGCCT AAAGCTAGTG 22200
CGATGCCGCT GCGCATCGCA CTTATCTTAC TGCCAACACC GCAGTTTGAA GTTAACTCTG 22260
TCGACCAGTC AGTATTAGCC AGCTATCAAA CACTGCAGCC TGAGCTAAAT GCCCTGCTTA 22320
ATAGTGCGCC GACACCTGAA ATGCTCAGCA TCACTATCTC AGATGATAGC GATGCAAACA 22380
GCTTTGAGTC GCAGCTAAAT GCTGCGACCA ACGCAATTAA CAATGGCTAT ATCGTCAAGC 22440
```

FIG. 4A-22

```
TTGCTACGGC AACTCACGCT TTGTTAATGC TGCCTGCATT AAAAGCGGGCG CAAATGCGGA  22500
TCCATCCTCA TGCGCAGCTT GCCGCTATGC AGCAAGCTAA ATCGACGCCA ATGAGTCAAG  22560
TATCTGGTGA GCTAAAGCTT GGCGCTAATG CGCTAAGCCT AGCTCAGACT AATGCGCTGT  22620
CTCATGCTTT AAGCCAAGCC AAGCGTAACT TAACTGATGT CAGCGTGAAT GAGTGTTTTG  22680
AGAACCTCAA AAGTGAACAG CAGTTCACAG AGGTTTATTC GCTTATTCAG CAACTTGCTA  22740
GCCGCACCCA TGTGAGAAAA GAGGTTAATC AAGGTGTGGA ACTTGGCCCT AAACAAGCCA  22800
AAAGCCACTA TTGGTTTAGC GAATTTCACC AAAACCGTGT TGCTGCCATC AACTTTATTA  22860
ATGGCCAACA AGCAACCAGC TATGTGCTTA CTCAAGGTTC AGGATTGTTA GCTGCGAAAT  22920
CAATGCTAAA CCAGCAAAGA TTAATGTTTA TCTTGCCGGG TAACAGTCAG CAACAAATAA  22980
CCGCATCAAT AACTCAGTTA ATGCAGCAAT CTAGAGCTGC CCGCTTATCA GAGGTTAATG  23040
AGCTTTCTCT AGAATGCCAA CTAGAGTAAGC TCAGCATAAT GTATGACAAC TTAGTCAACG  23100
CAGACAAACT CACTACTCGC GATAGTAAGC CCGCTTATCA GGCTGTGATT CAAGCAAGCT  23160
CTGTTAGCGC TGCAAAGCAA GAGTTAAGCG CGCTTAACGA TGCACTCACA GCGCTGTTTG  23220
CTGAGCAAAC AAACGCCACA TCAACGAATA AAGGCTTAAT CCAATACAAA ACACCGGCGG  23280
GCAGTTACTT AACCCTAACA CCGCTTGGCA GCAACAATGA CAACGCCCAA GCGGGTCTTG  23340
CTTTTGTCTA TCCGGGTGTG GGAACGGTTT ACGCCGATAT GCTTAATGAG CTGCATCAGT  23400
ACTTCCCTGC GCTTTACGCC AAACTTGAGC GTGAAGGCGA TTTAAAGGCG ATGCTACAAG  23460
```

FIG. 4A-23

```
CAGAAGATAT CTATCATCTT GACCCTAAAC ATGCTGCCCA AATGAGCTTA GGTGACTTAG 23520
CCATTGCTGG CGTGGGGAGC AGCTACCTGT TAACTCAGCT GCTCACCGAT GAGTTTAATA 23580
TTAAGCCTAA TTTTGCATTA GGTTACTCAA TGGGTGAAGC ATCAATGTGG GCAAGCTTAG 23640
GCGTATGGCA AAACCCGCAT GCGCTGATCA GCAAAACCCA AACCGACCCG CTATTTACTT 23700
CTGCTATTTC CGGCAAATTG ACCGCGGTTA GACAAGCTTG GCAGCTTGAT GATACCGCAG 23760
CGGAAATCCA GTGGAATAGC TTTGTGGTTA GAAGTGAAGC AGCGCCGATT GAAGCCTTGC 23820
TAAAAGATTA CCCACACGCT TACCTCGCGA TTATTCAAGG GGATACCTGC GTAATCGCTG 23880
GCTGTGAAAT CCAATGTAAA GCGCTACTTG CAGCACTGGG TAAACGCGGT ATTGCAGCTA 23940
ATCGTGTAAC GGCGATGCAT ACGCAGCCTG CGATGCAAGA GCATCAAAAT GTGATGGATT 24000
TTTATCTGCA ACCGTTAAAA GCAGAGCTTC CTAGTGAAAT AAGCTTTATC AGCGCCGCTG 24060
ATTTAACTGC CAAGCAAACG GTGAGTGAGC CAGCCAAGTC GTTGCTCAGT 24120
CTATTGCCGA CACCTTCTGC CAAACCCTTG ACTTTACCGC GCTAGTACAT CACGCCCAAC 24180
ATCAAGGCGC TAAGCTGTTT GTTGAAATTG GCGCGGATAG ACAAAACTGC ACCTTGATAG 24240
ACAAGATTGT TAAACAAGAT GGTGCCAGCA GTGTACAACA TCAACCTTGT TGCACAGTGC 24300
CTATGAACGC AAAAGGTAGC CAAGATATTA CCAGCGTGAT TAAAGGCGCTT GGCCAATTAA 24360
TTAGCCATCA GGTGCCATTA CATTTATTGA TGGACTCAAG CGCGAGCTAA 24420
CACTTTGCCA ATTGACCAGC CAACAGCTGG CAGCACATGC AAATGTTGAC AGCAAGTTTG 24480
```

FIG. 4A-24

```
AGTCTAACCA AGACCATTTA CTTCAAGGGG AAGTCTAATG TCATTACCAG ACAATGCTTC 24540
TAACCACCTT TCTGCCAACC AGAAAGGCGC ATCTCAGGCA AGTAAAACCA GTAAGCAAAG 24600
CAAAATCGCC ATTGTCGGTT TAGCCACTCT GTATCCAGAC GCTAAAACCC CGCAAGAATT 24660
TTGCAGAAT TTGCTGGATA AACGCGACTC TCGCAGCACC TTAACTAACG AAAAACTCGG 24720
CGCTAACAGC CAAGATTATC AAGGTGTGCA AGGCCAATCT GACCGTTTTT ATTGTAATAA 24780
AGGCGGCTAC ATTGAGAACT TGCTGCAGGC TACAAATTGC CGGAGCAAAG 24840
CTTAAATGGC TTGGACGACA GCTTCCTTTG GGCGCTCGAT ACTAGCCGTA ACGCACTAAT 24900
TGATGCTGGT ATTGATATCA ACGGCGCTGA TTTAAGCCGC GCAGGTGTAG TCATGGGCGC 24960
GCTGTCGTTC CCAACTACCC GCTCAAACGA TCTGTTTTTG CCAATTTATC ACAGCGCCGT 25020
TGAAAAAGCC CTGCAAGATA AACTAGGCGT AAAGGCATTT AAGCTAAGCC CAATAATGC 25080
TCATACCGCT CGCGCGGCAA ATGAGAGCAG CCTAAATGCA GCCAATGGTG CCATTGCCCA 25140
TAACAGCTCA AAAGTGGTGG CCGATGCACT TGGCCTTGGC GGCGCACAAC TAAGCCTAGA 25200
TGCTGCCTGT GCTAGTTCGG TTTACTCATT AAAGCTTGCC TGCGATTACC TAAGCACTGG 25260
CAAAGCCGAT ATCATGCTAG CAGGCGCAGT ATCTGGCGCG GATCCTTTCT TTATTAATAT 25320
GGGATTCTCA ATCTTCCACG CCTACCCAGA CCATGGTATC TCAGTACCGT TTGATGCCAG 25380
CAGTAAAAGT TTGTTTGCTG GCGAAGGCGC TGGCGTATTA GTGCTTAAAC GTCTTGAAGA 25440
TGCCGAGCGC GACAATGACA AAATCTATGC GGTTGTTAGC GGCGTAGGTC TATCAAACGA 25500
```

FIG. 4A-25

```
CGGTAAAGGC CAGTTTGTAT TAAGCCCTAA TCCAAAAGGT CAGGTGAAGG CCTTTGAACG  25560
TGCTTATGCT GCCAGTGACA TTGAGCCAAA AGACATTGAA GTGATTGAGT GCCACGCAAC  25620
AGGCACACCG CTTGGCGATA AAATTGAGCT CACTTCAATG GAAACCTTCT TTGAAGACAA  25680
GCTGCAAGGC ACCGATGCAC CGTTAATTGG CTCAGCTAAG TCTAACTTAG GCCACCTATT  25740
AACTGCAGCG CATGCGGGGA TCATGAAGAT GATCTTCGCC ATGAAAGAAG GTTACCTGCC  25800
GCCAAGTATC AATATTAGTG ATGCTATCGC TTCGCCGAAA AAACTCTTCG GTAAACCAAC  25860
CCTGCCTAGC ATGGTTCAAG GCTGGCCAGA TAAGCCATCG AATAATCATT TTGGTGTAAG  25920
AACCCGTCAC GCAGGCGTAT CGGTATTTGG CTTTGGTGGC TGTAACGCCC ATCTGTTGCT  25980
TGAGTCATAC AACGGCAAAG GAACAGTAAA GGCAGAAGCC ACTCAAGTAC CGCGTCAAGC  26040
TGAGCCGCTA AAAGTGGTTG GCCTTGCCTC GCACTTTGGG CCTCTTAGCA GCATTAATGC  26100
ACTCAACAAT GCTGTGACCC AAGATGGGAA TGGCTTTATC GAACTGCCGA AAAAGCGCTG  26160
GAAAGGCCTT GAAAAGCACA GTGAACTGTT AGCTGAATTT CTGCTTAGCAT CTGCGCCAAA  26220
AGGTGCTTAT GTTGATAACT TCGAGCTGGA CTTTTTACGC TTTAAACTGC CGCCAAACGA  26280
AGATGACCGT TTGATCTCAC AGCAGCTAAT GCTAATGCGA GTAACAGACG AAGCCATTCG  26340
TGATGCCAAG CTTGAGCCGG GGCAAAAAGT AGCTGTATTA GTGGCAATGG AAACTGAGCT  26400
TGAACTGCAT CAGTTCCGCG GCCGGGTTAA CTTGCATACT CAATTAGCGC AAAGTCTTGC  26460
CGCCATGGGC GTGAGTTTAT CAACGGATGA ATACCAAGCG CTTGAAGCCA TCGCCATGGA  26520
```

FIG. 4A-26

```
CAGCGTGCTT  GATGCTGCCA  AGCTCAATCA  GTACACCAGC  TTTATTGGTA  ATATTATGGC  26580
GTCACGCGTG  GCGTCACTAT  GGGACTTTAA  TGGCCCAGCC  TTCACTATTT  CAGCAGCAGA  26640
GCAATCTGTG  AGCCGCTGTA  TCGATGTGGC  GCAAAACCTC  ATCATGGAGG  ATAACCTAGA  26700
TGCGGTGGTG  ATTGCAGCGG  TCGATCTCTC  TGGTAGCTTT  GAGCAAGTCA  TTCTTAAAAA  26760
TGCCATTGCA  CCTGTAGCCA  TTGAGCCAAA  CCTCGAAGCA  AGCCTTAATC  CAACATCAGC  26820
AAGCTGGAAT  GTCGGTGAAG  GTGCTGGCGC  GGTCGTGCTT  GTTAAAAATG  AAGCTACATC  26880
GGGCTGCTCA  TACGGCCAAA  TTGATGCACT  TGGCTTTGCT  AAAACTGCCG  AAACAGCGTT  26940
GGCTACCGAC  AAGCTACTGA  GCCAAACTGC  CACAGACTTT  AATAAGGTTA  AAGTGATTGA  27000
AACTATGGCA  GCGCCTGCTA  GCCAAATTCA  ATTAGCGCCA  ATAGTTAGCT  CTCAAGTGAC  27060
TCACACTGCT  GCAGAGCAGC  GTGTTGGTCA  CTGCTTTGCT  AGCCCAAACC  TGGCAAGCCT  27120
ATTACACGGC  TTACTTAACT  TAAATACTGT  AGCCCAAACC  AATAAAGCCA  ATTGCGCGCT  27180
TATCAACAAT  ATCAGTGAAA  ACCAATTATC  ACAGCTGTTG  ATTAGCCAAA  CAGCGAGCGA  27240
ACAACAAGCA  TTAACCGCGC  GTTTAAGCAA  TGAGCTTAAA  TCCGATGCTA  AACACCAACT  27300
GGTTAAGCAA  GTCACCTTAG  GTGGCCGTGA  TATCTACCAG  CATATTGTTG  ATACACCGCT  27360
TGCAAGCCTT  GAAAGCATTA  CTCAGAAATT  GGCGCAAGCG  ACAGCATCGA  CAGTGGTCAA  27420
CCAAGTTAAA  CCTATTAAGG  CCGCTGGCTC  AGTCGAAATG  GCTAACTCAT  TCGAAACGGA  27480
AAGCTCAGCA  GAGCCCACAA  TAACAATTGC  AGCACAACAG  ACTGCAAACA  TTGGCGTCAC  27540
```

FIG. 4A-27

```
CGCTCAGGCA ACCAAACGTG AATTAGGTAC CCCACCAATG ACAACAAATA CCATTGCTAA 27600
TACAGCAAAT AATTTAGACA AGACTCTTGA GACTGTTGCT GGCAATACTG TTGCTAGCAA 27660
GGTTGGCTCT GGCGACATAG TCAATTTTCA ACAGAACCAA CAATTGGCTC AACAAGCTCA 27720
CCTCGCCTTT CTTGAAAGCC GCAGTGCGGG TATGAAGGTG GCTGATGCTT TATTGAAGCA 27780
ACAGCTAGCT CAAGTAACAG GCCAAACTAT CGATAATCAG GCCCTCGATA CTCAAGCCGT 27840
CGATACTCAA ACAAGCGAGA ATGTAGCGAT TGCCGCAGAA TCACCAGTTC AAGTTACAAC 27900
ACCTGTTCAA GTTACAACAC CTGTTCAAAT CAGTGTTGTG GAGTTAAAAC CAGATCACGC 27960
TAATGTGCCA CCATACACGC CGCCAGTGCC TGCATTAAAG CCGTGTATCT GGAACTATGC 28020
CGATTTAGTT GAGTACGCAG AAGGCGATAT CGCCAAGGTA TTTGGCAGTG ATTATGCCAT 28080
TATCGACAGC TACTCGCGCC GCGTACGTCT ACCGACCACT GACTACCTGT TGGTATCGCG 28140
CGTGACCAAA CTTGATGCGA CCATCAATCA ATTTAAGCCA TGCTCAATGA CCACTGAGTA 28200
CGACATCCCT GTTGATGCGC CGTACTTAGT AGACGGACAA ATCCCCTGGG CGGTAGCAGT 28260
AGAATCAGGC CAATGTGACT TGATGCTTAT TAGCTATCTC GGTATCGACT TTGAGAACAA 28320
AGGCGAGCGG GTTTATCGAC TACTCGATTG TACCCTCACC TTCCTAGGCG ACTTGCCACG 28380
TGGCGGAGAT ACCCTACGTT ACGACATTAA GATCAATAAC TATGCTCGCA ACGGCGACAC 28440
CCTGCTGTTC TTCTTCTCGT ATGAGTGTTT TGTTGGCGAC AAGATGATCC TCAAGATGGA 28500
TGGCGGCTGC GCTGGCTTCT TCACTGATGA AGAGCTTGCC GACGGTAAAG GCGTGATTCG 28560
```

FIG. 4A-28

| | | | | |
|---|---|---|---|---|
| CACAGAAGAA | GAGATTAAAG | CTCGCAGCCT | AGTGCAAAAG | CAACGCTTTA | ATCCGTTACT | 28620 |
| AGATTGTCCT | AAAACCCAAT | TTAGTTATGG | TGATATTCAT | AAGCTATTAA | CTGCTGATAT | 28680 |
| TGAGGGTTGT | TTTGGCCCAA | GCCACAGTGG | CGTCCACCAG | CCGTCACTTT | GTTTCGCATC | 28740 |
| TGAAAAATTC | TTGATGATTG | AACAAGTCAG | CAAGGTTGAT | CGCACTGGCG | GTACTTGGGG | 28800 |
| ACTTGGCTTA | ATTGAGGGTC | ATAAGCAGCT | TGAAGCAGAC | CACTGGTACT | TCCCATGTCA | 28860 |
| TTTCAAGGGC | GACCAAGTGA | TGGCTGGCTC | GCTAATGGCT | GAAGGTTGTG | GCCAGTTATT | 28920 |
| GCAGTTCTAT | ATGCTGCACC | TTGGTATGCA | TACCCAAACT | AAAAATGGTC | GTTTCCAACC | 28980 |
| TCTTGAAAAC | GCCCTCACAGC | AAGTACGCTG | TCGCGGTCAA | GTGCTGCCAC | AATCAGGCGT | 29040 |
| GCTAACTTAC | CGTATGGAAG | TGACTGAAAT | CGGTTTCAGT | CCACGCCCAT | ATGCTAAAGC | 29100 |
| TAACATGGAT | ATCTTGCTTA | ATGGCAAAGC | GGTAGTGGAT | TTCCACTTTTG | TAGGGGTGAT | 29160 |
| GATAAAAGAG | GAAGATGAGT | GTACTCGTTA | TCCACTTTTG | ACTGAATCAA | CAACGGCTAG | 29220 |
| CACTGCACAA | GTAAACGCTC | AAACAAGTGC | GAAAAAGGTA | TACAAGCCAG | CATCAGTCAA | 29280 |
| TGCGCCATTA | ATGGCACAAA | TTCCTGATCT | GACTAAAGAG | CCAAACAAGG | GCGTTATTCC | 29340 |
| GATTCCCCAT | GTTGAAGCAC | CAATTACGCC | AGACTACCCG | AACCGTGTAC | CTGATACAGT | 29400 |
| GCCATTCACG | CCGTATCACA | TGTTTGAGTT | TGCTACAGGC | AATATCGAAA | ACTGTTTCGG | 29460 |
| GCCAGAGTTC | TCAATCTATC | GCGGCATGAT | CCCACCACGT | ACACCATGCG | GTGACTTACA | 29520 |
| AGTGACCACA | CGTGTGATTG | AAGTTAACGG | TAAGCGTGGC | GACTTTAAAA | AGCCATCATC | 29580 |

FIG. 4A-29

| | | | | |
|---|---|---|---|---|
| GTGTATCGCT | GAATATGAAG | TGCCTGCAGA | TGCGTGGTAT | TTCGATAAAA | ACAGCCACGG | 29640 |
| CGCAGTGATG | CCATATTCAA | TTTTAATGGA | GATCTCACTG | CAACCTAACG | GCTTTATCTC | 29700 |
| AGTTACATG | GGCACAACCC | TAGGCTTCCC | TGGCCTTGAG | CTGTTCTTCC | GTAACTTAGA | 29760 |
| CGGTAGCGGT | GAGTTACTAC | GTGAAGTAGA | TTTACGTGGT | AAAACCATCC | GTAACGACTC | 29820 |
| ACGTTTATTA | TCAACAGTGA | TGGCCCGGCAC | TAACATCATC | CAAAGCTTTA | GCTTCGAGCT | 29880 |
| AAGCACTGAC | GGTGAGCCTT | TCTATCGCGG | CACTGCGGTA | TTTGGCTATT | TTAAAGGTGA | 29940 |
| CGCACTTAAA | GATCAGCTAG | GCCTAGATAA | CGGTAAAGTC | ACTCAGCCAT | GGCATGTAGC | 30000 |
| TAACGGCGTT | GCTGCAAGCA | CTAAGGTGAA | CCTGCTTGAT | AAGAGCTGCC | GTCACTTTAA | 30060 |
| TGCGCCAGCT | AACCAGCCAC | ACTATCGTCT | AGCCGGTGGT | CAGCTGAACT | TTATCGACAG | 30120 |
| TGTTGAAATT | GTTGATAATG | GCGGCACCGA | AGGTTTAGGT | TACTTGTATG | CCGAGCGCAC | 30180 |
| CATTGACCCA | AGTGATTGGT | TCTTCCAGTT | CCACTTCCAC | CAAGATCCGG | TTATGCCAGG | 30240 |
| CTCCTTAGGT | GTTGAAGCAA | TTATTGAAAC | CATGCAAGCT | TACGCTATTA | GTAAAGACTT | 30300 |
| GGGCGCAGAT | TTCAAAAATC | CTAAGTTTGG | TCAGATTTTA | TCGAACATCA | AGTGGAAGTA | 30360 |
| TCGCGGTCAA | ATCAATCCGC | TGAACAAGCA | GATGTCTATG | TTACTTCAAT | 30420 |
| CAAAGATGAA | GACGGTAAGA | AAGTCATCAC | AGTTAATGCC | AGCTTGAGTA | AAGATGGTCT | 30480 |
| GCGCATATAC | GAGGTCTTCG | ATATAGCTAT | CAGCATCGAA | GAATCTGTAT | AAATCGGAGT | 30540 |
| GACTGTCTGG | CTATTTTACT | CAATTTCTGT | GTCAAAAGTG | CTCACCTATA | TTCATAGGCT | 30600 |

FIG. 4A-30

```
GCGGCGCTTT TTCTGGAAAT TGAGCAAAAG TATCTGCGTC CTAACTCGAT TTATAAGAAT 30660
GGTTTAATTG AAAAGAACAA CAGCTAAGAG CCGCAAGCTC AATATAAATA ATTAAGGGTC 30720
TTACAAATAA TGAATCCTAC AGCAACTAAC GAAATGCTTT CTCCGTGGCC ATGGGCTGTG 30780
ACAGAGTCAA ATATCAGTTT TGACGTGCAA GTGATGGAAC AACAACTTAA AGATTTTAGC 30840
CGGGCATGTT ACGTGGTCAA TCATGCCGAC CACGGCTTTG GTATTGCGCA AACTGCCGAT 30900
ATCGTGACTG AACAAGCGGC AAACAGCACA GATTTACCTG TTAGTGCTTT TACTCCTGCA 30960
TTAGGTACCG AAAGCCTAGG CGACAATAAT TTCCGCCGCG TTCACGGCGT TAAATACGCT 31020
TATTACGCAG GCGCTATGGC AAACGGTATT TCATCTGAAG AGCTAGTGAT TGCCCTAGGT 31080
CAAGCTGGCA TTTTGTGTGG TTCGTTTGGA GCAGCCGGTC TTATTCCAAG TCGCGTTGAA 31140
GCGGCAATTA ACCGTATTCA AGCAGCGCTG CCAAATGGCC CTTATATGTT TAACCTTATC 31200
CATAGTCCTA GCGAGCCAGC ATTAGAGCGT GGCAGCGTAG AGCTATTTTT AAAGCATAAG 31260
GTACGCACCG TTGAAGCATC AGCTTTCTTA GGTCTAACAC CACAAATCGT CTATTACCGT 31320
GCAGCAGGAT TGAGCCGAGA CGCACAAGGT AAAGTTGTGG TTGGTAACAA GGTTATCGCT 31380
AAAGTAAGTC GCACCGAAGT GGCTGAAAAG TTTATGATGC CAGCGCCCGC AAAAATGCTA 31440
CAAAAACTAG TTGATGACGG TTCAATTACC GCTGAGCAAA TGGAGCTGGC GCAACTTGTA 31500
CCTATGGCTG ACGACATCAC TGCAGAGGCC GATTCAGGTG GCCATACTGA TAACCGTCCA 31560
TTAGTAACAT TGCTGCCAAC CATTTTAGCG CTGAAAGAAG AAATTCAAGC TAAATACCAA 31620
```

FIG. 4A-31

| | | | | | |
|---|---|---|---|---|---|
| TACGACACTC | CTATTCGTGT | CGGTTGTGGT | GGCGGTGTGG | GTACGCCTGA | TGCAGCGCTG 31680 |
| GCAACGTTTA | ACATGGGCGC | GGCGTATATT | GTTACCGGCT | CTATCAACCA | AGCTTGTGTT 31740 |
| GAAGCGGGCG | CAAGTGATCA | CACTCGTAAA | TTACTTGCCA | CCACTGAAAT | GGCCGATGTG 31800 |
| ACTATGGCAC | CAGCTGCAGA | TATGTTCGAG | ATGGGCGTAA | AACTGCAGGT | GGTTAAGCGC 31860 |
| GGCACGCTAT | TCCCAATGCG | CGCTAACAAG | CTATATGAGA | TCTACACCCG | TTACGATTCA 31920 |
| ATCGAAGCGA | TCCCATTAGA | CGAGCGTGAA | AAGCTTGAGA | AACAAGTATT | CCGTCAAGC 31980 |
| CTAGATGAAA | TATGGGCAGG | TACAGTGGCG | CACTTTAACG | AGCGCGACCC | TAAGCAAATC 32040 |
| GAACGCGCAG | AGGGTAACCC | TAAGCGTAAA | ATGGCATTGA | TTTTCCGTTG | GTACTTAGGT 32100 |
| CTTTCTAGTC | GCTGGTCAAA | CTCAGGCGAA | GTGGGTCGTG | AAATGGATTA | TCAAATTTGG 32160 |
| GCTGGCCCTG | CTCTCGGTGC | ATTTAACCAA | TGGGCAAAAG | GCAGTTACTT | AGATAACTAT 32220 |
| CAAGACCGAA | ATGCCGTCGA | TTTGGCAAAG | CACTTAATGT | ACGGGCGCGGC | TTACTTAAAT 32280 |
| CGTATTAACT | CGCTAACGGC | TCAAGGCGTT | AAAGTGCCAG | CACAGTTACT | TCGCTGGAAG 32340 |
| CCAAACCAAA | GAATGGCCTA | ATACACTTAC | AAAGCACCAG | TCTAAAAAGC | CACTAATCTT 32400 |
| GATTAGTGGC | TTTTTTTATT | GTGGTCAATA | TGAGGCTATT | TAGCCTGTAA | GCCTGAAAAT 32460 |
| ATCAGCACTC | TGACTTTACA | AGCAAATTAT | AATTAAGGCA | GGGCTCTACT | CATTTATACT 32520 |
| GCTAGCAAAC | AAGCAAGTTG | CCCAGTAAAA | CAACAAGGTA | CCTGATTTAT | ATCGTCATAA 32580 |
| AAGTTGGCTA | GAGATTCGTT | ATTGATCTTT | ACTGATTAGA | GTCGCTCTGT | TTGGAAAAAG 32640 |

FIG. 4A-32

```
GTTTCTCGTT ATCATCAAAA TACACTCTCA AACCTTTAAT CAATTACAAC TTAGGCTTTC 32700
TGCGGGCATT TTTATCTTAT TTGCCACAGC TGTATTTGCC TTTAGGTTTT GGGTGCAACT 32760
ACCATTAATT GAGGCCTCAT TAGTTAAATT ATCTGAGCAA GAGCTCACCT CTTTAAATTA 32820
CGCTTTTCAG CAAATGAGAA AGCCACTACA AACCATTAAT TACGACTATG CGGTGTGGGA 32880
CAGAACCTAC AGCTATATGA AATCAAACTC AGCGAGCGCT AAAAGGTACT ATGAAAAACA 32940
TGAGTACCCA GATGATACGT TCAAGAGTTT AAAAGTCGAC GGAGTATTTA TATTCAACCG 33000
TACAAATCAG CCAGTTTTTA GTAAAGTTT TAATCATAGA AATGATATAC CGCTGGTCTT 33060
TGAATTAACT GACTTTAAAC AACATCCACA AAACATCGCA TTATCTCCAC AAACCAAACA 33120
GGCACACCCA CCGGCAAGTA CTCCCCCTGA GATGTGCCTT CTACCCATGG 33180
GGTTATCGCC ACACGATACG GTCCAGCAAT TTATAGCTCT TAAAATCTGA 33240
TCGTAGCGGC TCCCAACTTG GTTATTTAGT CTTCATTAGG TTAATTGATG AATGGTTCAT 33300
CGCTGAGCTA TCGCAATACA CTGCCCGCAGG TGTTGAAATC GCTATGGCTG ATGCCGCAGA 33360
CGCACAATTA GCGAGATTAG GCGCAAACAC TAAGCTTAAT AAAGTAACCG CTACATCCGA 33420
ACGGTTAATA ACTAATGTCG ATGGTAAGCC TCTGTTGAAG TTAGTGCTTT ACCATACCAA 33480
TAACCAACCG CCGCCGATGC TAGATTACAG TATAATAATT CTATTAGTTG AGATGTCATT 33540
TTTACTGATC CTCGCTTATT TCCTTTACTC CTACTTCTTA GTCAGGCCAG TTAGAAAGCT 33600
GGCTTCAGAT ATTAAAAAAA TGGATAAAAG TCGTGAAATT AAAAAGCTAA GGTATCACTA 33660
```

FIG. 4A-33

```
CCCTATTACT GAGCTAGTCA AAGTTGCGAC TCACTTCAAC GCCCTAATGG GGACGATTCA 33720
GGAACAAACT AAACAGCTTA ATGAACAAGT TTTATTGAT AAATTAACCA ATATTCCCAA 33780
TCGTCGCGCT TTTGAGCAGC GACTTGAAAC CTATTGCCAA CTGCTAGCCC GGCAACAAAT 33840
TGGCTTTACT CTCATCATTG CCGATGTGGA TCATTTTAAA GAGTACAACG ATACTCTTGG 33900
GCACCTTGCT GGGGATGAAG CATTAATAAA AGTGGCACAA ACACTATCGC AACAGTTTTA 33960
CCGTGCAGAA GATATTTGTG CCCGTTTTGG TGGTGAAGAA TTTATTATGT TATTTCGAGA 34020
CATACCTGAT GAGCCCTTGC CGATGCGATG CTGCACTCTT TTGCAGAGCT 34080
CAACCTACCT CATCCAAACT CATCAACCGC TAATTACGTT ACTGTGAGCC TTGGGGTTTG 34140
CACAGTTGTT GCTGTTGATG ATTTTGAATT TAAAAGTGAG TCGCATATTA TTGGCAGTCA 34200
GGCTGCATTA ATCGCAGATA AGGCGCTTTA TCATGCTAAA GCCTGTGGTC GTAACCAGTT 34260
GTCAAAAACT ACTATTACTG TTGATGAGAT TGAGCAATTA GAAGCAAATA AAATCGGTCA 34320
TCAAGCCTAA ACTCGTTCGA GTACTTTCCC CTAAGTCAGA GCTATTTGCC ACTTCAAGAT 34380
GTGGCTACAA GGCTTACTCT TTCAAAACCT GCATCAATAG AACACAGCAA AATACAATAA 34440
TTTAAGTCAA TTTAGCCTAT TAAACAGAGT TAATGACAGC TCATGGTCGC AACTTATTAG 34500
CTATTTCTAG CAATATAAAA ACTTATCCAT TAGTAGTAAC CAATAAAAAA ACTAATATAT 34560
AAAACTATTT AATCATTATT TTACAGATGA TTAGCTACCA CCCACCTTAA GCTGGCTATA 34620
TTCGCACTAG TAAAAATAAA CATTAGATCG GGTTCAGATC AATTTACGAG TCTCGTATAA 34680
```

FIG. 4A-34

```
AATGTACAAT AATTCACTTA ATTTAATACT GCATATTTTT ACAAGTAGAG AGCGGGTGATG 34740
AAACAAAATA CGAAAGGCTT TACATTAATT GAATTAGTCA TCGTGATTAT TATTCTCGGT 34800
ATACTTGCTG CTGTGGCACT GCCGAAATTC ATCAATGTTC AAGATGACGC TAGGATCTCT 34860
GCGATGAGCG GTCAGTTTTC ATCATTTGAA AGTGCCGTAA AACTATACCA TAGCGGTTGG 34920
TTAGCCAAAG GCTACAACAC TGCGGTTGAA AAGCTCTCAG GCTTTGGCCA AGGTAATGTT 34980
GCATCAAGTG ACACAGGTTT TCCGTACTCA ACATCAGGCA CGAGTACTGA TGTGCATAAA 35040
GCTTGTGGTG AACTATGGCA TGGCATTACC GATACAGACT TCACAATTGG TGCGGTTAGT 35100
GATGGCGATC TAATGACTGC AGATGTCGAT ATTGCTTACA CCTATCGTGG TGATATGTGT 35160
ATCTATCGCG ATCTGTATTT TATTCAGCGC TCATTACCTA CTAAGGTGAT GAACTACAAA 35220
TTTAAAACTG GTGAAATAGA AATTATTGAT GCTTTCTAAG ACCCTGACGG CTCAACTGGT 35280
CAATTACCAT AAATTTGGCG CTTATCTAAG TTGTACTTGC TCTGACCGAC ACAAATAATG 35340
TCGTTTCTCA GCATATATCA AAATACACAG GGGTTAGCTA CAGTATCCAG TATAGCTAAC 35400
CCCAAATCAT ATCTAACTTT ACACTGCATC TAATTCCAAA CAGTGCAACA CCAAAAGCCT 35460
AAACTATTGT TGACTCAGCG CGATGCAACG AACAAGTCTT GGATCGCAAT 35520
ACCTGAGCTA TCAAAAATGG TCACCTCATC AGCACTTTGA CGTCCTGTTG CGGACTCGTT 35580
TATCACCTGA CCAATCTCAA TTATCGGCGT ATTTCTGCTA TGTTGAAACT CACCAATAAC 35640
AATAGATTGA GAAGCAAAGT CGCAAAACAA GCGAGCATGA CTATATAGGT CAGTTGGCAA 35700
```

FIG. 4A-35

```
CTCTTGCTTA CCCACTTTAT CAGCGCCCAT TGCAGAAATA TGCGTTCCTG CTTGTACCCA 35760
CTGCGCTTCA AATAAAGGCG CTTGAGCTGT GGTTGCTGTG ATAATAATAT CTGCTTGTTC 35820
ACAAGCAGCT TGTGCATCAC AAGCTTCGGC ATTAATGCCT TTTTCTAATA AACGCTTAAC 35880
CAAGTTTTCA GTTTTGCTAG CACTACGGCC AACTACCAAT ACCTTAGTTA ATGAACGAAC 35940
CTTGCTCACT GCTAGCACTT CATATTCAGC CTGATGACCG GTACCAAAAA CAGTTAATAC 36000
CGTAGCATCT TCTCTCGCGA GGTAACTCAC TGCTACTGCA TCGGCAGCAC CAGTGCGGTA 36060
AGCATTAACG GTAGTGGCAG CAATCACCGN CTGCAACATA CCGGTTAATG GATCGAGTAA 36120
AAATACGTTA GTGCCGTGGC ATGGTAAACC ATGTTTATGG TTATCAGGCC AATAGCTGCC 36180
TGTTTTCCAG CCGACAAGGT TTGGCGTTGA AGCCGACTTT AATGAGAACA TTTCATTAAG 36240
GTTCGCGCCC TGTGCATTAA CTACCGGGAA CAAGGTTGCT TTATCATCTA CGGCAGCGAC 36300
AAACGCTTCT TTAACAGCGA ATGGTAAACC CTCATGGGAG ATGAGCTTTG ATGTTTGCGC 36360
TTCAGTTAAA TAGATCATAT TACCACCCCT GCACTCGATT CCAGATCTCA TAGCCACCAT 36420
TATCACCATC AGTATCAAAT ACATGGTACT GAGCGTGCAT TGAAGCTGTT GCACAGGCGT 36480
GGTTCGGCAA AATATGTAGA CGACTACCTA CCGGAACTG CGCTAAATCA ATAACGCCGC 36540
CATCAACTGC TTCAATAATG CCGTGCTCTT GATTAACAGT TATAACCTGT AGACCTGATA 36600
ACACGTGACC GCTGTCGTCA CACACTAAAC CATAACCACA ATCTTTTGGC TGCTCTGCAG 36660
TACCTCTATC ACCCGAAAGA GCCATCCAAC CCGCATCAAT GAAAATCCAG TTTTTATCAG 36720
```

FIG. 4A-36

```
GATTATGACC AATAACACTG GTCACTACCG TTGCGGCAAT ATCAGTTAAC TGACACACGT 36780
TTAGCCCTGC CATGACTAAA TCGAAGAAGG TGTACACACC CGCTCTAACC TCGGTGATCC 36840
CATCAAGGTT TTGATAGCTT TGCGCTGTTG GTGTTGAACC AATACTAACG ATGTCACATT 36900
GCATACCCGC TGCGCGAATG CGTCAGCAGC TTGTACAGCC GCTGCAACTT CATTTGCGC 36960
CGCATCAATT AATTGCTGTT TTTCAAAACA TTGATATGAC TCACCAGCGT GAGTNAGTAC 37020
GCCGTGAAAA CTCGCTGCGC CAGACGTTAG TATCTGAGCA ATTTCAATCA ACTTATCGGC 37080
TTCCGGTGGA ATACCACCAC GATGGCCATC ACAATCAATT TCAATTAATG CTGGTATTTG 37140
GCAGTCATAA GAACCACAGA AATGATTTAG CTGATGCGCT TGCTCAACAC TATCAAGTAA 37200
AACTCTTGCA TTAATACCTT GGTCCAACAT TGTCTGTGTA TTTAGCAATA CGCGGCAACT TACCATCGGC 37260
AATACCTACT GCATAAATAA ACAGTGACTG GTGAGTTTTT ACCTTTAGAT GCTAAGGCCT CGGCCTCTTT 37320
TACCGTTGAT GTTTTAAAAT GCGGTCTTAG GTTTGCACCT AAAAACTCGG CTGCTTCAAG 37380
TAGTTGACTG AGGTTATTAA TAAATACTGG CTTATTTACA AATCCTTCAA TTTTTTGGCG 37440
TGCTTGATAC TGACTTTGCT GAGTCGTGGA AAGTATTTGA TATAAAAACG GTGTATCAAT 37500
CCTAGTTCAT CAATCAATCT AACAAGTTTG ATGCCTAGCC ACAGTGGCTT TCTTTAATAT 37560
TGCTTTGGAA AATGCTTATA TTCAAAGTAT TTGAAAGACA TCAAACTTCT GTATTCATGA 37620
TCAGTATCCA CCAGCACGCA TTTATTTTAT ATTAACTATT ATCAAGATAT TGTTTAATGC 37680
                                                            AGATTAGGTT 37740
```

FIG. 4A-37

```
CAAACCAAAT GATTAGTACT GAAGATCTAC GTTTTATCAG CGTAATCGCC AGTCATCGCA  37800
CCTTAGCTGA TGCCGCTAGA ACACTAAATA TCACGCCACC ATCAGTGACA TTAAGGTTGC  37860
AGCATATTGA AAAGAAACTA TCGATTAGCC TGATC                             37895
```

FIG. 4A-38

6121
*
| MKQTLMAISI | MSLFSFNALA | AQHEHDHITV | DYEGKAATEH |
| TIAHNQAVAK | TLNFADTRAF | EQSSKNLVAK | FDKATADILR |
| AEFAFISDEI | PDSVNPSLYR | QAQLNMVPNG | YKVSDGIYQV |
| RGTDLSNLTL | IRSDNGWIAY | DVLLTKEAAK | ASLQFALKNL |
| PKDGDPVVAM | IYSHSHADHF | GGARGVQEMF | PDVKVYGSDN |
| ITKEIVDENV | LAGNAMSRRA | AYQYGATLGK | HDHGIVDAAL |
| GKGLSKGEIT | YVAPDYTLNS | EGKWETLTID | GLEMVFMDAS |
| GTEAESEMIT | YIPSKKALWT | AELTYQGMHN | IYTLRGAKVR |
| DALKWSKDIN | EMINAFGQDV | EVLFASHSAP | VWGNQAINDF |
| LRLQRDNYGL | VHNQTLRLAN | DGVGIQDIGD | AIQDTIPESI |
| YKTWHTNGYH | GTYSHNAKAV | YNKYLGYFD | MNPANLNPLP |
| TKQESAKFVE | YMGGADAAIK | RAKDDYAQGE | YRFVATALNK |
| VVMAEPENDS | ARQLLADTYE | QLGYQAEGAG | WRNIYLTGAQ |
| ELRVGIQAGA | PKTASADVIS | EMDMPTLFDF | LAVKIDSQQA |
| AKHGLVKMNV | ITPDTKDILY | IELSNGNLSN | AVVDKEQAAD |
| ANLMVNKADV | NRILLGQVTL | KALLASGDAK | LTGDKTAFSK |
| IADSMVEFTP | DFEIVPTPVK | | |

8186
*
STKASARVVA KFNVEEAAIS IQQCQGISLA FRYSDDLHGL

LCHWNDAANM QQEKAEILGL GSKQPEANPK NSSSELLALG

IDQKLLVQRQ NLQHEVKHDA IADSIDVCHS LSKPANVGLF

TESLASFDFA FSKLSLALGL GKAKIYSEKL AWLDFFRDRQ

LAEPLALLAR KESESFYHSL ISHINTSNRC REIDVGFEIS

ASDTEEKSAQ SAGKNDATCI GVLLWDGSHS VNFHVGTQAF

QADSLRPKGK DGYEFRWENP RIESHQSLLA RLYGRVM
                                        *
                                      9016

GCTAGTCTTA GCTGASRTHR YSAASRAGCT CGAACAACAG CTTTAAAATT
CACTTCTTCT GCTGCAATAC TTATTTGCTG ACACTGACCA ATACTCAGTG
CAAAACGATA ACTATCATCA AGATGAAAR GVAVAAAYSH ASNVAGGAAA
ASRGNGNCYS GNGYSRAAHA RGTYRSRASA SHSCCCAGTA AACAATGCCA
ATTATCAGCA GCGTTCATTT GCTGTTCTTT AGCCTCAATC AAACCTAAAC
CAGACTTTTG TGGCTCAGCG TTAGGCTTAT TAGGYCYSHS TRASNASAAA
AASNMTGNGN GYSAAGGYGY SRYSGNRGAA ASNRYSASNS RAACTCGACT
CTAGTAAAGC AAGACCAATA TCTTGTTTTA ACAAACCTG TCGCTGATTA
AGTTGATGCT CAACCTTGTG ATCCGCAATA GCATCGGAAA TSRSRGAAGY
ASGNYSVAGN ARGGNASNGN HSGVAYSHSA SAAAAASSRA TCAACACAAT
GGCTCAAGCT TTTAGGTGCA TTAACTCCAA GAAAAGTTTC GCTCAGTGCA
GAGAAGTCAA ACGCAAAAGA TTTTAGCGAT AATGCCAGCA SVACYSHSSR
SRYSRAAASN VAGYHTHRGS RAASRHASHA AHSRYSSRAA CCAAGTCCTT
TCGCTTTAAT GTAAGACTCC TTGAGCGCCC ACAAATCAAA AAAGCGGTCT
CGCTGCAAGG CCTCTGGTAA CGCTAACAAG GCTCGCTTTT GYGYYSAAYS
TYRSRGYSAA TRASHHARGA SARGGNAAGR AAAAARGYSG CTGATTCAGA
GAAATAATGA CTAAGAATAG AGTGGATATT GGTGCTGTTA CGGCAACGCT
CAATGTCGAC GCCAAACTCA ATACTAGCAG AGTCAGTTTC SRGSRHTYRH
SSRSRHSASN THRSRASNAR GCYSARGGAS VAGYHGSRAA SRASTHRGCT
CCTTGCTTGC CTGACTGGCG CCTTTATTAT CAGCAGTGCA AATGCCTACT
AATAGCCAAT CTCCACTATG ACTCACATTA AAGTGGACCC CGGTTTGAGY
SSRAAGNSRA AGYYSASNAS AATHRCYSGY VATRASGYSR HSSRVAASNH
HSVAGYTHRG NGCAAATTGC GCATCACTCA ATCTAGGCTT ACCTTTGTCG

FIG. 4D-1

```
CCATATTCAA AGCGCCATTC ATTGGGGCGT ATTTCACTAT GTTGTGACAA
TAAAGCGCGC AAAHGNAAAS SRARGRYSGY YSASGYTYRG HARGTRGASN
RARGGSRHSG NSRAAARGAA TAGCCTCTTA CCATTAAACC TTGAGTTTTA
GCTTCTTGTT TAATGTAGCG ATTAACCTTA ATTAACTCAT CTTCAGGCAG
CCATGACTTA ACCAACTCTY RGYARGVAMT GYGNTHRYSA AGGNYSTYRA
RGASNVAYSG ASGRTRSRYS VAGTGTAGTC TGGTTATCGC ACTCTTGTAT
TGTTAACGGA CAGAAGTATA AGGAAATCAA
                              *
                             9157
```

MSMFLNSKLS RSVKLAISAG LTASLAMPVF AEETAAEEQI ERVAVTGSRI
AKAELTQPAP VVSLSAEELT KFGNQDLGSV LAELPAIGAT NTIIGNNNSN
SSAGVSSADL RRLGANRTLV LVNGKRYVAG QPGSAEVDLS TIPTSMISRV
EIVTGGASAI YGSDAVSGVI NVILKEDFEG FEFNARTSGS TESVGTQEHS
FDILGGANVA DGRGNVTFYA GYERTKEVMA TDIRQFDAWG TIKNEADGGE
DDGIPDRLRV PRVYSEMINA TGVINAFGGG IGRSTFDSNG NPIAQQERDG
TNSFAFGSFP NGCDTCFNTE AYENYIPGVE RINVGSSFNF DFTDNIQFYT
DFRYVKSDIQ QQFQPSFRFG NININVEDNA FLNDDLRQQM LDAGQTNASF
AKFFDELGNR SAENKRELFR YVGGFKGGFD ISETIFDYDL YYVYGETNNR
RKTLNDLIPD NFVAAVDSVI DPDTGLAACR SQVASAQGDD YTDPASVNGS
DCVAYNPFGM GQASAEARDW VSADVTREDK ITQQVIGGTL GTDSEELFEL
QGGAIAMVVG FEYREETSGS TTDEFTKAGF LTSAATPDSY GEYDVTEYFV
EVNIPVLKEL PFAHELSFDG AYRNADYSHA GKTEAWKAGM FYSPLEQLAL
RGTVGEAVRA PNIAEAFSPR SPGFGRVSDP CDADNINDDP DRVSNCAALG
IPPGFQANDN VSVDTLSGGN PDLKPETSTS FTGGLVWTPT FADNLSFTVD
YYDIQIEDAI LSVATQTVAD NCVDSTGGPD TDFCSQVDRN PTTYDIELVR
SGYLNAAALN TKGIEFQAAY SLDLESFNAP GELRFNLLGN QLLELERLEF
QNRPDEINDE KGEVGDPELQ FRLGIDYRLD DLSVSWNTRY IDSVVTYDVS
ENGGSPEDLY PGHIGSMTTH DLSATYYINE NFMINGGVRN LFDALPPGYT
NDALYDLVGR RAFLGIKVMM

13040
MAKINSEHLD EATITSNKCT QTETEARHRN ATTTPEMRRF IQESDLSVSQ
LSKILNISEA TVRKWRKRDS VENCPNTPHH LNTTLTPLQE YVVVGLRYQL
KMPLDRLLKA TQEFINPNVS RSGLARCLKR YGVSRVSDIQ SPHVPMRYFN
QIPVTQGSDV QTYTLHYETL AKTLALPSTD GDNVVQVVSL TIPPKLTEEA
PSSILLGIDP HSDWIYLDIY QDGNTQATNR YMAYVLKHGP FHLRKLLVRN
YHTFLQRFPG ATQNRRPSKD MPETINKTPE TQAPSGDS
                                        13903

MSQTSKPTNS ATEQAQDSQA DSRLNKRLKD MPIAIVGMAS IFANSRYLNK
FWDLISEKID AITELPSTHW QPEEYYDADK TAADKSYCKR GGFLPDVDFN
PMEFGLPPNI LELTDSSQLL SLIVAKEVLA DANLPENYDR DKIGITLGVG
GGQKISHSLT ARLQYPVLKK VFANSGISDT DSEMLIKKFQ DQYVHWEENS
FPGSLGNVIA GRIANRFDFG GMNCVVDAAC AGSLAAMRMA LTELTEGRSE
MMITGGVCTD NSPSMYMSFS KTPAFTTNET IQPFDIDSKG MMIGEGIGMV
ALKRLEDAER DGDRIYSVIK GVGASSDGKF KSIYAPRPSG QAKALNRAYD
DAGFAPHTLG LIEAHGTGTA AGDAAEFAGL CSVFAEGNDT KQHIALGSVK
SQIGHTKSTA GTAGLIKAAL ALHHKVLPPT INVSQPSPKL DIENSPFYLN
TETRPWLPRV DGTPRRAGIS SFGFGGTNFH FVLEEYNQEH SRTDSEKAKY
RQRQVAQSFL VSASDKASLI NELNVLAASA SQAEFILKDA AANYGVRELD
KNAPRIGLVA NTAEELAGLI KQALAKLAAS DDNAWQLPGG TSYRAAAVEG
KVAALFAGQG SQYLNMGRDL TCYYPEMRQQ FVTADKVFAA NDKTPLSQTL
YPKPVFNKDE LKAQEAILTN TANAQSAIGA ISMGQYDLFT AAGFNADMVA
GHSFGELSAL CAAGVISADD YYKLAFARGE AMATKAPAKD GVEADAGAMF
AIITKSAADL ETVEATIAKF DGVKVANYNA PTQSVIAGPT ATTADAAKAL
TELGYKAINL PVSGAFHTEL VGHAQAPFAK AIDAAKFTKT SRALYSNATG
GLYESTAAKI KASFKKHMLQ SVRFTSQLEA MYNDGARVFV EFGPKNILQK
LVQGTLVNTE NEVCTISINP NPKVDSDLQL KQAAMQLAVT GVVLSEIDPY
QADIAAPAKK SPMSISLNAA NHISKATRAK MAKSLETGIV TSQIEHVIEE
KIVEVEKLVE VEKIVEKVVE VEKVVEVEAP VNSVQANAIQ TRSVVAPVIE
NQVVSKNSKP AVQSISGDAL SNFFAAQQQT AQLHQQFLAI PQQYGETFTT
LMTEQAKLAS SGVAIPESLQ RSMEQFHQLQ AQTLQSHTQF LEMQAGSNIA
ALNLLNSSQA TYAPAIHNEA IQSQVVQSQT AVQPVISTQV NHVSEQPTQA
PAPKAQPAPV TTAVQTAPAQ VVRQAAPVQA AIEPINTSVA TTTPSAFSAE

FIG. 4G-1

TALSATKVQA TMLEVVAEKT GYPTEMLELE MDMEADLGID SIKRVEILGT
VQDELPGLPE LSPEDLAECR TLGEIVDYMG SKLPAEGSMN SQLSTGSAAA
TPAANGLSAE KVQATMMSVV AEKTGYPTEM LELEMDMEAD LGIDSIKRVE
ILGTVQDELP GLPELSPEDL AECRTLGEIV DYMNSKLADG SKLPAEGSMN
SQLSTSAAAA TPAANGLSAE KVQATMMSVV AEKTGYPTEM LELEMDMEAD
LGIDSIKRVE ILGTVQDELP GLPELNPEDL AECRTLGEIV TYMNSKLADG
SKLPAEGSMH YQLSTSTAAA TPVANGLSAE KVQATMMSVV ADKTGYPTEM
LELEMDMEAD LGIDSIKRVE ILGTVQDELP GLPELNPEDL AECRTLGEIV
DYMGSKLPAE GSANTSAAAS LNVSAVAAPQ AAATPVSNGL SAEKVQSTMM
SVVAEKTGYP TEMLELGMDM EADLGIDSIK RVEILGTVQD ELPGLPELNP
EDLAECRTLG EIVDYMNSKL ADGSKLPAEG SANTSATAAT PAVNGLSADK
VQATMMSVVA EKTGYPTEML ELGMDMEADL GIDSIKRVEI LGTVQDELPG
LPELNPEDLA ECRTLGEIVS YMNSQLADGS KLSTSAAEGS ADTSAANAAK
PAAISAEPSV ELPPHSEVAL KKLNAANKLE NCFAADASVV INDDGHNAGV
LAEKLIKQGL KVAVVRLPKG QPQSPLSSDV ASFELASSQE SELEASITAV
IAQIETQVGA IGGFIHLQPE ANTEEQTAVN LDAQSFTHVS NAFLWAKLLQ
PKLVAGADAR RCFVTVSRID GGFGYLNTDA LKDAELNQAA LAGLTKTLSH
EWPQVFCRAL DIATDVDATH LADAITSELF DSQAQLPEVG LSLIDGKVNR
VTLVAAEAAD KTAKAELNST DKILVTGGAK GVTFECALAL ASRSQSHFIL
AGRSELQALP SWAEGKQTSE LKSAAIAHII STGQKPTPKQ VEAAVWPVQS
SIEINAALAA FNKVGASAEY VSMDVTDSAA ITAALNGRSN EITGLIHGAG
VLADKHIQDK TLAELAKVYG TKVNGLKALL AALEPSKIKL LAMFSSAAGF
YGNIGQSDYA MSNDILNKAA LQFTARNPQA KVMSFNWGPW DGGMVNPALK

FIG. 4G-2

```
KMFTERGVYV  IPLKAGAELF  ATQLLAETGV  QLLIGTSMQG  GSDTKATETA
SVKKLNAGEV  LSASHPRAGA  QKTPLQAVTA  TRLLTPSAMV  FIEDHRIGGN
SVLPTVCAID  WMREAASDML  GAQVKVLDYK  LLKGIVFETD  EPQELTLELT
PDDSDEATLQ  ALISCNGRPQ  YKATLISDNA  DIKQLNKQFD  LSAKAITTAK
ELYSNGTLFH  GPRLQGIQSV  VQFDDQGLIA  KVALPKVELS  DCGEFLPQTH
MGGSQPFAED  LLLQAMLVWA  RLKTGSASLP  SSIGEFTSYQ  PMAFGETGTI
ELEVIKHNKR  SLEANVALYR  DNGELSAMFK  SAKITISKSL  NSAFLPAVLA
NDSEAN
     *
  22173
```

FIG. 4G-3

22203
*MPLRIALILL PTPQFEVNSV DQSVLASYQT LQPELNALLN SAPTPEMLSI
TISDDSDANS FESQLNAATN AINNGYIVKL ATATHALLML PALKAAQMRI
HPHAQLAAMQ QAKSTPMSQV SGELKLGANA LSLAQTNALS HALSQAKRNL
TDVSVNECFE NLKSEQQFTE VYSLIQQLAS RTHVRKEVNQ GVELGPKQAK
SHYWFSEFHQ NRVAAINFIN GQQATSYVLT QGSGLLAAKS MLNQQRLMFI
LPGNSQQQIT ASITQLMQQL ERLQVTEVNE LSLECQLELL SIMYDNLVNA
DKLTTRDSKP AYQAVIQASS VSAAKQELSA LNDALTALFA EQTNATSTNK
GLIQYKTPAG SYLTLTPLGS NNDNAQAGLA FVYPGVGTVY ADMLNELHQY
FPALYAKLER EGDLKAMLQA EDIYHLDPKH AAQMSLGDLA IAGVGSSYLL
TQLLTDEFNI KPNFALGYSM GEASMWASLG VWQNPHALIS KTQTDPLFTS
AISGKLTAVR QAWQLDDTAA EIQWNSFVVR SEAAPIEALL KDYPHAYLAI
IQGDTCVIAG CEIQCKALLA ALGKRGIAAN RVTAMHTQPA MQEHQNVMDF
YLQPLKAELP SEISFISAAD LTAKQTVSEQ ALSSQVVAQS IADTFCQTLD
FTALVHHAQH QGAKLFVEIG ADRQNCTLID KIVKQDGASS VQHQPCCTVP
MNAKGSQDIT SVIKALGQLI SHQVPLSVQP FIDGLKRELT LCQLTSQQLA
AHANVDSKFE SNQDHLLQGE V
                     *
                   24515

```
 *
 MSLPDNASNH LSANQKGASQ ASKTSKQSKI AIVGLATLYP DAKTPQEFWQ
 NLLDKRDSRS TLTNEKLGAN SQDYQGVQGQ SDRFYCNKGG YIENFSFNAA
 GYKLPEQSLN GLDDSFLWAL DTSRNALIDA GIDINGADLS RAGVVMGALS
 FPTTRSNDLF LPIYHSAVEK ALQDKLGVKA FKLSPTNAHT ARAANESSLN
 AANGAIAHNS SKVVADALGL GGAQLSLDAA CASSVYSLKL ACDYLSTGKA
 DIMLAGAVSG ADPFFINMGF SIFHAYPDHG ISVPFDASSK GLFAGEGAGV
 LVLKRLEDAE RDNDKIYAVV SGVGLSNDGK GQFVLSPNPK GQVKAFERAY
 AASDIEPKDI EVIECHATGT PLGDKIELTS METFFEDKLQ GTDAPLIGSA
 KSNLGHLLTA AHAGIMKMIF AMKEGYLPPS INISDAIASP KKLFGKPTLP
 SMVQGWPDKP SNNHFGVRTR HAGVSVFGFG GCNAHLLLES YNGKGTVKAE
 ATQVPRQAEP LKVVGLASHF GPLSSINALN NAVTQDGNGF IELPKKRWKG
 LEKHSELLAE FGLASAPKGA YVDNFELDFL RFKLPPNEDD RLISQQLMLM
 RVTDEAIRDA KLEPGQKVAV LVAMETELEL HQFRGRVNLH TQLAQSLAAM
 GVSLSTDEYQ ALEAIAMDSV LDAAKLNQYT SFIGNIMASR VASLWDFNGP
 AFTISAAEQS VSRCIDVAQN LIMEDNLDAV VIAAVDLSGS FEQVILKNAI
 APVAIEPNLE ASLNPTSASW NVGEGAGAVV LVKNEATSGC SYGQIDALGF
 AKTAETALAT DKLLSQTATD FNKVKVIETM AAPASQIQLA PIVSSQVTHT
 AAEQRVGHCF AAAGMASLLH GLLNLNTVAQ TNKANCALIN NISENQLSQL
 LISQTASEQQ ALTARLSNEL KSDAKHQLVK QVTLGGRDIY QHIVDTPLAS
 LESITQKLAQ ATASTVVNQV KPIKAAGSVE MANSFETESS AEPQITIAAQ
 QTANIGVTAQ ATKRELGTPP MTTNTIANTA NNLDKTLETV AGNTVASKVG
 SGDIVNFQQN QQLAQQAHLA FLESRSAGMK VADALLKQQL AQVTGQTIDN
 QALDTQAVDT QTSENVAIAA ESPVQVTTPV QVTTPVQISV VELKPDHANV
 PPYTPPVPAL KPCIWNYADL VEYAEGDIAK VFGSDYAIID SYSRRVRLPT
 TDYLLVSRVT KLDATINQFK PCSMTTEYDI PVDAPYLVDG QIPWAVAVES
 GQCDLMLISY LGIDFENKGE RVYRLLDCTL TFLGDLPRGG DTLRYDIKIN
 NYARNGDTLL FFFSYECFVG DKMILKMDGG CAGFFTDEEL ADGKGVIRTE
```

FIG. 4I-1

EEIKARSLVQ KQRFNPLLDC PKTQFSYGDI HKLLTADIEG CFGPSHSGVH
QPSLCFASEK FLMIEQVSKV DRTGGTWGLG LIEGHKQLEA DHWYFPCHFK
GDQVMAGSLM AEGCGQLLQF YMLHLGMHTQ TKNGRFQPLE NASQQVRCRG
QVLPQSGVLT YRMEVTEIGF SPRPYAKANI DILLNGKAVV DFQNLGVMIK
EEDECTRYPL LTESTTASTA QVNAQTSAKK VYKPASVNAP LMAQIPDLTK
EPNKGVIPIS HVEAPITPDY PNRVPDTVPF TPYHMFEFAT GNIENCFGPE
FSIYRGMIPP RTPCGDLQVT TRVIEVNGKR GDFKKPSSCI AEYEVPADAW
YFDKNSHGAV MPYSILMEIS LQPNGFISGY MGTTLGFPGL ELFFRNLDGS
GELLREVDLR GKTIRNDSRL LSTVMAGTNI IQSFSFELST DGEPFYRGTA
VFGYFKGDAL KDQLGLDNGK VTQPWHVANG VAASTKVNLL DKSCRHFNAP
ANQPHYRLAG GQLNFIDSVE IVDNGGTEGL GYLYAERTID PSDWFFQFHF
HQDPVMPGSL GVEAIIETMQ AYAISKDLGA DFKNPKFGQI LSNIKWKYRG
QINPLNKQMS MDVSITSIKD EDGKKVITGN ASLSKDGLRI YEVFDIAISI
EESV

30730
\*
MNPTATNEML SPWPWAVTES NISFDVQVME QQLKDFSRAC
YVVNHADHGF GIAQTADIVT EQAANSTDLP VSAFTPALGT
ESLGDNNFRR VHGVKYAYYA GAMANGISSE ELVIALGQAG
ILCGSFGAAG LIPSRVEAAI NRIQAALPNG PYMFNLIHSP
SEPALERGSV ELFLKHKVRT VEASAFLGLT PQIVYYRAAG
LSRDAQGKVV VGNKVIAKVS RTEVAEKFMM PAPAKMLQKL
VDDGSITAEQ MELAQLVPMA DDITAEADSG GHTDNRPLVT
LLPTILALKE EIQAKYQYDT PIRVGCGGGV GTPDAALATF
NMGAAYIVTG SINQACVEAG ASDHTRKLLA TTEMADVTMA
PAADMFEMGV KLQVVKRGTL FPMRANKLYE IYTRYDSIEA
IPLDEREKLE KQVFRSSLDE IWAGTVAHFN ERDPKQIERA
EGNPKRKMAL IFRWYLGLSS RWSNSGEVGR EMDYQIWAGP
ALGAFNQWAK GSYLDNYQDR NAVDLAKHLM YGAAYLNRIN
SLTAQGVKVP AQLLRWKPNQ RMA
\*
32358

```
MRKPLQTINY  DYAVWDRTYS  YMKSNSASAK  RYYEKHEYPD
DTFKSLKVDG  VFIFNRTNQP  VFSKGFNHRN  DIPLVFELTD
FKQHPQNIAL  SPQTKQAHPP  ASKPLDSPDD  VPSTHGVIAT
RYGPAIYYSS  TSILKSDRSG  SQLGYLVFIR  LIDEWFIAEL
SQYTAAGVEI  AMADAADAQL  ARLGANTKLN  KVTATSERLI
TNVDGKPLLK  LVLYHTNNQP  PPMLDYSIII  LLVEMSFLLI
LAYFLYSYFL  VRPVRKLASD  IKKMDKSREI  KKLRYHYPIT
ELVKVATHFN  ALMGTIQEQT  KQLNEQVFID  KLTNIPNRRA
FEQRLETYCQ  LLARQQIGFT  LIIADVDHFK  EYNDTLGHLA
GDEALIKVAQ  TLSQQFYRAE  DICARFGGEE  FIMLFRDIPD
EPLQRKLDAM  LHSFAELNLP  HPNSSTANYV  TVSLGVCTVV
AVDDFEFKSE  SHIIGSQAAL  IADKALYHAK  ACGRNQALSK
TTITVDEIEQ  LEANKIGHQ
```
\*
34327

FIG. 4K

1
AATAGATCGACTCGCAAAAGTTGCTTAAGATAGTGTCAATATAGCTTCTTATTTGTA
AATATTGTTTTTTATGTGTAAACATGTTTAGTGTGTGTAAATGCTGTTAATTATCCT
TTTGGGATTGTAATAGCTGATGTTGCTGGCTAATGAGTACTTTTAGTTCGGCAATAT
CTTGCTTTAAATCGCTAACTTCAGTTTTTAATTCACCCACACTTGTTGTATTTTTAA
GGCTCTCTTCCCCACCATCGACAAACCAGGATGATATGAAACCGGTAAACGTACCAA
AGAGACCGACACCTGCAGTCATGAGTAATGCCGCAATGATACGTCCGCCAGTGGTGA
CGGGGTAGTAGTCACCGTAACCAACAGTCGTTATTGTCACAAATGACCACCAAAGTG
CGTCGATGCCGTTATTGATGTTACTGCCTACTTGATCCTGTTCTAACAATAAAATAC
CGATAGCACCAAAGGTGACAAGGATGAAGGATATCGCAGATACCAGCGAAAAGGTGG
CTTTAAACCGATGTTCAAAATCATTTTTAAGATAATTTTTGATGAGCGTATATTCT
GAATAGATCTTAATACTCTAGCGATACGAATTATGCGAATAAACTGCAGTTGCTCGA
CCATCGGAATACTCGACAGTAGGTCAATCCAACCCCATTTCATAAACTGAAATTTAT
TCTCAGCTTGGTGAAAGCGAATTACAAAGTCAGTGAAAAGAATAAGCAAATCGTAT
TATCTACGCTCGTTAATATTTCAGTGACGTTACTTGAAAAGGTAAAAATAAGTTGCA
GTAGTGATGATACGACCACATGAAGTGATAAAATAAGCATGAAAATCTGAAATGGAT
TTACATCACTGTTGTTTTGGTGCCACTTTTAAGGTTCGTTTTCACAATCTGCTGCC
TCGGTTCATTGATTTGTTAATATAAACCTTAGTCAGTAGCAAGACAAAATATATTT
ACATCAATGTCATCGTATTATTCAACCGCGCGTCGTGTATTCAGACCAAGATCGTTG
TATATGTTAGTCATGTAGCGATGAGATTATCATGCGACAGGAGAGAATTATGTTTGT
TATTATTTTTTACGTACCTAAAGTTAATGTTGAAGAAGTAAAACAGGCGTTATTTAA
CGTCGGAGCTGGCACCATCGGTGATTATGATAGTTGTGCTTGGCAATGTTTGGGGAC
TGGGCAGTTCCAACCTTTACTTGGTAGCCAGCCACATATTGGTAAGCTAAATGAGGT
TGAATTCGTTGATGAGTTTAGAGTAGAAATGGTTTGTCGAGCAGAAAATGTAAGGGC
AGCAATAAATGCACTTATTGCTGCGCACCCTTATGAAGAACCTGCTTATCATATTCT
GCAAACATTGAATCTTGATGAGTTACCTTAAGTTAGATGCACTGCACTTAATTGGTT
CGCTGTGCTAGGTTAGCAATTAGCAATTTTGACCATGTTAGCGATAGTTTTGGCACA

FIG. 5A

```
AGTGATCGATATTAAACTATCCGATTCAGATCCCATTTTTACTGCTGAATTAGGTTT
CATTACACTTGTTCTAGTGGTTTTTCCCGACAGGTGTAACTCTGTTACTTGCGTAAG
GTTGATAATCTCTACCGCATTGGCAGGAGTTACACCTGCACCAGGCATAATACTAAT
TCTACCATCTGCTTGGTTAACTAACGTTTGGATTAAGGCGCAGCCTTCTAGCGCTTG
AGCTTGTTGACCAGAGGTTAAAATACGCTCACAACCAGCAGTGATCAAGGTCTCCAA
GGCTTGTTGTGGATCATTACACAAGTCGAAAGCGCGGTGGAAGGTTACGCCGAGATC
ACGTGATGCCACCATTAAGCGTTTTAAAGCTGGCTCGTCAATATTACCATCTGCTGT
TAACGCGCCAATAACGACCCCTTGGACACCGAGTAACTTCATGAATTTGATGTCGGA
AACCATAATATCAACTTCTTGTTCGCTATATACAAAATCACCGGCGCGAGGGCGAAT
AATGGCATAAATGGGGATCGTTGCTAGATCAATAGACTTTTGTACAAAACCTGCGTT
GGCGGTCAAGCCACCTAATGCTAATGCCGAGCACAACTCAATACGATCGGCGCCAGA
TGCTTGAGCCGTCAGCAGTGATTCTATATTATCGACACATACTTCTATTGTCATTGT
CATATACTTCTCTTTAAAAAGTTTATTAAAAATAATAAAGCCAGCATAAGTCGTTTT
ATACAATATGAAAGGGGAAAAGGCGACTTAGCTCGCCTAGATCAATTATTATGGCAG
AATACTGCCGTATTGTGATTAGAAAGACAGTTTTTTAAGCTCAATAGCCGTTATCGC
GTTGTTATCTACCATCGTGTAACTTTTCTGGCCTGGGTGCTTTATTAACACTGTTTC
AGTGGCTGGATTAGGGTGAAATGATTCTTTTTTCAAATCTGTTTTTTTGTATTTGAA
CGTACCTGTAATGTCTTGCTGCTCACGAAGACGTACAAATATTGGTTGCGCATAGCT
TGGTAGTGCCGCATTGACATGTTGATAGAATTCAGACGCTGAAAATTCATGAATAGG
GCAATTCAAAGTCAGCGCGACCATGCCTGCTCGGCCATCGTGATGTGGGAGCTTGAC
ACCATAAGCCACACTTTGCTCAATTTGCACAAAATCGTTAACTTGAGCTTCTACTTG
CGTCGTGGCGACATTTTCACCTTTCCAGCGGAATGTATCACCTAATCTATCCACAAA
GGAAATATGGCGATAACCTTGGTAATGAACGAGATCGCCGGTATTAAAATAACAGTC
ACCGTCTTTTAATACTGACTTAAATAGCTTTTTATTACTTTCGTTGTCATCGGTATA
ACCATCAAATGGTGAACGTTTAGTTATCTTTGTTAGCAGTAGCCCTGTTTCTCCCGT
```

FIG. 5B

```
TTTTACTTTGGTCATTTTCCCTTTCGCATTATACACAGGTTTGTCATTGTCAATATC
ATATTGTATGACGGTAAAAGCAAGTGGAGTAACCCCGCTGTATGCGGTAAGTTCAG
CGCATTGGAGAACACAAGATTACACTCACTGGCGCCATAGAATTCATTAATATGCTC
GATCCCAAAACGTTGTTGGAAATGATCCCAAATTTCGGGGCGTAATCCATTACCTAT
GATTTTCTTTATATTATGCTGTTTGTCTTTATTGCTAGGCGGTACATTTAATAAATA
ACGGCAGAGCTCGCCGATGTAAGTAAACGCAGTGGCATTATGAGCACGAACTTCATC
CCAAAAGCGACTTGAACTGAATTTTTCAGAAAGTGCGAGGGTTGCTGCGCTACCAAA
CACGGCGCTTAATGACACTGTCAGTGCATTGTTATGGTATAGGGGAGTGATAAATA
CAATACATCATCAGCTGTTAAGCGTAATGATGCCATCCCCATGCCTGCCATGGATTT
AAACCAACGGTGATGGCTCATTCTTGCTGCTTTTGGCAGTCCAGTTTTTCCCGAGGT
AAAGATATAAAACGCGCAATGCTTAAGCTGTATTTGTGCTGTTGATTCAGGGTTCAA
TACTGAATATCCTGCGACTAGTGTAGATATGTTTTTATAACCATCACTCATGTCTGG
CGTTTCTAAAGCGGGTACGTAAAAGACATTCTGTTGTAATGTCGATGACAAATTGGT
TTCAATATTATTAATGGCGGATGTGTATAGTTCATCTGCGATGAGTAATTTGGTATC
GACCACGCTAAGACTATGTTCGAGGATTGAATCCCGTTGTGTCGTATTTATCATACA
AGCAATCGCGCCAAGCTTGACAACTGCGAGGGCAATAATGATGGTTTCAGGCCTGTT
ATCGAGCATGATGGCGACTTTATCATTTTTACCAATGCCGTATTCATGAAGGAAATG
GGCATATTGATTTGCTTGCTTATTCAATGAATCGTAACTATAACGCTGGTCTTTAAA
TTGTATTGCGATCAAGTCAGAGTTATTGACAGCTTGCTGCTCTAGTAATAAACCAAT
AGACATAAAACGTTCGGGCTTTGCTTGTTGTAAGTGCCATAAGCCTTTGATGATTGG
CTTTGGGGTTTTTAATAGATTGATGGTACTTTTCAGGAATTGTTTGCCGGTTATAAC
AGTCATAAGCTAATTCTTTTTATCAAGAAGAGGGGTTATGACACCAAATAAATGGGT
CACGCGTTGGTTTAATTTGGTTAGACTAAATGTGTTGTTTTGCTGTGATAATGCGAC
GTTCAAACAAACTTGAGAAGGTAAAAAAATAGCATTTTTAAATTGAACATCAATACT
AATGTGTTGAATATCAATCAAGTTTTCTAACTGTGCGAGCACGCGTGCTTTAGCAAA
```

FIG. 5C

CATGCCATGTGCTATTGCTGTTTTAAACCCCATTAGTTTCGCTGGGATAAAATGTAA
ATGGATTGGATTTGTGTCTTTGGAGATATAAGCATATTTATATACGTCAAAAGGACT
AAATTTAAACAATGAAATCGGCTCGTAAGCATAATTCGCTGGCGTATTTACTATTTT
CTCACCGCTGGAACGTTGAGATCGTTGGCACGTTTTCGCTGTTTCGTTTTCTGTAA
GAATGTCGATGTACACTCCCACGCAAATTGTCCATCTACAAACACATCAATATGAGT
ATCAATGAAACGTCCTGTATCCGTTATGTACTCCTTAATTACACGACATGTGCTCGT
CAATATCGCGTTTAATGCTATCGGTTGATGTTGTGTTATGCGATTTCGATAATGGAC
TAGTCCTAATATAGATATCGGAAATTGTGTTGATGTCATGAGTTTCATCAATAATGG
AAAGATCATCACAAATGGATAAGTAACCGGTACATAGTTTGTGTTATTAAACCCACA
GCATTTAATATATTGCTTTAAATTTCGCTGATCTATTTTTTGTCCACTGATACTAAA
TTGCTCAGTACACACTTGTGTCGACCAAGTGTTCATCAGTGTTTTAACAATTGTATT
GACCACTGCTTTCACATATAAAAGCGAGATAATCGGTTGCTTTGTTAACAGTGTGAT
CTGGTTAGCGTGCATTGAAATAATTCATATAAGAGTATGTAGCATTTATGTTAATAT
TTTGTTTTGGAAGTTGAATTGGCGAATCCGTAATCGGTTTATGGCAGTTCGGTCAAA
TACTTCAGGTAAACTCGTTACTCATACCATTGATAGTGTTAAAGTGATTGACTGAAT
AAAGAATAGAGCTAAAAGTGGAAAAATTATGCAAGATGCGGGTATGTTATTACGCAT
TGCTTATGAGGCAATGAAAGAGTTAGAGGTTGATGTCATTGAAGTACTTTCTCGTTG
TAACATAAGTGAAGAAGTACTGAATGATAAGGATCTTCGCACACCTAATCATGCACA
AACACATTTTTGGCAAGTATTAGAAGACATATCACAAGATCCTAACATCGGCATTTC
ACTTGGTGAGAGAATGCCAGTGTTCACGGGGCAGGTATTACAGTATCTTTTTCTCAG
TAGTCCTACATTTGGTACTGGCTGGGAACGCGCAACAAAATACTTTCGATTAATCAG
TGATGCGGCGAGTGTTTCTATCAAGATGGAAGGCTGTGAAGCGCGATTATCTGTGAA
CTTAGATGGTTTAGCGGAAGATGCGAATCGTCATTTGAATGATTGCCTAGTGATCGG
TGCATTTAAATTTTGTTTATATGTGACAGAAGGCGAATTTAAAGTAAGCAAAATAGC
CTTTGCTCATGCTCGCCCGAAAGATATTACTGCCTATACCAATGTATTTACATGTCC

FIG. 5D

```
GATTGAGTTTGCTGCCGAAGATAATTATATTTATTTCGATGCTGATTTACTCGAACG
TCCTTCTTCGCATGCGGAGCCTGAGCTATTCGCCTTACACGATCAGCTTGCAAGCCG
TAAAATAGCCAAGTTAGAACTGCAAGATTTAGTGGATAAAGTACGTAAGGTTATTGC
ACAACAACTTGAGTCTGGTGTGGTGACTTTAGAAAGTATCGCCACTGAACTTGACAT
GAAACCACGTATGCTAAGAGCGAAGTTAGCTGACATTGATTATAACTTTAATCAAAT
ACTCGCTGATTTTCGTTGCGAGTTATCAAAAAACTGTTGGCGAATACGGACGAGTC
TATTGATCAGATTGTCTATCTCACTGGTTTTTCTGAACCAAGTACTTTTTATCGTGC
CTTTAAGCGCTGGGTTAAAATGACGCCAATTGAATATCGCCGTAGCAAACTCGCGGT
TAGGCATGCTAATCAACACGAGTCCTAAAAATTCGCTGCTTAGTGCATAGTGCATAG
TGCATAGTGCTAGTAAGCCAAGTACAAAGCGTTAAAGTTAAGTACTTGAGCGAACCA
TCAGACACCACTTACTAGATTAAGCACCTATTAATGATTGACCACAAATTCTGATCG
TATTGCCTGTGATCCCTGCAGCTTGAGGTTGCGCAAAAAAGCTATCGCTTCAGCAA
CATCAACTGGCTTACCACCTTGTTTTAATGAATTCATACGACGACCAGCTTCACGAA
CTGTAAATGGAATCGCTGCTGTCATTTTTGTTTCAATAAAGCCTGGTGCAACAGCAT
TAATGGTGATGTATTTGTCTGCAAGCGGAGTTTGCATTGCATCAACATAACCAATGA
CTGCGGCCTTAGACGTTGCATAATTAGTCTGACCAAAGTTACCCGCAATCCCACTCA
TCGAAGACACACAAACAATGCGGCCATAGTCGTTGAGCAGATCATCATTTAGCAGTC
GCTCATTGATTCTTTCCATTGCCGACAAGTTAATATCCATCAGTACATCCCAATGGT
TATCCGGCATACGTGCTAGCGTTTTGTCTTTTGTTACCCCGGCATTATGGACGATGA
TATCAAGCGACTGTTCTCGCACAAGTCAGCAATGATATTTGGGGCGTCAGCAGCGG
TAATATCAGCAACAATGCTGCTACCTTTCAAGCAATGAGCTACTTTTTCAAGGTCCT
GTTTTAATGCCGGAATGTCTAAGCAAATAACATGTGCGCCATCACGGGCGAGTGTTT
CAGCAATAGCAGCCCCGATGCCACGTGATGCACCAGTGACAAGTGCTGTCTTTCCTT
GTAATGGTTTTGCCGTGTTACTTGTTTCGTTAATAACTTCGTTAATAACTTCGTTAA
```

FIG. 5E

```
TAACTTCGTTAATAGCCCCATTAATCGAACCGGGTTTTACGTTAATAACCTGTGCTG
AGATATAGGCTGATTTTGCTGAGGTTAAGAAACGTAGCGGGGCCTCTAATAATTGCT
CACTACCAGGTTGTACATAGATAAGTTGACAGGTACTACCATTCTTGCCTATTTCTT
TGGCGACACTGCGACAAAACCCTTCTAAAGATCTTTGTACAGTCGCGTAGCTTACAT
CGTCAAGATGTTCACTCGGATGACCTAACACGATCACTCTGCTGCATGGCGAGAGCT
GCTTAATTACAGGTTGAAAAAACGATGTAATGCACTTAATTGCTTGCTGTTCTTAA
TGCCTGAGGCGTCGAAGATAATACCGTTGAAGCGATCTGTTTTAGCGATAGCATTAA
GGCTAATAGGTGTCGCGACTAAAGACGTTTGATTAAATTCAATATTAAGATCGGCTA
ACGCTGACGTGTTATTAGGATAAGAAATCGTGACTTCAGCATCTTTAAATGTGTTAA
GAATGGGTTTAATTAATTTGCTGTTGCTGGCTGCGCCGATGAGTAAGTTGCCAGAGA
TGAGATCGGTTCCCTGATCGTAGCGTGTTAACGTAACCGGTCGTGGCAGATTAAGCG
CTTTAAATAAACCTGATGTCCACTTGCCATTAGCGAGTTTTGCGTATGTATCCGTCA
TTTTCTAATCCTTGTTATAGTGAACAGTTTGAATCTCGAAGATGTACATGTGTTAAA
AATTATCTGATAGCTATGACTTATCTGCCACTACGTAATAATAAATAGACCAGTTCA
TTACATCGTTAATCGATATAGTATAACTAAATACTAAGTAAATTATAATGATAAGAC
TGTTATCGTACTCGGATCAAACTCTGATCAGCAAATAATCAAATTAGAGTTTTTATT
TTAAACTTGTATCAACAATGTTACATTAATGTATCTTACGTCTAATGTGCTACGGGC
ATATTTAAGTCACTAAATTAAAGGAATAAACCATGACAGGTCAAACAATAAGAAGAG
TAGCAATTATCGGCGGTAACCGTATCCCGTTTGCACGTTCAAATACAGCGTATTCAA
AACTAAGTAACCAAGATATGCTGACGGAAACTATCCGTGGCTTGGTGGTTAAATATA
ACCTACGTGGTGAACAACTGGGGGAAGTTGTTGCTGGTGCGGTAATTAAGCATTCTC
GTGATTTTAACTTAACACGTGAAGCCGTGCTAAGTGCAGGTCTTGCACCTGAAACGC
CTTGTTATGACATTCAACAAGCTTGTGGTACTGGTCTAGCTGCAGCTATCCAAGTAG
CAAACAAAATTGCGCTTGGTCAAATAGAAGCGGGTATTGCTGGTGGTTCTGATACGA
```

FIG. 5F

```
CATCAGATGCACCGATTGCAGTCAGTGAAGGCATGCGTAGTGTATTACTTGAGCTTA
ATCGAGCTAAAACGGGTAAGCAACGTTTGAAAGCACTATCTCGTCTACGTCTAAAAC
ACTTTGCGCCACTAACGCCTGCAAATAAAGAGCCGCGTACCAAAATGGCGATGGGCG
ATCATTGTCAAGTAACAGCGAAAGAGTGGAATATCTCACGTGAAGCACAAGATGCAT
TGGCCTGCGCAAGTCATCAAAAATTAGCTGCAGCATATGAAGAAGGTTTCTTTGATA
CGTTAGTTTCACCTATGGCCGGCTTAACGAAAGATAACGTATTACGCGCAGATACAA
CAGTTGAGAAACTGGCTAAATTGAAACCTTGTTTTGATAAAGTAAACGGCACTATGA
CGGCGGGTAACAGTACTAACCTTACCGATGGAGCATCAGCTGTATTACTTGCAAGTG
AAGAATGGGCAGCGGCACATAACTTACCAGTACAAGCTTATCTAACATTTGGTGAAA
CGGCCGCTATCGACTTCGTTGATAAGAAAGAAGGTCTGTTAATGGCGCCTGCATACG
CAGTGCCAAAAATGTTGAAGCGTGCTGGCCTTACATTACAAGACTTCGATTACTATG
AAATACATGAAGCATTTGCTGCGCAGTTATTAGCAACGCTAGCAGCTTGGGAAGACG
AAAAATTCTGTAAAGAAAACTGGGTCTAGATGCTGCGCTTGGTTCAATTGATATGA
CCAAGTTAAACGTGAAAGGGAGTAGCTTAGCCACGGGTCACCCATTTGCCGCAACTG
GTGGTCGTGTTGTCGCTACGCTAGCGCAATTACTTGATCAGAAAGGTTCAGGTCGTG
GTTTGATCTCGATTTGTGCTGCTGGTGGTCAAGGTATCACGGCAATTTTAGAGAAAT
AAACGCACTGTTTATTATCTATTGATTAAGCTGTCCTGAGATACTGGATATTTTTAA
ATAAAACGCCAATACTGCAGAGTATTGGCGTTTTTTTGTAATACCAATTCCTATATA
ACGGTGCATTTTAAACACTTAATTTCCGGCATTGGTATCATAAAAAGCAGCACCGA
AGTGCTGCTTGATTGTAGATTAACCTATTAAAATAGAGAGGCTAGAATTAGTCTTCG
TATGCTTCATTATGTACGCCAGCTGCACGACCCGATGGATCAGCATTGTTTTGGAAA
CTTTCATCCAAGCTAATGCTTCTACAGTTGAACAAGCAACGGATTTACCAAACGGT
ACGCATTTCGCTGCTGAATCACCTGGGAAGTGATCTTCAAAGATGGCACGATAGTAG
TAACCTTCTTTCGTATCTGGTGTGTTAATTGGGAACTTAAATGCTGCACTTGCTAAC
ATTTGATCAGTTACCGCTTCTTCAACGTGTACTTTAAGTTGGTCAATCCAAGAATAA
```

FIG. 5G

```
CCAACACCATCAGAGAATTGTTCTTTTTGACGCCATACAATTTCTTCAGGTAGTAAA
TCTTCAAATGCTTCTCGAATGATGTTTTTCTCAATGCGGTCGCCCGTGATCATTTTT
AGTTCAGGGTTTAGACGCATTGACGCATCAACAAATTCTTTATCTAAGAAAGGAACA
CGTGCTTCGATGCCCCAAGCTGCCATAGATTTGTTTGCACGTAAGCAATCAAACATA
TGTAATTTATTTACTTTACGTACCGTCTCTTCATGGAATTCTTTCGCATTTGGCGCT
TTGTGGAAGTACAAGTAACCACCGAACAGTTCATCAGCACCTTCACCAGAAAGCACC
ATCTTAATCCCCATGGCTTTAATTTTACGTGCCATTAGGTACATAGGGGTTGATGCA
CGAATTGTTGTTACATCGTAGGTTTCAATGTGGTAAATCACGTCGCGTAAAGCGTCG
ATACCTTCTTGCACAGTAAATTCAATTGAATGATGGATAGTACCTAAGTGATCTGCC
ACTTTTTGTGCAGCGGCTAAATCTGGAGAACCATTTAGGCCTACAGAGAAAGAGTGT
AGTTGTGGCCACCATGCTTCGGTTTTACCACCGTCTTCAATACGACGTTTTGCATAC
TGTTGGGTGATTGCTGAAATAACAGATGAATCTAACCCGCCTGATAATAATACGCCG
TAAGGTACATCACACATTAATTGACGTTTAACTGCATCTTCCAAACCTTGCTTAACA
ACGCTTTTATCACCACCATTTTGTGCAACGTTATCAAAATCTTTCCAATCACGTTGA
TAATAAGGCGTGACTACACCATCCTTACTCCACAGGTAATGACCTGCTGGGAATTCT
TCAATTTGAGTACAAATTGGCACTAGTGCTTTCATTTCAGAGGCAACATAAAAGTTA
CCGTGTTCATCATAGCCCGTATAAAGAGGGATGATACCGATATGGTCACGGCCAATC
AGGTAAGCGTCCTCTGTTTCGTCATATAAAGCGAAAGCAAAATACCATTTAGATCA
TCTAAAAATTGTGTGCCTTTTTCTTTATATAGCGCAAGTATCACTTCGCAATCTGAT
TCTGTTTGGAATTCAAAGTCTACGTTCAGCGTTTTCTTTAAATCTTTGTGGTTATAA
ATTTCACCATTAACAGCAAGTACGTGTGTCTTTTCTTCATTATATAGCGGCTGTGCA
CCATTATTTACATCGACAATAGCAAGACGTTCATGAACTAAAATAGCATTGTCACTT
GTATAGATACCTGACCAATCTGGGCCGCGGTGACGTAGTAACTTTGATAGTTCTAGT
GCTTGTTCGCGAAGAGGTTTAATGTCTGATTTGATGTCTAGAATTCCGAATATTGAG
```

FIG. 5H

```
CACATAACTAATTCCTTCTGGGGCTGCGTCTGCAGCTAACTTTCTAAATAGTGTGTC
TAATTTGCCACATTGTAGATTTAATGCAAACATTAATGATAAACATTTATAAAAAA
TGTAATTCAATGTGGAATCGATAATTTAATGGCTTAAAAGTGAAGATCCATTAATTG
TGATGGCGAGGTGATAGACCAATGTAGACCTTAATGAATAAAGCAGGCACGATTGAA
TCCATTCAACGCAAAGTGGTACTAACTATTGTTTTAAACGTTATAAATAGTGTTTTA
AAGGTTATAAGTAAATAATTTAAAAACAATAATAATCCACATGCATTAAATTTATCA
TGATAAACCGCTATATCTCAATGGCAATTTGGGATAAGTGTAAAATATATGTAAAAT
GAATGAGTTGACTTGCTTTTTTTACACTAAGTGATGAAATTAAAGCTAGATGTCGTT
GTTAGCATTGATTAATAACGTACTAAAATACGACATCTAGTATAGAAATTTAAAAAA
CAGTTGGTTTTGATAGCATAACTGCATAAACTAATCAGCTTATTGTCTGTAATATTT
TTGTAATTTAAATAGGTTTAATAAAATTATATGTCTGATAAATATAAACCGTACGAC
CTTTCCTTTAAAAAGACGTTTTTGCTGCCTAAGTTTTGGCCTGTGTGGTTCGGGGTG
TTTGCAATATACTTATTAGCTTTTATGCCAGTAAAGCCGCGTGATAAATTTGCTCGA
TTCATAGCGAAGAAATTGTTTAGTCTAAAATGATGGCAAAGCGTAAAAGGTAGCA
AAGATCAATTTATCTATGTGCTTCCCTGAAATGGATGATACGGAACAAGACCGTATA
ATCATGGTCAATCTAGTTACTTTTGTCAAACTATCTTAAGTTATGCAGAGCCAAGT
GCGCGTAGTCGTGCTTATAACCGTGACCGTATGATAGTGCATGGTGGCGAGAATTTA
TTTCCGCTACTTGAACAAGGTAAGGCTTGTATCTTATTAGTGCCGCATAGCTTCGCT
ATTGATTTTGCAGGTTTACACATTGCTTCTTATGGCGCGCCATTTTGTACTATGTTT
AACAATTCTGAGAATGAGTTGTTCGATTGGCTGATGACACGTCAACGCGCTATGTTT
GGAGGCACTGTTTATCACCGCAAGGCAGGGCTAGGGGCTCTAGTTAAATCACTTAAG
AGCGGTGAAAGCTGTTATTACTTACCTGATGAAGACCATGGACCTAAGCGTAGTGTA
TTTGCGCCTTTATTTGCGACTCAAAAAGCAACTTTACCTGTAATGGGCAAGCTAGCA
GAAAAAACAAATGCACTCGTTGTTCCTGTTTATGCGGCATATAATGAATCACTAGGT
AAATTTGAAACCTTTATTCGACCAGCAATGCAAAACTTTCCATCAGAAAGCCCAGAA
CAAGATGCAGTGATGATGAATAAAGAGATTGAAGCCTTGATTGAATGTGGTGTTGAT
```

FIG. 5I

```
CAATATATGTGGACACTTAGATTATTGAGAACACGTCCGGACGGTAAAAAATCTAC
TAATAAAGTTTAATAAACACCATAATCTTCGTTGAATATGGTGTTTACCCCCCTGAA
TACCCTCTAAATTAATAACAAAAAAGCCATTTACGTAACATCTAATGATGATTTAG
CCTGCACTTGCTTTGTTTTAGTCTTAAGAGCCTAATAAACTTGATCTAGGTATAGA
TTCTGTCTTTCTTTACGTAACGCGATCTATTTTTTTTAACCGATAGTTGTTATAATT
AGTTTCATATGAAAGAGATATCGTTTCAGTAAAAGCTATTTCGTTTCAATAGATAAT
TTATTTATAGTCATATTTTCTGTAATGACAATCATTTTCTCATCTAGACTATAGATA
AGAATACGAATTAAGTAAGAACATTAATTTTACAAGAATATAAAATATCCCATCGGA
GCTATAAGAATGAAAAGACTAAAATTGTTTGTACAATTGGTCCAAAAACTGAATCA
GTAGAGAAACTAACAGAGCTTGTTAATGCAGGCATGAACGTTATGCGTTTAAATTTC
TCTCATGGTAACTTTGCTGAACATTCAGTGCGTATTCAAAATATCCGTCAAGTAAGT
GAAAACCTGAATAAGAAAATTGCTGTTTTACTGGATACTAAAGGTCCAGAAATCCGT
ACGATTAAACTAGAAAACGGTGACGATGTAATGTTGACCGCTGGTCAGTCATTCACG
TTTACAACAGACATTAACGTGGTAGGTAATAAAGACTGTGTTGCTGTAACATATGCT
GGTTTTGCTAAAGACCTTAATCCTGGTGCAATCATCCTTGTTGATGATGGTTTAATT
GAAATGGAAGTTGTTGCAACAACTGACACTGAAGTTAAATGTACAGTATTAAATACT
GGTGCACTTGGTGAAAATAAAGGCGTTAACTTACCTAACATCAGTGTAGGTCTACCT
GCATTGTCAGAAAAGATAAAGCTGATTTAGCGTTTGGTTGTGAGCAAGAAGTTGAT
TTTGTTGCTGCATCATTTATTCGTAAGGCTGATGATGTAAGAGAAATTCGTGAAATC
CTATTTAATAATGGTGGCGAAAACATTCAGATTATCTCGAAAATTGAAAACCAAGAA
GGTGTAGACAATTTCGATGAAATCTTAGCTGAATCAGACGGTATCATGGTTGCTCGT
GGCGATCTCGGTGTTGAGATCCCAGTTGAAGAAGTGATCATGGCACAGAAGATGATG
ATCAAAAAATGTAATAAAGCAGGTAAAGTTGTAATTACTGCAACACAAATGCTTGAT
TCAATGATCAGTAACCCACGTCCAACACGTGCAGAAGCGGGCGATGTTGCCAATGCT
GTGCTTGACGGTACCGACGCGGTAATGCTTTCTGGTGAAACTGCGAAAGGTAAATAC
```

FIG. 5J

```
CCAGTTGAAGCTGTGTCTATCATGGCAAACATCTGTGAACGTACTGATAACTCAATG
TCTTCGGATTTAGGTGCGAACATTGTTGCTAAAAGCATGCGCATTACAGAAGCTGTG
TGTAAAGGTGCGGTAGAAACAACAGAAAATTGTGTGCTCCACTTATTGTTGTTGCA
ACTCGTGGCGGTAAATCAGCAAATCTGTTCGTAAATACTTCCCGAAAGCAAATATT
CTTGCTATCACAACAAATGAAAAGCAGCGCAACAGTTATGCCTAACTAAAGGCGTA
AGCAGCTGCATCGTTGAGCAGATTGATAGCACTGATGAGTTCTACCGTAAAGGTAAA
GAGCTTGCATTAGCAACTGGTTTAGCTAAAGAAGGCGATATCGTTGTTATGGTATCA
GGTGCGTTAGTACCATCAGGTACAACGAATACGGCATCTGTTCACCAACTTTAAGTT
GCCATATTGATATTATAAAAAGAGAGCGTATGCTCTCTTTTTTTATATCTGTAGTT
TATATGTCTGTACAAAAAATGATAAAGAGTACATAAACTATTAATATAGCGTAATA
TATAATGATTAACGGTGATGAAAGGGTTAAATAAATGGATAGTGCTAAACATAAAAT
TGGCTTAGTCCTTTCTGGCGGTGGTGCGAAAGGTATTGCTCATCTTGGTGTATTAAA
ATACCTGTTAGAGCAAGATATAAGACCGAATGTAATTGCGGGTACAAGTGCTGGCTC
TATGGTTGGTGCACTTTATTGCTCAGGACTTGAGATTGATGACATTTTACAATTCTT
CATCGATGTAAAACCTTTTTCTTGGAAGTTTACCCGTGCCCGTGCTGGCTTTATAGA
CCCGGCAAAATTATATCCTGAAGTGCTAAAATATATCCCCGAGGATAGCTTTGAGTA
CCTTCAACCTGAATTGCGCATTGTTGCCACCAACATGTTACTCGGTAAAGAGCATAT
ATTTAAAGATGGCTCCGTGATTAATGCCTTATTAGCATCAGCCAGCTACCCTTTAGT
TTTTTCTCCGATGATCATTGACGATCAAGTGTATTCAGATGGCGGTATTGTTAATCA
TTTCCCCGTGAGTGTCATTGAAGATGATTGCGATAAAATAATCGGCGTATACGTGTC
GCCCATTCGTCAGGTCGAAGCTGACGAACTCTCGAGTATAAAAGACGTGGTATTACG
TGCGTTCACGCTGCAGGGTAGTGGTGCTGAATTAGATAAACTATCGCAATGTGATGT
GCAAATTTATCCAGAAGCGCTATTGAATTACAATACGTTTGCAACCGATGAAAAATC
ATTACGGGAGATCTACCAGATTGGTTATGATGCTGCAAAAGATCAACATGACAACCT
TATGGCATTGAAAGAAAGTATCACCACCAGCGAGGTTAAAAAGAACGTCTTTAGCAA
```

FIG. 5K

ATGGTTTGGTGATAAACTTGCTAGCAACAGCGGCAAATAGCGGCCCACACGGATTTA
TACACTAGGATAATGGGCGTTAATAGCCTCACTGTCGTTGTGTGGTCTCTAATTTTA
GCTAAATCTTGTGTTATACTGACTTCCTATTAATCATAAACGATTTATCACGGTAAA
CATGACTCAAATAAATAACCCGCTTCACGGCATGACACTCGAAAAGTAATTAACAG
TCTCGTTGAACAATATGGCTGGGATGGTCTTGGATACTACATCAACATTCGTTGCTT
TACTGAAAATCCAAGTGTTAAGTCTAGTCTTAAATTTTACGTAAAACCCCTTGGGC
ACGTGATAAAGTAGAAGCGCTATATATCAAAATGGTGACTGAAGGCTAACTGTCTCC
ACGCTAGCGAACCGCTGTTTATAGTTAATATAAGTACTATAAGCAGGGCTCGTTAAT
TCAGTATGTAATTAATCCTGAATACCTCCGCTTATTTCAACATTGTACTCTCTAGAT
AACACTCTCAACATTACACCTTCAACATCACAGCCTCCACATAACATCCGATGACAT
AGCCCTGTTATTTTCACATTTATCTATATGCTATATATTTTAGCCATTTGATCAAT
TGAGTTAATTTCTGCAATGACAAAGATATACCATCATCCAGTACAAATTTATTATGA
AGATACCGACCATTCTGGTGTTGTTTACCACCCTAACTTTTTAAAATACTTTGAACG
TGCACGTGAGCATGTGATAAATAGTGACTTACTAGCAACATTGTGGAATGAACGCGG
TTTAGGTTTTGCGGTGTATAAAGCCAATATGACTTTTCAGGATGGGGTCGAATTTGC
TGAAGTGTGTGATATTCGCACTTCTTTTGTCCTAGACGGTAAGTACAAAACGATCTG
GCGCCAAGAAGTATGGCGTCCGAATGCGACTAGGGCTGCCGTTATCGGTGATATTGA
AATGGTGTGCTTAGACAAACAAAAACGTTTACAGCCCATCCCTGATGATGTGTTAGC
TGCAATGGTTAGTGAATAAATGGTTCATGCATAAATAGTTAATACATGATTCTGGCC
CGTCACGTTTACAGATAAGAGGCATCCGATGCCTCCTTCCTATTACCAATACTACTG
CTTATCCCTTTCTAACTATCTTTAGCGTCCATAACACACTGAGCATTTATTCTATTA
ATCAGTGATTGTGATTTAATTATCTTCTATATATGTAATTTAATGTAATTTTCAATT
TATTTTTAGCTACATTAAGGCTTACGAATGTACGCTAAAATGAGATGTCAGACTAAT
TTTAGCTTATTAATCTGTTAGCCGTTTATATTTTATAAAGATGGGATTTAACTTAAA

FIG. 5L

```
TGCAATTAATTATGGCGTAAATAGAGTGAAAACATGGCTAATATTCACTAAGTCCTG
AATTTTATATAAAGTTTAATCTGTTATTTTAGCGTTTACCTGGTCTTATCAGTGAGG
TTTATAGCCATTATTAGTGGGATTGAAGTGATTTTTAAAGCTATGTATATTATTGCA
AATATAAATTGTAACAATTAAGACTTTGGACACTTGAGTTCAATTTCGAATTGATTG
GCATAAAATTTAAAACAGCTAAATCTACCTCAATCATTTTAGCAAATGTATGCAGGT
AGATTTTTTTCGCCATTTAAGAGTACACTTGTACGCTAGGTTTTTGTTTAGTGTGCA
AATGAACGTTTTGATGAGCATTGTTTTAGAGCACAAAATAGATCCTTACAGGAGCA
ATAACGCAATGGCTAAAAGAACACCACATCGATTAAGCACGCCAAGGATGTGTTAA
GTAGTGATGATCAACAGTTAAATTCTCGCTTGCAAGAATGTCCGATTGCCATCATTG
GTATGGCATCGGTTTTTGCAGATGCTAAAAACTTGGATCAATTCTGGGATAACATCG
TTGACTCTGTGGACGCTATTATTGATGTGCCTAGCGATCGCTGGAACATTGACGACC
ATTACTCGGCTGATAAAAAGCAGCTGACAAGACATACTGCAAACGCGGTGGTTTCA
TTCCAGAGCTTGATTTTGATCCGATGGAGTTTGGTTTACCGCCAAATATCCTCGAGT
TAACTGACATCGCTCAATTGTTGTCATTAATTGTTGCTCGTGATGTATTAAGTGATG
CTGGCATTGGTAGTGATTATGACCATGATAAAATTGGTATCACGCTGGGTGTCGGTG
GTGGTCAGAAACAAATTTCGCCATTAACGTCGCGCCTACAAGGCCCGGTATTAGAAA
AAGTATTAAAAGCCTCAGGCATTGATGAAGATGATCGCGCTATGATCATCGACAAAT
TTAAAAAAGCCTACATCGGCTGGGAAGAGAACTCATTCCCAGGCATGCTAGGTAACG
TTATTGCTGGTCGTATCGCCAATCGTTTTGATTTTGGTGGTACTAACTGTGTGGTTG
ATGCGGCATGCGCTGGCTCCCTTGCAGCTGTTAAAATGGCGATCTCAGACTTACTTG
AATATCGTTCAGAAGTCATGATATCGGGTGGTGTATGTTGTGATAACTCGCCATTCA
TGTATATGTCATTCTCGAAAACACCAGCATTTACCACCAATGATGATATCCGTCCGT
TTGATGACGATTCAAAAGGCATGCTGGTTGGTGAAGGTATTGGCATGATGGCGTTTA
AACGTCTTGAAGATGCTGAACGTGACGGCGACAAAATTTATTCTGTACTGAAAGGTA
TCGGTACATCTTCAGATGGTCGTTTCAAATCTATTTACGCTCCACGCCCAGATGGCC
AAGCAAAAGCGCTAAAACGTGCTTATGAAGATGCCGGTTTTGCCCCTGAAACATGTG
```

FIG. 5M

```
GTCTAATTGAAGGCCATGGTACGGGTACCAAAGCGGGTGATGCCGCAGAATTTGCTG
GCTTGACCAAACACTTTGGCGCCGCCAGTGATGAAAGCAATATATCGCCTTAGGCT
CAGTTAAATCGCAAATTGGTCATACTAAATCTGCGGCTGGCTCTGCGGGTATGATTA
AGGCGGCATTAGCGCTGCATCATAAAATCTTACCTGCAACGATCCATATCGATAAAC
CAAGTGAAGCCTTGGATATCAAAAACAGCCCGTTATACCTAAACAGCGAAACGCGTC
CTTGGATGCCACGTGAAGATGGTATTCCACGTCGTGCAGGTATCAGCTCATTTGGTT
TTGGCGGCACCAACTTCCATATTATTTAGAAGAGTATCGCCCAGGTCACGATAGCG
CATATCGCTTAAACTCAGTGAGCCAAACTGTTGATCTCGGCAAACGACCAACAAG
GTATTGTTGCTGAGTTAAATAACTGGCGTACTAAACTGGCTGTCGATGCTGATCATC
AAGGGTTTGTATTTAATGAGTTAGTGACAACGTGGCCATTAAAAACCCCATCCGTTA
ACCAAGCTCGTTTAGGTTTTGTTGCGCGTAATGCAAATGAAGCGATCGCGATGATTG
ATACGGCATTGAAACAATTCAATGCGAACGCAGATAAAATGACATGGTCAGTACCTA
CCGGGGTTTACTATCGTCAAGCCGGTATTGATGCAACAGGTAAAGTGGTTGCGCTAT
TCTCAGGGCAAGGTTCGCAATACGTGAACATGGGTCGTGAATTAACCTGTAACTTCC
CAAGCATGATGCACAGTGCTGCGGCGATGGATAAAGAGTTCAGTGCCGCTGGTTTAG
GCCAGTTATCTGCAGTTACTTTCCCTATCCCTGTTTATACGGATGCCGAGCGTAAGC
TACAAGAAGAGCAATTACGTTTAACGCAACATGCGCAACCAGCGATTGGTAGTTTGA
GTGTTGGTCTGTTCAAAACGTTTAAGCAAGCAGGTTTTAAAGCTGATTTTGCTGCCG
GTCATAGTTTCGGTGAGTTAACCGCATTATGGGCTGCCGATGTATTGAGCGAAAGCG
ATTACATGATGTTAGCGCGTAGTCGTGGTCAAGCAATGGCTGCGCCAGAGCAACAAG
ATTTTGATGCAGGTAAGATGGCCGCTGTTGTTGGTGATCCAAAGCAAGTCGCTGTGA
TCATTGATACCCTTGATGATGTCTCTATTGCTAACTTCAACTCGAATAACCAAGTTG
TTATTGCTGGTACTACGGAGCAGGTTGCTGTAGCGGTTACAACCTTAGGTAATGCTG
GTTTCAAAGTTGTGCCACTGCCGGTATCTGCTGCGTTCCATACACCTTTAGTTCGTC
ACGCGCAAAAACCATTTGCTAAAGCGGTTGATAGCGCTAAATTTAAAGCGCCAAGCA
TTCCAGTGTTTGCTAATGGCACAGGCTTGGTGCATTCAAGCAAACCGAATGACATTA
```

FIG. 5N

```
AGAAAAACCTGAAAAACCACATGCTGGAATCTGTTCATTTCAATCAAGAAATTGACA
ACATCTATGCTGATGGTGGCCGCGTATTTATCGAATTTGGTCCAAAGAATGTATTAA
CTAAATTGGTTGAAAACATTCTCACTGAAAAATCTGATGTGACTGCTATCGCGGTTA
ATGCTAATCCTAAACAACCTGCGGACGTACAAATGCGCCAAGCTGCGCTGCAAATGG
CAGTGCTTGGTGTCGCATTAGACAATATTGACCCGTACGACGCCGTTAAGCGTCCAC
TTGTTGCGCCGAAAGCATCACCAATGTTGATGAAGTTATCTGCAGCGTCTTATGTTA
GTCCGAAAACGAAGAAAGCGTTTGCTGATGCATTGACTGATGGCTGGACTGTTAAGC
AAGCGAAAGCTGTACCTGCTGTTGTGTCACAACCACAAGTGATTGAAAAGATCGTTG
AAGTTGAAAAGATAGTTAACGCATTGTCGAAGTAGAGCGTATTGTCGAAGTAGAAA
AAATCGTCTACGTTAATGCTGACGGTTCGCTTATATCGCAAAATAATCAAGACGTTA
ACAGCGCTGTTGTTAGCAACGTGACTAATAGCTCAGTGACTCATAGCAGTGATGCTG
ACCTTGTTGCCTCTATTAACGCAGTGTTGGTCAATTTGTTGCACACCAACAGCAAT
TATTAAATGTACATGAACAGTTTATGCAAGGTCCACAAGACTACGCGAAAACAGTGC
AGAACGTACTTGCTGCGCAGACGAGCAATGAATTACCGGAAAGTTTAGACCGTACAT
TGTCTATGTATAACGAGTTCCAATCAGAAACGCTACGTGTACATGAAACGTACCTGA
ACAATCAGACGAGCAACATGAACACCATGCTTACTGGTGCTGAAGCTGATGTGCTAG
CAACCCCAATAACTCAGGTAGTGAATACAGCCGTTGCCACTAGTCACAAGGTAGTTG
CTCCAGTTATTGCTAATACAGTGACGAATGTTGTATCTAGTGTCAGTAATAACGCGG
CGGTTGCAGTGCAAACTGTGGCATTAGCGCCTACGCAAGAAATCGCTCCAACAGTCG
CTACTACGCCAGCACCCGCATTGGTTGCTATCGTGGCTGAACCTGTGATTGTTGCGC
ATGTTGCTACAGAAGTTGCACCAATTACACCATCAGTTACACCAGTTGTCGCAACTC
AAGCGGCTATCGATGTAGCAACTATTAACAAAGTAATGTTAGAAGTTGTTGCTGATA
AAACCGGTTATCCAACGGATATGCTGGAACTGAGCATGGACATGGAAGCTGACTTAG
GTATCGACTCAATCAAACGTGTTGAGATATTAGGCGCAGTACAGGAATTGATCCCTG
ACTTACCTGAACTTAATCCTGAAGATCTTGCTGAGCTACGCACGCTTGGTGAGATTG
TCGATTACATGAATTCAAAAGCCCAGGCTGTAGCTCCTACAACAGTACCTGTAACAA
```

FIG. 50

GTGCACCTGTTTCGCCTGCATCTGCTGGTATTGATTTAGCCCACATCCAAAACGTAA
TGTTAGAAGTGGTTGCAGACAAAACCGGTTACCCAACAGACATGCTAGAACTGAGCA
TGGATATGGAAGCTGACTTAGGTATTGATTCAATCAAGCGTGTGGAAATCTTAGGTG
CAGTACAGGAGATCATAACTGATTTACCTGAGCTAAACCCTGAAGATCTTGCTGAAT
TACGCACCCTAGGTGAAATCGTTAGTTACATGCAAAGCAAAGCGCCAGTCGCTGAAA
GTGCGCCAGTGGCGACGGCTCCTGTAGCAACAAGCTCAGCACCGTCTATCGATTTGA
ACCACATTCAAACAGTGATGATGGATGTAGTTGCAGATAAGACTGGTTATCCAACTG
ACATGCTAGAACTTGGCATGGACATGGAAGCTGATTTAGGTATCGATTCAATCAAAC
GTGTGGAAATATTAGGCGCAGTGCAGGAGATCATCACTGATTTACCTGAGCTAAACC
CAGAAGACCTCGCTGAATTACGCACGCTAGGTGAAATCGTTAGTTACATGCAAAGCA
AAGCGCCAGTCGCTGAGAGTGCGCCAGTAGCGACGGCTTCTGTAGCAACAAGCTCTG
CACCGTCTATCGATTTAAACCATATCCAAACAGTGATGATGGAAGTGGTTGCAGACA
AAACCGGTTATCCAGTAGACATGTTAGAACTTGCTATGGACATGGAAGCTGACCTAG
GTATCGATTCAATCAAGCGTGTAGAAATTTTAGGTGCGGTACAGGAAATCATTACTG
ACTTACCTGAGCTTAACCCTGAAGATCTTGCTGAACTACGTACATTAGGTGAAATCG
TTAGTTACATGCAAAGCAAAGCGCCCGTAGCTGAAGCGCCTGCAGTACCTGTTGCAG
TAGAAAGTGCACCTACTAGTGTAACAAGCTCAGCACCGTCTATCGATTTAGACCACA
TCCAAAATGTAATGATGGATGTTGTTGCTGATAAGACTGGTTATCCTGCCAATATGC
TTGAATTAGCAATGGACATGGAAGCCGACCTTGGTATTGATTCAATCAAGCGTGTTG
AAATTCTAGGCGCGGTACAGGAGATCATTACTGATTTACCTGAACTAAACCCAGAAG
ACTTAGCTGAACTACGTACGTTAGAAGAAATTGTAACCTACATGCAAAGCAAGGCGA
GTGGTGTTACTGTAAATGTAGTGGCTAGCCCTGAAAATAATGCTGTATCAGATGCAT
TTATGCAAAGCAATGTGGCGACTATCACAGCGGCCGCAGAACATAAGGCGGAATTTA
AACCGGCGCCGAGCGCAACCGTTGCTATCTCTCGTCTAAGCTCTATCAGTAAAATAA
GCCAAGATTGTAAAGGTGCTAACGCCTTAATCGTAGCTGATGGCACTGATAATGCTG

FIG. 5P

```
TGTTACTTGCAGACCACCTATTGCAAACTGGCTGGAATGTAACTGCATTGCAACCAA
CTTGGGTAGCTGTAACAACGACGAAAGCATTTAATAAGTCAGTGAACCTGGTGACTT
TAAATGGCGTTGATGAAACTGAAATCAACAACATTATTACTGCTAACGCACAATTGG
ATGCAGTTATCTATCTGCACGCAAGTAGCGAAATTAATGCTATCGAATACCCACAAG
CATCTAAGCAAGGCCTGATGTTAGCCTTCTTATTAGCGAAATTGAGTAAAGTAACTC
AAGCCGCTAAAGTGCGTGGCGCCTTTATGATTGTTACTCAGCAGGGTGGTTCATTAG
GTTTTGATGATATCGATTCTGCTACAAGTCATGATGTGAAAACAGACCTAGTACAAA
GCGGCTTAAACGGTTTAGTTAAGACACTGTCTCACGAGTGGGATAACGTATTCTGTC
GTGCGGTTGATATTGCTTCGTCATTAACGGCTGAACAAGTTGCAAGCCTTGTTAGTG
ATGAACTACTTGATGCTAACACTGTATTAACAGAAGTGGGTTATCAACAAGCTGGTA
AAGGCCTTGAACGTATCACGTTAACTGGTGTGGCTACTGACAGCTATGCATTAACAG
CTGGCAATAACATCGATGCTAACTCGGTATTTTAGTGAGTGGTGGCGCAAAAGGTG
TAACTGCACATTGTGTTGCTCGTATAGCTAAAGAATATCAGTCTAAGTTCATCTTAT
TGGGACGTTCAACGTTCTCAAGTGACGAACCGAGCTGGGCAAGTGGTATTACTGATG
AAGCGGCGTTAAAGAAAGCAGCGATGCAGTCTTTGATTACAGCAGGTGATAAACCAA
CACCCGTTAAGATCGTACAGCTAATCAAACCAATCCAAGCTAATCGTGAAATTGCGC
AAACCTTGTCTGCAATTACCGCTGCTGGTGGCCAAGCTGAATATGTTTCTGCAGATG
TAACTAATGCAGCAAGCGTACAAATGGCAGTCGCTCCAGCTATCGCTAAGTTCGGTG
CAATCACTGGCATCATTCATGGCGCGGGTGTGTTAGCTGACCAATTCATTGAGCAAA
AAACACTGAGTGATTTTGAGTCTGTTTACAGCACTAAAATTGACGGTTTGTTATCGC
TACTATCAGTCACTGAAGCAAGCAACATCAAGCAATTGGTATTGTTCTCGTCAGCGG
CTGGTTTCTACGGTAACCCCGGCCAGTCTGATTACTCGATTGCCAATGAGATCTTAA
ATAAAACCGCATACCGCTTTAAATCATTGCACCCACAAGCTCAAGTATTGAGCTTTA
ACTGGGGTCCTTGGGACGGTGGCATGGTAACGCCTGAGCTTAAACGTATGTTTGACC
AACGTGGTGTTTACATTATTCCACTTGATGCAGGTGCACAGTTATTGCTGAATGAAC
```

FIG. 5Q

```
TAGCCGCTAATGATAACCGTTGTCCACAAATCCTCGTGGGTAATGACTTATCTAAAG
ATGCTAGCTCTGATCAAAAGTCTGATGAAAAGAGTACTGCTGTAAAAAAGCCACAAG
TTAGTCGTTTATCAGATGCTTTAGTAACTAAAAGTATCAAAGCGACTAACAGTAGCT
CTTTATCAAACAAGACTAGTGCTTTATCAGACAGTAGTGCTTTTCAGGTTAACGAAA
ACCACTTTTTAGCTGACCACATGATCAAAGGCAATCAGGTATTACCAACGGTATGCG
CGATTGCTTGGATGAGTGATGCAGCAAAAGCGACTTATAGTAACCGAGACTGTGCAT
TGAAGTATGTCGGTTTCGAAGACTATAAATTGTTTAAAGGTGTGGTTTTTGATGGCA
ATGAGGCGGCGGATTACCAAATCCAATTGTCGCCTGTGACAAGGGCGTCAGAACAGG
ATTCTGAAGTCCGTATTGCCGCAAAGATCTTTAGCCTGAAAAGTGACGGTAAACCTG
TGTTTCATTATGCAGCGACAATATTGTTAGCAACTCAGCCACTTAATGCTGTGAAGG
TAGAACTTCCGACATTGACAGAAAGTGTTGATAGCAACAATAAAGTAACTGATGAAG
CACAAGCGTTATACAGCAATGGCACCTTGTTCCACGGTGAAAGTCTGCAGGGCATTA
AGCAGATATTAAGTTGTGACGACAAGGGCCTGCTATTGGCTTGTCAGATAACCGATG
TTGCAACAGCTAAGCAGGGATCCTTCCCGTTAGCTGACAACAATATCTTTGCCAATG
ATTTGGTTTATCAGGCTATGTTGGTCTGGGTGCGCAAACAATTTGGTTTAGGTAGCT
TACCTTCGGTGACAACGGCTTGGACTGTGTATCGTGAAGTGGTTGTAGATGAAGTAT
TTTATCTGCAACTTAATGTTGTTGAGCATGATCTATTGGGTTCACGCGGCAGTAAAG
CCCGTTGTGATATTCAATTGATTGCTGCTGATATGCAATTACTTGCCGAAGTGAAAT
CAGCGCAAGTCAGTGTCAGTGACATTTTGAACGATATGTCATGATCGAGTAAATAAT
AACGATAGGCGTCATGGTGAGCATGGCGTCTGCTTTCTTCATTTTTTAACATTAACA
ATATTAATAGCTAAACGCGGTTGCTTTAAACCAAGTAAACAAGTGCTTTTAGCTATT
ACTATTCCAAACAGGATATTAAAGAGAATATGACGGAATTAGCTGTTATTGGTATGG
ATGCTAAATTTAGCGGACAAGACAATATTGACCGTGTGGAACGCGCTTTCTATGAAG
GTGCTTATGTAGGTAATGTTAGCCGCGTTAGTACCGAATCTAATGTTATTAGCAATG
GCGAAGAACAAGTTATTACTGCCATGACAGTTCTTAACTCTGTCAGTCTACTAGCGC
```

FIG. 5R

```
AAACGAATCAGTTAAATATAGCTGATATCGCGGTGTTGCTGATTGCTGATGTAAAAA
GTGCTGATGATCAGCTTGTAGTCCAAATTGCATCAGCAATTGAAAAACAGTGTGCGA
GTTGTGTTGTTATTGCTGATTTAGGCCAAGCATTAAATCAAGTAGCTGATTTAGTTA
ATAACCAAGACTGTCCTGTGGCTGTAATTGGCATGAATAACTCGGTTAATTTATCTC
GTCATGATCTTGAATCTGTAACTGCAACAATCAGCTTTGATGAAACCTTCAATGGTT
ATAACAATGTAGCTGGGTTCGCGAGTTTACTTATCGCTTCAACTGCGTTTGCCAATG
CTAAGCAATGTTATATATACGCCAACATTAAGGGCTTCGCTCAATCGGGCGTAAATG
CTCAATTTAACGTTGGAAACATTAGCGATACTGCAAAGACCGCATTGCAGCAAGCTA
GCATAACTGCAGAGCAGGTTGGTTTGTTAGAAGTGTCAGCAGTCGCTGATTCGGCAA
TCGCATTGTCTGAAAGCCAAGGTTTAATGTCTGCTTATCATCATACGCAAACTTTGC
ATACTGCATTAAGCAGTGCCCGTAGTGTGACTGGTGAAGGCGGGTGTTTTTCACAGG
TCGCAGGTTTATTGAAATGTGTAATTGGTTTACATCAACGTTATATTCCGGCGATTA
AAGATTGGCAACAACCGAGTGACAATCAAATGTCACGGTGGCGGAATTCACCATTCT
ATATGCCTGTAGATGCTCGACCTTGGTTCCCACATGCTGATGGCTCTGCACACATTG
CCGCTTATAGTTGTGTGACTGCTGACAGCTATTGTCATATTCTTTTACAAGAAAACG
TCTTACAAGAACTTGTTTTGAAAGAAACAGTCTTGCAAGATAATGACTTAACTGAAA
GCAAGCTTCAGACTCTTGAACAAAACAATCCAGTAGCTGATCTGCGCACTAATGGTT
ACTTTGCATCGAGCGAGTTAGCATTAATCATAGTACAAGGTAATGACGAAGCACAAT
TACGCTGTGAATTAGAAACTATTACAGGGCAGTTAAGTACTACTGGCATAAGTACTA
TCAGTATTAAACAGATCGCAGCAGACTGTTATGCCCGTAATGATACTAACAAAGCCT
ATAGCGCAGTGCTTATTGCCGAGACTGCTGAAGAGTTAAGCAAAGAAATAACCTTGG
CGTTTGCTGGTATCGCTAGCGTGTTTAATGAAGATGCTAAAGAATGGAAAACCCCGA
AGGGCAGTTATTTTACCGCGCAGCCTGCAAATAAACAGGCTGCTAACAGCACACAGA
ATGGTGTCACCTTCATGTACCCAGGTATTGGTGCTACATATGTTGGTTTAGGGCGTG
ATCTATTTCATCTATTCCCACAGATTTATCAGCCTGTAGCGGCTTTAGCCGATGACA
```

FIG. 5S

```
TTGGCGAAAGTCTAAAAGATACTTTACTTAATCCACGCAGTATTAGTCGTCATAGCT
TTAAAGAACTCAAGCAGTTGGATCTGGACCTGCGCGGTAACTTAGCCAATATCGCTG
AAGCCGGTGTGGGTTTTGCTTGTGTGTTTACCAAGGTATTTGAAGAAGTCTTTGCCG
TTAAAGCTGACTTTGCTACAGGTTATAGCATGGGTGAAGTAAGCATGTATGCAGCAC
TAGGCTGCTGGCAGCAACCGGGATTGATGAGTGCTCGCCTTGCACAATCGAATACCT
TTAATCATCAACTTTGCGGCGAGTTAAGAACACTACGTCAGCATTGGGGCATGGATG
ATGTAGCTAACGGTACGTTCGAGCAGATCTGGGAAACCTATACCATTAAGGCAACGA
TTGAACAGGTCGAAATTGCCTCTGCAGATGAAGATCGTGTGTATTGCACCATTATCA
ATACACCTGATAGCTTGTTGTTAGCCGGTTATCCAGAAGCCTGTCAGCGAGTCATTA
AGAATTTAGGTGTGCGTGCAATGGCATTGAATATGGCGAACGCAATTCACAGCGCGC
CAGCTTATGCCGAATACGATCATATGGTTGAGCTATACCATATGGATGTTACTCCAC
GTATTAATACCAAGATGTATTCAAGCTCATGTTATTTACCGATTCCACAACGCAGCA
AAGCGATTTCCCACAGTATTGCTAAATGTTTGTGTGATGTGGTGGATTTCCCACGTT
TGGTTAATACCTTACATGACAAAGGTGCGCGGGTATTCATTGAAATGGGTCCAGGTC
GTTCGTTATGTAGCTGGGTAGATAAGATCTTAGTTAATGGCGATGGCGATAATAAAA
AGCAAAGCCAACATGTATCTGTTCCTGTGAATGCCAAAGGCACCAGTGATGAACTTA
CTTATATTCGTGCGATTGCTAAGTTAATTAGTCATGGCGTGAATTTGAATTTAGATA
GCTTGTTTAACGGGTCAATCCTGGTTAAAGCAGGCCATATAGCAAACACGAACAAAT
AGTCAACATCGATATCTAGCGCTGGTGAGTTATACCTCATTAGTTGAAATATGGATT
TAAAGAGAGTAATTATGGAAAATATTGCAGTAGTAGGTATTGCTAATTTGTTCCCGG
GCTCACAAGCACCGGATCAATTTTGGCAGCAATTGCTTGAACAACAAGATTGCCGCA
GTAAGGCGACCGCTGTTCAAATGGGCGTTGATCCTGCTAAATATACCGCCAACAAAG
GTGACACAGATAAATTTTACTGTGTGCACGGCGGTTACATCAGTGATTTCAATTTTG
ATGCTTCAGGTTATCAACTCGATAATGATTATTTAGCCGGTTTAGATGACCTTAATC
AATGGGGGCTTTATGTTACGAAACAAGCCCTTACCGATGCGGGTTATTGGGGCAGTA
```

FIG. 5T

```
CTGCACTAGAAAACTGTGGTGTGATTTTAGGTAATTTGTCATTCCCAACTAAATCAT
CTAATCAGCTGTTTATGCCTTTGTATCATCAAGTTGTTGATAATGCCTTAAAGGCGG
TATTACATCCTGATTTTCAATTAACGCATTACACAGCACCGAAAAAAACACATGCTG
ACAATGCATTAGTAGCAGGTTATCCAGCTGCATTGATCGCGCAAGCGGCGGGTCTTG
GTGGTTCACATTTTGCACTGGATGCGGCTTGTGCTTCATCTTGTTATAGCGTTAAGT
TAGCGTGTGATTACCTGCATACGGGTAAAGCCAACATGATGCTTGCTGGTGCGGTAT
CTGCAGCAGATCCTATGTTCGTAAATATGGGTTTCTCGATATTCCAAGCTTACCCAG
CTAACAATGTACATGCCCCGTTTGACCAAAATTCACAAGGTCTATTTGCCGGTGAAG
GCGCGGGCATGATGGTATTGAAACGTCAAGTGATGCAGTACGTGATGGTGATCATA
TTTACGCCATTATTAAAGGCGGCGCATTATCGAATGACGGTAAAGGCGAGTTTGTAT
TAAGCCCGAACACCAAGGGCCAAGTATTAGTATATGAACGTGCTTATGCCGATGCAG
ATGTTGACCCGAGTACAGTTGACTATATTGAATGTCATGCAACGGGCACACCTAAGG
GTGACAATGTTGAATTGCGTTCGATGGAAACCTTTTTCAGTCGCGTAAATAACAAAC
CATTACTGGGCTCGGTTAAATCTAACCTTGGTCATTTGTTAACTGCCGCTGGTATGC
CTGGCATGACCAAAGCTATGTTAGCGCTAGGTAAAGGTCTTATTCCTGCAACGATTA
ACTTAAAGCAACCACTGCAATCTAAAAACGGTTACTTTACTGGCGAGCAAATGCCAA
CGACGACTGTGTCTTGGCCAACAACTCCGGGTGCCAAGGCAGATAAACCGCGTACCG
CAGGTGTGAGCGTATTTGGTTTTGGTGGCAGCAACGCCCATTTGGTATTACAACAGC
CAACGCAAACACTCGAGACTAATTTTAGTGTTGCTAAACCACGTGAGCCTTTGGCTA
TTATTGGTATGGACAGCCATTTTGGTAGTGCCAGTAATTTAGCGCAGTTCAAAACCT
TATTAAATAATAATCAAAATACCTTCCGTGAATTACCAGAACAACGCTGGAAAGGCA
TGGAAAGTAACGCTAACGTCATGCAGTCGTTACAATTACGCAAAGCGCCTAAAGGCA
GTTACGTTGAACAGCTAGATATTGATTTCTTGCGTTTTAAAGTACCGCCTAATGAAA
AAGATTGCTTGATCCCGCAACAGTTAATGATGATGCAAGTGGCAGACAATGCTGCGA
AAGACGGAGGTCTAGTTGAAGGTCGTAATGTTGCGGTATTAGTAGCGATGGGCATGG
```

FIG. 5U

```
AACTGGAATTACATCAGTATCGTGGTCGCGTTAATCTAACCACCCAAATTGAAGACA
GCTTATTACAGCAAGGTATTAACCTGACTGTTGAGCAACGTGAAGAACTGACCAATA
TTGCTAAAGACGGTGTTGCCTCGGCTGCACAGCTAAATCAGTATACGAGTTTCATTG
GTAATATTATGGCGTCACGTATTTCGGCGTTATGGATTTTTCTGGTCCTGCTATTA
CCGTATCGGCTGAAGAAACTCTGTTTATCGTTGTGTTGAATTAGCTGAAAATCTAT
TTCAAACCAGTGATGTTGAAGCCGTTATTATTGCTGCTGTTGATTTGTCTGGTTCAA
TTGAAAACATTACTTTACGTCAGCACTACGGTCCAGTTAATGAAAAGGGATCTGTAA
GTGAATGTGGTCCGGTTAATGAAAGCAGTTCAGTAACCAACAATATTCTTGATCAGC
AACAATGGCTGGTGGGTGAAGGCGCAGCGGCTATTGTCGTTAAACCGTCATCGCAAG
TCACTGCTGAGCAAGTTTATGCGCGTATTGATGCGGTGAGTTTTGCCCCTGGTAGCA
ATGCGAAAGCAATTACGATTGCAGCGGATAAAGCATTAACACTTGCTGGTATCAGTG
CTGCTGATGTAGCTAGTGTTGAAGCACATGCAAGTGGTTTTAGTGCCGAAAATAATG
CTGAAAAACCGCGTTACCGACTTTATACCCAAGCGCAAGTATCAGTTCGGTGAAAG
CCAATATTGGTCATACGTTTAATGCCTCGGGTATGGCGAGTATTATTAAAACGGCGC
TGCTGTTAGATCAGAATACGAGTCAAGATCAGAAAAGCAAACATATTGCTATTAACG
GTCTAGGTCGTGATAACAGCTGCGCGCATCTTATCTTATCGAGTTCAGCGCAAGCGC
ATCAAGTTGCACCAGCGCCTGTATCTGGTATGGCCAAGCAACGCCCACAGTTAGTTA
AAACCATCAAACTCGGTGGTCAGTTAATTAGCAACGCGATTGTTAACAGTGCGAGTT
CATCTTTACACGCTATTAAAGCGCAGTTTGCCGGTAAGCACTTAAACAAAGTTAACC
AGCCAGTGATGATGGATAACCTGAAGCCCCAAGGTATTAGCGCTCATGCAACCAATG
AGTATGTGGTGACTGGAGCTGCTAACACTCAAGCTTCTAACATTCAAGCATCTCATG
TTCAAGCGTCAAGTCATGCACAAGAGATAGCACCAAACCAAGTTCAAAATATGCAAG
CTACAGCAGCCGCTGTAAGTTCACCCCTTTCTCAACATCAACACACAGCGCAGCCCG
TAGCGGCACCGAGCGTTGTTGGAGTGACTGTGAAACATAAAGCAAGTAACCAAATTC
ATCAGCAAGCGTCTACGCATAAAGCATTTTTAGAAAGTCGTTTAGCTGCACAGAAAA
```

FIG. 5V

```
ACCTATCGCAACTTGTTGAATTGCAAACCAAGCTGTCAATCCAAACTGGTAGTGACA
ATACATCTAACAATACTGCGTCAACAAGCAATACAGTGCTAACAAATCCTGTATCAG
CAACGCCATTAACACTTGTGTCTAATGCGCCTGTAGTAGCGACAAACCTAACCAGTA
CAGAAGCAAAAGCGCAAGCAGCTGCTACACAAGCTGGTTTTCAGATAAAAGGACCTG
TTGGTTACAACTATCCACCGCTGCAGTTAATTGAACGTTATAATAAACCAGAAACG
TGATTTACGATCAAGCTGATTTGGTTGAATTCGCTGAAGGTGATATTGGTAAGGTAT
TTGGTGCTGAATACAATATTATTGATGGCTATTCGCGTCGTGTACGTCTGCCAACCT
CAGATTACTTGTTAGTAACACGTGTTACTGAACTTGATGCCAAGGTGCATGAATACA
AGAAATCATACATGTGTACTGAATATGATGTGCCTGTTGATGCACCGTTCTTAATTG
ATGGTCAGATCCCTTGGTCTGTTGCCGTCGAATCAGGCCAGTGTGATTTGATGTTGA
TTTCATATATCGGTATTGATTTCCAAGCGAAAGGCGAACGTGTTTACCGTTTACTTG
ATTGTGAATTAACTTTCCTTGAAGAGATGGCTTTTGGTGGCGATACTTTACGTTACG
AGATCCACATTGATTCGTATGCACGTAACGGCGAGCAATTATTATTCTTCTTCCATT
ACGATTGTTACGTAGGGGATAAGAAGGTACTTATCATGCGTAATGGTTGTGCTGGTT
TCTTTACTGACGAAGAACTTTCTGATGGTAAAGGCGTTATTCATAACGACAAAGACA
AAGCTGAGTTTAGCAATGCTGTTAAATCATCATTCACGCCGTTATTACAACATAACC
GTGGTCAATACGATTATAACGACATGATGAAGTTGGTTAATGGTGATGTTGCCAGTT
GTTTTGGTCCGCAATATGATCAAGGTGGCCGTAATCCATCATTGAAATTCTCGTCTG
AGAAGTTCTTGATGATTGAACGTATTACCAAGATAGACCCAACCGGTGGTCATTGGG
GACTAGGCCTGTTAGAAGGTCAGAAAGATTTAGACCCTGAGCATTGGTATTTCCCTT
GTCACTTTAAAGGTGATCAAGTAATGGCTGGTTCGTTGATGTCGGAAGGTTGTGGCC
AAATGGCGATGTTCTTCATGCTGTCTCTTGGTATGCATACCAATGTGAACAACGCTC
GTTTCCAACCACTACCAGGTGAATCACAAACGGTACGTTGTCGTGGGCAAGTACTGC
CACAGCGCAATACCTTAACTTACCGTATGGAAGTTACTGCGATGGGTATGCATCCAC
AGCCATTCATGAAAGCTAATATTGATATTTTGCTTGACGGTAAAGTGGTTGTTGATT
```

FIG. 5W

```
TCAAAAACTTGAGCGTGATGATCAGCGAACAAGATGAGCATTCAGATTACCCTGTAA
CACTGCCGAGTAATGTGGCGCTTAAAGCGATTACTGCACCTGTTGCGTCAGTAGCAC
CAGCATCTTCACCCGCTAACAGCGCGGATCTAGACGAACGTGGTGTTGAACCGTTTA
AGTTTCCTGAACGTCCGTTAATGCGTGTTGAGTCAGACTTGTCTGCACCGAAAAGCA
AAGGTGTGACACCGATTAAGCATTTTGAAGCGCCTGCTGTTGCTGGTCATCATAGAG
TGCCTAACCAAGCACCGTTTACACCTTGGCATATGTTTGAGTTTGCGACGGGTAATA
TTTCTAACTGTTTCGGTCCTGATTTTGATGTTTATGAAGGTCGTATTCCACCTCGTA
CACCTTGTGGCGATTTACAAGTTGTTACTCAGGTTGTAGAAGTGCAGGGCGAACGTC
TTGATCTTAAAAATCCATCAAGCTGTGTAGCTGAATACTATGTACCGGAAGACGCTT
GGTACTTTACTAAAAACAGCCATGAAACTGGATGCCTTATTCATTAATCATGGAAA
TTGCATTGCAACCAAATGGCTTTATTTCTGGTTACATGGGCACGACGCTTAAATACC
CTGAAAAGATCTGTTCTTCCGTAACCTTGATGGTAGCGGCACGTTATTAAAGCAGA
TTGATTTACGCGGCAAGACCATTGTGAATAAATCAGTCTTGGTTAGTACGGCTATTG
CTGGTGGCGCGATTATTCAAAGTTTCACGTTTGATATGTCTGTAGATGGCGAGCTAT
TTTATACTGGTAAAGCTGTATTTGGTTACTTTAGTGGTGAATCACTGACTAACCAAC
TGGGCATTGATAACGGTAAAACGACTAATGCGTGGTTTGTTGATAACAATACCCCCG
CAGCGAATATTGATGTGTTTGATTTAACTAATCAGTCATTGGCTCTGTATAAAGCGC
CTGTGGATAAACCGCATTATAAATTGGCTGGTGGTCAGATGAACTTTATCGATACAG
TGTCAGTGGTTGAAGGCGGTGGTAAAGCGGGCGTGGCTTATGTTTATGGCGAACGTA
CGATTGATGCTGATGATTGGTTCTTCCGTTATCACTTCCACCAAGATCCGGTGATGC
CAGGTTCATTAGGTGTTGAAGCTATTATTGAGTTGATGCAGACCTATGCGCTTAAAA
ATGATTTGGGTGGCAAGTTTGCTAACCCACGTTTCATTGCCGATGACGCAAGTTG
ATTGGAAATACCGTGGGCAAATTACGCCGCTGAATAAACAGATGTCACTGGACGTGC
ATATCACTGAGATCGTGAATGACGCTGGTGAAGTGCGAATCGTTGGTGATGCGAATC
TGTCTAAAGATGGTCTGCGTATTTATGAAGTTAAAAACATCGTTTTAAGTATTGTTG
```

FIG. 5X

AAGCGTAAAGGGTCAAGTGTAACGTGCTTAAGCGCCGCATTGGTTAAAGACGCTTTG
CACGCCGTGAATCCGTCCATGGAGGCTTGGGGTTGGCATCCATGCCAACAACAGCAA
GCTTACTTTAATCAATACGGCTTGGTGTCCATTTAGACGCCTCGAACTTAGTAGTTA
ATAGACAAATAATTTAGCTGTGGAATGAATATAGTAAGTAATCATTCGGCAGCTAC
AAAAAAGGAATTAAGAATGTCGAGTTTAGGTTTTAACAATAACAACGCAATTAACTG
GCTTGGAAAGTAGATCCAGCGTCAGTTCATACACAAGATGCAGAAATTAAAGCAGC
TTTAATGGATCTAACTAAACCTCTCTATGTGGCGAATAATTCAGGCGTAACTGGTAT
AGCTAATCATACGTCAGTAGCAGGTGCGATCAGCAATAACATCGATGTTGATGTATT
GGCGTTTGCGCAAAAGTTAAACCCAGAAGATCTGGGTGATGATGCTTACAAGAAACA
GCACGGCGTTAAATATGCTTATCATGGCGGTGCGATGGCAAATGGTATTGCCTCGGT
TGAATTGGTTGTTGCGTTAGGTAAAGCAGGGCTGTTATGTTCATTTGGTGCTGCAGG
TCTAGTGCCTGATGCGGTTGAAGATGCAATTCGTCGTATTCAAGCTGAATTACCAAA
TGGCCCTTATGCGGTTAACTTGATCCATGCACCAGCAGAAGAAGCATTAGAGCGTGG
CGCGGTTGAACGTTTCCTAAAACTTGGCGTCAAGACGGTAGAGGCTTCAGCTTACCT
TGGTTTAACTGAACACATTGTTTGGTATCGTGCTGCTGGTCTAACTAAAAACGCAGA
TGGCAGTGTTAATATCGGTAACAAGGTTATCGCTAAAGTATCGCGTACCGAAGTTGG
TCGCCGCTTTATGGAACCTGCACCGCAAAAATTACTGGATAAGTTATTAGAACAAAA
TAAGATCACCCCTGAACAAGCTGCTTTAGCGTTGCTTGTACCTATGGCTGATGATAT
TACTGGGGAAGCGGATTCTGGTGGTCATACAGATAACCGTCCGTTTTTAACATTATT
ACCGACGATTATTGGTCTGCGTGATGAAGTGCAAGCGAAGTATAACTTCTCTCCTGC
ATTACGTGTTGGTGCTGGTGGTGGTATCGGAACGCCTGAAGCAGCACTCGCTGCATT
TAACATGGGCGCGGCTTATATCGTTCTGGGTTCTGTGAATCAGGCGTGTGTTGAAGC
GGGTGCATCTGAATATACTCGTAAACTGTTATCGACAGTTGAAATGGCTGATGTGAC
TATGGCACCTGCTGCAGATATGTTTGAAATGGGTGTGAAGCTGCAAGTATTAAAACG
CGGTTCTATGTTCGCGATGCGTGCGAAGAAACTGTATGACTTGTATGTGGCTTATGA

FIG. 5Y

```
CTCGATTGAAGATATCCCAGCTGCTGAACGTGAGAAGATTGAAAAACAAATCTTCCG
TGCAAACCTAGACGAGATTTGGGATGGCACTATCGCTTTCTTTACTGAACGCGATCC
AGAAATGCTAGCCCGTGCAACGAGTAGTCCTAAACGTAAAATGGCACTTATCTTCCG
TTGGTATCTTGGCCTTTCTTCACGCTGGTCAAACACAGGCGAGAAGGGACGTGAAAT
GGATTATCAGATTTGGGCAGGCCCAAGTTTAGGTGCATTCAACAGCTGGGTGAAGG
TTCTTACCTTGAAGACTATACCCGCCGTGGCGCTGTAGATGTTGCTTTGCATATGCT
TAAAGGTGCTGCGTATTTACAACGTGTAAACCAGTTGAAATTGCAAGGTGTTAGCTT
AAGTACAGAATTGGCAAGTTATCGTACGAGTGATTAATGTTACTTGATGATATGTGA
ATTAATTAAAGCGCCTGAGGGCGCTTTTTTTGGTTTTTAACTCAGGTGTTGTAACTC
GAAATTGCCCCTTTCAAGTTAGATCGATTACTCACTCACAATATGTTGATATCGCAC
TTGCCATATACTTGCTCATCCAAAGCCCTATATTGATAATGGTGTTAATAGTCTTTA
ATATCCGAGTCTTTCTTCAGCATAATACTAATATAGAGACTCGACCAATGTTAAACA
CAACAAAGAATATATTCTTGTGTACTGCCTTATTATTAACGAGTGCGAGTACGACAG
CTACTACGCTAAACAATTCGATATCAGCAATTGAACAACGTATTTCTGGTCGTATCG
GTGTGGCTGTTTTAGATACGCAAAATAAACAAACGTGGGCTTACAATGGTGATGCAC
ATTTTCCGATGATGAGTACATTCAAAACCCTCGCTTGCGCGAAAATGCTAAGTGAAT
CGACAAATGGTAATCTGGATCCCAGTACTAGCTCATTGATAAAGGCTGAAGAATTAA
TCCCTTGGTCACCAGTCACTAAAACGTTTGTAATAACACTATTACAGTGGCGAAAG
CGTGTGAAGCAACAATGCTGACCAGTGATAATACCGCGGCTAATATTGTTTTACAGT
ATATCGGAGGCCCTCAAGGCGTTACTGCATTCTTGCGAGAAATTGGTGATGAAGAGA
GTCAGTTAGATCGTATAGAACCTGAATTGAATGAAGCTAAGGTCGGAGACTTGCGTG
ATACCACGACACCGAAGCCATAGTTACCACGCTCAACAAACTACTACTTGGTGATG
TTCTACTTGATTTGGATAAAAACCAACTTAAAACATGGATGCAAAATAATAAAGTGT
CAGATCCTTTACTGCGTTCTATATTACCGCAAGGCTGGTTTATTGCCGACCGCTCAG
GTGCGGGTGGTAATGGTTCTCGAGGTATAACTGCTATGCTTTGGCACTCCGAGCGTC
```

FIG. 5Z

```
AACCGCTAATCATCAGTATTTATTTAACCGAAACTGAGTTAGCAATGGCAATGCGCA
ATGAGATTATTGTTGAGATCGGTAAGCTGATATTCAAAGAATACGCGGTGAAATAAT
AAGTTATTTTTTGATAATACTTTAACGAGCGTAGCTATCGAAGTGAGGGCGTCAATT
AGACACCTTTGCTTCCCCTACAAAATCTAATGTGTATTACCTCGGCTAGTACAATTG
CCCTAAGTTATTTCTGTCCAGCTTTGGCTTAGTGCAATTGCGTTAGCCAATGTGAAC
ACCAAGGGACTTTGTCGTACCATAACTACCAAGCGACTTTGTCGTTTTATCTTTTC
TTAGACAAACAGAGGTTAAATGAGTGACGCCTTCCAAATCACAGGAATGAATCCGCA
TTTCAATAAAATCTAACCCGTACCAACTCCGTACAAGTTGATCTTTAGTTGTTTAAA
ATCTATAATAAATTCAATTACGGAATTAATCCGTACAACTGGAGGTTTTATGGCTAC
TGCAAGACTTGATATCCGTTTGGATGAAGAAATCAAAGCTAAGGCTGAGAAAGCATC
AGCTTTACTCGGCTTAAAAAGTTTAACCGAATACGTTGTTCGCTTAATGGACGAAGA
TTCAACTAAAGTAGTTTCTGAGCATGAGAGTATTACCGTTGAAGCGAATGTATTCGA
CCAATTTATGGCTGCTTGTGATGAAGCGAAAGCCCCAAATAAAGCATTACTTGAAGC
CGCTGTATTTACTCAGAATGGTGAGTTTAAGTGAGTTATTCCAAACGTTTCAAAGAA
CTGGATAAATCAAAACATGACAGAGCATCATTTGACTGTGGCGAAAAAGAGCTAAAT
GATTTTATCCAAACTCAAGCAGCCAAACATATGCAAGCAGGTATTAGCCGCACTCTG
GTTTTACCTGCTTCTGCGCCGTTACCAAACAAAAAATATCCAATTTGCTCATTTTAT
AGTATCGCGCCAAGCTCAATTAGCCGCGATACGTTACCACAAGCAATGGCTAAAAAG
TTACCACGTTATCCTATCCCTGTTTTTCTTTTGGCTCAACTTGCCGTCCATAAAGAG
TTTCATGGGAGTGGGTTAGGCAAAGTTAGCTTAATTAAAGCGTTAGAGTACCTTTGG
GAAATTAACTCTCACATGAGAGCTTACGCCATCGTTGTTGATTGTTTAACTGAACAA
GCTGAGTCATTCTACGCTAAATATGGTTTCGACGTTCTCTGCGAAATAAATGGTCGA
GTAAGAATGTTCATATCAATGAAAACAGTCAATCAGTTATTCACTTAACAGTAAGAG
TTAGTATAACAGTTGTATGAATTAAATTTATTATATTCGGTAATCTCATTGCGATCA
CGCTAGAAGTGCGAGCGGGTCAGACCGAGGCCACAATAGCAGCCGTTACGTTTAGGG
```

FIG. 5AA

```
GATGACTTAAAAAGATAACTACTACGTCAGTGGCGATCCTAGAGGATTAAAGGTTTA
TGATTCACAACATTTATTTATTGTGCTTAATTTTTTCTATCCAATATGCGCAAGCTG
TAAATATCACTGAAGTAGACTTTTATGTCAGTGATGATATCCCTAAAGATGTTGCCA
AATTAAAGATAGGTGAATCCATAACGAACTCCAGCCTTATTCTAAGTAACTCATCTA
TTCCACTCTCGCGGGAGACGGGTAACATATATTACTCTTCATCAATTGCTAACTTGA
ACTATGACTCGATAGAATTTGTTATGGCTCAATTGATGGCCGAAGATTCCAGCCTTT
ACAAGATGCTGGTAAATAGCGATAGGTTGTCCGTGCTAGTAATGACATCTTCCCAGT
CCACAGATCTCTATGGCTCGACTTACTCGGCTTATTTTCCTAATGTTGCGGTCATCG
ATTTGAATTGTGACTCGCTAACTTTAGAACATGAGCTCGGCCATCTATACGGAGCTG
AACATGAAGAAATATATGACGACTATGTCTTCTATGCTGCGATATGTGGAGACTATA
CGACTATCATGAACTCTATGCAGCCTGAAATGAAAGAAAAACAAATGATAAAGGCAT
ATTCATTCCCTGAATTAAAAGTGGATGGCTTGCAGTGCGGAAATGAAAATACGAATA
ACAAAAAGGTTATTTTAGACAATATTGGTCGGTTTAGATAGGATTGGGATATTATTC
TCATTCGGCTCTACTTAGTGCTGTTATTATGAGTGCCAGTGCTTCTATCTACGATAT
TGGTCTTAACAAGTATTTATCTATAGACGCTAAGGTGTTATGTATTTAAGGGATGTT
CAAGATGAAACTAGGTGTAAACGATGTATAGTTGTATAACATTTTTTCAACGGTTGG
AACGTTCGATTCTATCGGGTAACAAGACCGCGACGATCCGCGATAAGTCCGATAGTC
ATTACTTAGTTGGTCAGATGTTAGATGCTTGTACTCACGAAGATAATCGGAAAATGT
GTCAAATAGAAATACTGAGCATTGAATATGTGACGTTTAGTGAATTAAACCGTGCGC
ACGCCAATGCTGAAGGTTTACCGTTTTGTTTATGCTTAAGTGGATAGTTCGAAAGA
TTTATCCGACTTCAAATGATTTATTTTCATAAGTTTCAGAGTTGTAACTATCGATA
TCTTATAAGTCTTAGTGCACAAACAGAACTATTTATAGCGCTCAAGAAGGCGATAA
TTTGATAATGAATTATCGCCTTGTTACTATTAAGAGACTTTAAATGACTGAGATATA
AGATATGACACGGAAGAACATATTGATCACAGGCGCAAGTTCAGGGTTGGGCCGAGG
TATGGCCATCGAATTTGCAAAATCAGGTCATAACTTAGCACTTTGTGCACGTAGACT
```

FIG. 5BB

TGATAATTTAGTTGCACTGAAAGCAGAACTCTTAGCCCTCAATCCTCACATCCAAAT
CGAAATAAAACCTCTTGATGTCAATGAACATGAACAAGTCTTCACTGTTTTCCATGA
ATTCAAAGCTGAATTTGGTACGCTTGATCGTATTATTGTTAATGCTGGATTAGGCAA
GGGTGGATCC
    *
  40138

*AAATGCAATTAATTATGGCGTAAATAGAGTGAAAACATGGCTAATATTCACTAAGTC
CTGAATTTTATATAAAGTTTAATCTGTTATTTTAGCGTTTACCTGGTCTTATCAGTG
AGGTTTATAGCCATTATTAGTGGGATTGAAGTGATTTTTAAAGCTATGTATATTATT
GCAAATATAAATTGTAACAATTAAGACTTTGGACACTTGAGTTCAATTTCGAATTGA
TTGGCATAAAATTTAAAACAGCTAAATCTACCTCAATCATTTTAGCAAATGTATGCA
GGTAGATTTTTTTCGCCATTTAAGAGTACACTTGTACGCTAGGTTTTTGTTTAGTGT
GCAAATGAACGTTTTGATGAGCATTGTTTTAGAGCACAAAATAGATCCTTACAGGA
GCAATAACGCAATGGCTAAAAGAACACCACATCGATTAAGCACGCCAAGGATGTGT
TAAGTAGTGATGATCAACAGTTAAATTCTCGCTTGCAAGAATGTCCGATTGCCATCA
TTGGTATGGCATCGGTTTTTGCAGATGCTAAAAACTTGGATCAATTCTGGGATAACA
TCGTTGACTCTGTGGACGCTATTATTGATGTGCCTAGCGATCGCTGGAACATTGACG
ACCATTACTCGGCTGATAAAAAGCAGCTGACAAGACATACTGCAAACGCGGTGGTT
TCATTCCAGAGCTTGATTTTGATCCGATGGAGTTTGGTTTACCGCCAAATATCCTCG
AGTTAACTGACATCGCTCAATTGTTGTCATTAATTGTTGCTCGTGATGTATTAAGTG
ATGCTGGCATTGGTAGTGATTATGACCATGATAAAATTGGTATCACGCTGGGTGTCG
GTGGTGGTCAGAAACAAATTTCGCCATTAACGTCGCGCCTACAAGGCCCGGTATTAG
AAAAAGTATTAAAAGCCTCAGGCATTGATGAAGATGATCGCGCTATGATCATCGACA
AATTTAAAAAAGCCTACATCGGCTGGGAAGAGAACTCATTCCCAGGCATGCTAGGTA
ACGTTATTGCTGGTCGTATCGCCAATCGTTTTGATTTGGTGGTACTAACTGTGTGG
TTGATGCGGCATGCGCTGGCTCCCTTGCAGCTGTTAAAATGGCGATCTCAGACTTAC
TTGAATATCGTTCAGAAGTCATGATATCGGGTGGTGTATGTTGTGATAACTCGCCAT
TCATGTATATGTCATTCTCGAAAACACCAGCATTTACCACCAATGATGATATCCGTC
CGTTTGATGACGATTCAAAAGGCATGCTGGTTGGTGAAGGTATTGGCATGATGGCGT
TTAAACGTCTTGAAGATGCTGAACGTGACGGCGACAAAATTTATTCTGTACTGAAAG
GTATCGGTACATCTTCAGATGGTCGTTTCAAATCTATTTACGCTCCACGCCCAGATG
GCCAAGCAAAAGCGCTAAAACGTGCTTATGAAGATGCCGGTTTTGCCCCTGAAACAT
GTGGTCTAATTGAAGGCCATGGTACGGGTACCAAAGCGGGTGATGCCGCAGAATTTG

FIG. 6A

```
CTGGCTTGACCAAACACTTTGGCGCCGCCAGTGATGAAAAGCAATATATCGCCTTAG
GCTCAGTTAAATCGCAAATTGGTCATACTAAATCTGCGGCTGGCTCTGCGGGTATGA
TTAAGGCGGCATTAGCGCTGCATCATAAAATCTTACCTGCAACGATCCATATCGATA
AACCAAGTGAAGCCTTGGATATCAAAAACAGCCCGTTATACCTAAACAGCGAAACGC
GTCCTTGGATGCCACGTGAAGATGGTATTCCACGTCGTGCAGGTATCAGCTCATTTG
GTTTTGGCGGCACCAACTTCCATATTATTTTAGAAGAGTATCGCCCAGGTCACGATA
GCGCATATCGCTTAAACTCAGTGAGCCAAACTGTGTTGATCTCGGCAAACGACCAAC
AAGGTATTGTTGCTGAGTTAAATAACTGGCGTACTAAACTGGCTGTCGATGCTGATC
ATCAAGGGTTTGTATTTAATGAGTTAGTGACAACGTGGCCATTAAAAACCCCATCCG
TTAACCAAGCTCGTTTAGGTTTTGTTGCGCGTAATGCAAATGAAGCGATCGCGATGA
TTGATACGGCATTGAAACAATTCAATGCAACGCAGATAAAATGACATGGTCAGTAC
CTACCGGGGTTTACTATCGTCAAGCCGGTATTGATGCAACAGGTAAAGTGGTTGCGC
TATTCTCAGGGCAAGGTTCGCAATACGTGAACATGGGTCGTGAATTAACCTGTAACT
TCCCAAGCATGATGCACAGTGCTGCGGCGATGGATAAAGAGTTCAGTGCCGCTGGTT
TAGGCCAGTTATCTGCAGTTACTTTCCCTATCCCTGTTTATACGGATGCCGAGCGTA
AGCTACAAGAAGAGCAATTACGTTTAACGCAACATGCGCAACCAGCGATTGGTAGTT
TGAGTGTTGGTCTGTTCAAAACGTTTAAGCAAGCAGGTTTTAAAGCTGATTTTGCTG
CCGGTCATAGTTTCGGTGAGTTAACCGCATTATGGGCTGCCGATGTATTGAGCGAAA
GCGATTACATGATGTTAGCGCGTAGTCGTGGTCAAGCAATGGCTGCGCCAGAGCAAC
AAGATTTTGATGCAGGTAAGATGGCCGCTGTTGTTGGTGATCCAAAGCAAGTCGCTG
TGATCATTGATACCCTTGATGATGTCTCTATTGCTAACTTCAACTCGAATAACCAAG
TTGTTATTGCTGGTACTACGGAGCAGGTTGCTGTAGCGGTTACAACCTTAGGTAATG
CTGGTTTCAAAGTTGTGCCACTGCCGGTATCTGCTGCGTTCCATACACCTTTAGTTC
GTCACGCGCAAAAACCATTTGCTAAAGCGGTTGATAGCGCTAAATTTAAAGCGCCAA
GCATTCCAGTGTTTGCTAATGGCACAGGCTTGGTGCATTCAAGCAAACCGAATGACA
TTAAGAAAAACCTGAAAAACCACATGCTGGAATCTGTTCATTTCAATCAAGAAATTG
```

FIG. 6B

```
ACAACATCTATGCTGATGGTGGCCGCGTATTTATCGAATTTGGTCCAAAGAATGTAT
TAACTAAATTGGTTGAAAACATTCTCACTGAAAAATCTGATGTGACTGCTATCGCGG
TTAATGCTAATCCTAAACAACCTGCGGACGTACAAATGCGCCAAGCTGCGCTGCAAA
TGGCAGTGCTTGGTGTCGCATTAGACAATATTGACCCGTACGACGCCGTTAAGCGTC
CACTTGTTGCGCCGAAAGCATCACCAATGTTGATGAAGTTATCTGCAGCGTCTTATG
TTAGTCCGAAAACGAAGAAAGCGTTTGCTGATGCATTGACTGATGGCTGGACTGTTA
AGCAAGCGAAAGCTGTACCTGCTGTTGTGTCACAACCACAAGTGATTGAAAGATCG
TTGAAGTTGAAAAGATAGTTGAACGCATTGTCGAAGTAGAGCGTATTGTCGAAGTAG
AAAAAATCGTCTACGTTAATGCTGACGGTTCGCTTATATCGCAAAATAATCAAGACG
TTAACAGCGCTGTTGTTAGCAACGTGACTAATAGCTCAGTGACTCATAGCAGTGATG
CTGACCTTGTTGCCTCTATTGAACGCAGTGTTGGTCAATTTGTTGCACACCAACAGC
AATTATTAAATGTACATGAACAGTTTATGCAAGGTCCACAAGACTACGCGAAAACAG
TGCAGAACGTACTTGCTGCGCAGACGAGCAATGAATTACCGGAAAGTTTAGACCGTA
CATTGTCTATGTATAACGAGTTCCAATCAGAAACGCTACGTGTACATGAAACGTACC
TGAACAATCAGACGAGCAACATGAACACCATGCTTACTGGTGCTGAAGCTGATGTGC
TAGCAACCCCAATAACTCAGGTAGTGAATACAGCCGTTGCCACTAGTCACAAGGTAG
TTGCTCCAGTTATTGCTAATACAGTGACGAATGTTGTATCTAGTGTCAGTAATAACG
CGGCGGTTGCAGTGCAAACTGTGGCATTAGCGCCTACGCAAGAAATCGCTCCAACAG
TCGCTACTACGCCAGCACCCGCATTGGTTGCTATCGTGGCTGAACCTGTGATTGTTG
CGCATGTTGCTACAGAAGTTGCACCAATTACACCATCAGTTACACCAGTTGTCGCAA
CTCAAGCGGCTATCGATGTAGCAACTATTAACAAAGTAATGTTAGAAGTTGTTGCTG
ATAAAACCGGTTATCCAACGGATATGCTGGAACTGAGCATGGACATGGAAGCTGACT
TAGGTATCGACTCAATCAAACGTGTTGAGATATTAGGCGCAGTACAGGAATTGATCC
CTGACTTACCTGAACTTAATCCTGAAGATCTTGCTGAGCTACGCACGCTTGGTGAGA
TTGTCGATTACATGAATTCAAAAGCCCAGGCTGTAGCTCCTACAACAGTACCTGTAA
```

FIG. 6C

CAAGTGCACCTGTTTCGCCTGCATCTGCTGGTATTGATTTAGCCCACATCCAAAACG
TAATGTTAGAAGTGGTTGCAGACAAAACCGGTTACCCAACAGACATGCTAGAACTGA
GCATGGATATGGAAGCTGACTTAGGTATTGATTCAATCAAGCGTGTGGAAATCTTAG
GTGCAGTACAGGAGATCATAACTGATTTACCTGAGCTAAACCCTGAAGATCTTGCTG
AATTACGCACCCTAGGTGAAATCGTTAGTTACATGCAAAGCAAAGCGCCAGTCGCTG
AAAGTGCGCCAGTGGCGACGGCTCCTGTAGCAACAAGCTCAGCACCGTCTATCGATT
TGAACCACATTCAAACAGTGATGATGGATGTAGTTGCAGATAAGACTGGTTATCCAA
CTGACATGCTAGAACTTGGCATGGACATGGAAGCTGATTTAGGTATCGATTCAATCA
AACGTGTGGAAATATTAGGCGCAGTGCAGGAGATCATCACTGATTTACCTGAGCTAA
ACCCAGAAGACCTCGCTGAATTACGCACGCTAGGTGAAATCGTTAGTTACATGCAAA
GCAAAGCGCCAGTCGCTGAGAGTGCGCCAGTAGCGACGGCTTCTGTAGCAACAAGCT
CTGCACCGTCTATCGATTTAAACCATATCCAAACAGTGATGATGGAAGTGGTTGCAG
ACAAAACCGGTTATCCAGTAGACATGTTAGAACTTGCTATGGACATGGAAGCTGACC
TAGGTATCGATTCAATCAAGCGTGTAGAAATTTTAGGTGCGGTACAGGAAATCATTA
CTGACTTACCTGAGCTTAACCCTGAAGATCTTGCTGAACTACGTACATTAGGTGAAA
TCGTTAGTTACATGCAAAGCAAAGCGCCCGTAGCTGAAGCGCCTGCAGTACCTGTTG
CAGTAGAAAGTGCACCTACTAGTGTAACAAGCTCAGCACCGTCTATCGATTTAGACC
ACATCCAAAATGTAATGATGGATGTTGTTGCTGATAAGACTGGTTATCCTGCCAATA
TGCTTGAATTAGCAATGGACATGGAAGCCGACCTTGGTATTGATTCAATCAAGCGTG
TTGAAATTCTAGGCGCGGTACAGGAGATCATTACTGATTTACCTGAACTAAACCCAG
AAGACTTAGCTGAACTACGTACGTTAGAAGAAATTGTAACCTACATGCAAAGCAAGG
CGAGTGGTGTTACTGTAAATGTAGTGGCTAGCCCTGAAAATAATGCTGTATCAGATG
CATTTATGCAAAGCAATGTGGCGACTATCACAGCGGCCGCAGAACATAAGGCGGAAT
TTAAACCGGCGCCGAGCGCAACCGTTGCTATCTCTCGTCTAAGCTCTATCAGTAAAA
TAAGCCAAGATTGTAAAGGTGCTAACGCCTTAATCGTAGCTGATGGCACTGATAATG
CTGTGTTACTTGCAGACCACCTATTGCAAACTGGCTGGAATGTAACTGCATTGCAAC
CAACTTGGGTAGCTGTAACAACGACGAAAGCATTTAATAAGTCAGTGAACCTGGTGA

FIG. 6D

```
CTTTAAATGGCGTTGATGAAACTGAAATCAACAACATTATTACTGCTAACGCACAAT
TGGATGCAGTTATCTATCTGCACGCAAGTAGCGAAATTAATGCTATCGAATACCCAC
AAGCATCTAAGCAAGGCCTGATGTTAGCCTTCTTATTAGCGAAATTGAGTAAAGTAA
CTCAAGCCGCTAAAGTGCGTGGCGCCTTTATGATTGTTACTCAGCAGGGTGGTTCAT
TAGGTTTTGATGATATCGATTCTGCTACAAGTCATGATGTGAAAACAGACCTAGTAC
AAAGCGGCTTAAACGGTTTAGTTAAGACACTGTCTCACGAGTGGGATAACGTATTCT
GTCGTGCGGTTGATATTGCTTCGTCATTAACGGCTGAACAAGTTGCAAGCCTTGTTA
GTGATGAACTACTTGATGCTAACACTGTATTAACAGAAGTGGGTTATCAACAAGCTG
GTAAAGGCCTTGAACGTATCACGTTAACTGGTGTGGCTACTGACAGCTATGCATTAA
CAGCTGGCAATAACATCGATGCTAACTCGGTATTTTAGTGAGTGGTGGCGCAAAAG
GTGTAACTGCACATTGTGTTGCTCGTATAGCTAAAGAATATCAGTCTAAGTTCATCT
TATTGGGACGTTCAACGTTCTCAAGTGACGAACCGAGCTGGGCAAGTGGTATTACTG
ATGAAGCGGCGTTAAAGAAAGCAGCGATGCAGTCTTTGATTACAGCAGGTGATAAAC
CAACACCCGTTAAGATCGTACAGCTAATCAAACCAATCCAAGCTAATCGTGAAATTG
CGCAAACCTTGTCTGCAATTACCGCTGCTGGTGGCCAAGCTGAATATGTTTCTGCAG
ATGTAACTAATGCAGCAAGCGTACAAATGGCAGTCGCTCCAGCTATCGCTAAGTTCG
GTGCAATCACTGGCATCATTCATGGCGCGGGTGTGTTAGCTGACCAATTCATTGAGC
AAAAAACACTGAGTGATTTTGAGTCTGTTTACAGCACTAAAATTGACGGTTTGTTAT
CGCTACTATCAGTCACTGAAGCAAGCAACATCAAGCAATTGGTATTGTTCTCGTCAG
CGGCTGGTTTCTACGGTAACCCCGGCCAGTCTGATTACTCGATTGCCAATGAGATCT
TAAATAAAACCGCATACCGCTTTAAATCATTGCACCCACAAGCTCAAGTATTGAGCT
TTAACTGGGGTCCTTGGGACGGTGGCATGGTAACGCCTGAGCTTAAACGTATGTTTG
ACCAACGTGGTGTTTACATTATTCCACTTGATGCAGGTGCACAGTTATTGCTGAATG
AACTAGCCGCTAATGATAACCGTTGTCCACAAATCCTCGTGGGTAATGACTTATCTA
AGATGCTAGCTCTGATCAAAAGTCTGATGAAAGAGTACTGCTGTAAAAAAGCCAC
AAGTTAGTCGTTTATCAGATGCTTTAGTAACTAAAAGTATCAAAGCGACTAACAGTA
```

FIG. 6E

GCTCTTTATCAAACAAGACTAGTGCTTTATCAGACAGTAGTGCTTTTCAGGTTAACG
AAAACCACTTTTTAGCTGACCACATGATCAAAGGCAATCAGGTATTACCAACGGTAT
GCGCGATTGCTTGGATGAGTGATGCAGCAAAAGCGACTTATAGTAACCGAGACTGTG
CATTGAAGTATGTCGGTTTCGAAGACTATAAATTGTTTAAAGGTGTGGTTTTTGATG
GCAATGAGGCGGCGGATTACCAAATCCAATTGTCGCCTGTGACAAGGGCGTCAGAAC
AGGATTCTGAAGTCCGTATTGCCGCAAAGATCTTTAGCCTGAAAAGTGACGGTAAAC
CTGTGTTTCATTATGCAGCGACAATATTGTTAGCAACTCAGCCACTTAATGCTGTGA
AGGTAGAACTTCCGACATTGACAGAAAGTGTTGATAGCAACAATAAAGTAACTGATG
AAGCACAAGCGTTATACAGCAATGGCACCTTGTTCCACGGTGAAAGTCTGCAGGGCA
TTAAGCAGATATTAAGTTGTGACGACAAGGGCCTGCTATTGGCTTGTCAGATAACCG
ATGTTGCAACAGCTAAGCAGGGATCCTTCCCGTTAGCTGACAACAATATCTTTGCCA
ATGATTTGGTTTATCAGGCTATGTTGGTCTGGGTGCGCAAACAATTTGGTTTAGGTA
GCTTACCTTCGGTGACAACGGCTTGGACTGTGTATCGTGAAGTGGTTGTAGATGAAG
TATTTTATCTGCAACTTAATGTTGTTGAGCATGATCTATTGGGTTCACGCGGCAGTA
AAGCCCGTTGTGATATTCAATTGATTGCTGCTGATATGCAATTACTTGCCGAAGTGA
AATCAGCGCAAGTCAGTGTCAGTGACATTTTGAACGATATGTCATGATCGAGTAAAT
AATAACGATAGGCGTCATGGTGAGCATGGCGTCTGCTTTCTTCATTTTTTAACATTA
ACAATATTAATAGCTAAACGCGGTTGCTTTAAACCAAGTAAACAAGTGCTTTTAGCT
ATTACTATTCCAAACAGGATATTAAAGAGAATATGACGGAATTAGCTGTTATTGGTA
TGGATGCTAAATTTAGCGGACAAGACAATATTGACCGTGTGGAACGCGCTTTCTATG
AAGGTGCTTATGTAGGTAATGTTAGCCGCGTTAGTACCGAATCTAATGTTATTAGCA
ATGGCGAAGAACAAGTTATTACTGCCATGACAGTTCTTAACTCTGTCAGTCTACTAG
CGCAAACGAATCAGTTAAATATAGCTGATATCGCGGTGTTGCTGATTGCTGATGTAA
AAAGTGCTGATGATCAGCTTGTAGTCCAAATTGCATCAGCAATTGAAAAACAGTGTG
CGAGTTGTGTTGTTATTGCTGATTTAGGCCAAGCATTAAATCAAGTAGCTGATTTAG

FIG. 6F

```
TTAATAACCAAGACTGTCCTGTGGCTGTAATTGGCATGAATAACTCGGTTAATTTAT
CTCGTCATGATCTTGAATCTGTAACTGCAACAATCAGCTTTGATGAAACCTTCAATG
GTTATAACAATGTAGCTGGGTTCGCGAGTTTACTTATCGCTTCAACTGCGTTTGCCA
ATGCTAAGCAATGTTATATATACGCCAACATTAAGGGCTTCGCTCAATCGGGCGTAA
ATGCTCAATTTAACGTTGGAAACATTAGCGATACTGCAAAGACCGCATTGCAGCAAG
CTAGCATAACTGCAGAGCAGGTTGGTTTGTTAGAAGTGTCAGCAGTCGCTGATTCGG
CAATCGCATTGTCTGAAAGCCAAGGTTTAATGTCTGCTTATCATCATACGCAAACTT
TGCATACTGCATTAAGCAGTGCCCGTAGTGTGACTGGTGAAGGCGGGTGTTTTCAC
AGGTCGCAGGTTTATTGAAATGTGTAATTGGTTTACATCAACGTTATATTCCGGCGA
TTAAAGATTGGCAACAACCGAGTGACAATCAAATGTCACGGTGGCGGAATTCACCAT
TCTATATGCCTGTAGATGCTCGACCTTGGTTCCCACATGCTGATGGCTCTGCACACA
TTGCCGCTTATAGTTGTGTGACTGCTGACAGCTATTGTCATATTCTTTTACAAGAAA
ACGTCTTACAAGAACTTGTTTTGAAAGAAACAGTCTTGCAAGATAATGACTTAACTG
AAAGCAAGCTTCAGACTCTTGAACAAAACAATCCAGTAGCTGATCTGCGCACTAATG
GTTACTTTGCATCGAGCGAGTTAGCATTAATCATAGTACAAGGTAATGACGAAGCAC
AATTACGCTGTGAATTAGAAACTATTACAGGGCAGTTAAGTACTACTGGCATAAGTA
CTATCAGTATTAAACAGATCGCAGCAGACTGTTATGCCCGTAATGATACTAACAAAG
CCTATAGCGCAGTGCTTATTGCCGAGACTGCTGAAGAGTTAAGCAAAGAAATAACCT
TGGCGTTTGCTGGTATCGCTAGCGTGTTTAATGAAGATGCTAAAGAATGGAAAACCC
CGAAGGGCAGTTATTTTACCGCGCAGCCTGCAAATAAACAGGCTGCTAACAGCACAC
AGAATGGTGTCACCTTCATGTACCCAGGTATTGGTGCTACATATGTTGGTTTAGGGC
GTGATCTATTTCATCTATTCCCACAGATTTATCAGCCTGTAGCGGCTTTAGCCGATG
ACATTGGCGAAAGTCTAAAAGATACTTTACTTAATCCACGCAGTATTAGTCGTCATA
GCTTTAAAGAACTCAAGCAGTTGGATCTGGACCTGCGCGGTAACTTAGCCAATATCG
CTGAAGCCGGTGTGGGTTTTGCTTGTGTGTTTACCAAGGTATTTGAAGAAGTCTTTG
CCGTTAAAGCTGACTTTGCTACAGGTTATAGCATGGGTGAAGTAAGCATGTATGCAG
CACTAGGCTGCTGGCAGCAACCGGGATTGATGAGTGCTCGCCTTGCACAATCGAATA
```

FIG. 6G

```
CCTTTAATCATCAACTTTGCGGCGAGTTAAGAACACTACGTCAGCATTGGGGCATGG
ATGATGTAGCTAACGGTACGTTCGAGCAGATCTGGGAAACCTATACCATTAAGGCAA
CGATTGAACAGGTCGAAATTGCCTCTGCAGATGAAGATCGTGTGTATTGCACCATTA
TCAATACACCTGATAGCTTGTTGTTAGCCGGTTATCCAGAAGCCTGTCAGCGAGTCA
TTAAGAATTTAGGTGTGCGTGCAATGGCATTGAATATGGCGAACGCAATTCACAGCG
CGCCAGCTTATGCCGAATACGATCATATGGTTGAGCTATACCATATGGATGTTACTC
CACGTATTAATACCAAGATGTATTCAAGCTCATGTTATTTACCGATTCCACAACGCA
GCAAAGCGATTTCCCACAGTATTGCTAAATGTTTGTGTGATGTGGTGGATTTCCCAC
GTTTGGTTAATACCTTACATGACAAAGGTGCGCGGGTATTCATTGAAATGGGTCCAG
GTCGTTCGTTATGTAGCTGGGTAGATAAGATCTTAGTTAATGGCGATGGCGATAATA
AAAAGCAAAGCCAACATGTATCTGTTCCTGTGAATGCCAAAGGCACCAGTGATGAAC
TTACTTATATTCGTGCGATTGCTAAGTTAATTAGTCATGGCGTGAATTTGAATTTAG
ATAGCTTGTTTAACGGGTCAATCCTGGTTAAAGCAGGCCATATAGCAAACACGAACA
AATAGTCAACATCGATATCTAGCGCTGGTGAGTTATACCTCATTAGTTGAAATATGG
ATTTAAAGAGAGTAATTATGGAAAATATTGCAGTAGTAGGTATTGCTAATTTGTTCC
CGGGCTCACAAGCACCGGATCAATTTTGGCAGCAATTGCTTGAACAACAAGATTGCC
GCAGTAAGGCGACCGCTGTTCAAATGGGCGTTGATCCTGCTAAATATACCGCCAACA
AAGGTGACACAGATAAATTTTACTGTGTGCACGGCGGTTACATCAGTGATTTCAATT
TTGATGCTTCAGGTTATCAACTCGATAATGATTATTTAGCCGGTTTAGATGACCTTA
ATCAATGGGGGCTTTATGTTACGAAACAAGCCCTTACCGATGCGGGTTATTGGGGCA
GTACTGCACTAGAAACTGTGGTGTGATTTTAGGTAATTTGTCATTCCCAACTAAAT
CATCTAATCAGCTGTTTATGCCTTTGTATCATCAAGTTGTTGATAATGCCTTAAAGG
CGGTATTACATCCTGATTTTCAATTAACGCATTACACAGCACCGAAAAAACACATG
CTGACAATGCATTAGTAGCAGGTTATCCAGCTGCATTGATCGCGCAAGCGGCGGGTC
TTGGTGGTTCACATTTTGCACTGGATGCGGCTTGTGCTTCATCTTGTTATAGCGTTA
AGTTAGCGTGTGATTACCTGCATACGGGTAAAGCCAACATGATGCTTGCTGGTGCGG
```

FIG. 6H

TATCTGCAGCAGATCCTATGTTCGTAAATATGGGTTTCTCGATATTCCAAGCTTACC
CAGCTAACAATGTACATGCCCCGTTTGACCAAAATTCACAAGGTCTATTTGCCGGTG
AAGGCGCGGGCATGATGGTATTGAAACGTCAAAGTGATGCAGTACGTGATGGTGATC
ATATTTACGCCATTATTAAAGGCGGCGCATTATCGAATGACGGTAAAGGCGAGTTTG
TATTAAGCCCGAACACCAAGGGCCAAGTATTAGTATATGAACGTGCTTATGCCGATG
CAGATGTTGACCCGAGTACAGTTGACTATATTGAATGTCATGCAACGGGCACACCTA
AGGGTGACAATGTTGAATTGCGTTCGATGGAAACCTTTTTCAGTCGCGTAAATAACA
AACCATTACTGGGCTCGGTTAAATCTAACCTTGGTCATTTGTTAACTGCCGCTGGTA
TGCCTGGCATGACCAAAGCTATGTTAGCGCTAGGTAAAGGTCTTATTCCTGCAACGA
TTAACTTAAAGCAACCACTGCAATCTAAAAACGGTTACTTTACTGGCGAGCAAATGC
CAACGACGACTGTGTCTTGGCCAACAACTCCGGGTGCCAAGGCAGATAAACCGCGTA
CCGCAGGTGTGAGCGTATTTGGTTTTGGTGGCAGCAACGCCCATTTGGTATTACAAC
AGCCAACGCAAACACTCGAGACTAATTTTAGTGTTGCTAAACCACGTGAGCCTTTGG
CTATTATTGGTATGGACAGCCATTTTGGTAGTGCCAGTAATTTAGCGCAGTTCAAAA
CCTTATTAAATAATAATCAAAATACCTTCCGTGAATTACCAGAACAACGCTGGAAAG
GCATGGAAAGTAACGCTAACGTCATGCAGTCGTTACAATTACGCAAAGCGCCTAAAG
GCAGTTACGTTGAACAGCTAGATATTGATTTCTTGCGTTTTAAAGTACCGCCTAATG
AAAAAGATTGCTTGATCCCGCAACAGTTAATGATGATGCAAGTGGCAGACAATGCTG
CGAAAGACGGAGGTCTAGTTGAAGGTCGTAATGTTGCGGTATTAGTAGCGATGGGCA
TGGAACTGGAATTACATCAGTATCGTGGTCGCGTTAATCTAACCACCCAAATTGAAG
ACAGCTTATTACAGCAAGGTATTAACCTGACTGTTGAGCAACGTGAAGAACTGACCA
ATATTGCTAAAGACGGTGTTGCCTCGGCTGCACAGCTAAATCAGTATACGAGTTTCA
TTGGTAATATTATGGCGTCACGTATTTCGGCGTTATGGGATTTTCTGGTCCTGCTA
TTACCGTATCGGCTGAAGAAACTCTGTTTATCGTTGTGTTGAATTAGCTGAAAATC
TATTTCAAACCAGTGATGTTGAAGCCGTTATTATTGCTGCTGTTGATTTGTCTGGTT
CAATTGAAAACATTACTTTACGTCAGCACTACGGTCCAGTTAATGAAAAGGGATCTG

FIG. 6I

```
TAAGTGAATGTGGTCCGGTTAATGAAAGCAGTTCAGTAACCAACAATATTCTTGATC
AGCAACAATGGCTGGTGGGTGAAGGCGCAGCGGCTATTGTCGTTAAACCGTCATCGC
AAGTCACTGCTGAGCAAGTTTATGCGCGTATTGATGCGGTGAGTTTTGCCCCTGGTA
GCAATGCGAAAGCAATTACGATTGCAGCGGATAAAGCATTAACACTTGCTGGTATCA
GTGCTGCTGATGTAGCTAGTGTTGAAGCACATGCAAGTGGTTTTAGTGCCGAAAATA
ATGCTGAAAAACCGCGTTACCGACTTTATACCCAAGCGCAAGTATCAGTTCGGTGA
AAGCCAATATTGGTCATACGTTTAATGCCTCGGGTATGGCGAGTATTATTAAAACGG
CGCTGCTGTTAGATCAGAATACGAGTCAAGATCAGAAAAGCAAACATATTGCTATTA
ACGGTCTAGGTCGTGATAACAGCTGCGCGCATCTTATCTTATCGAGTTCAGCGCAAG
CGCATCAAGTTGCACCAGCGCCTGTATCTGGTATGGCCAAGCAACGCCCACAGTTAG
TTAAACCATCAAACTCGGTGGTCAGTTAATTAGCAACGCGATTGTTAACAGTGCGA
GTTCATCTTTACACGCTATTAAAGCGCAGTTTGCCGGTAAGCACTTAAACAAAGTTA
ACCAGCCAGTGATGATGGATAACCTGAAGCCCCAAGGTATTAGCGCTCATGCAACCA
ATGAGTATGTGGTGACTGGAGCTGCTAACACTCAAGCTTCTAACATTCAAGCATCTC
ATGTTCAAGCGTCAAGTCATGCACAAGAGATAGCACCAAACCAAGTTCAAAATATGC
AAGCTACAGCAGCCGCTGTAAGTTCACCCCTTTCTCAACATCAACACACAGCGCAGC
CCGTAGCGGCACCGAGCGTTGTTGGAGTGACTGTGAAACATAAAGCAAGTAACCAAA
TTCATCAGCAAGCGTCTACGCATAAAGCATTTTTAGAAAGTCGTTTAGCTGCACAGA
AAAACCTATCGCAACTTGTTGAATTGCAAACCAAGCTGTCAATCCAAACTGGTAGTG
ACAATACATCTAACAATACTGCGTCAACAAGCAATACAGTGCTAACAAATCCTGTAT
CAGCAACGCCATTAACACTTGTGTCTAATGCGCCTGTAGTAGCGACAAACCTAACCA
GTACAGAAGCAAAAGCGCAAGCAGCTGCTACACAAGCTGGTTTTCAGATAAAAGGAC
CTGTTGGTTACAACTATCCACCGCTGCAGTTAATTGAACGTTATAATAAACCAGAAA
ACGTGATTTACGATCAAGCTGATTTGGTTGAATTCGCTGAAGGTGATATTGGTAAGG
TATTTGGTGCTGAATACAATATTATTGATGGCTATTCGCGTCGTGTACGTCTGCCAA
CCTCAGATTACTTGTTAGTAACACGTGTTACTGAACTTGATGCCAAGGTGCATGAAT
```

FIG. 6J

```
ACAAGAAATCATACATGTGTACTGAATATGATGTGCCTGTTGATGCACCGTTCTTAA
TTGATGGTCAGATCCCTTGGTCTGTTGCCGTCAATCAGGCCAGTGTGATTTGATGT
TGATTTCATATATCGGTATTGATTTCCAAGCGAAAGGCGAACGTGTTTACCGTTTAC
TTGATTGTGAATTAACTTTCCTTGAAGAGATGGCTTTTGGTGGCGATACTTTACGTT
ACGAGATCCACATTGATTCGTATGCACGTAACGGCGAGCAATTATTATTCTTCTTCC
ATTACGATTGTTACGTAGGGGATAAGAAGGTACTTATCATGCGTAATGGTTGTGCTG
GTTTCTTTACTGACGAAGAACTTTCTGATGGTAAAGGCGTTATTCATAACGACAAAG
ACAAAGCTGAGTTTAGCAATGCTGTTAAATCATCATTCACGCCGTTATTACAACATA
ACCGTGGTCAATACGATTATAACGACATGATGAAGTTGGTTAATGGTGATGTTGCCA
GTTGTTTTGGTCCGCAATATGATCAAGGTGGCCGTAATCCATCATTGAAATTCTCGT
CTGAGAAGTTCTTGATGATTGAACGTATTACCAAGATAGACCCAACCGGTGGTCATT
GGGGACTAGGCCTGTTAGAAGGTCAGAAAGATTTAGACCCTGAGCATTGGTATTTCC
CTTGTCACTTTAAAGGTGATCAAGTAATGGCTGGTTCGTTGATGTCGGAAGGTTGTG
GCCAAATGGCGATGTTCTTCATGCTGTCTCTTGGTATGCATACCAATGTGAACAACG
CTCGTTTCCAACCACTACCAGGTGAATCACAAACGGTACGTTGTCGTGGGCAAGTAC
TGCCACAGCGCAATACCTTAACTTACCGTATGGAAGTTACTGCGATGGGTATGCATC
CACAGCCATTCATGAAAGCTAATATTGATATTTTGCTTGACGGTAAAGTGGTTGTTG
ATTTCAAAAACTTGAGCGTGATGATCAGCGAACAAGATGAGCATTCAGATTACCCTG
TAACACTGCCGAGTAATGTGGCGCTTAAAGCGATTACTGCACCTGTTGCGTCAGTAG
CACCAGCATCTTCACCCGCTAACAGCGCGGATCTAGACGAACGTGGTGTTGAACCGT
TTAAGTTTCCTGAACGTCCGTTAATGCGTGTTGAGTCAGACTTGTCTGCACCGAAAA
GCAAAGGTGTGACACCGATTAAGCATTTTGAAGCGCCTGCTGTTGCTGGTCATCATA
GAGTGCCTAACCAAGCACCGTTTACACCTTGGCATATGTTTGAGTTTGCGACGGGTA
ATATTTCTAACTGTTTCGGTCCTGATTTTGATGTTTATGAAGGTCGTATTCCACCTC
GTACACCTTGTGGCGATTTACAAGTTGTTACTCAGGTTGTAGAAGTGCAGGGCGAAC
GTCTTGATCTTAAAAATCCATCAAGCTGTGTAGCTGAATACTATGTACCGGAAGACG
```

FIG. 6K

```
CTTGGTACTTTACTAAAAACAGCCATGAAAACTGGATGCCTTATTCATTAATCATGG
AAATTGCATTGCAACCAAATGGCTTTATTTCTGGTTACATGGGCACGACGCTTAAAT
ACCCTGAAAAAGATCTGTTCTTCCGTAACCTTGATGGTAGCGGCACGTTATTAAAGC
AGATTGATTTACGCGGCAAGACCATTGTGAATAAATCAGTCTTGGTTAGTACGGCTA
TTGCTGGTGGCGCGATTATTCAAAGTTTCACGTTTGATATGTCTGTAGATGGCGAGC
TATTTTATACTGGTAAAGCTGTATTTGGTTACTTTAGTGGTGAATCACTGACTAACC
AACTGGGCATTGATAACGGTAAAACGACTAATGCGTGGTTTGTTGATAACAATACCC
CCGCAGCGAATATTGATGTGTTTGATTTAACTAATCAGTCATTGGCTCTGTATAAAG
CGCCTGTGGATAAACCGCATTATAAATTGGCTGGTGGTCAGATGAACTTTATCGATA
CAGTGTCAGTGGTTGAAGGCGGTGGTAAAGCGGGCGTGGCTTATGTTTATGGCGAAC
GTACGATTGATGCTGATGATTGGTTCTTCCGTTATCACTTCCACCAAGATCCGGTGA
TGCCAGGTTCATTAGGTGTTGAAGCTATTATTGAGTTGATGCAGACCTATGCGCTTA
AAAATGATTTGGGTGGCAAGTTTGCTAACCCACGTTTCATTGCGCCGATGACGCAAG
TTGATTGGAAATACCGTGGGCAAATTACGCCGCTGAATAAACAGATGTCACTGGACG
TGCATATCACTGAGATCGTGAATGACGCTGGTGAAGTGCGAATCGTTGGTGATGCGA
ATCTGTCTAAAGATGGTCTGCGTATTTATGAAGTTAAAAACATCGTTTTAAGTATTG
TTGAAGCGTAAAGGGTCAAGTGTAACGTGCTTAAGCGCCGCATTGGTTAAAGACGCT
TTGCACGCCGTGAATCCGTCCATGGAGGCTTGGGGTTGGCATCCATGCCAACAACAG
CAAGCTTACTTTAATCAATACGGCTTGGTGTCCATTTAGACGCCTCGAACTTAGTAG
TTAATAGACAAAATAATTTAGCTGTGGAATGAATATAGTAAGTAATCATTCGGCAGC
TACAAAAAGGAATTAAGAATGTCGAGTTTAGGTTTTAACAATAACAACGCAATTAA
CTGGGCTTGGAAAGTAGATCCAGCGTCAGTTCATACACAAGATGCAGAAATTAAAGC
AGCTTTAATGGATCTAACTAAACCTCTCTATGTGGCGAATAATTCAGGCGTAACTGG
TATAGCTAATCATACGTCAGTAGCAGGTGCGATCAGCAATAACATCGATGTTGATGT
ATTGGCGTTTGCGCAAAAGTTAAACCCAGAAGATCTGGGTGATGATGCTTACAAGAA
ACAGCACGGCGTTAAATATGCTTATCATGGCGGTGCGATGGCAAATGGTATTGCCTC
```

FIG. 6L

```
GGTTGAATTGGTTGTTGCGTTAGGTAAAGCAGGGCTGTTATGTTCATTTGGTGCTGC
AGGTCTAGTGCCTGATGCGGTTGAAGATGCAATTCGTCGTATTCAAGCTGAATTACC
AAATGGCCCTTATGCGGTTAACTTGATCCATGCACCAGCAGAAGAAGCATTAGAGCG
TGGCGCGGTTGAACGTTTCCTAAAACTTGGCGTCAAGACGGTAGAGGCTTCAGCTTA
CCTTGGTTTAACTGAACACATTGTTTGGTATCGTGCTGCTGGTCTAACTAAAAACGC
AGATGGCAGTGTTAATATCGGTAACAAGGTTATCGCTAAAGTATCGCGTACCGAAGT
TGGTCGCCGCTTTATGGAACCTGCACCGCAAAAATTACTGGATAAGTTATTAGAACA
AAATAAGATCACCCCTGAACAAGCTGCTTTAGCGTTGCTTGTACCTATGGCTGATGA
TATTACTGGGGAAGCGGATTCTGGTGGTCATACAGATAACCGTCCGTTTTTAACATT
ATTACCGACGATTATTGGTCTGCGTGATGAAGTGCAAGCGAAGTATAACTTCTCTCC
TGCATTACGTGTTGGTGCTGGTGGTGGTATCGGAACGCCTGAAGCAGCACTCGCTGC
ATTTAACATGGGCGCGGCTTATATCGTTCTGGGTTCTGTGAATCAGGCGTGTGTTGA
AGCGGGTGCATCTGAATATACTCGTAAACTGTTATCGACAGTTGAAATGGCTGATGT
GACTATGGCACCTGCTGCAGATATGTTTGAAATGGGTGTGAAGCTGCAAGTATTAAA
ACGCGGTTCTATGTTCGCGATGCGTGCGAAGAAACTGTATGACTTGTATGTGGCTTA
TGACTCGATTGAAGATATCCCAGCTGCTGAACGTGAGAAGATTGAAAAACAAATCTT
CCGTGCAAACCTAGACGAGATTTGGGATGGCACTATCGCTTTCTTTACTGAACGCGA
TCCAGAAATGCTAGCCCGTGCAACGAGTAGTCCTAAACGTAAAATGGCACTTATCTT
CCGTTGGTATCTTGGCCTTTCTTCACGCTGGTCAAACACAGGCGAGAAGGGACGTGA
AATGGATTATCAGATTTGGGCAGGCCCAAGTTTAGGTGCATTCAACAGCTGGGTGAA
AGGTTCTTACCTTGAAGACTATACCCGCCGTGGCGCTGTAGATGTTGCTTTGCATAT
GCTTAAAGGTGCTGCGTATTTACAACGTGTAAACCAGTTGAAATTGCAAGGTGTTAG
CTTAAGTACAGAATTGGCAAGTTATCGTACGAGTGATTAATGTTACTTGATGATATG
TGAATTAATTAAAGCGCCTGAGGGCGCTTTTTTTGGTTTTTAACTCAGGTGTTGTAA
CTCGAAATTGCCCCTTTC
                *
              19227
```

FIG. 6M

| EPA (%Fatty acids) | DHA (%Fatty acids) | 20 deg C |
|---|---|---|
| 0.00 | 0.06 | pEPAD8 |
| 0.60 | 0.70 | *4* |
| 0.64 | 0.66 | *5* |
| 0.33 | 0.22 | *6s* |
| 0.45 | 0.59 | *6l* |
| | | 23 deg C |
| 0.02 | 0.06 | pEPAD8 |
| 0.32 | 0.62 | *4* |
| 0.27 | 0.22 | *6s* |
| 0.18 | 0.65 | *6l* |

FIGURE 16

```
 ↓
ATT GGT AAA AAT AGG GGT TAT GTT TGT TGC TTT AAA GAG TGT CCT GAA
 I   G   K   N   R   G   Y   V   C   C   F   K   E   C   P   E

↓              9157↓   ↓
AAA TTG CTA ACT TCT CGA TTG ATT TCC TTA TAC TTC TGT CCG TTA ACA
 K   L   L   T   S   R   L   I   S   L   Y   F   C   P   L   T

↓
ATA CAA GAG TGC GAT AAC CAG ACT ACA GAG TTG GTT AAG TCA TGG CTG
 I   Q   E   C   D   N   Q   T   T   E   L   V   K   S   W   L

↓                       ↓
CCT GAA GAT GAG TTA ATT AAG GTT AAT CGC TAC ATT AAA CAA GAA GCT
 P   E   D   E   L   I   K   V   N   R   Y   I   K   Q   E   A

9016↓
AAA ACT CAA GGT TTA ATG GTA AGA G
 K   T   Q   G   L   M   V   R
```

FIG. 24

```
AGCGAAATGC TTATCAAGAA ATTCCAAGAT CAATACATCA CTGGGAAGAA AATTCATTCC    60
CTGGTTCACT GGGTAACGTT ATTCCGGCC  GTATTGCTAA CCGCTTCGAC CTTGGTGGCA   120
TGAACTGTGT CGTTGATGCA GCATGTGCAG GCCCTCTTGC TGCATTGCGT ATGGCATTAA   180
GCGAGCTTGT TGAAGGCCGC AGCGAAATGA TGATTACAGG TGGTGTGTGT ACCGATAACT   240
CACCAACCAT GTACATGAGC TTCTCTAAAA CACCGGCATT CACGACAAAC GAAACAATTC   300
AACCATTCGA TATTGACTCG AAAGGTATGA TGATTGGTGA AGGTATCGGT ATGATTGCGC   360
TTAAACGTCT TGAAGACGCA GAGCGTGATG GCGACCGTAT CTATTCCGTG ATTAAAGGTG   420
TTGGGTGCAT CTTCAGACGG TAATTTATTA AGAGTANTTA TGCGCNTCGT CCTGAAGGTC   480
AGGCTAAGGC ACTTAAACGT GCTTACGACG ATGCAGGTTT CGCACCGCAC ACACTTGGCT   540
TACTTGAAGC CCACGGCACA GGCACAGCAG CAGGTGATGT GGCAGAATTC AGTGGTCTTA   600
ACTCTGTATT CAGTGAAGGC AATGACGAAA AGCAACACAT CGCATTAGGT TCAGTGAAAT   660
CACAGATTGG TCACACTAAA TCAACAGCGG GTACTGCGGG TCTAATCAAA GCGTCTTTAG   720
CACTGCACCA TAAAGTACTG CCGCCCAACAA TCAATGTAAC CAGCCCTAAC CAACGTGTCG   780
ATATTGAAGA CTCGCCCTTTC TACCTCAATA CACAGACGCG TCCATGGATG CAACGTGTCG   840
ATGGTACACC GCGTCGTGCT GGTATTAGCT CATTTGGTTT TGGTG                   885
```

FIG. 25

```
                        20                 40                  60
                         *                  *                   *
3-2(-VECTO   CCAAGCTAAA GCACTTAACC GTGCTTATGA AGATGCCGGT TTTGCCCCTG AAACATGTGG
             |||||||||| |||||||||| |||||||||| |||||||||| |||||||||| ||||||||||
jmpl str +   CCAAGCTAAA GCACTTAACC GTGCCTATGA TGATGCCGGT TTTGCCCCTG AAACATGTGG
             |||||||||| |||||||||| |||| ||||| | |||||||| |||||||||| ||||||||||
3-2(-VECTO   CCAAGCTAAA GCACTTAACC GTGCTTATGA AGATGCCGGT TTTGCCCCTG AAACATGTGG 80                 100                 120
                         *                  *                   *
3-2(-VECTO   TCTAATTGAA GGCCATGGTA CGGGTACCAA AGCGGGTGAT GCCGCAGAAT TGCTGGCTT
             |||||||||| |||||||||| |      |    ||||||||| |||| ||||| |||| ||||
jmpl str +   TCTAATTGAA GGCCATGGTA C                                          
             |||||||||| |||||||||| |                                          
3-2(-VECTO   TCTAATTGAA GGCCATGGTA C AGA ACGCAAAGTT GCCGCACTGT TTGGTCGCCA
             |   ||       | |||||||||| |||||||| |
             CAA AGCGGGTGAT GCCGCACTGT TTGGTCGCTT
```

FIG. 26A

```
                            140                 160                 180
                             *                   *                   *
3-2(-VECTO  GACCAAACAC TTTGGGCCCG CCAGTGATGA AAAGCAATAT ATCGCCTTAG GCTCAGTTAA jmpl str +                                             C ATTGCGCTAG GTTCAGTTAA
                                                       |  ||  ||||  ||||||||
3-2(-VECTO                                             T ATCGCCTTAG GCTCAGTTAA jmpl str +  AGGTTCACAA
            ||    |||
3-2(-VECTO  GACCTAACAC 200                 220                 240
                             *                   *                   *
3-2(-VECTO  ATCGCAAATT GGTCATACTA AATCTGCGGC TGGCTCTGCG GGTATGATTA AGGCGGCATT jmpl str +                                             CG GCTTCGATTT TGGCGGCATG
                                                       || |  ||  || |    ||||
3-2(-VECTO                                             CG CGTATGATTA AGGCGGCATT jmpl str +  ATCACAAATT GGTCATACTA AATCAACTGC AGGT
            |||  |||||| |||||||||| ||||  |||  ||
3-2(-VECTO  ATCGCAAATT GGTCATACTA AATCTGCGGC TGGC
```

FIG. 26B

```
jmpl st +                                             GCACTGCT GCAAGCATGA ACGCGTCGTT
                                                      || ||| | |||| |||||||
                                                      GCTCTGCCG GCTATCATTA ACGCGGCATT
                       *        *         *         *         *        300
                      260                280
3-2(-VECTO AGCGCTGCAT CATAAAATCT TACCTGCAAC GATCCATATC GATAAACCAA GTGAAGCCTT jmpl st +  AACGGTG
           ||  |  |
3-2(-VECTO AGCGCTG jmpl st +       T
                |
3-2(-VECTO      A jmpl st +                                  TCCCTGGTGC TAACCATATC AGCAAACCA
                                           |  |||  |  |||||||    ||| ||
                                           TACCTGCAAC GATCCATATC GATAAACCA
                       *        *         *         *         *        360
                      320                340
3-2(-VECTO GGATATCAAA AACAGCCCGT TATACCTAAA CAGGGAAACG CGTCCTTGGA TGCCACGTGA
```

FIG. 26C

```
jmpl str +                                              CTCACCTT TGTATCTAAA CACTGAGACT TCGTCCATGG TTACCACGTGT
                                                        - -  - | ||||| |  || || |||||  ||| |||||||
3-2(-VECTO                                              CAGCCCGT TATACCTAAA CAGCGAAACG GCGTCCTTGG ATGCCACGTGA

*                   380                    *               400             *
3-2(-VECTO    AGATGGTATT CCACGTCGTG CCGCGCCGCG CGGGTATTAG CAGGTATTAG CTCATTTGGT TTTGGTGGC>
              |||||||    |=||||||||  | ||| ||  - ||||||| |||||||||| |||||||||| ||||||||
jmpl str +    TGATGGTACG CCGCGCCGCG CGGGTATTAG CTCATTTGGT TTTGGTGGC
              ||||||||  |=||||||||               |||||||||| |||||||||| ||||||||
3-2(-VECTO    AGATGGTATT CCACGTCGTG                        CAGGTATTAG CTCATTTGGT TTTGGTGGC
```

FIG. 26D

SEQUENCE LISTING

```
<160> NUMBER OF SEQ ID NOS: 66

<210> SEQ ID NO 1
<211> LENGTH: 37895
<212> TYPE: DNA
<213> ORGANISM: Shewanella putrefaciens

<400> SEQUENCE: 1
gatctcttac aaagaaacta tctcaatgtg aatttaacct taattccgtt taattacggc      60
```

```
ctgatagagc atcacccaat cagccataaa actgtaaagt gggtactcaa aggtggctgg      120
gcgattcttc tcaaatacaa agtgcccaac ccaagcaaat ccatatccga taacaggtaa      180
aagtagcaat aaaccccagc gctgagttag taatacataa gcgaataata ggatcactaa      240
actactgccg aaatagtgta atattcgaca gtttctatgc tgatgttgag ataaataaaa      300
agggtaaaat tcagcaaaag aacgatagcg cttactcatt actcacacct cggtaaaaaa      360
gcaactcgcc attaacttgg ccaatcgtca gttgttctat cgtctcaaag ttatgccgac      420
taaataactc tatatgtgca ttatgattag caaaaactcc gataccatca agatgaagtt      480
gttcatcaca ccaactcaaa actgcgtcga taagcttact gccatagccc ttgccttgct      540
ccacatttgc gatagcaata aactgtaaaa tgccacattg gccacttggt aagctctcta      600
taatctgatt ttctttgtta ataagtgcct gagttgaata ccaaccagta cttaacaaca      660
tctttaaacg ccaatgccaa aaacgcgctt cacctaaggg aacctgctga gtcactatgc      720
aggctacgcc tatcaatcta tccccaacga acataccaat aagtgcttgc tcctgttgcc      780
agagctcatt gagttcttct cgaatagccc cgcgaagctt ttgctcatac tgcgcttgat      840
caccactaaa aagtgtttcg ataaaaaagg gatcatcatg ataggcgtta tagagaatag      900
aggctgctat gcgtaaatct tctgccgtga gataaactgc acgacactct tccatggctt      960
gatcttccat tgttattgtc cttgaccttg atcacacaac accaatgtaa caagactgta     1020
tagaagtgca attaataatc aattcgtgca ttaagcaggt cagcatttct ttgctaaaca     1080
agctttattg gctttgacaa aactttgcct agactttaac gatagaaatc ataatgaaag     1140
agaaaagcta caacctagag gggaataatc aaacaactgc taagatctag ataatgtaat     1200
aaacaccgag tttatcgacc atacttagat agagtcatag caacgagaat agttatggat     1260
acaacgccgc aagatctatc acacctgttt ttacagctag gattagcaaa tgatcaaccc     1320
gcaattgaac agtttatcaa tgaccatcaa ttagcggaca atatattgct acatcaagca     1380
agcttttgga gcccatcgca aaagcacttc ttaattgagt catttaatga agatgcccag     1440
tggaccgaag tcatcgacca cttagacacc ttattaagaa aaaactaacc attacaacag     1500
caactttaaa ttttgccgta agccatctcc ccccacccca caacagcgtt gttgcttatg     1560
accactggag tacattcgtc tttagtcgtt ttaccatcac catgggtacg ttgagtgcga     1620 taaaaagca cataaacttc tttatcggcc tgaatatagg cttcgttaaa atcagctgtt     1680
cccattaaag taaccacttg ctctttactc atgcctagag atatctttgt caaattgtca     1740 cggttttat cttgagtttt ctcccaagca ccgtgattat cccagtcaga ttccccatca     1800
ccaacattga ccacacagcc cgttagccct aagcttgcaa tcccaaaaca tgctaaacct     1860
aataatttat ttttcatttt aacttcctgt tatgacatta ttttgctta gaagaaaagc     1920 aacttacatg ccaaaacaca agctgttgtt ttaaatgact ttatttatta ttagccttt     1980 aggatatgcc tagagcaata ataattacca atgtttaagg aatttgacta actatgagtc     2040
cgattgagca agtgctaaca gctgctaaaa aaatcaatga acaaggtaga gaaccaacat     2100
tagcattgat taaaaccaaa cttggtaata gcatcccaat gcgcgagtta atccaaggtt     2160
tgcaacagtt taagtctatg agtgcagaag aaagacaagc aatacctagc agcttagcaa     2220
cagcaaaaga aactcaatat ggtcaatcaa gcttatctca atctgaacaa gctgatagga     2280
tcctccagct agaaaacgcc ctcaatgaat taagaaacga atttaatggg ctaaaaagtc     2340
aatttgataa cttacaacaa aacctgatga ataaagagcc tgacaccaaa tgcatgtaat     2400
```

-continued

```
tgaactacga tttgaatgtt ttgataacac cacgattact gcagcagaaa aagccattaa    2460
tggtttgctt gaagcttatc gagccaatgg ccaggttcta ggtcgtgaat tgccgttgc    2520
atttaacgat ggtgagttta aagcacgcat gttaaccccca gaaaaaagca gcttatctaa    2580
acgctttaat agtccttggg taaatagtgc actcgaagag ctaaccgaag ccaaattgct    2640
tgcgccacgt gaaaagtata ttggccaaga tattaattct gaagcatcta gccaagacac    2700
accaagttgg cagctacttt acacaagtta tgtgcacatg tgctcaccac taagaaatgg    2760
cgacaccttg cagcctattc cactgtatca aattccagca actgccaacg gcgatcataa    2820
acgaatgatc cgttggcaaa cagaatggca agcttgtgat gaattgcaaa tggccgcagc    2880
tactaaagct gaatttgccg cacttgaaga gctaaccagt catcagagtg atctatttag    2940
gcgtggttgg gacttacgtg gcagagtcga atacttgacg aaaattccga cctattacta    3000
tttataccgt gttggcggtg aaagcttagc agtagaaaag cagcgctctt gtcctaagtg    3060
tggcagtcaa gaatggctgc tcgataaacc attattggat atgttccatt ttcgctgtga    3120
cacctgccgc atcgtatcta atatctcttg ggaccattta taactcttcc gagtcttatc    3180
acactagagt ttagtcagca taaaaatggc gcttatattt caattaaaag aaatataagc    3240
gccattttca tcgatactat atatcagcag actattttcc gcgtaaatta gcccacatta    3300
atttcattct ttgccagatc cctggatgat ctagttgtgg catcgactct tcaataggtt    3360
taaccgcagg tgtaacccctt ggagtcaatt cgtttataaa ctcgtttaaa ctgtcactta    3420
atttaacgct ttgtacttca cctggaattt caatccatac gctgccatca ctattattaa    3480
ccgtcaacat tttatcttca tcatcaagaa taccaataaa ccaagtcggc tcttgcttaa    3540
gctttctctt catcattaaa tgaccaatga tgttttgttg taagtattca aaatcagttt    3600
gatcccacac ttggattagc tcaccttggc cccattgtga gtcaaaaaat agcggtgcag    3660
aaaaatgact gccaaaaaat ggattaattt ctgcagataa tgtcatttca agtgctgttt    3720
caacattagc aaattcacca ggttgttgac gtacaaccga ttgccaaaac actgcgccat    3780
cggagcccgc ttcggcgaca acacactcag acttttgtcc ttgcgcataa tatcttggct    3840
gttcaccaag cttatccatg taggcttgtt gatatttaga taaaaaaaga tctaaagcag    3900
gtaaagaaga cacttaagcc agttccaaaa tcagttataa taggggtcta ttttgacatg    3960
gaaaccgtat tgatgacaca acatcatgat ccctacagta acgcccccga actttctgaa    4020
ttaactttag gaaagtcgac cggttatcaa gagcagtatg atgcatcttt actacaagcg    4080
tgccgcgtaa attaaaccgt gatgctatcg gtctaaccaa tgagctacct tttcatggct    4140
gtgatatttg gactggctac gaactgtctt ggctaaatgc taaaggcaag ccaatgattg    4200
ctattgcaga cttttaaccta gttttgata gtaaaaatct gatcgagtct aagtcgttta    4260
agctgtattt aaacagctat aaccaaacac gatttgatag cgttcaagcg gttcaagaac    4320
gtttaactga agacttaagc gcctgtgccc aaggcacagt tacggtaaaa gtgattgaac    4380
ctaagcaatt taaccacctg agagtggttg atatgccagg tacctgcatt gacgatttag    4440
atattgaagt tgatgactat agctttaact ctgactatct caccgacagt gttgatgaca    4500
aagtcatggt tgctgaaacg ctaacgtcaa acttattgaa atcaaactgc ctaatcactt    4560
ctcagcctga ctggggtaca gtgatgatcc ggttatcaagg gcctaagata gaccgtgaaa    4620
agctacttag atatctgatt tcatttagac agcacaatga atttcatgag cagtgtgttg    4680
agcgtatatt tgttgattta aagcactatt gccaatgtgc caaacttact gtctatgcac    4740
gttatacccg ccgtggtggt ttagatatca acccatatcg tagcgacttt gaaaaccctg    4800
```

```
cagaaaatca gcgcctagcg agacagtaat tgattgcagt acctacaaaa aacaatgcct    4860
ataagccaag cttatgggca tttttatatt atcaacttgt catcaaacct cagccgccaa    4920
gccttttagt tttatcgcta aattaagccg ctctctcagc caaatatttg caggattttg    4980
ctgtaattta tggctccaca ccatgaaata ctctatcggc tctaccgcaa aaggtaagtc    5040
aaatacctgt aagccaaaca gcttggcata ttcgtcagtg tgggcttttg acgcgatagc    5100
taacgcatca cttttgagg caaccgacat catacttaat attgatgatt gctcgctgtg     5160
catttgcctt gccggtaaca cctgtttagt cagcaagtcg gcaacactta aattgtagcg    5220
gcgcatctta aaaataatat gcttttcatt aaagtattgc tcttgcgtca acccaccttg    5280
gatccttggg tgagcatttc gtgccacaca aactaattta tcctgcatta cttttgact    5340 cttaaatgcc gcagattctg gcagccaaat atctaaggct aaatccacct tttctagttg    5400
taggtccatc tgcaactctt cttcaatgag cggcggctca cgaaatacaa tattaattgc    5460
agtgccctgt aacacttgct caatttgatc ttgcaagagt tgtattgccg actcgctggc    5520
atacacataa aaagttcgct cacttgaagt ggggtcaaat gcttcaaagc tagtcgcaac    5580
ttgctcaatt gttgacatag cgcccgcgag ctgttgataa agcgtcatcg cacttgcggt    5640
aggtttaact cccctaccca ctcgagtaaa caactcttct ccaacaatac ttttttagcct   5700 cgaaatcgca ttactaaccg acgactgagt caaatccagc tcttctgccg cccggctaaa    5760
agatgaggtg cgatacaccg cagtaaaaac gcgaaataaa ttaagatcaa agcttttg     5820 ctgcgacata aatcagctat ctccttatcc ttatccttat ccttataaaa agttagctcc    5880
agagcactct agctcaaaaa caactcagcg tattaagcca atattttggg aactcaatta    5940
atattcataa taaagtatt cataatataa ataccaagtc ataatttagc cctaattatt     6000
aatcaattca agttacctat actggcctca attaagcaaa tgtctcatca gtctccctgc    6060
aactaaatgc aatattgaga cataaagctt tgaactgatt caatcttacg agggtaactt    6120
atgaaacaga ctctaatggc tatctcaatc atgtcgcttt tttcattcaa tgcgctagca    6180
gcgcaacatg aacatgacca catcactgtt gattacgaag ggaaagccgc aacagaacac    6240
accatagctc acaaccaagc tgtagctaaa acacttaact ttgccgacac gcgtgcattt    6300
gagcaatcgt ctaaaaatct agtcgccaag tttgataaag caactgccga tatattacgt    6360
gccgaatttg cttttattag cgatgaaatc cctgactcgg ttaacccgtc tctctaccgt    6420
caggctcagc ttaatatggt gcctaatggt ctgtataaag tgagcgatgg catttaccag    6480
gtccgcggta ccgacttatc taaccttaca cttatccgca gtgataacgg ttggatagca    6540
tacgatgttt tgttaaccaa agaagcagca aaagcctcac tacaatttgc gttaaagaat    6600
ctacctaaag atggcgattt acccgttgtt gcgatgattt actcccatag ccatgcggac    6660
cactttggcg gagctcgcgg tgttcaagag atgttccctg atgtcaaagt ctacggctca    6720
gataacatca ctaaagaaat tgtcgatgag aacgtacttg ccggtaacgc catgagccgc    6780
cgcgcagctt atcaatacgg cgcaacactg ggcaaacatg accacggtat tgttgatgct    6840
gcgctaggta aggtctatc aaaggtgaa atcacttacg tcgccccaga ctacaccttaa    6900 aacagtgaag gcaaatggga aacgctgacg attgatggtc tagagatggt gtttatggat    6960
gcctcgggca ccgaagctga gtcagaaatg atcacttata ttccctctaa aaaagcgctc    7020
tggacgcgcg agcttaccta tcaaggtatg cacaacattt atacgctgcg cggcgctaaa    7080
gtacgtgatg cgctcaagtg gtcaaaagat atcaacgaaa tgatcaatgc ctttggtcaa    7140
```

```
gatgtcgaag tgctgtttgc ctcgcactct gcgccagtgt ggggtaacca agcgatcaac    7200
gatttcttac gcctacagcg tgataactac ggcctagtgc acaatcaaac cttgagactt    7260
gccaacgatg tgtcggtat  acaagatatt ggcgatgcga ttcaagacac gattccagag    7320
tctatctaca agacgtggca taccaatggt taccacggca cttatagcca taacgctaaa    7380
gcggtttata acaagtatct aggctacttc gatatgaacc cagccaacct taatccgctg    7440
ccaaccaagc aagaatctgc caagtttgtc gaatacatgg gcggcgcaga tgccgcaatt    7500
aagcgcgcta agatgatta  cgctcaaggt gaataccgct tgttgcaac  ggcattaaat    7560 aaggtggtga tggccgagcc agaaaatgac tccgctcgtc aattgctagc cgatacctat    7620
gagcaacttg gttatcaagc agaagggget ggctggagaa acatttactt aactggcgca    7680
caagagctac gagtaggtat tcaagctggc gcgcctaaaa ccgcatcggc agatgtcatc    7740
agtgaaatgg acatgccgac tctatttgac ttcctcgcgg tgaagattga tagtcaacag    7800
gcggctaagc acggcttagt taagatgaat gttatcaccc ctgatactaa agatattctc    7860
tatattgagc taagcaacgg taacttaagc aacgcagtgg tcgacaaaga gcaagcagct    7920
gacgcaaacc ttatggttaa taaagctgac gttaaccgca tcttacttgg ccaagtaacc    7980
ctaaaagcgt tattagccag cggcgatgcc aagctcactg gtgataaaac ggcatttagt    8040
aaaatagccg atagcatggt cgagtttaca cctgacttcg aaatcgtacc aacgcctgtt    8100
aaatgaggca ttaatctcaa caagtgcaag ctagacataa aaatgggcg  attagacgcc    8160 ccattttta  tgcaattttg aactagctag tcttagctga agctcgaaca acagctttaa    8220
aattcacttc ttctgctgca atacttattt gctgacactg accaatactc agtgcaaaac    8280
gataactatc atcaagatgg cccagtaaac aatgccaatt atcagcagcg ttcatttgct    8340
gttctttagc ctcaatcaaa cctaaaccag acttttgtgg ctcagcgtta ggcttattag    8400
aactcgactc tagtaaagca agaccaatat cttgttttaa caaaacctgt cgctgattaa    8460
gttgatgctc aaccttgtga tccgcaatag catcggaaat atcaacacaa tggctcaagc    8520
ttttaggtgc attaactcca agaaaagttt cgctcagtgc agagaagtca aacgcaaaag    8580
attttagcga taatgccagc ccaagtcctt tcgctttaat gtaagactcc ttgagcgccc    8640
acaaatcaaa aaagcggtct cgctgcaagg cctctggtaa cgctaacaag gctcgctttt    8700
ctgattcaga gaaataatga ctaagaatag agtggatatt ggtgctgtta cggcaacgct    8760
caatgtcgac gccaaactca atactagcag agtcagtttc ctccttgctt gcctgactgg    8820
cgcctttatt atcagcagtg caaatgccta ctaatagcca atctccacta tgactcacat    8880
taaagtggac cccggtttga gcaaattgcg catcactcaa tctaggctta cctttgtcgc    8940
catattcaaa gcgccattca ttggggcgta tttcactatg ttgtgacaat aaagcgcgca    9000
aatagcctct taccattaaa ccttgagttt tagcttcttg tttaatgtag cgattaacct    9060
taattaactc atcttcaggc agccatgact taaccaactc tgtagtctgg ttatcgcact    9120
cttgtattgt taacggacag aagtataagg aaatcaatcg agaagttagc aatttttcag    9180
gacactcttt aaagcaacaa acataacccc tattttttacc aatttaagat caaaactaaa    9240
gccaaaacta attgagaata gtgtcaaact agctttaaag gaaaaaaata taaaagaac    9300 attatacttg tataaattat tttacacacc aaagccatga tcttcacaaa attagctccc    9360
tctccctaaa acaagattga ataaaaaaat aaacctaac  tttcatatag ataaaacaaa    9420
ccaatgggat aaagtatatt gaattcattt ttaaggaaaa attcaaattg aattcaagct    9480
cttcagtaaa agcatatttt gccgttagtg tgaaaaaaaa caaatttaaa aaccaacata    9540
```

-continued

```
gaacaaataa gcagacaata aaaccaaggc gcaacacaaa caacgcgctt acaattttca   9600
caaaaaagca acaagagtaa cgtttagtat ttggatatgg ttattgtaat tgagaatttt   9660
ataacaatta tattaaggga atgagtatgt ttttaaattc aaaactttcg cgctcagtca   9720
aacttgccat atccgcaggc ttaacagcct cgctagctat gcctgttttt gcagaagaaa   9780
ctgctgctga agaacaaata gaaagagtcg cagtgaccgg atcgcgaatc gctaaagcag   9840
agctaactca accagctcca gtcgtcagcc tttcagccga agaactgaca aaatttggta   9900
atcaagattt aggtagcgta ctagcagaat tacctgctat tggtgcaacc aacactatta   9960
ttggtaataa caatagcaac tcaagcgcag gtgttagctc agcagacttg cgtcgtctag  10020
gtgctaacag aaccttagta ttagtcaacg gtaagcgcta cgttgccggc caaccgggct  10080
cagctgaggt agatttgtca actataccaa ctagcatgat ctcgcgagtt gagattgtaa  10140
ccggcggtgc ttcagcaatt tatggttcgg acgctgtatc aggtgttatc aacgttatcc  10200
ttaaagaaga cttttgaaggc tttgagttta acgcacgtac tagcggttct actgaaagtg  10260
taggcactca agagcactct tttgacattt tgggtggtgc aaacgttgca gatgacgtg   10320 gtaatgtaac cttctacgca ggttatgaac gtacaaaaga agtcatggct accgacattc  10380
gccaattcga tgcttgggga acaattaaaa acgaagccga tggtggtgaa gatgatggta  10440
ttccagacag actacgtgta ccacgagttt attctgaaat gattaatgct accggtgtta  10500
tcaatgcatt tggtggtgga attggtcgct caacctttga cagtaacggc aatcctattg  10560
cacaacaaga acgtgatggg actaacagct ttgcatttgg ttcattccct aatggctgtg  10620
acacatgttt caacactgaa gcatacgaaa actatattcc aggggtagaa agaataaacg  10680
ttggctcatc attcaacttt gattttaccg ataacattca attttacact gacttcagat  10740
atgtaaagtc agatattcag caacaatttc agccttcatt ccgttttggt aacattaata  10800
tcaatgttga agataacgcc tttttgaatg acgacttgcg tcagcaaatg ctcgatgcgg  10860
gtcaaaccaa tgctagtttt gccaagtttt ttgatgaatt aggaaatcgc tcagcagaaa  10920
ataaacgcga acttttccgt tacgtaggtg gctttaaagg tggctttgat attagcgaaa  10980
ccatatttga ttacgacctt tactatgttt atggcgagac taataaccgt cgtaaaaccc  11040
ttaatgacct aattcctgat aactttgtcg cagctgtcga ctctgttatt gatcctgata  11100
ctggcttagc agcgtgtcgc tcacaagtag caagcgctca aggcgatgac tatacagatc  11160
ccgcgtctgt aaatggtagc gactgtgttg cttataaccc atttggcatg ggtcaagctt  11220
cagcagaagc ccgcgactgg gtttctgctg atgtgactcg tgaagacaaa ataactcaac  11280
aagtgattgg tggtactctc ggtaccgatt ctgaagaact atttgagctt caaggtggtg  11340
caatcgctat ggttgttggt tttgaatacc gtgaagaaac gtctggttca acaaccgatg  11400
aatttactaa agcaggtttc ttgacaagcg ctgcaacgcc agattcttat ggcgaatacg  11460
acgtgactga gtattttgtt gaggtgaaca tcccagtact aaaagaatta ccttttgcac  11520
atgagttgag ctttgacggt gcataccgta atgctgatta ctcacatgcc ggtaagactg  11580
aagcatggaa agctggtatg ttctactcac cattagagca acttgcatta cgtggtacgg  11640
taggtgaagc agtacgagca ccaaacattg cagaagcctt tagtccacgc tctcctggtt  11700
ttggccgcgt ttcagatcca tgtgatgcag ataacattaa tgacgatccg gatcgcgtgt  11760
caaactgtgc agcattgggg atccctccag gattccaagc taatgataac gtcagtgtag  11820
ataccttatc tggtggtaac ccagatctaa aacctgaaac atcaacatcc tttacaggtg  11880
```

-continued

```
gtcttgtttg gacaccaacg tttgctgaca atctatcatt cactgtcgat tattatgata   11940
ttcaaattga ggatgctatt ttgtcagtag ccacccagac tgtggctgat aactgtgttg   12000
actcaactgg cggacctgac accgacttct gtagtcaagt tgatcgtaat ccaacgacct   12060
atgatattga acttgttcgc tctggttatc taaatgccgc ggcattgaat accaaaggta   12120
ttgaatttca agctgcatac tcattagatc tagagtcttt caacgcgcct ggtgaactac   12180
gcttcaacct attggggaac caattacttg aactagaacg tcttgaattc caaatcgtc    12240 ctgatgagat taatgatgaa aaaggcgaag taggtgatcc agagctgcag ttccgcctag   12300
gcatcgatta ccgtctagat gatctaagtg ttagctggaa cacgcgttat attgatagcg   12360
tagtaactta tgatgtctct gaaaatggtg gctctcctga agatttatat ccaggccaca   12420
taggctcaat gacaactcat gacttgagcg ctacatacta catcaatgag aacttcatga   12480
ttaacggtgg tgtacgtaac ctatttgacg cacttccacc tggatacact aacgatgcgc   12540
tatatgatct agttggtcgc cgtgcattcc taggtattaa ggtaatgatg taattaatta   12600
ttacgcctct aactaataaa aatgcaatct cttcgtagag attgcatttt tttatgaaat   12660
ccaatcttaa actggttctc cgagcatctt acgccttaaa aaccccgccc ctcaatgtaa   12720
cgccaaagtt aattgcttac acgcacttac acaaacgaac aatttcatta acacgagaca   12780
cagctcacgc ttttattttt acccttgatt ttactacata aaattgcgtt ttagcgcaca   12840
agtgttctcc caagctggtc gtatctgtaa ttattcagtc ccaggtgatt gtattgaccc   12900
ataagctcag gtagtctgct ctgccattag ctaaacaata ttgacaaaat ggcgataaaa   12960
tgtggcttag cgctaagttc accgtaagtt ttatcggcat taagtcccaa cagattatta   13020
acggaaaccc gctaaactga tggcaaaaat aaatagtgaa cacttggatg aagctactat   13080
tacttcgaat aagtgtacgc aaacagagac tgaggctcgg catagaaatg ccactacaac   13140
acctgagatg cgccgattca tacaagagtc ggatctcagt gttagccaac tgtctaaaat   13200
attaaatatc agtgaagcta ccgtacgtaa gtggcgcaag cgtgactctg tcgaaaactg   13260
tcctaatacc ccgcaccatc tcaataccac gctaaccct ttgcaagaat atgtggttgt    13320
gggcctgcgt tatcaattga aaatgccatt agacagattg ctcaaagcaa cccaagagtt   13380
tatcaatcca aacgtgtcgc gctcaggttt agcaagatgt ttgaagcgtt atggcgtttc   13440
acgggtgagt gatatccaaa gcccacacgt accaatgcgc tactttaatc aaattccagt   13500
cactcaaggc agcgatgtgc aaacctacac cctgcactat gaaacgctgg caaaaacctt   13560
agccttacct agtaccgatg gtgacaatgt ggtgcaagtg gtgtctctca ccattccacc   13620
aaagttaacc gaagaagcac ccagttcaat tttgctcggc attgatcctc atagcgactg   13680
gatctatctc gacatatacc aagatggcaa tacacaagcc acgaatagat atatggctta   13740
tgtgctaaaa cacgggccat tccatttacg aaagttactc gtgcgtaact atcacacctt   13800
tttacagcgc tttcctggag cgacgcaaaa tcgccgcccc tctaaagata tgcctgaaac   13860
aatcaacaag acgcctgaaa cacaggcacc cagtggagac tcataatgag ccagacctct   13920
aaacctacaa actcagcaac tgagcaagca caagactcac aagctgactc tcgtttaaat   13980
aaacgactaa aagatatgcc aattgctatt gttggcatgg cgagtatttt tgcaaactct   14040
cgctatttga ataagttttg ggacttaatc agcgaaaaaa ttgatgcgat tactgaatta   14100
ccatcaactc actggcagcc tgaagaatat tacgacgcag ataaaaccgc agcagacaaa   14160
agctactgta aacgtggtgg ctttttgcca gatgtagact tcaacccaat ggagtttggc   14220
ctgccgccaa acattttgga actgaccgat tcatcgcaac tattatcact catcgttgct   14280
```

-continued

```
aaagaagtgt tggctgatgc taacttacct gagaattacg accgcgataa aattggtatc    14340
accttaggtg tcggcggtgg tcaaaaaatt agccacagcc taacagcgcg tctgcaatac    14400
ccagtattga agaaagtatt cgccaatagc ggcattagtg acaccgacag cgaaatgctt    14460
atcaagaaat tccaagacca atatgtacac tgggaagaaa actcgttccc aggttcactt    14520
ggtaacgtta ttgcgggccg tatcgccaac cgcttcgatt ttggcggcat gaactgtgtg    14580
gttgatgctg cctgtgctgg atcacttgct gctatgcgta tggcgctaac agagctaact    14640
gaaggtcgct ctgaaatgat gatcaccggt ggtgtgtgta ctgataactc accctctatg    14700
tatatgagct tttcaaaaac gcccgccttt accactaacg aaaccattca gccatttgat    14760
atcgactcaa aaggcatgat gattggtgaa ggtattggca tggtggcgct aaagcgtctt    14820
gaagatgcag agcgcgatgg cgaccgcatt tactctgtaa ttaaaggtgt gggtgcatca    14880
tctgacggta agtttaaatc aatctatgcc cctcgcccat caggccaagc taaagcactt    14940
aaccgtgcct atgatgacgc aggttttgcg ccgcatacct aggtctaat tgaagctcac    15000 ggaacaggta ctgcagcagg tgacgcggca gagtttgccg gcctttgctc agtatttgct    15060
gaaggcaacg ataccaagca acacattgcg ctaggttcag ttaaatcaca aattggtcat    15120
actaaatcaa ctgcaggtac agcaggttta attaaagctg ctcttgcttt gcatcacaag    15180
gtactgccgc cgaccattaa cgttagtcag ccaagcccta aacttgatat cgaaaactca    15240 ccgtttttatc taaacactga gactcgtcca tggttaccac gtgttgatgg tacgccgcgc    15300
cgcgcgggta ttagctcatt tggttttggt ggcactaact tccattttgt actagaagag    15360
tacaaccaag aacacagccg tactgatagc gaaaaagcta agtatcgtca acgccaagtg    15420
gcgcaaagct tccttgttag cgcaagcgat aaagcatcgc taattaacga gttaaacgta    15480
ctagcagcat ctgcaagcca agctgagttt atcctcaaag atgcagcagc aaactatggc    15540
gtacgtgagc ttgataaaaa tgcaccacgg atcggtttag ttgcaaacac agctgaagag    15600
ttagcaggcc taattaagca agcacttgcc aaactagcag ctagcgatga taacgcatgg    15660
cagctacctg gtggcactag ctaccgcgcc gctgcagtag aaggtaaagt tgccgcactg    15720
tttgctggcc aaggttcaca atatctcaat atgggccgtg accttacttg ttattaccca    15780
gagatgcgtc agcaatttgt aactgcagat aaagtatttg ccgcaaatga taaaacgccg    15840
ttatcgcaaa ctctgtatcc aaagcctgta tttaataaag atgaattaaa ggctcaagaa    15900
gccattttga ccaataccgc caatgcccaa agcgcaattg gtgcgatttc aatgggtcaa    15960
tacgatttgt ttactgcggc tggctttaat gccgacatgg ttgcaggcca tagctttggt    16020
gagctaagtg cactgtgtgc tgcaggtgtt atttcagctg atgactacta caagctggct    16080
tttgctcgtg gtgaggctat ggcaacaaaa gcaccggcta agacggcgt tgaagcagat    16140 gcaggagcaa tgtttgcaat cataaccaag agtgctgcag accttgaaac cgttgaagcc    16200
accatcgcta aatttgatgg ggtgaaagtc gctaactata cgcgccaac gcaatcagta    16260 attgcaggcc caacagcaac taccgctgat gcggctaaag cgctaactga gcttggttac    16320
aaagcgatta acctgccagt atcaggtgca ttccacactg aacttgttgg tcacgctcaa    16380
gcgccatttg ctaaagcgat tgacgcagcc aaatttacta aaacaagccg agcactttac    16440
tcaaatgcaa ctggcggact ttatgaaagc actgctgcaa agattaaagc ctcgtttaag    16500
aaacatatgc ttcaatcagt gcgctttact agccagctag aagccatgta caacgacggc    16560
gcccgtgtat ttgttgaatt tggtccaaag aacatcttac aaaaattagt tcaaggcacg    16620
```

-continued

```
cttgtcaaca ctgaaaatga agtttgcact atctctatca accctaatcc taaagttgat    16680
agtgatctgc agcttaagca agcagcaatg cagctagcgg ttactggtgt ggtactcagt    16740
gaaattgacc cataccaagc cgatattgcc gcaccagcga aaaagtcgcc aatgagcatt    16800
tcgcttaatg ctgctaacca tatcagcaaa gcaactcgcg ctaagatggc caagtcttta    16860
gagacaggta tcgtcacctc gcaaatagaa catgttattg aagaaaaaat cgttgaagtt    16920
gagaaactgg ttgaagtcga aaagatcgtc gaaaaagtgg ttgaagtaga aaagttgtt     16980 gaggttgaag ctcctgttaa ttcagtgcaa gccaatgcaa ttcaaacccg ttcagttgtc    17040
gctccagtaa tagagaacca agtcgtgtct aaaaacagta agccagcagt ccagagcatt    17100
agtggtgatg cactcagcaa cttttttgct gcacagcagc aaaccgcaca gttgcatcag    17160
cagttcttag ctattccgca gcaatatggt gagacgttca ctacgctgat gaccgagcaa    17220
gctaaactgg caagttctgg tgttgcaatt ccagagagtc tgcaacgctc aatggagcaa    17280
ttccaccaac tacaagcgca aacactacaa agccacaccc agttccttga gatgcaagcg    17340
ggtagcaaca ttgcagcgtt aaacctactc aatagcagcc aagcaactta cgctccagcc    17400
attcacaatg aagcgattca aagccaagtg gttcaaagcc aaactgcagt ccagccagta    17460
atttcaacac aagttaacca tgtgtcagag cagccaactc aagctccagc tccaaaagcg    17520
cagccagcac ctgtgacaac tgcagttcaa actgctccgg cacaagttgt tcgtcaagcc    17580
gcaccagttc aagccgctat tgaaccgatt aatacaagtg ttgcgactac aacgccttca    17640
gccttcagcg ccgaaacagc cctgagcgca acaaaagtcc aagccactat gcttgaagtg    17700
gttgctgaga aaaccggtta cccaactgaa atgctagagc ttgaaatgga tatggaagcc    17760
gatttaggca tcgattctat caagcgtgta gaaattcttg gcacagtaca agatgagcta    17820
ccgggtctac ctgagcttag ccctgaagat ctagctgagt gtcgaacgct aggcgaaatc    17880
gttgactata tgggcagtaa actgccggct gaaggctcta tgaattctca gctgtctaca    17940
ggttccgcag ctgcgactcc tgcagcgaat ggtctttctg cggagaaagt tcaagcgact    18000
atgatgtctg tggttgccga aaagactggc tacccaactg aaatgctaga gcttgaaatg    18060
gatatggaag ccgatttagg catagattct atcaagcgcg ttgaaattct tggcacagta    18120
caagatgagc taccgggtct acctgagctt agccctgaag atctagctga gtgtcgtact    18180
ctaggcgaaa tcgttgacta tatgaactct aaactcgctg acggctctaa gctgccggct    18240
gaaggctcta tgaattctca gctgtctaca agtgccgcag ctgcgactcc tgcagcgaat    18300
ggtctctctg cggagaaagt tcaagcgact atgatgtctg tggttgccga aaagactggc    18360
tacccaactg aaatgctaga acttgaaatg gatatggaag ctgaccttgg catcgattca    18420
atcaagcgcg ttgaaattct tggcacagta caagatgagc taccgggttt acctgagcta    18480
aatccagaag atttggcaga gtgtcgtact cttggcgaaa tcgtgactta tatgaactct    18540
aaactcgctg acggctctaa gctgccagct gaaggctcta tgcactatca gctgtctaca    18600
agtaccgctg ctgcgactcc tgtagcgaat ggtctctctg cagaaaaagt tcaagcgacc    18660
atgatgtctg tagttgcaga taaaactggc tacccaactg aaatgcttga acttgaaatg    18720
gatatggaag ccgatttagg tatcgattct atcaagcgcg ttgaaattct tggcacagta    18780
caagatgagc taccgggttt acctgagcta aatccagaag atctagcaga gtgtcgcacc    18840
ctaggcgaaa tcgttgacta tatgggcagt aaactgccgg ctgaaggctc tgctaataca    18900
agtgccgctg cgtctcttaa tgttagtgcc gttgcggcgc tcaagctgc tgcgactcct    18960 gtatcgaacg gtctctctgc agagaaagtg caaagcacta tgatgtcagt agttgcagaa    19020
```

-continued

```
aagaccggct acccaactga aatgctagaa cttggcatgg atatggaagc cgatttaggt    19080
atcgactcaa ttaaacgcgt tgagattctt ggcacagtac aagatgagct accgggtcta    19140
ccagagctta atcctgaaga tttagctgag tgccgtacgc tgggcgaaat cgttgactat    19200
atgaactcta agctggctga cggctctaag cttccagctg aaggctctgc taatacaagt    19260
gccactgctg cgactcctgc agtgaatggt ctttctgctg acaaggtaca ggcgactatg    19320
atgtctgtag ttgctgaaaa gaccggctac ccaactgaaa tgctagaact tggcatggat    19380
atggaagcag accttggtat tgattctatt aagcgcgttg aaattcttgg cacagtacaa    19440
gatgagctcc caggtttacc tgagcttaat cctgaagatc tcgctgagtg ccgcacgctt    19500
ggcgaaatcg ttagctatat gaactctcaa ctggctgatg gctctaaact ttctacaagt    19560
gcggctgaag gctctgctga tacaagtgct gcaaatgctg caaagccggc agcaatttcg    19620
gcagaaccaa gtgttgagct tcctcctcat agcgaggtag cgctaaaaaa gcttaatgcg    19680
gcgaacaagc tagaaaattg tttcgccgca gacgcaagtg ttgtgattaa cgatgatggt    19740
cacaacgcag gcgttttagc tgagaaactt attaaacaag gcctaaaagt agccgttgtg    19800
cgtttaccga aaggtcagcc tcaatcgcca cttttcaagcg atgttgctag ctttgagctt    19860
gcctcaagcc aagaatctga gcttgaagcc agtatcactg cagttatcgc gcagattgaa    19920
actcaggttg gcgctattgg tggctttatt cacttgcaac cagaagcgaa tacagaagag    19980
caaacggcag taaacctaga tgcgcaaagt tttactcacg ttagcaatgc gttcttgtgg    20040
gccaaattat tgcaaccaaa gctcgttgct ggagcagatg cgcgtcgctg ttttgtaaca    20100
gtaagccgta tcgacggtgg ctttggttac ctaaatactg acgccctaaa agatgctgag    20160
ctaaaccaag cagcattagc tggtttaact aaaaccttaa gccatgaatg gccacaagtg    20220
ttctgtcgcg cgctagatat tgcaacagat gttgatgcaa cccatcttgc tgatgcaatc    20280
accagtgaac tatttgatag ccaagctcag ctacctgaag tgggcttaag cttaattgat    20340
ggcaaagtta accgcgtaac tctagttgct gctgaagctg cagataaaac agcaaaagca    20400
gagcttaaca gcacagataa aatcttagtg actggtgggg caaaagggt gacatttgaa     20460 tgtgcactgg cattagcatc tcgcagccag tctcacttta tcttagctgg gcgcagtgaa    20520
ttacaagctt taccaagctg ggctgagggt aagcaaacta gcgagctaaa atcagctgca    20580
atcgcacata ttatttctac tggtcaaaag ccaacgccta agcaagttga agccgctgtg    20640
tggccagtgc aaagcagcat tgaaattaat gccgccctag ccgcctttaa caaagttggc    20700
gcctcagctg aatacgtcag catggatgtt accgatagcg ccgcaatcac agcagcactt    20760
aatggtcgct caaatgagat caccggtctt attcatggcg caggtgtact agccgacaag    20820
catattcaag acaagactct tgctgaactt gctaaagttt atggcactaa agtcaacggc    20880
ctaaaagcgc tgctcgcggc acttgagcca agcaaaatta aattacttgc tatgttctca    20940
tctgcagcag gtttttacgg taatatcggc caaagcgatt acgcgatgtc gaacgatatt    21000
cttaacaagg cagcgctgca gttcaccgct cgcaacccac aagctaaagt catgagcttt    21060
aactggggtc cttgggatgg cggcatggtt aacccagcgc ttaaaaagat gtttaccgag    21120
cgtggtgtgt acgttattcc actaaaaagca ggtgcagagc tatttgccac tcagctattg    21180
gctgaaactg gcgtgcagtt gctcattggt acgtcaatgc aaggtggcag cgacactaaa    21240
gcaactgaga ctgcttctgt aaaaaagctt aatgcgggtg aggtgctaag tgcatcgcat    21300
ccgcgtgctg gtgcacaaaa aacaccacta caagctgtca ctgcaacgcg tctgttaacc    21360
```

```
ccaagtgcca tggtcttcat tgaagatcac cgcattggcg gtaacagtgt gttgccaacg   21420
gtatgcgcca tcgactggat gcgtgaagcg gcaagcgaca tgcttggcgc tcaagttaag   21480
gtacttgatt acaagctatt aaaaggcatt gtatttgaga ctgatgagcc gcaagagtta   21540
acacttgagc taacgccaga cgattcagac gaagctacgc tacaagcatt aatcagctgt   21600
aatgggcgtc cgcaatacaa ggcgacgctt atcagtgata atgccgatat taagcaactt   21660
aacaagcagt ttgatttaag cgctaaggcg attaccacag caaaagagct ttatagcaac   21720
ggcaccttgt tccacggtcc gcgtctacaa gggatccaat ctgtagtgca gttcgatgat   21780
caaggcttaa ttgctaaagt cgctctgcct aaggttgaac ttagcgattg tggtgagttc   21840
ttgccgcaaa cccacatggg tggcagtcaa ccttttgctg aggacttgct attacaagct   21900
atgctggttt gggctcgcct taaaactggc tcggcaagtt tgccatcaag cattggtgag   21960
tttacctcat accaaccaat ggcctttggt gaaactggta ccatagagct tgaagtgatt   22020
aagcacaaca aacgctcact tgaagcgaat gttgcgctat atcgtgacaa cggcgagtta   22080
agtgccatgt ttaagtcagc taaaatcacc attagcaaaa gcttaaattc agcatttta   22140 cctgctgtct tagcaaacga cagtgaggcg aattagtgga acaaacgcct aaagctagtg   22200
cgatgccgct gcgcatcgca cttatcttac tgccaacacc gcagtttgaa gttaactctg   22260
tcgaccagtc agtattagcc agctatcaaa cactgcagcc tgagctaaat gccctgctta   22320
atagtgcgcc gacacctgaa atgctcagca tcactatctc agatgatagc gatgcaaaca   22380
gctttgagtc gcagctaaat gctgcgacca acgcaattaa caatggctat atcgtcaagc   22440
ttgctacggc aactcacgct ttgttaatgc tgcctgcatt aaaagcggcg caaatgcgga   22500
tccatcctca tgcgcagctt gccgctatgc agcaagctaa atcgacgcca atgagtcaag   22560
tatctggtga gctaaagctt ggcgctaatg cgctaagcct agctcagact aatgcgctgt   22620
ctcatgcttt aagccaagcc aagcgtaact taactgatgt cagcgtgaat gagtgttttg   22680
agaacctcaa aagtgaacag cagttcacag aggtttattc gcttattcag caacttgcta   22740
gccgcaccca tgtgagaaaa gaggttaatc aaggtgtgga acttggccct aaacaagcca   22800
aaagccacta ttggtttagc gaatttcacc aaaaccgtgt tgctgccatc aactttatta   22860
atggccaaca agcaaccagc tatgtgctta ctcaaggttc aggattgtta gctgcgaaat   22920
caatgctaaa ccagcaaaga ttaatgttta tcttgccggg taacagtcag caacaaataa   22980
ccgcatcaat aactcagtta atgcagcaat tagagcgttt gcaggtaact gaggttaatg   23040
agctttctct agaatgccaa ctagagctgc tcagcataat gtatgacaac ttagtcaacg   23100
cagacaaact cactactcgc gatagtaagc ccgcttatca ggctgtgatt caagcaagct   23160
ctgttagcgc tgcaaagcaa gagttaagcg cgcttaacga tgcactcaca gcgctgtttg   23220
ctgagcaaac aaacgccaca tcaacgaata aaggcttaat ccaatacaaa acaccggcgg   23280
gcagttactt aaccctaaca ccgcttggca gcaacaatga caacgcccaa gcgggtcttg   23340
cttttgtcta tccgggtgtg ggaacggttt acgccgatat gcttaatgag ctgcatcagt   23400
acttccctgc gctttacgcc aaacttgagc gtgaaggcga tttaaaggcg atgctacaag   23460
cagaagatat ctatcatctt gaccctaaac atgctgccca aatgagctta ggtgacttag   23520
ccattgctgg cgtggggagc agctacctgt taactcagct gctcaccgat gagtttaata   23580
ttaagcctaa ttttgcatta ggttactcaa tgggtgaagc atcaatgtgg gcaagcttag   23640
gcgtatggca aaacccgcat gcgctgatca gcaaaaccca aaccgacccg ctatttactt   23700
ctgctatttc cggcaaattg accgcggtta gacaagcttg gcagcttgat gataccgcag   23760
```

```
cggaaatcca gtggaatagc tttgtggtta aagtgaagc agcgccgatt gaagccttgc    23820
taaaagatta cccacacgct tacctcgcga ttattcaagg ggatacctgc gtaatcgctg    23880
gctgtgaaat ccaatgtaaa gcgctacttg cagcactggg taaacgcggt attgcagcta    23940
atcgtgtaac ggcgatgcat acgcagcctg cgatgcaaga gcatcaaaat gtgatggatt    24000
tttatctgca accgttaaaa gcagagcttc ctagtgaaat aagctttatc agcgccgctg    24060
atttaactgc caagcaaacg gtgagtgagc aagcacttag cagccaagtc gttgctcagt    24120
ctattgccga caccttctgc caaaccttgg actttaccgc gctagtacat cacgcccaac    24180
atcaaggcgc taagctgttt gttgaaattg gcgcggatag acaaaactgc accttgatag    24240
acaagattgt taaacaagat ggtgccagca gtgtacaaca tcaaccttgt tgcacagtgc    24300
ctatgaacgc aaaaggtagc caagatatta ccagcgtgat taaagcgctt ggccaattaa    24360
ttagccatca ggtgccatta tcggtgcaac catttattga tggactcaag cgcgagctaa    24420
cactttgcca attgaccagc caacagctgg cagcacatgc aaatgttgac agcaagtttg    24480
agtctaacca agaccattta cttcaagggg aagtctaatg tcattaccag acaatgcttc    24540
taaccacctt tctgccaacc agaaaggcgc atctcaggca agtaaaacca gtaagcaaag    24600
caaaatcgcc attgtcggtt tagccactct gtatccagac gctaaaaccc gcaagaatt    24660 ttggcagaat ttgctggata aacgcgactc tcgcagcacc ttaactaacg aaaaactcgg    24720
cgctaacagc caagattatc aaggtgtgca aggccaatct gaccgtttt attgtaataa    24780 aggcggctac attgagaact tcagctttaa tgctgcaggc tacaaattgc cggagcaaag    24840
cttaaatggc ttggacgaca gcttcctttg ggcgctcgat actagccgta acgcactaat    24900
tgatgctggt attgatatca acggcgctga tttaagccgc gcaggtgtag tcatgggcgc    24960
gctgtcgttc ccaactaccc gctcaaacga tctgttttg ccaatttatc acagcgccgt    25020
tgaaaaagcc ctgcaagata aactaggcgt aaaggcattt aagctaagcc caactaatgc    25080
tcataccgct cgcgcggcaa atgagagcag cctaaatgca gccaatggtg ccattgccca    25140
taacagctca aaagtggtgg ccgatgcact tggccttggc ggcgcacaac taagcctaga    25200
tgctgcctgt gctagttcgg tttactcatt aaagcttgcc tgcgattacc taagcactgg    25260
caaagccgat atcatgctag caggcgcagt atctggcgcg gatcctttct ttattaatat    25320
gggattctca atcttccacg cctacccaga ccatggtatc tcagtaccgt ttgatgccag    25380
cagtaaaggt ttgtttgctg gcgaaggcgc tggcgtatta gtgcttaaac gtcttgaaga    25440
tgccgagcgc gacaatgaca aaatctatgc ggttgttagc ggcgtaggtc tatcaaacga    25500
cggtaaaggc cagtttgtat taagccctaa tccaaaaggt caggtgaagg cctttgaacg    25560
tgcttatgct gccagtgaca ttgagccaaa agacattgaa gtgattgagt gccacgcaac    25620
aggcacaccg cttggcgata aaattgagct cacttcaatg gaaaccttct ttgaagacaa    25680
gctgcaaggc accgatgcac cgttaattgg ctcagctaag tctaacttag gccacctatt    25740
aactgcagcg catgcgggga tcatgaagat gatcttcgcc atgaaagaag gttacctgcc    25800
gccaagtatc aatattagtg atgctatcgc ttcgccgaaa aaactcttcg gtaaaccaac    25860
cctgcctagc atggttcaag gctggccaga taagccatcg aataatcatt ttggtgtaag    25920
aacccgtcac gcaggcgtat cggtatttgg ctttggtggc tgtaacgccc atctgttgct    25980
tgagtcatac aacggcaaag gaacagtaaa ggcagaagcc actcaagtac cgcgtcaagc    26040
tgagccgcta aaagtggttg gccttgcctc gcactttggg cctcttagca gcattaatgc    26100
```

```
actcaacaat gctgtgaccc aagatgggaa tggctttatc gaactgccga aaaagcgctg  26160
gaaaggcctt gaaaagcaca gtgaactgtt agctgaattt ggcttagcat ctgcgccaaa  26220
aggtgcttat gttgataact tcgagctgga cttttacgc tttaaactgc cgccaaacga  26280
agatgaccgt tgatctcac agcagctaat gctaatgcga gtaacagacg aagccattcg  26340
tgatgccaag cttgagccgg ggcaaaaagt agctgtatta gtggcaatgg aaactgagct  26400
tgaactgcat cagttccgcg gccgggttaa cttgcatact caattagcgc aaagtcttgc  26460
cgccatgggc gtgagtttat caacggatga ataccaagcg cttgaagcca tcgccatgga  26520
cagcgtgctt gatgctgcca agctcaatca gtacaccagc tttattggta atattatggc  26580
gtcacgcgtg gcgtcactat gggactttaa tggcccagcc ttcactattt cagcagcaga  26640
gcaatctgtg agccgctgta tcgatgtggc gcaaaacctc atcatggagg ataacctaga  26700
tgcggtggtg attgcagcgg tcgatctctc tggtagcttt gagcaagtca ttcttaaaaa  26760
tgccattgca cctgtagcca ttgagccaaa cctcgaagca agccttaatc caacatcagc  26820
aagctggaat gtcggtgaag gtgctggcgc ggtcgtgctt gttaaaaatg aagctacatc  26880
gggctgctca tacggccaaa ttgatgcact tggctttgct aaaactgccg aaacagcgtt  26940
ggctaccgac aagctactga gccaaactgc cacagacttt aataaggtta aagtgattga  27000
aactatggca gcgcctgcta gccaaattca attagcgcca atagttagct ctcaagtgac  27060
tcacactgct gcagagcagc gtgttggtca ctgctttgct gcagcgggta tggcaagcct  27120
attacacggc ttacttaact taaatactgt agcccaaacc aataaagcca attgcgcgct  27180
tatcaacaat atcagtgaaa accaattatc acagctgttg attagccaaa cagcgagcga  27240
acaacaagca ttaaccgcgc gtttaagcaa tgagcttaaa tccgatgcta acaccaact  27300 ggttaagcaa gtcaccttag gtggccgtga tatctaccag catattgttg ataccgct  27360 tgcaagcctt gaaagcatta ctcagaaatt ggcgcaagcg acagcatcga cagtggtcaa  27420
ccaagttaaa cctattaagg ccgctggctc agtcgaaatg gctaactcat tcgaaacgga  27480
aagctcagca gagccacaaa taacaattgc agcacaacag actgcaaaca ttggcgtcac  27540
cgctcaggca accaaacgtg aattaggtac cccaccaatg acaacaaata ccattgctaa  27600
tacagcaaat aatttagaca agactcttga gactgttgct ggcaatactg ttgctagcaa  27660
ggttggctct ggcgacatag tcaattttca acagaaccaa caattggctc aacaagctca  27720
cctcgccttt cttgaaagcc gcagtgcggg tatgaaggtg gctgatgctt tattgaagca  27780
acagctagct caagtaacag gccaaactat cgataatcag gccctcgata ctcaagccgt  27840
cgatactcaa acaagcgaga atgtagcgat tgccgcagaa tcaccagttc aagttacaac  27900
acctgttcaa gttacaacac ctgttcaaat cagtgttgtg gagttaaaac cagatcacgc  27960
taatgtgcca ccatacacgc cgccagtgcc tgcattaaag ccgtgtatct ggaactatgc  28020
cgatttagtt gagtacgcag aaggcgatat cgccaaggta tttggcagtg attatgccat  28080
tatcgacagc tactcgcgcc gcgtacgtct accgaccact gactacctgt tggtatcgcg  28140
cgtgaccaaa cttgatgcga ccatcaatca attgaagcca tgctcaatga ccactgagta  28200
cgacatccct gttgatgcgc cgtacttagt agacggacaa atcccttggg cggtagcagt  28260
agaatcaggc caatgtgact tgatgcttat tagctatctc ggtatcgact ttgagaacaa  28320
aggcgagcgg gtttatcgac tactcgattg taccctcacc ttcctaggcg acttgccacg  28380
tggcggagat accctacgtt acgacattaa gatcaataac tatgctcgca acggcgacac  28440
cctgctgttc ttcttctcgt atgagtgttt tgttggcgac aagatgatcc tcaagatgga  28500
```

```
tggcggctgc gctggcttct tcactgatga agagcttgcc gacggtaaag gcgtgattcg   28560
cacagaagaa gagattaaag ctcgcagcct agtgcaaaag caacgcttta atccgttact   28620
agattgtcct aaaacccaat ttagttatgg tgatattcat aagctattaa ctgctgatat   28680
tgagggttgt tttggcccaa gccacagtgg cgtccaccag ccgtcacttt gtttcgcatc   28740
tgaaaaattc ttgatgattg aacaagtcag caaggttgat cgcactggcg gtacttgggg   28800
acttggctta attgagggtc ataagcagct tgaagcagac cactggtact tcccatgtca   28860
tttcaagggc gaccaagtga tggctggctc gctaatggct gaaggttgtg gccagttatt   28920
gcagttctat atgctgcacc ttggtatgca tacccaaact aaaaatggtc gtttccaacc   28980
tcttgaaaac gcctcacagc aagtacgctg tcgcggtcaa gtgctgccac aatcaggcgt   29040
gctaacttac cgtatggaag tgactgaaat cggtttcagt ccacgcccat atgctaaagc   29100
taacatcgat atcttgctta atggcaaagc ggtagtggat ttccaaaacc tagggtgat   29160 gataaaagag gaagatgagt gtactcgtta tccacttttg actgaatcaa caacggctag   29220
cactgcacaa gtaaacgctc aaacaagtgc gaaaaggta tacaagccag catcagtcaa   29280
tgcgccatta atggcacaaa ttcctgatct gactaaagag ccaaacaagg gcgttattcc   29340
gatttcccat gttgaagcac caattacgcc agactacccg aaccgtgtac ctgatacagt   29400
gccattcacg ccgtatcaca tgtttgagtt tgctacaggc aatatcgaaa actgtttcgg   29460
gccagagttc tcaatctatc gcggcatgat cccaccacgt acaccatgcg gtgacttaca   29520
agtgaccaca cgtgtgattg aagttaacgg taagcgtggc gactttaaaa agccatcatc   29580
gtgtatcgct gaatatgaag tgcctgcaga tcgtggtat ttcgataaaa acagccacgg   29640
cgcagtgatg ccatattcaa ttttaatgga gatctcactg caacctaacg gctttatctc   29700
aggttacatg ggcacaaccc taggcttccc tggccttgag ctgttcttcc gtaacttaga   29760
cggtagcggt gagttactac gtgaagtaga tttacgtggt aaaaccatcc gtaacgactc   29820
acgtttatta tcaacagtga tggccggcac taacatcatc caaagcttta gcttcgagct   29880
aagcactgac ggtgagcctt tctatcgcgg cactgcggta tttggctatt ttaaaggtga   29940
cgcacttaaa gatcagctag gcctagataa cggtaaagtc actcagccat ggcatgtagc   30000
taacggcgtt gctgcaagca ctaaggtgaa cctgcttgat aagagctgcc gtcactttaa   30060
tgcgccagct aaccagccac actatcgtct agccggtggt cagctgaact ttatcgacag   30120
tgttgaaatt gttgataatg cggcaccgga aggtttaggt tacttgtatg ccgagcgcac   30180
cattgaccca agtgattggt tcttccagtt ccacttccac caagatccgg ttatgccagg   30240
ctccttaggt gttgaagcaa ttattgaaac catgcaagct tacgctatta gtaaagactt   30300
gggcgcagat ttcaaaaatc ctaagtttgg tcagattta tcgaacatca agtggaagta   30360
tcgcggtcaa atcaatccgc tgaacaagca gatgtctatg gatgtcagca ttacttcaat   30420
caaagatgaa gacggtaaga aagtcatcac aggtaatgcc agcttgagta aagatggtct   30480
gcgcatatac gaggtcttcg atatagctat cagcatcgaa gaatctgtat aaatcggagt   30540
gactgtctgg ctattttact caatttctgt gtcaaaagtg ctcacctata ttcataggct   30600
gcgcgctttt ttctggaaat tgagcaaaag tatctgcgtc ctaactcgat ttataagaat   30660
ggtttaattg aaaagaacaa cagctaagag ccgcaagctc aatataaata attaagggtc   30720
ttacaaataa tgaatcctac agcaactaac gaaatgcttt ctccgtggcc atgggctgtg   30780
acagagtcaa atatcagttt tgacgtgcaa gtgatggaac aacaacttaa agattttagc   30840
```

```
cgggcatgtt acgtggtcaa tcatgccgac cacggctttg gtattgcgca aactgccgat   30900
atcgtgactg aacaagcggc aaacagcaca gatttacctg ttagtgcttt tactcctgca   30960
ttaggtaccg aaagcctagg cgacaataat ttccgccgcg ttcacggcgt taaatacgct   31020
tattacgcag gcgctatggc aaacggtatt tcatctgaag agctagtgat tgccctaggt   31080
caagctggca ttttgtgtgg ttcgtttgga gcagccggtc ttattccaag tcgcgttgaa   31140
gcggcaatta accgtattca agcagcgctg ccaaatggcc cttatatgtt taaccttatc   31200
catagtccta gcgagccagc attagagcgt ggcagcgtag agctatttt aaagcataag   31260 gtacgcaccg ttgaagcatc agctttctta ggtctaacac cacaaatcgt ctattaccgt   31320
gcagcaggat tgagccgaga cgcacaaggt aaagttgtgg ttggtaacaa ggttatcgct   31380
aaagtaagtc gcaccgaagt ggctgaaaag tttatgatgc cagcgcccgc aaaaatgcta   31440
caaaaactag ttgatgacgg ttcaattacc gctgagcaaa tggagctggc gcaacttgta   31500
cctatggctg acgacatcac tgcagaggcc gattcaggtg gccatactga taaccgtcca   31560
ttagtaacat tgctgccaac cattttagcg ctgaaagaag aaattcaagc taaataccaa   31620
tacgacactc ctattcgtgt cggttgtggt ggcggtgtgg gtacgcctga tgcagcgctg   31680
gcaacgttta acatgggcgc ggcgtatatt gttaccggct ctatcaacca agcttgtgtt   31740
gaagcgggcg caagtgatca cactcgtaaa ttacttgcca ccactgaaat ggccgatgtg   31800
actatggcac cagctgcaga tatgttcgag atgggcgtaa aactgcaggt ggttaagcgc   31860
ggcacgctat tcccaatgcg cgctaacaag ctatatgaga tctacacccg ttacgattca   31920
atcgaagcga tcccattaga cgagcgtgaa aagcttgaga aacaagtatt ccgctcaagc   31980
ctagatgaaa tatgggcagg tacagtggcg cactttaacg agcgcgaccc taagcaaatc   32040
gaacgcgcag agggtaaccc taagcgtaaa atggcattga ttttccgttg gtacttaggt   32100 cttttctagtc gctggtcaaa ctcaggcgaa gtgggtcgtg aaatggatta tcaaatttgg   32160
gctggccctg ctctcggtgc atttaaccaa tgggcaaaag gcagttactt agataactat   32220
caagaccgaa atgccgtcga tttggcaaag cacttaatgt acggcgcggc ttacttaaat   32280
cgtattaact cgctaacggc tcaaggcgtt aaagtgccag cacagttact tcgctggaag   32340
ccaaaccaaa gaatggccta atacacttac aaagcaccag tctaaaaagc cactaatctt   32400
gattagtggc tttttttatt gtggtcaata tgaggctatt tagcctgtaa gcctgaaaat   32460
atcagcactc tgactttaca agcaaattat aattaaggca gggctctact catttatact   32520
gctagcaaac aagcaagttg cccagtaaaa caacaaggta cctgatttat atcgtcataa   32580
aagttggcta gagattcgtt attgatcttt actgattaga gtcgctctgt ttggaaaaag   32640
gtttctcgtt atcatcaaaa tacactctca aacctttaat caattacaac ttaggctttc   32700
tgcgggcatt tttatcttat ttgccacagc tgtatttgcc tttaggtttt gggtgcaact   32760
accattaatt gaggcctcat tagttaaatt atctgagcaa gagctcacct ctttaaatta   32820
cgcttttcag caaatgagaa agccactaca aaccattaat tacgactatg cggtgtggga   32880
cagaacctac agctatatga aatcaaactc agcgagcgct aaaaggtact atgaaaaaca   32940
tgagtaccca gatgatacgt tcaagagttt aaaagtcgac ggagtattta tattcaaccg   33000
tacaaatcag ccagtttta gtaaaggttt taatcataga aatgatatac cgctggtctt   33060
tgaattaact gactttaaac aacatccaca aaacatcgca ttatctccac aaaccaaaca   33120
ggcacaccca ccggcaagta agccgttaga ctcccctgat gatgtgcctt ctacccatgg   33180
ggttatcgcc acacgatacg gtccagcaat ttatagctct accagcattt taaaatctga   33240
```

```
tcgtagcggc tcccaacttg gttatttagt cttcattagg ttaattgatg aatggttcat    33300
cgctgagcta tcgcaataca ctgccgcagg tgttgaaatc gctatggctg atgccgcaga    33360
cgcacaatta gcgagattag gcgcaaacac taagcttaat aaagtaaccg ctacatccga    33420
acggttaata actaatgtcg atggtaagcc tctgttgaag ttagtgcttt accataccaa    33480
taaccaaccg ccgccgatgc tagattacag tataataatt ctattagttg agatgtcatt    33540
tttactgatc ctcgcttatt tcctttactc ctacttctta gtcaggccag ttagaaagct    33600
ggcttcagat attaaaaaaa tggataaaag tcgtgaaatt aaaaagctaa ggtatcacta    33660
ccctattact gagctagtca aagttgcgac tcacttcaac gccctaatgg ggacgattca    33720
ggaacaaact aaacagctta atgaacaagt ttttattgat aaattaacca atattcccaa    33780
tcgtcgcgct tttgagcagc gacttgaaac ctattgccaa ctgctagccc ggcaacaaat    33840
tggctttact ctcatcattg ccgatgtgga tcattttaaa gagtacaacg atactcttgg    33900
gcaccttgct ggggatgaag cattaataaa agtggcacaa acactatcgc aacagtttta    33960
ccgtgcagaa gatatttgtg cccgttttgg tggtgaagaa tttattatgt tatttcgaga    34020
catacctgat gagcccttgc agagaaagct cgatgcgatg ctgcactctt ttgcagagct    34080
caacctacct catccaaact catcaaccgc taattacgtt actgtgagcc ttggggtttg    34140
cacagttgtt gctgttgatg attttgaatt taaaagtgag tcgcatatta ttggcagtca    34200
ggctgcatta atcgcagata aggcgcttta tcatgctaaa gcctgtggtc gtaaccagtt    34260
gtcaaaaact actattactg ttgatgagat tgagcaatta gaagcaaata aaatcggtca    34320
tcaagcctaa actcgttcga gtactttccc ctaagtcaga gctatttgcc acttcaagat    34380
gtggctacaa ggcttactct ttcaaaacct gcatcaatag aacacagcaa aatacaataa    34440
tttaagtcaa tttagcctat taaacagagt taatgacagc tcatggtcgc aacttattag    34500
ctatttctag caatataaaa acttatccat tagtagtaac caataaaaaa actaatatat    34560
aaaactattt aatcattatt ttacagatga ttagctacca cccaccttaa gctggctata    34620
ttcgcactag taaaaataaa cattagatcg ggttcagatc aatttacgag tctcgtataa    34680
aatgtacaat aattcactta atttaatact gcatattttt acaagtagag agcggtgatg    34740
aaacaaaata cgaaaggctt tacattaatt gaattagtca tcgtgattat tattctcggt    34800
atacttgctg ctgtggcact gccgaaattc atcaatgttc aagatgacgc taggatctct    34860
gcgatgagcg gtcagttttc atcatttgaa agtgccgtaa aactatacca tagcggttgg    34920
ttagccaaag gctacaacac tgcggttgaa aagctctcag gctttggcca aggtaatgtt    34980
gcatcaagtg acacaggttt tccgtactca acatcaggca cgagtactga tgtgcataaa    35040
gcttgtggtg aactatggca tggcattacc gatacagact tcacaattgg tgcggttagt    35100
gatggcgatc taatgactgc agatgtcgat attgcttaca cctatcgtgg tgatatgtgt    35160
atctatcgcg atctgtattt tattcagcgc tcattaccta ctaaggtgat gaactacaaa    35220
tttaaaactg gtgaaataga aattattgat gctttctaca accctgacgg ctcaactggt    35280
caattaccat aaatttggcg cttatctaag ttgtacttgc tctgaccgac acaaataatg    35340
tcgtttctca gcatatatca aaatacacag caaaaatttg gggttagcta tatagctaac    35400
cccaaatcat atctaacttt acactgcatc taattccaaa cagtatccag ccaaaagcct    35460
aaactattgt tgactcagcg ctaaaatatg cgatgcaaca aacaagtctt ggatcgcaat    35520
acctgagcta tcaaaaatgg tcacctcatc agcactttga cgtcctgttg cggactcgtt    35580
```

-continued

```
tatcacctga ccaatctcaa ttatcggcgt atttctgcta tgttgaaact caccaataac   35640
aatagattga gaagcaaagt cgcaaaacaa gcgagcatga ctatataggt cagttggcaa   35700
ctcttgctta cccactttat cagcgcccat tgcagaaata tgcgttcctg cttgtaccca   35760
ctgcgcttca aataaaggcg cttgagctgt ggttgctgtg ataataatat ctgcttgttc   35820
acaagcagct tgtgcatcac aagcttcggc attaatgcct ttttctaata aacgcttaac   35880
caagttttca gttttgctag cactacggcc aactaccaat accttagtta atgaacgaac   35940
cttgctcact gctagcactt catattcagc ctgatgaccg gtaccaaaaa cagttaatac   36000
cgtagcatct tctctcgcga ggtaactcac tgctactgca tcggcagcac cagtgcggta   36060
agcattaacg gtagtggcag caatcaccgn ctgcaacata ccggttaatg gatcgagtaa   36120
aaatacgtta gtgccgtggc atggtaaacc atgtttatgg ttatcaggcc aatagctgcc   36180
tgttttccag ccgacaaggt ttggcgttga agccgacttt aatgagaaca tttcattaag   36240
gttcgcgccc tgtgcattaa ctaccgggaa caaggttgct ttatcatcta cggcagcgac   36300
aaacgcttct ttaacagcga tataagccag ctcatgggag atgagctttg atgtttgcgc   36360
ttcagttaaa tagatcatat taccacccct gcactcgatt ccagatctca tagccaccat   36420
tatcaccatc agtatcaaat acatggtact gagcgtgcat tgaagctgtt gcacaggcgt   36480
ggttcggcaa aatatgtaga cgactaccta ccgggaactg cgctaaatca ataacgccgc   36540
catcaactgc ttcaataatg ccgtgctctt gattaacagt tataacctgt agacctgata   36600
acacgtgacc gctgtcgtca cactaaac cataaccaca atcttttggc tgctctgcag   36660
tacctctatc acccgaaaga gccatccaac ccgcatcaat gaaaatccag tttttatcag   36720
gattatgacc aataacactg gtcactaccg ttgcggcaat atcagttaac tgacacacgt   36780
ttagccctgc catgactaaa tcgaagaagg tgtacacacc cgctctaacc tcggtgatcc   36840
catcaaggtt ttgatagctt tgcgctgttg gtgttgaacc aatactaacg atgtcacatt   36900
gcatacccgc tgcgcgaatg cgtcagcagc ttgtacagcc gctgcaactt cattttgcgc   36960
cgcatcaatt aattgctgtt tttcaaaaca ttgatatgac tcaccagcgt gagtnagtac   37020
gccgtgaaaa ctcgctgcgc cagacgttag tatctgagca atttcaatca acttatcggc   37080
ttccggtgga ataccaccac gatggccatc acaatcaatt tcaattaatg ctggtatttg   37140
gcagtcataa gaaccacaga aatgatttag ctgatgcgct tgctcaacac tatcaagtaa   37200
aactcttgca ttaataccctt ggtccaacat tttagcaata cgcggcaact taccatcggc   37260
aatacctact gcataaataa tgtctgtgta acctttagat gctaaggcct cggcctcttt   37320
taccgttgat acagtgactg gtgagttttt agtgggtaat aaaaactcgg ctgcttcaag   37380
tgatcttaac gttttaaaat gcggtcttag gtttgcacct aatccttcaa ttttttggcg   37440
tagttgactg aggttattaa taaatactgg cttatttaca tataaaaacg gtgtatcaat   37500
tgcttgatac tgactttgct gagtcgtgga aagtatttga gtagatggca tctttaatat   37560
cctagttcat caatcaatct aacaagtttg atgcctagcc acagtggctt gtattcatga   37620
tgctttggaa aatgcttata ttcaaagtat ttgaaagaca tcaaacttct tgtttaatgc   37680
tcagtatcca ccagcacgca tttattttat attaactatt atcaagatat agattaggtt   37740
caaaccaaat gattagtact gaagatctac gttttatcag cgtaatcgcc agtcatcgca   37800
ccttagctga tgccgctaga acactaaata tcacgccacc atcagtgaca ttaaggttgc   37860
agcatattga aaagaaacta tcgattagcc tgatc                             37895
```

```
<210> SEQ ID NO 2
<211> LENGTH: 654
<212> TYPE: PRT
<213> ORGANISM: Shewanella putrefaciens

<400> SEQUENCE: 2

Met Lys Gln Thr Leu Met Ala Ile Ser Ile Met Ser Leu Phe Ser Phe
 1               5                  10                  15

Asn Ala Leu Ala Ala Gln His Glu His Asp His Ile Thr Val Asp Tyr
             20                  25                  30

Glu Gly Lys Ala Ala Thr Glu His Thr Ile Ala His Asn Gln Ala Val
         35                  40                  45

Ala Lys Thr Leu Asn Phe Ala Asp Thr Arg Ala Phe Glu Gln Ser Ser
     50                  55                  60

Lys Asn Leu Val Ala Lys Phe Asp Lys Ala Thr Ala Asp Ile Leu Arg
 65                  70                  75                  80

Ala Glu Phe Ala Phe Ile Ser Asp Glu Ile Pro Asp Ser Val Asn Pro
                 85                  90                  95

Ser Leu Tyr Arg Gln Ala Gln Leu Asn Met Val Pro Asn Gly Tyr Lys
            100                 105                 110

Val Ser Asp Gly Ile Tyr Gln Val Arg Gly Thr Asp Leu Ser Asn Leu
        115                 120                 125

Thr Leu Ile Arg Ser Asp Asn Gly Trp Ile Ala Tyr Asp Val Leu Leu
    130                 135                 140

Thr Lys Glu Ala Ala Lys Ala Ser Leu Gln Phe Ala Leu Lys Asn Leu
145                 150                 155                 160

Pro Lys Asp Gly Asp Pro Val Val Ala Met Ile Tyr Ser His Ser His
                165                 170                 175

Ala Asp His Phe Gly Gly Ala Arg Gly Val Gln Glu Met Phe Pro Asp
            180                 185                 190

Val Lys Val Tyr Gly Ser Asp Asn Ile Thr Lys Glu Ile Val Asp Glu
        195                 200                 205

Asn Val Leu Ala Gly Asn Ala Met Ser Arg Arg Ala Ala Tyr Gln Tyr
    210                 215                 220

Gly Ala Thr Leu Gly Lys His Asp His Gly Ile Val Asp Ala Ala Leu
225                 230                 235                 240

Gly Lys Gly Leu Ser Lys Gly Glu Ile Thr Tyr Val Ala Pro Asp Tyr
                245                 250                 255

Thr Leu Asn Ser Glu Gly Lys Trp Glu Thr Leu Thr Ile Asp Gly Leu
            260                 265                 270

Glu Met Val Phe Met Asp Ala Ser Gly Thr Glu Ala Glu Ser Glu Met
        275                 280                 285

Ile Thr Tyr Ile Pro Ser Lys Lys Ala Leu Trp Thr Ala Glu Leu Thr
    290                 295                 300

Tyr Gln Gly Met His Asn Ile Tyr Thr Leu Arg Gly Ala Lys Val Arg
305                 310                 315                 320

Asp Ala Leu Lys Trp Ser Lys Asp Ile Asn Glu Met Ile Asn Ala Phe
                325                 330                 335

Gly Gln Asp Val Glu Val Leu Phe Ala Ser His Ser Ala Pro Val Trp
            340                 345                 350

Gly Asn Gln Ala Ile Asn Asp Phe Leu Arg Leu Gln Arg Asp Asn Tyr
        355                 360                 365

Gly Leu Val His Asn Gln Thr Leu Arg Leu Ala Asn Asp Gly Val Gly
    370                 375                 380
```

-continued

```
Ile Gln Asp Ile Gly Asp Ala Ile Gln Asp Thr Ile Pro Glu Ser Ile
385                 390                 395                 400

Tyr Lys Thr Trp His Thr Asn Gly Tyr His Gly Thr Tyr Ser His Asn
            405                 410                 415

Ala Lys Ala Val Tyr Asn Lys Tyr Leu Gly Tyr Phe Asp Met Asn Pro
        420                 425                 430

Ala Asn Leu Asn Pro Leu Pro Thr Lys Gln Ser Ala Lys Phe Val
    435                 440                 445

Glu Tyr Met Gly Gly Ala Asp Ala Ala Ile Lys Arg Ala Lys Asp Asp
450                 455                 460

Tyr Ala Gln Gly Glu Tyr Arg Phe Val Ala Thr Ala Leu Asn Lys Val
465                 470                 475                 480

Val Met Ala Glu Pro Glu Asn Asp Ser Ala Arg Gln Leu Leu Ala Asp
            485                 490                 495

Thr Tyr Glu Gln Leu Gly Tyr Gln Ala Glu Gly Ala Gly Trp Arg Asn
        500                 505                 510

Ile Tyr Leu Thr Gly Ala Gln Glu Leu Arg Val Gly Ile Gln Ala Gly
    515                 520                 525

Ala Pro Lys Thr Ala Ser Ala Asp Val Ile Ser Glu Met Asp Met Pro
530                 535                 540

Thr Leu Phe Asp Phe Leu Ala Val Lys Ile Asp Ser Gln Gln Ala Ala
545                 550                 555                 560

Lys His Gly Leu Val Lys Met Asn Val Ile Thr Pro Asp Thr Lys Asp
            565                 570                 575

Ile Leu Tyr Ile Glu Leu Ser Asn Gly Asn Leu Ser Asn Ala Val Val
        580                 585                 590

Asp Lys Glu Gln Leu Met Val Asn Lys Ala Asp Val Asn Arg Ile Leu
    595                 600                 605

Leu Gly Gln Val Thr Leu Lys Ala Leu Leu Ala Ser Gly Asp Ala Lys
610                 615                 620

Leu Thr Gly Asp Lys Thr Ala Phe Ser Lys Ile Ala Asp Ser Met Val
625                 630                 635                 640

Glu Phe Thr Pro Asp Phe Glu Ile Val Pro Thr Pro Val Lys
            645                 650

<210> SEQ ID NO 3
<211> LENGTH: 277
<212> TYPE: PRT
<213> ORGANISM: Shewanella putrefaciens

<400> SEQUENCE: 3

Ser Thr Lys Ala Ser Ala Arg Val Val Ala Lys Phe Asn Val Glu Glu
1               5                   10                  15

Ala Ala Ile Ser Ile Gln Gln Cys Gln Gly Ile Ser Leu Ala Phe Arg
            20                  25                  30

Tyr Ser Asp Asp Leu His Gly Leu Leu Cys His Trp Asn Asp Ala Ala
        35                  40                  45

Asn Met Gln Gln Glu Lys Ala Glu Ile Leu Gly Leu Gly Ser Lys Gln
    50                  55                  60

Pro Glu Ala Asn Pro Lys Asn Ser Ser Glu Leu Leu Ala Leu Gly
65                  70                  75                  80

Ile Asp Gln Lys Leu Leu Val Gln Arg Gln Asn Leu Gln His Glu Val
            85                  90                  95

Lys His Asp Ala Ile Ala Asp Ser Ile Asp Val Cys His Ser Leu Ser
        100                 105                 110
```

```
Lys Pro Ala Asn Val Gly Leu Phe Thr Glu Ser Leu Ala Ser Phe Asp
        115                 120                 125

Phe Ala Phe Ser Lys Leu Ser Leu Ala Leu Gly Leu Gly Lys Ala Lys
    130                 135                 140

Ile Tyr Ser Glu Lys Leu Ala Trp Leu Asp Phe Phe Arg Asp Arg Gln
145                 150                 155                 160

Leu Ala Glu Pro Leu Ala Leu Leu Ala Arg Lys Glu Ser Glu Ser Phe
                165                 170                 175

Tyr His Ser Leu Ile Ser His Ile Asn Thr Ser Asn Arg Cys Arg Glu
            180                 185                 190

Ile Asp Val Gly Phe Glu Ile Ser Ala Ser Asp Thr Glu Glu Lys Ser
        195                 200                 205

Ala Gln Ser Ala Gly Lys Asn Asp Ala Thr Cys Ile Gly Val Leu Leu
    210                 215                 220

Trp Asp Gly Ser His Ser Val Asn Phe His Val Gly Thr Gln Ala Phe
225                 230                 235                 240

Gln Ala Asp Ser Leu Arg Pro Lys Gly Lys Asp Gly Tyr Glu Phe Arg
                245                 250                 255

Trp Glu Asn Pro Arg Ile Glu Ser His Gln Ser Leu Leu Ala Arg Leu
            260                 265                 270

Tyr Gly Arg Val Met
            275

<210> SEQ ID NO 4
<211> LENGTH: 1480
<212> TYPE: DNA
<213> ORGANISM: Shewanella putrefaciens

<400> SEQUENCE: 4
gctagtctta gctgasrthr ysaasragct cgaacaacag ctttaaaatt cacttcttct      60
gctgcaatac ttatttgctg acactgacca atactcagtg caaaacgata actatcatca     120
agatggaaar gvavaaaysh asnvaggaaa asrgngncys gngysraaha rgtyrsrasa     180
shscccagta acaatgcca attatcagca gcgttcattt gctgttcttt agcctcaatc     240
aaacctaaac cagacttttg tggctcagcg ttaggcttat taggycyshs trasnasaaa     300
aasnmtgngn gysaaggygy srysgnrgaa asnrysasns raactcgact ctagtaaagc     360
aagaccaata tcttgttta acaaaacctg tcgctgatta agttgatgct caaccttgtg     420
atccgcaata gcatcggaaa tsrsrgaagy asgnysvagn arggnasngn hsgvayshsa     480
saaaaassra tcaacacaat ggctcaagct tttaggtgca ttaactccaa gaaagtttc     540
gctcagtgca gagaagtcaa acgcaaaaga ttttagcgat aatgccagca svacyshssr     600
srysraaasn vagyhthrgs raasrhasha ahsryssraa ccaagtcctt tcgctttaat     660
gtaagactcc ttgagcgccc acaaatcaaa aaagcggtct cgctgcaagg cctctggtaa     720
cgctaacaag gctcgctttt gygyysaays tyrsrgysaa trashharga sarggnaagr     780
aaaaargysg ctgattcaga gaaataatga ctaagaatag agtggatatt ggtgctgtta     840
cggcaacgct caatgtcgac gccaaactca atactagcag agtcagtttc srgsrhtyrh     900
ssrsrhsasn thrsrasnar gcysarggas vagyhgsraa srasthrgct ccttgcttgc     960
ctgactggcg cctttattat cagcagtgca aatgcctact aatagccaat ctccactatg    1020
actcacatta aagtggaccc cggtttgagy ssraagnsra agyysasnas aathrcysgy    1080
vatrasgysr hssrvaasnh hsvagythrg ngcaaattgc gcatcactca atctaggctt    1140
```

```
accctttgtcg ccatattcaa agcgccattc attggggcgt atttcactat gttgtgacaa    1200
taaagcgcgc aaahgnaaas srargrysgy ysasgytyrg hargtrgasn rarggsrhsg    1260
nsraaargaa tagcctctta ccattaaacc ttgagtttta gcttcttgtt taatgtagcg    1320
attaacctta attaactcat cttcaggcag ccatgactta accaactcty rgyargvamt    1380
gygnthrysa aggnystyra rgasnvaysg asgrtrsrys vagtgtagtc tggttatcgc    1440
actcttgtat tgttaacgga cagaagtata aggaaatcaa                         1480
```

<210> SEQ ID NO 5
<211> LENGTH: 970
<212> TYPE: PRT
<213> ORGANISM: Shewanella putrefaciens

<400> SEQUENCE: 5

```
Met Ser Met Phe Leu Asn Ser Lys Leu Ser Arg Ser Val Lys Leu Ala
 1               5                  10                  15

Ile Ser Ala Gly Leu Thr Ala Ser Leu Ala Met Pro Val Phe Ala Glu
            20                  25                  30

Glu Thr Ala Ala Glu Glu Gln Ile Glu Arg Val Ala Val Thr Gly Ser
        35                  40                  45

Arg Ile Ala Lys Ala Glu Leu Thr Gln Pro Ala Pro Val Val Ser Leu
    50                  55                  60

Ser Ala Glu Glu Leu Thr Lys Phe Gly Asn Gln Asp Leu Gly Ser Val
65                  70                  75                  80

Leu Ala Glu Leu Pro Ala Ile Gly Ala Thr Asn Thr Ile Ile Gly Asn
                85                  90                  95

Asn Asn Ser Asn Ser Ser Ala Gly Val Ser Ser Ala Asp Leu Arg Arg
            100                 105                 110

Leu Gly Ala Asn Arg Thr Leu Val Leu Val Asn Gly Lys Arg Tyr Val
        115                 120                 125

Ala Gly Gln Pro Gly Ser Ala Glu Val Asp Leu Ser Thr Ile Pro Thr
    130                 135                 140

Ser Met Ile Ser Arg Val Glu Ile Val Thr Gly Gly Ala Ser Ala Ile
145                 150                 155                 160

Tyr Gly Ser Asp Ala Val Ser Gly Val Ile Asn Val Ile Leu Lys Glu
                165                 170                 175

Asp Phe Glu Gly Phe Glu Phe Asn Ala Arg Thr Ser Gly Ser Thr Glu
            180                 185                 190

Ser Val Gly Thr Gln Glu His Ser Phe Asp Ile Leu Gly Gly Ala Asn
        195                 200                 205

Val Ala Asp Gly Arg Gly Asn Val Thr Phe Tyr Ala Gly Tyr Glu Arg
    210                 215                 220

Thr Lys Glu Val Met Ala Thr Asp Ile Arg Gln Phe Asp Ala Trp Gly
225                 230                 235                 240

Thr Ile Lys Asn Glu Ala Asp Gly Gly Glu Asp Asp Gly Ile Pro Asp
                245                 250                 255

Arg Leu Arg Val Pro Arg Val Tyr Ser Glu Met Ile Asn Ala Thr Gly
            260                 265                 270

Val Ile Asn Ala Phe Gly Gly Ile Gly Arg Ser Thr Phe Asp Ser
        275                 280                 285

Asn Gly Asn Pro Ile Ala Gln Gln Glu Arg Asp Gly Thr Asn Ser Phe
    290                 295                 300

Ala Phe Gly Ser Phe Pro Asn Gly Cys Asp Thr Cys Phe Asn Thr Glu
```

-continued

```
305                 310                 315                 320
Ala Tyr Glu Asn Tyr Ile Pro Gly Val Glu Arg Ile Asn Val Gly Ser
                325                 330                 335
Ser Phe Asn Phe Asp Phe Thr Asp Asn Ile Gln Phe Tyr Thr Asp Phe
                340                 345                 350
Arg Tyr Val Lys Ser Asp Ile Gln Gln Gln Phe Gln Pro Ser Phe Arg
                355                 360                 365
Phe Gly Asn Ile Asn Ile Asn Val Glu Asp Asn Ala Phe Leu Asn Asp
                370                 375                 380
Asp Leu Arg Gln Gln Met Leu Asp Ala Gly Gln Thr Asn Ala Ser Phe
385                 390                 395                 400
Ala Lys Phe Phe Asp Glu Leu Gly Asn Arg Ser Ala Glu Asn Lys Arg
                405                 410                 415
Glu Leu Phe Arg Tyr Val Gly Phe Lys Gly Gly Phe Asp Ile Ser
                420                 425                 430
Glu Thr Ile Phe Asp Tyr Asp Leu Tyr Tyr Val Tyr Gly Glu Thr Asn
                435                 440                 445
Asn Arg Arg Lys Thr Leu Asn Asp Leu Ile Pro Asp Asn Phe Val Ala
                450                 455                 460
Ala Val Asp Ser Val Ile Asp Pro Asp Thr Gly Leu Ala Ala Cys Arg
465                 470                 475                 480
Ser Gln Val Ala Ser Ala Gln Gly Asp Asp Tyr Thr Asp Pro Ala Ser
                485                 490                 495
Val Asn Gly Ser Asp Cys Val Ala Tyr Asn Pro Phe Gly Met Gly Gln
                500                 505                 510
Ala Ser Ala Glu Ala Arg Asp Trp Val Ser Ala Asp Val Thr Arg Glu
                515                 520                 525
Asp Lys Ile Thr Gln Gln Val Ile Gly Gly Thr Leu Gly Thr Asp Ser
                530                 535                 540
Glu Glu Leu Phe Glu Leu Gln Gly Gly Ala Ile Ala Met Val Val Gly
545                 550                 555                 560
Phe Glu Tyr Arg Glu Glu Thr Ser Gly Ser Thr Thr Asp Glu Phe Thr
                565                 570                 575
Lys Ala Gly Phe Leu Thr Ser Ala Ala Thr Pro Asp Ser Tyr Gly Glu
                580                 585                 590
Tyr Asp Val Thr Glu Tyr Phe Val Glu Val Asn Ile Pro Val Leu Lys
                595                 600                 605
Glu Leu Pro Phe Ala His Glu Leu Ser Phe Asp Gly Ala Tyr Arg Asn
                610                 615                 620
Ala Asp Tyr Ser His Ala Gly Lys Thr Glu Ala Trp Lys Ala Gly Met
625                 630                 635                 640
Phe Tyr Ser Pro Leu Glu Gln Leu Ala Leu Arg Gly Thr Val Gly Glu
                645                 650                 655
Ala Val Arg Ala Pro Asn Ile Ala Glu Ala Phe Ser Pro Arg Ser Pro
                660                 665                 670
Gly Phe Gly Arg Val Ser Asp Pro Cys Asp Ala Asp Asn Ile Asn Asp
                675                 680                 685
Asp Pro Asp Arg Val Ser Asn Cys Ala Ala Leu Gly Ile Pro Pro Gly
                690                 695                 700
Phe Gln Ala Asn Asp Asn Val Ser Val Asp Thr Leu Ser Gly Gly Asn
705                 710                 715                 720
Pro Asp Leu Lys Pro Glu Thr Ser Thr Ser Phe Thr Gly Gly Leu Val
                725                 730                 735
```

```
Trp Thr Pro Thr Phe Ala Asp Asn Leu Ser Phe Thr Val Asp Tyr Tyr
            740                 745                 750

Asp Ile Gln Ile Glu Asp Ala Ile Leu Ser Val Ala Thr Gln Thr Val
            755                 760                 765

Ala Asp Asn Cys Val Asp Ser Thr Gly Gly Pro Asp Thr Asp Phe Cys
            770                 775                 780

Ser Gln Val Asp Arg Asn Pro Thr Thr Tyr Asp Ile Glu Leu Val Arg
785                 790                 795                 800

Ser Gly Tyr Leu Asn Ala Ala Ala Leu Asn Thr Lys Gly Ile Glu Phe
                805                 810                 815

Gln Ala Ala Tyr Ser Leu Asp Leu Glu Ser Phe Asn Ala Pro Gly Glu
                820                 825                 830

Leu Arg Phe Asn Leu Leu Gly Asn Gln Leu Leu Glu Leu Glu Arg Leu
                835                 840                 845

Glu Phe Gln Asn Arg Pro Asp Glu Ile Asn Asp Glu Lys Gly Glu Val
            850                 855                 860

Gly Asp Pro Glu Leu Gln Phe Arg Leu Gly Ile Asp Tyr Arg Leu Asp
865                 870                 875                 880

Asp Leu Ser Val Ser Trp Asn Thr Arg Tyr Ile Asp Ser Val Val Thr
                885                 890                 895

Tyr Asp Val Ser Glu Asn Gly Gly Ser Pro Glu Asp Leu Tyr Pro Gly
                900                 905                 910

His Ile Gly Ser Met Thr Thr His Asp Leu Ser Ala Thr Tyr Tyr Ile
                915                 920                 925

Asn Glu Asn Phe Met Ile Asn Gly Gly Val Arg Asn Leu Phe Asp Ala
            930                 935                 940

Leu Pro Pro Gly Tyr Thr Asn Asp Ala Leu Tyr Asp Leu Val Gly Arg
945                 950                 955                 960

Arg Ala Phe Leu Gly Ile Lys Val Met Met
                965                 970

<210> SEQ ID NO 6
<211> LENGTH: 288
<212> TYPE: PRT
<213> ORGANISM: Shewanella putrefaciens

<400> SEQUENCE: 6

Met Ala Lys Ile Asn Ser Glu His Leu Asp Glu Ala Thr Ile Thr Ser
1               5                   10                  15

Asn Lys Cys Thr Gln Thr Glu Thr Glu Ala Arg His Arg Asn Ala Thr
            20                  25                  30

Thr Thr Pro Glu Met Arg Arg Phe Ile Gln Glu Ser Asp Leu Ser Val
            35                  40                  45

Ser Gln Leu Ser Lys Ile Leu Asn Ile Ser Glu Ala Thr Val Arg Lys
    50                  55                  60

Trp Arg Lys Arg Asp Ser Val Glu Asn Cys Pro Asn Thr Pro His His
65                  70                  75                  80

Leu Asn Thr Thr Leu Thr Pro Leu Gln Glu Tyr Val Val Gly Leu
                85                  90                  95

Arg Tyr Gln Leu Lys Met Pro Leu Asp Arg Leu Leu Lys Ala Thr Gln
                100                 105                 110

Glu Phe Ile Asn Pro Asn Val Ser Arg Ser Gly Leu Ala Arg Cys Leu
            115                 120                 125

Lys Arg Tyr Gly Val Ser Arg Val Ser Asp Ile Gln Ser Pro His Val
```

```
                130                 135                 140
Pro Met Arg Tyr Phe Asn Gln Ile Pro Val Thr Gln Gly Ser Asp Val
145                 150                 155                 160

Gln Thr Tyr Thr Leu His Tyr Glu Thr Leu Ala Lys Thr Leu Ala Leu
                165                 170                 175

Pro Ser Thr Asp Gly Asp Asn Val Val Gln Val Val Ser Leu Thr Ile
            180                 185                 190

Pro Pro Lys Leu Thr Glu Glu Ala Pro Ser Ser Ile Leu Leu Gly Ile
        195                 200                 205

Asp Pro His Ser Asp Trp Ile Tyr Leu Asp Ile Tyr Gln Asp Gly Asn
    210                 215                 220

Thr Gln Ala Thr Asn Arg Tyr Met Ala Tyr Val Leu Lys His Gly Pro
225                 230                 235                 240

Phe His Leu Arg Lys Leu Leu Val Arg Asn Tyr His Thr Phe Leu Gln
                245                 250                 255

Arg Phe Pro Gly Ala Thr Gln Asn Arg Arg Pro Ser Lys Asp Met Pro
            260                 265                 270

Glu Thr Ile Asn Lys Thr Pro Glu Thr Gln Ala Pro Ser Gly Asp Ser
        275                 280                 285

<210> SEQ ID NO 7
<211> LENGTH: 2756
<212> TYPE: PRT
<213> ORGANISM: Shewanella putrefaciens

<400> SEQUENCE: 7

Met Ser Gln Thr Ser Lys Pro Thr Asn Ser Ala Thr Glu Gln Ala Gln
1               5                   10                  15

Asp Ser Gln Ala Asp Ser Arg Leu Asn Lys Arg Leu Lys Asp Met Pro
            20                  25                  30

Ile Ala Ile Val Gly Met Ala Ser Ile Phe Ala Asn Ser Arg Tyr Leu
        35                  40                  45

Asn Lys Phe Trp Asp Leu Ile Ser Glu Lys Ile Asp Ala Ile Thr Glu
    50                  55                  60

Leu Pro Ser Thr His Trp Gln Pro Glu Glu Tyr Tyr Asp Ala Asp Lys
65                  70                  75                  80

Thr Ala Ala Asp Lys Ser Tyr Cys Lys Arg Gly Gly Phe Leu Pro Asp
                85                  90                  95

Val Asp Phe Asn Pro Met Glu Phe Gly Leu Pro Pro Asn Ile Leu Glu
            100                 105                 110

Leu Thr Asp Ser Ser Gln Leu Leu Ser Leu Ile Val Ala Lys Glu Val
        115                 120                 125

Leu Ala Asp Ala Asn Leu Pro Glu Asn Tyr Asp Arg Asp Lys Ile Gly
    130                 135                 140

Ile Thr Leu Gly Val Gly Gly Gln Lys Ile Ser His Ser Leu Thr
145                 150                 155                 160

Ala Arg Leu Gln Tyr Pro Val Leu Lys Lys Val Phe Ala Asn Ser Gly
                165                 170                 175

Ile Ser Asp Thr Asp Ser Glu Met Leu Ile Lys Lys Phe Gln Asp Gln
            180                 185                 190

Tyr Val His Trp Glu Glu Asn Ser Phe Pro Gly Ser Leu Gly Asn Val
        195                 200                 205

Ile Ala Gly Arg Ile Ala Asn Arg Phe Asp Phe Gly Gly Met Asn Cys
    210                 215                 220
```

-continued

Val Val Asp Ala Ala Cys Ala Gly Ser Leu Ala Ala Met Arg Met Ala
225                 230                 235                 240

Leu Thr Glu Leu Thr Glu Gly Arg Ser Glu Met Met Ile Thr Gly Gly
            245                 250                 255

Val Cys Thr Asp Asn Ser Pro Ser Met Tyr Met Ser Phe Ser Lys Thr
            260                 265                 270

Pro Ala Phe Thr Thr Asn Glu Thr Ile Gln Pro Phe Asp Ile Asp Ser
            275                 280                 285

Lys Gly Met Met Ile Gly Glu Gly Ile Gly Met Val Ala Leu Lys Arg
290                 295                 300

Leu Glu Asp Ala Glu Arg Asp Gly Asp Arg Ile Tyr Ser Val Ile Lys
305                 310                 315                 320

Gly Val Gly Ala Ser Ser Asp Gly Lys Phe Lys Ser Ile Tyr Ala Pro
            325                 330                 335

Arg Pro Ser Gly Gln Ala Lys Ala Leu Asn Arg Ala Tyr Asp Asp Ala
            340                 345                 350

Gly Phe Ala Pro His Thr Leu Gly Leu Ile Glu Ala His Gly Thr Gly
            355                 360                 365

Thr Ala Ala Gly Asp Ala Ala Glu Phe Ala Gly Leu Cys Ser Val Phe
370                 375                 380

Ala Glu Gly Asn Asp Thr Lys Gln His Ile Ala Leu Gly Ser Val Lys
385                 390                 395                 400

Ser Gln Ile Gly His Thr Lys Ser Thr Ala Gly Thr Ala Gly Leu Ile
            405                 410                 415

Lys Ala Ala Leu Ala Leu His His Lys Val Leu Pro Pro Thr Ile Asn
            420                 425                 430

Val Ser Gln Pro Ser Pro Lys Leu Asp Ile Glu Asn Ser Pro Phe Tyr
            435                 440                 445

Leu Asn Thr Glu Thr Arg Pro Trp Leu Pro Arg Val Asp Gly Thr Pro
450                 455                 460

Arg Arg Ala Gly Ile Ser Ser Phe Gly Phe Gly Gly Thr Asn Phe His
465                 470                 475                 480

Phe Val Leu Glu Glu Tyr Asn Gln Glu His Ser Arg Thr Asp Ser Glu
            485                 490                 495

Lys Ala Lys Tyr Arg Gln Arg Gln Val Ala Gln Ser Phe Leu Val Ser
            500                 505                 510

Ala Ser Asp Lys Ala Ser Leu Ile Asn Glu Leu Asn Val Leu Ala Ala
            515                 520                 525

Ser Ala Ser Gln Ala Glu Phe Ile Leu Lys Asp Ala Ala Asn Tyr
530                 535                 540

Gly Val Arg Glu Leu Asp Lys Asn Ala Pro Arg Ile Gly Leu Val Ala
545                 550                 555                 560

Asn Thr Ala Glu Glu Leu Ala Gly Leu Ile Lys Gln Ala Leu Ala Lys
            565                 570                 575

Leu Ala Ala Ser Asp Asp Asn Ala Trp Gln Leu Pro Gly Gly Thr Ser
            580                 585                 590

Tyr Arg Ala Ala Ala Val Glu Gly Lys Val Ala Ala Leu Phe Ala Gly
            595                 600                 605

Gln Gly Ser Gln Tyr Leu Asn Met Gly Arg Asp Leu Thr Cys Tyr Tyr
            610                 615                 620

Pro Glu Met Arg Gln Gln Phe Val Thr Ala Asp Lys Val Phe Ala Ala
625                 630                 635                 640

Asn Asp Lys Thr Pro Leu Ser Gln Thr Leu Tyr Pro Lys Pro Val Phe

-continued

Asn Lys Asp Glu Leu Lys Ala Gln Glu Ala Ile Leu Thr Asn Thr Ala
        645                 650                 655
                660                 665                 670
Asn Ala Gln Ser Ala Ile Gly Ala Ile Ser Met Gly Gln Tyr Asp Leu
                675                 680                 685
Phe Thr Ala Ala Gly Phe Asn Ala Asp Met Val Ala Gly His Ser Phe
            690                 695                 700
Gly Glu Leu Ser Ala Leu Cys Ala Ala Gly Val Ile Ser Ala Asp Asp
705                 710                 715                 720
Tyr Tyr Lys Leu Ala Phe Ala Arg Gly Glu Ala Met Ala Thr Lys Ala
                    725                 730                 735
Pro Ala Lys Asp Gly Val Glu Ala Asp Ala Gly Ala Met Phe Ala Ile
                740                 745                 750
Ile Thr Lys Ser Ala Ala Asp Leu Glu Thr Val Glu Ala Thr Ile Ala
                755                 760                 765
Lys Phe Asp Gly Val Lys Val Ala Asn Tyr Asn Ala Pro Thr Gln Ser
        770                 775                 780
Val Ile Ala Gly Pro Thr Ala Thr Thr Ala Asp Ala Ala Lys Ala Leu
785                 790                 795                 800
Thr Glu Leu Gly Tyr Lys Ala Ile Asn Leu Pro Val Ser Gly Ala Phe
                    805                 810                 815
His Thr Glu Leu Val Gly His Ala Gln Ala Pro Phe Ala Lys Ala Ile
                820                 825                 830
Asp Ala Ala Lys Phe Thr Lys Thr Ser Arg Ala Leu Tyr Ser Asn Ala
            835                 840                 845
Thr Gly Gly Leu Tyr Glu Ser Thr Ala Ala Lys Ile Lys Ala Ser Phe
        850                 855                 860
Lys Lys His Met Leu Gln Ser Val Arg Phe Thr Ser Gln Leu Glu Ala
865                 870                 875                 880
Met Tyr Asn Asp Gly Ala Arg Val Phe Val Glu Phe Gly Pro Lys Asn
                    885                 890                 895
Ile Leu Gln Lys Leu Val Gln Gly Thr Leu Val Asn Thr Glu Asn Glu
                900                 905                 910
Val Cys Thr Ile Ser Ile Asn Pro Asn Pro Lys Val Asp Ser Asp Leu
            915                 920                 925
Gln Leu Lys Gln Ala Ala Met Gln Leu Ala Val Thr Gly Val Val Leu
        930                 935                 940
Ser Glu Ile Asp Pro Tyr Gln Ala Asp Ile Ala Ala Pro Ala Lys Lys
945                 950                 955                 960
Ser Pro Met Ser Ile Ser Leu Asn Ala Ala Asn His Ile Ser Lys Ala
                    965                 970                 975
Thr Arg Ala Lys Met Ala Lys Ser Leu Glu Thr Gly Ile Val Thr Ser
                980                 985                 990
Gln Ile Glu His Val Ile Glu Glu Lys Ile Val Glu Val Glu Lys Leu
            995                 1000                1005
Val Glu Val Glu Lys Ile Val Glu Lys Val Val Glu Val Glu Lys Val
    1010                1015                1020
Val Glu Val Glu Ala Pro Val Asn Ser Val Gln Ala Asn Ala Ile Gln
1025                1030                1035                1040
Thr Arg Ser Val Val Ala Pro Val Ile Glu Asn Gln Val Val Ser Lys
                1045                1050                1055
Asn Ser Lys Pro Ala Val Gln Ser Ile Ser Gly Asp Ala Leu Ser Asn
            1060                1065                1070

-continued

```
Phe Phe Ala Ala Gln Gln Gln Thr Ala Gln Leu His Gln Gln Phe Leu
        1075                1080                1085

Ala Ile Pro Gln Gln Tyr Gly Glu Thr Phe Thr Thr Leu Met Thr Glu
    1090                1095                1100

Gln Ala Lys Leu Ala Ser Ser Gly Val Ala Ile Pro Glu Ser Leu Gln
1105                1110                1115                1120

Arg Ser Met Glu Gln Phe His Gln Leu Gln Ala Gln Thr Leu Gln Ser
            1125                1130                1135

His Thr Gln Phe Leu Glu Met Gln Ala Gly Ser Asn Ile Ala Ala Leu
        1140                1145                1150

Asn Leu Leu Asn Ser Ser Gln Ala Thr Tyr Ala Pro Ala Ile His Asn
    1155                1160                1165

Glu Ala Ile Gln Ser Gln Val Val Gln Ser Gln Thr Ala Val Gln Pro
1170                1175                1180

Val Ile Ser Thr Gln Val Asn His Val Ser Glu Gln Pro Thr Gln Ala
1185                1190                1195                1200

Pro Ala Pro Lys Ala Gln Pro Ala Pro Val Thr Thr Ala Val Gln Thr
            1205                1210                1215

Ala Pro Ala Gln Val Val Arg Gln Ala Ala Pro Val Gln Ala Ala Ile
        1220                1225                1230

Glu Pro Ile Asn Thr Ser Val Ala Thr Thr Thr Pro Ser Ala Phe Ser
    1235                1240                1245

Ala Glu Thr Ala Leu Ser Ala Thr Lys Val Gln Ala Thr Met Leu Glu
1250                1255                1260

Val Val Ala Glu Lys Thr Gly Tyr Pro Thr Glu Met Leu Glu Leu Glu
1265                1270                1275                1280

Met Asp Met Glu Ala Asp Leu Gly Ile Asp Ser Ile Lys Arg Val Glu
            1285                1290                1295

Ile Leu Gly Thr Val Gln Asp Glu Leu Pro Gly Leu Pro Glu Leu Ser
        1300                1305                1310

Pro Glu Asp Leu Ala Glu Cys Arg Thr Leu Gly Glu Ile Val Asp Tyr
    1315                1320                1325

Met Gly Ser Lys Leu Pro Ala Glu Gly Ser Met Asn Ser Gln Leu Ser
1330                1335                1340

Thr Gly Ser Ala Ala Ala Thr Pro Ala Ala Asn Gly Leu Ser Ala Glu
1345                1350                1355                1360

Lys Val Gln Ala Thr Met Met Ser Val Val Ala Glu Lys Thr Gly Tyr
            1365                1370                1375

Pro Thr Glu Met Leu Glu Leu Glu Met Asp Met Glu Ala Asp Leu Gly
        1380                1385                1390

Ile Asp Ser Ile Lys Arg Val Glu Ile Leu Gly Thr Val Gln Asp Glu
    1395                1400                1405

Leu Pro Gly Leu Pro Glu Leu Ser Pro Glu Asp Leu Ala Glu Cys Arg
1410                1415                1420

Thr Leu Gly Glu Ile Val Asp Tyr Met Asn Ser Lys Leu Ala Asp Gly
1425                1430                1435                1440

Ser Lys Leu Pro Ala Glu Gly Ser Met Asn Ser Gln Leu Ser Thr Ser
            1445                1450                1455

Ala Ala Ala Ala Thr Pro Ala Ala Asn Gly Leu Ser Ala Glu Lys Val
        1460                1465                1470

Gln Ala Thr Met Met Ser Val Val Ala Glu Lys Thr Gly Tyr Pro Thr
    1475                1480                1485
```

```
Glu Met Leu Glu Leu Glu Met Asp Met Glu Ala Asp Leu Gly Ile Asp
    1490                1495                1500

Ser Ile Lys Arg Val Glu Ile Leu Gly Thr Val Gln Asp Glu Leu Pro
1505            1510                1515                1520

Gly Leu Pro Glu Leu Asn Pro Glu Asp Leu Ala Glu Cys Arg Thr Leu
                1525                1530                1535

Gly Glu Ile Val Thr Tyr Met Asn Ser Lys Leu Ala Asp Gly Ser Lys
                1540                1545                1550

Leu Pro Ala Glu Gly Ser Met His Tyr Gln Leu Ser Thr Ser Thr Ala
            1555                1560                1565

Ala Ala Thr Pro Val Ala Asn Gly Leu Ser Ala Glu Lys Val Gln Ala
            1570                1575                1580

Thr Met Met Ser Val Val Ala Asp Lys Thr Gly Tyr Pro Thr Glu Met
1585                1590                1595                1600

Leu Glu Leu Glu Met Asp Met Glu Ala Asp Leu Gly Ile Asp Ser Ile
                1605                1610                1615

Lys Arg Val Glu Ile Leu Gly Thr Val Gln Asp Glu Leu Pro Gly Leu
                1620                1625                1630

Pro Glu Leu Asn Pro Glu Asp Leu Ala Glu Cys Arg Thr Leu Gly Glu
            1635                1640                1645

Ile Val Asp Tyr Met Gly Ser Lys Leu Pro Ala Glu Gly Ser Ala Asn
1650                1655                1660

Thr Ser Ala Ala Ala Ser Leu Asn Val Ser Ala Val Ala Ala Pro Gln
1665                1670                1675                1680

Ala Ala Ala Thr Pro Val Ser Asn Gly Leu Ser Ala Glu Lys Val Gln
                1685                1690                1695

Ser Thr Met Met Ser Val Val Ala Glu Lys Thr Gly Tyr Pro Thr Glu
            1700                1705                1710

Met Leu Glu Leu Gly Met Asp Met Glu Ala Asp Leu Gly Ile Asp Ser
            1715                1720                1725

Ile Lys Arg Val Glu Ile Leu Gly Thr Val Gln Asp Glu Leu Pro Gly
        1730                1735                1740

Leu Pro Glu Leu Asn Pro Glu Asp Leu Ala Glu Cys Arg Thr Leu Gly
1745                1750                1755                1760

Glu Ile Val Asp Tyr Met Asn Ser Lys Leu Ala Asp Gly Ser Lys Leu
                1765                1770                1775

Pro Ala Glu Gly Ser Ala Asn Thr Ser Ala Thr Ala Ala Thr Pro Ala
            1780                1785                1790

Val Asn Gly Leu Ser Ala Asp Lys Val Gln Ala Thr Met Met Ser Val
            1795                1800                1805

Val Ala Glu Lys Thr Gly Tyr Pro Thr Glu Met Leu Glu Leu Gly Met
    1810                1815                1820

Asp Met Glu Ala Asp Leu Gly Ile Asp Ser Ile Lys Arg Val Glu Ile
1825                1830                1835                1840

Leu Gly Thr Val Gln Asp Glu Leu Pro Gly Leu Pro Glu Leu Asn Pro
                1845                1850                1855

Glu Asp Leu Ala Glu Cys Arg Thr Leu Gly Glu Ile Val Ser Tyr Met
            1860                1865                1870

Asn Ser Gln Leu Ala Asp Gly Ser Lys Leu Ser Thr Ser Ala Ala Glu
            1875                1880                1885

Gly Ser Ala Asp Thr Ser Ala Ala Asn Ala Ala Lys Pro Ala Ala Ile
    1890                1895                1900

Ser Ala Glu Pro Ser Val Glu Leu Pro Pro His Ser Glu Val Ala Leu
```

-continued

```
            1905                1910                1915                1920
Lys Lys Leu Asn Ala Ala Asn Lys Leu Glu Asn Cys Phe Ala Ala Asp
            1925                1930                1935

Ala Ser Val Val Ile Asn Asp Asp Gly His Asn Ala Gly Val Leu Ala
            1940                1945                1950

Glu Lys Leu Ile Lys Gln Gly Leu Lys Val Ala Val Arg Leu Pro
            1955                1960                1965

Lys Gly Gln Pro Gln Ser Pro Leu Ser Ser Asp Val Ala Ser Phe Glu
            1970                1975                1980

Leu Ala Ser Ser Gln Glu Ser Glu Leu Glu Ala Ser Ile Thr Ala Val
1985                1990                1995                2000

Ile Ala Gln Ile Glu Thr Gln Val Gly Ala Ile Gly Gly Phe Ile His
            2005                2010                2015

Leu Gln Pro Glu Ala Asn Thr Glu Glu Gln Thr Ala Val Asn Leu Asp
            2020                2025                2030

Ala Gln Ser Phe Thr His Val Ser Asn Ala Phe Leu Trp Ala Lys Leu
            2035                2040                2045

Leu Gln Pro Lys Leu Val Ala Gly Ala Asp Ala Arg Arg Cys Phe Val
            2050                2055                2060

Thr Val Ser Arg Ile Asp Gly Gly Phe Gly Tyr Leu Asn Thr Asp Ala
2065                2070                2075                2080

Leu Lys Asp Ala Glu Leu Asn Gln Ala Ala Leu Ala Gly Leu Thr Lys
            2085                2090                2095

Thr Leu Ser His Glu Trp Pro Gln Val Phe Cys Arg Ala Leu Asp Ile
            2100                2105                2110

Ala Thr Asp Val Asp Ala Thr His Leu Ala Asp Ala Ile Thr Ser Glu
            2115                2120                2125

Leu Phe Asp Ser Gln Ala Gln Leu Pro Glu Val Gly Leu Ser Leu Ile
            2130                2135                2140

Asp Gly Lys Val Asn Arg Val Thr Leu Val Ala Ala Glu Ala Ala Asp
2145                2150                2155                2160

Lys Thr Ala Lys Ala Glu Leu Asn Ser Thr Asp Lys Ile Leu Val Thr
            2165                2170                2175

Gly Gly Ala Lys Gly Val Thr Phe Glu Cys Ala Leu Ala Leu Ala Ser
            2180                2185                2190

Arg Ser Gln Ser His Phe Ile Leu Ala Gly Arg Ser Glu Leu Gln Ala
            2195                2200                2205

Leu Pro Ser Trp Ala Glu Gly Lys Gln Thr Ser Glu Leu Lys Ser Ala
            2210                2215                2220

Ala Ile Ala His Ile Ile Ser Thr Gly Gln Lys Pro Thr Pro Lys Gln
2225                2230                2235                2240

Val Glu Ala Ala Val Trp Pro Val Gln Ser Ser Ile Glu Ile Asn Ala
            2245                2250                2255

Ala Leu Ala Ala Phe Asn Lys Val Gly Ala Ser Ala Glu Tyr Val Ser
            2260                2265                2270

Met Asp Val Thr Asp Ser Ala Ala Ile Thr Ala Ala Leu Asn Gly Arg
            2275                2280                2285

Ser Asn Glu Ile Thr Gly Leu Ile His Gly Ala Gly Val Leu Ala Asp
            2290                2295                2300

Lys His Ile Gln Asp Lys Thr Leu Ala Glu Leu Ala Lys Val Tyr Gly
2305                2310                2315                2320

Thr Lys Val Asn Gly Leu Lys Ala Leu Leu Ala Ala Leu Glu Pro Ser
            2325                2330                2335
```

```
Lys Ile Lys Leu Leu Ala Met Phe Ser Ser Ala Ala Gly Phe Tyr Gly
        2340                2345                2350

Asn Ile Gly Gln Ser Asp Tyr Ala Met Ser Asn Asp Ile Leu Asn Lys
        2355                2360                2365

Ala Ala Leu Gln Phe Thr Ala Arg Asn Pro Gln Ala Lys Val Met Ser
        2370                2375                2380

Phe Asn Trp Gly Pro Trp Asp Gly Gly Met Val Asn Pro Ala Leu Lys
2385                2390                2395                2400

Lys Met Phe Thr Glu Arg Gly Val Tyr Val Ile Pro Leu Lys Ala Gly
        2405                2410                2415

Ala Glu Leu Phe Ala Thr Gln Leu Leu Ala Glu Thr Gly Val Gln Leu
        2420                2425                2430

Leu Ile Gly Thr Ser Met Gln Gly Gly Ser Asp Thr Lys Ala Thr Glu
        2435                2440                2445

Thr Ala Ser Val Lys Lys Leu Asn Ala Gly Glu Val Leu Ser Ala Ser
        2450                2455                2460

His Pro Arg Ala Gly Ala Gln Lys Thr Pro Leu Gln Ala Val Thr Ala
2465                2470                2475                2480

Thr Arg Leu Leu Thr Pro Ser Ala Met Val Phe Ile Glu Asp His Arg
        2485                2490                2495

Ile Gly Gly Asn Ser Val Leu Pro Thr Val Cys Ala Ile Asp Trp Met
        2500                2505                2510

Arg Glu Ala Ala Ser Asp Met Leu Gly Ala Gln Val Lys Val Leu Asp
        2515                2520                2525

Tyr Lys Leu Leu Lys Gly Ile Val Phe Glu Thr Asp Glu Pro Gln Glu
        2530                2535                2540

Leu Thr Leu Glu Leu Thr Pro Asp Asp Ser Asp Glu Ala Thr Leu Gln
2545                2550                2555                2560

Ala Leu Ile Ser Cys Asn Gly Arg Pro Gln Tyr Lys Ala Thr Leu Ile
        2565                2570                2575

Ser Asp Asn Ala Asp Ile Lys Gln Leu Asn Lys Gln Phe Asp Leu Ser
        2580                2585                2590

Ala Lys Ala Ile Thr Thr Ala Lys Glu Leu Tyr Ser Asn Gly Thr Leu
        2595                2600                2605

Phe His Gly Pro Arg Leu Gln Gly Ile Gln Ser Val Val Gln Phe Asp
2610                2615                2620

Asp Gln Gly Leu Ile Ala Lys Val Ala Leu Pro Lys Val Glu Leu Ser
2625                2630                2635                2640

Asp Cys Gly Glu Phe Leu Pro Gln Thr His Met Gly Gly Ser Gln Pro
        2645                2650                2655

Phe Ala Glu Asp Leu Leu Leu Gln Ala Met Leu Val Trp Ala Arg Leu
        2660                2665                2670

Lys Thr Gly Ser Ala Ser Leu Pro Ser Ser Ile Gly Glu Phe Thr Ser
        2675                2680                2685

Tyr Gln Pro Met Ala Phe Gly Glu Thr Gly Thr Ile Glu Leu Glu Val
        2690                2695                2700

Ile Lys His Asn Lys Arg Ser Leu Glu Ala Asn Val Ala Leu Tyr Arg
2705                2710                2715                2720

Asp Asn Gly Glu Leu Ser Ala Met Phe Lys Ser Ala Lys Ile Thr Ile
        2725                2730                2735

Ser Lys Ser Leu Asn Ser Ala Phe Leu Pro Ala Val Leu Ala Asn Asp
        2740                2745                2750
```

```
Ser Glu Ala Asn
        2755

<210> SEQ ID NO 8
<211> LENGTH: 771
<212> TYPE: PRT
<213> ORGANISM: Shewanella putrefaciens

<400> SEQUENCE: 8

Met Pro Leu Arg Ile Ala Leu Ile Leu Leu Pro Thr Pro Gln Phe Glu
 1               5                  10                  15

Val Asn Ser Val Asp Gln Ser Val Leu Ala Ser Tyr Gln Thr Leu Gln
                20                  25                  30

Pro Glu Leu Asn Ala Leu Leu Asn Ser Ala Pro Thr Pro Glu Met Leu
            35                  40                  45

Ser Ile Thr Ile Ser Asp Asp Ser Asp Ala Asn Ser Phe Glu Ser Gln
        50                  55                  60

Leu Asn Ala Ala Thr Asn Ala Ile Asn Asn Gly Tyr Ile Val Lys Leu
 65                  70                  75                  80

Ala Thr Ala Thr His Ala Leu Leu Met Leu Pro Ala Leu Lys Ala Ala
                85                  90                  95

Gln Met Arg Ile His Pro His Ala Gln Leu Ala Ala Met Gln Gln Ala
            100                 105                 110

Lys Ser Thr Pro Met Ser Gln Val Ser Gly Glu Leu Lys Leu Gly Ala
        115                 120                 125

Asn Ala Leu Ser Leu Ala Gln Thr Asn Ala Leu Ser His Ala Leu Ser
    130                 135                 140

Gln Ala Lys Arg Asn Leu Thr Asp Val Ser Val Asn Glu Cys Phe Glu
145                 150                 155                 160

Asn Leu Lys Ser Glu Gln Gln Phe Thr Glu Val Tyr Ser Leu Ile Gln
                165                 170                 175

Gln Leu Ala Ser Arg Thr His Val Arg Lys Glu Val Asn Gln Gly Val
            180                 185                 190

Glu Leu Gly Pro Lys Gln Ala Lys Ser His Tyr Trp Phe Ser Glu Phe
        195                 200                 205

His Gln Asn Arg Val Ala Ala Ile Asn Phe Ile Asn Gly Gln Gln Ala
    210                 215                 220

Thr Ser Tyr Val Leu Thr Gln Gly Ser Gly Leu Leu Ala Ala Lys Ser
225                 230                 235                 240

Met Leu Asn Gln Gln Arg Leu Met Phe Ile Leu Pro Gly Asn Ser Gln
                245                 250                 255

Gln Gln Ile Thr Ala Ser Ile Thr Gln Leu Met Gln Gln Leu Glu Arg
            260                 265                 270

Leu Gln Val Thr Glu Val Asn Glu Leu Ser Leu Glu Cys Gln Leu Glu
        275                 280                 285

Leu Leu Ser Ile Met Tyr Asp Asn Leu Val Asn Ala Asp Lys Leu Thr
    290                 295                 300

Thr Arg Asp Ser Lys Pro Ala Tyr Gln Ala Val Ile Gln Ala Ser Ser
305                 310                 315                 320

Val Ser Ala Ala Lys Gln Glu Leu Ser Ala Leu Asn Asp Ala Leu Thr
                325                 330                 335

Ala Leu Phe Ala Glu Gln Thr Asn Ala Thr Ser Thr Asn Lys Gly Leu
            340                 345                 350

Ile Gln Tyr Lys Thr Pro Ala Gly Ser Tyr Leu Thr Leu Thr Pro Leu
        355                 360                 365
```

-continued

```
Gly Ser Asn Asn Asp Asn Ala Gln Ala Gly Leu Ala Phe Val Tyr Pro
    370                 375                 380
Gly Val Gly Thr Val Tyr Ala Asp Met Leu Asn Glu Leu His Gln Tyr
385                 390                 395                 400
Phe Pro Ala Leu Tyr Ala Lys Leu Glu Arg Glu Gly Asp Leu Lys Ala
                405                 410                 415
Met Leu Gln Ala Glu Asp Ile Tyr His Leu Asp Pro Lys His Ala Ala
                420                 425                 430
Gln Met Ser Leu Gly Asp Leu Ala Ile Ala Gly Val Gly Ser Ser Tyr
            435                 440                 445
Leu Leu Thr Gln Leu Leu Thr Asp Glu Phe Asn Ile Lys Pro Asn Phe
            450                 455                 460
Ala Leu Gly Tyr Ser Met Gly Glu Ala Ser Met Trp Ala Ser Leu Gly
465                 470                 475                 480
Val Trp Gln Asn Pro His Ala Leu Ile Ser Lys Thr Gln Thr Asp Pro
                485                 490                 495
Leu Phe Thr Ser Ala Ile Ser Gly Lys Leu Thr Ala Val Arg Gln Ala
            500                 505                 510
Trp Gln Leu Asp Asp Thr Ala Ala Glu Ile Gln Trp Asn Ser Phe Val
            515                 520                 525
Val Arg Ser Glu Ala Ala Pro Ile Glu Ala Leu Leu Lys Asp Tyr Pro
530                 535                 540
His Ala Tyr Leu Ala Ile Ile Gln Gly Asp Thr Cys Val Ile Ala Gly
545                 550                 555                 560
Cys Glu Ile Gln Cys Lys Ala Leu Leu Ala Leu Gly Lys Arg Gly
                565                 570                 575
Ile Ala Ala Asn Arg Val Thr Ala Met His Thr Gln Pro Ala Met Gln
                580                 585                 590
Glu His Gln Asn Val Met Asp Phe Tyr Leu Gln Pro Leu Lys Ala Glu
            595                 600                 605
Leu Pro Ser Glu Ile Ser Phe Ile Ser Ala Ala Asp Leu Thr Ala Lys
            610                 615                 620
Gln Thr Val Ser Glu Gln Ala Leu Ser Ser Gln Val Val Ala Gln Ser
625                 630                 635                 640
Ile Ala Asp Thr Phe Cys Gln Thr Leu Asp Phe Thr Ala Leu Val His
                645                 650                 655
His Ala Gln His Gln Gly Ala Lys Leu Phe Val Glu Ile Gly Ala Asp
                660                 665                 670
Arg Gln Asn Cys Thr Leu Ile Asp Lys Ile Val Lys Gln Asp Gly Ala
            675                 680                 685
Ser Ser Val Gln His Gln Pro Cys Cys Thr Val Pro Met Asn Ala Lys
            690                 695                 700
Gly Ser Gln Asp Ile Thr Ser Val Ile Lys Ala Leu Gly Gln Leu Ile
705                 710                 715                 720
Ser His Gln Val Pro Leu Ser Val Gln Pro Phe Ile Asp Gly Leu Lys
                725                 730                 735
Arg Glu Leu Thr Leu Cys Gln Leu Thr Ser Gln Gln Leu Ala Ala His
                740                 745                 750
Ala Asn Val Asp Ser Lys Phe Glu Ser Asn Gln Asp His Leu Leu Gln
            755                 760                 765
Gly Glu Val
    770
```

-continued

```
<210> SEQ ID NO 9
<211> LENGTH: 2004
<212> TYPE: PRT
<213> ORGANISM: Shewanella putrefaciens

<400> SEQUENCE: 9

Met Ser Leu Pro Asp Asn Ala Ser Asn His Leu Ser Ala Asn Gln Lys
 1               5                  10                  15

Gly Ala Ser Gln Ala Ser Lys Thr Ser Lys Gln Ser Lys Ile Ala Ile
            20                  25                  30

Val Gly Leu Ala Thr Leu Tyr Pro Asp Ala Lys Thr Pro Gln Glu Phe
        35                  40                  45

Trp Gln Asn Leu Leu Asp Lys Arg Asp Ser Arg Ser Thr Leu Thr Asn
    50                  55                  60

Glu Lys Leu Gly Ala Asn Ser Gln Asp Tyr Gln Gly Val Gln Gly Gln
65                  70                  75                  80

Ser Asp Arg Phe Tyr Cys Asn Lys Gly Gly Tyr Ile Glu Asn Phe Ser
                85                  90                  95

Phe Asn Ala Ala Gly Tyr Lys Leu Pro Glu Gln Ser Leu Asn Gly Leu
            100                 105                 110

Asp Asp Ser Phe Leu Trp Ala Leu Asp Thr Ser Arg Asn Ala Leu Ile
        115                 120                 125

Asp Ala Gly Ile Asp Ile Asn Gly Ala Asp Leu Ser Arg Ala Gly Val
    130                 135                 140

Val Met Gly Ala Leu Ser Phe Pro Thr Thr Arg Ser Asn Asp Leu Phe
145                 150                 155                 160

Leu Pro Ile Tyr His Ser Ala Val Glu Lys Ala Leu Gln Asp Lys Leu
                165                 170                 175

Gly Val Lys Ala Phe Lys Leu Ser Pro Thr Asn Ala His Thr Ala Arg
            180                 185                 190

Ala Ala Asn Glu Ser Ser Leu Asn Ala Ala Asn Gly Ala Ile Ala His
        195                 200                 205

Asn Ser Ser Lys Val Val Ala Asp Ala Leu Gly Leu Gly Gly Ala Gln
    210                 215                 220

Leu Ser Leu Asp Ala Ala Cys Ala Ser Ser Val Tyr Ser Leu Lys Leu
225                 230                 235                 240

Ala Cys Asp Tyr Leu Ser Thr Gly Lys Ala Asp Ile Met Leu Ala Gly
                245                 250                 255

Ala Val Ser Gly Ala Asp Pro Phe Phe Ile Asn Met Gly Phe Ser Ile
            260                 265                 270

Phe His Ala Tyr Pro Asp His Gly Ile Ser Val Pro Phe Asp Ala Ser
        275                 280                 285

Ser Lys Gly Leu Phe Ala Gly Glu Gly Ala Gly Val Leu Val Leu Lys
    290                 295                 300

Arg Leu Glu Asp Ala Glu Arg Asp Asn Asp Lys Ile Tyr Ala Val Val
305                 310                 315                 320

Ser Gly Val Gly Leu Ser Asn Asp Gly Lys Gly Gln Phe Val Leu Ser
                325                 330                 335

Pro Asn Pro Lys Gly Gln Val Lys Ala Phe Glu Arg Ala Tyr Ala Ala
            340                 345                 350

Ser Asp Ile Glu Pro Lys Asp Ile Glu Val Ile Glu Cys His Ala Thr
        355                 360                 365

Gly Thr Pro Leu Gly Asp Lys Ile Glu Leu Thr Ser Met Glu Thr Phe
    370                 375                 380
```

-continued

```
Phe Glu Asp Lys Leu Gln Gly Thr Asp Ala Pro Leu Ile Gly Ser Ala
385                 390                 395                 400

Lys Ser Asn Leu Gly His Leu Leu Thr Ala Ala His Ala Gly Ile Met
            405                 410                 415

Lys Met Ile Phe Ala Met Lys Glu Gly Tyr Leu Pro Pro Ser Ile Asn
        420                 425                 430

Ile Ser Asp Ala Ile Ala Ser Pro Lys Lys Leu Phe Gly Lys Pro Thr
            435                 440                 445

Leu Pro Ser Met Val Gln Gly Trp Pro Asp Lys Pro Ser Asn Asn His
        450                 455                 460

Phe Gly Val Arg Thr Arg His Ala Gly Val Ser Val Phe Gly Phe Gly
465                 470                 475                 480

Gly Cys Asn Ala His Leu Leu Leu Glu Ser Tyr Asn Gly Lys Gly Thr
                485                 490                 495

Val Lys Ala Glu Ala Thr Gln Val Pro Arg Gln Ala Glu Pro Leu Lys
            500                 505                 510

Val Val Gly Leu Ala Ser His Phe Gly Pro Leu Ser Ser Ile Asn Ala
        515                 520                 525

Leu Asn Asn Ala Val Thr Gln Asp Gly Asn Gly Phe Ile Glu Leu Pro
530                 535                 540

Lys Lys Arg Trp Lys Gly Leu Glu Lys His Ser Glu Leu Leu Ala Glu
545                 550                 555                 560

Phe Gly Leu Ala Ser Ala Pro Lys Gly Ala Tyr Val Asp Asn Phe Glu
                565                 570                 575

Leu Asp Phe Leu Arg Phe Lys Leu Pro Pro Asn Glu Asp Asp Arg Leu
            580                 585                 590

Ile Ser Gln Gln Leu Met Leu Met Arg Val Thr Asp Glu Ala Ile Arg
            595                 600                 605

Asp Ala Lys Leu Glu Pro Gly Gln Lys Val Ala Val Leu Val Ala Met
        610                 615                 620

Glu Thr Glu Leu Glu Leu His Gln Phe Arg Gly Arg Val Asn Leu His
625                 630                 635                 640

Thr Gln Leu Ala Gln Ser Leu Ala Ala Met Gly Val Ser Leu Ser Thr
                645                 650                 655

Asp Glu Tyr Gln Ala Leu Glu Ala Ile Ala Met Asp Ser Val Leu Asp
            660                 665                 670

Ala Ala Lys Leu Asn Gln Tyr Thr Ser Phe Ile Gly Asn Ile Met Ala
        675                 680                 685

Ser Arg Val Ala Ser Leu Trp Asp Phe Asn Gly Pro Ala Phe Thr Ile
690                 695                 700

Ser Ala Ala Glu Gln Ser Val Ser Arg Cys Ile Asp Val Ala Gln Asn
705                 710                 715                 720

Leu Ile Met Glu Asp Asn Leu Asp Ala Val Ile Ala Ala Val Asp
                725                 730                 735

Leu Ser Gly Ser Phe Glu Gln Val Ile Leu Lys Asn Ala Ile Ala Pro
            740                 745                 750

Val Ala Ile Glu Pro Asn Leu Glu Ala Ser Leu Asn Pro Thr Ser Ala
        755                 760                 765

Ser Trp Asn Val Gly Glu Gly Ala Gly Ala Val Val Leu Val Lys Asn
770                 775                 780

Glu Ala Thr Ser Gly Cys Ser Tyr Gly Gln Ile Asp Ala Leu Gly Phe
785                 790                 795                 800
```

-continued

```
Ala Lys Thr Ala Glu Thr Ala Leu Ala Thr Asp Lys Leu Leu Ser Gln
            805                 810                 815

Thr Ala Thr Asp Phe Asn Lys Val Lys Val Ile Glu Thr Met Ala Ala
            820                 825                 830

Pro Ala Ser Gln Ile Gln Leu Ala Pro Ile Val Ser Ser Gln Val Thr
            835                 840                 845

His Thr Ala Ala Glu Gln Arg Val Gly His Cys Phe Ala Ala Ala Gly
            850                 855                 860

Met Ala Ser Leu Leu His Gly Leu Leu Asn Leu Asn Thr Val Ala Gln
865                 870                 875                 880

Thr Asn Lys Ala Asn Cys Ala Leu Ile Asn Asn Ile Ser Glu Asn Gln
            885                 890                 895

Leu Ser Gln Leu Leu Ile Ser Gln Thr Ala Ser Glu Gln Gln Ala Leu
            900                 905                 910

Thr Ala Arg Leu Ser Asn Glu Leu Lys Ser Asp Ala Lys His Gln Leu
            915                 920                 925

Val Lys Gln Val Thr Leu Gly Gly Arg Asp Ile Tyr Gln His Ile Val
            930                 935                 940

Asp Thr Pro Leu Ala Ser Leu Glu Ser Ile Thr Gln Lys Leu Ala Gln
945                 950                 955                 960

Ala Thr Ala Ser Thr Val Val Asn Gln Val Lys Pro Ile Lys Ala Ala
            965                 970                 975

Gly Ser Val Glu Met Ala Asn Ser Phe Glu Thr Glu Ser Ser Ala Glu
            980                 985                 990

Pro Gln Ile Thr Ile Ala Ala Gln Gln Thr Ala Asn Ile Gly Val Thr
            995                1000                1005

Ala Gln Ala Thr Lys Arg Glu Leu Gly Thr Pro Pro Met Thr Thr Asn
1010                1015                1020

Thr Ile Ala Asn Thr Ala Asn Asn Leu Asp Lys Thr Leu Glu Thr Val
1025                1030                1035                1040

Ala Gly Asn Thr Val Ala Ser Lys Val Gly Ser Gly Asp Ile Val Asn
            1045                1050                1055

Phe Gln Gln Asn Gln Gln Leu Ala Gln Gln Ala His Leu Ala Phe Leu
            1060                1065                1070

Glu Ser Arg Ser Ala Gly Met Lys Val Ala Asp Ala Leu Leu Lys Gln
            1075                1080                1085

Gln Leu Ala Gln Val Thr Gly Gln Thr Ile Asp Asn Gln Ala Leu Asp
            1090                1095                1100

Thr Gln Ala Val Asp Thr Gln Thr Ser Glu Asn Val Ala Ile Ala Ala
1105                1110                1115                1120

Glu Ser Pro Val Gln Val Thr Thr Pro Val Gln Val Thr Thr Pro Val
            1125                1130                1135

Gln Ile Ser Val Val Glu Leu Lys Pro Asp His Ala Asn Val Pro Pro
            1140                1145                1150

Tyr Thr Pro Pro Val Pro Ala Leu Lys Pro Cys Ile Trp Asn Tyr Ala
            1155                1160                1165

Asp Leu Val Glu Tyr Ala Glu Gly Asp Ile Ala Lys Val Phe Gly Ser
            1170                1175                1180

Asp Tyr Ala Ile Ile Asp Ser Tyr Ser Arg Arg Val Arg Leu Pro Thr
1185                1190                1195                1200

Thr Asp Tyr Leu Leu Val Ser Arg Val Thr Lys Leu Asp Ala Thr Ile
            1205                1210                1215

Asn Gln Phe Lys Pro Cys Ser Met Thr Thr Glu Tyr Asp Ile Pro Val
```

-continued

```
                1220               1225               1230
Asp Ala Pro Tyr Leu Val Asp Gly Gln Ile Pro Trp Ala Val Ala Val
            1235               1240               1245

Glu Ser Gly Gln Cys Asp Leu Met Leu Ile Ser Tyr Leu Gly Ile Asp
       1250               1255               1260

Phe Glu Asn Lys Gly Glu Arg Val Tyr Arg Leu Leu Asp Cys Thr Leu
1265               1270               1275               1280

Thr Phe Leu Gly Asp Leu Pro Arg Gly Gly Asp Thr Leu Arg Tyr Asp
            1285               1290               1295

Ile Lys Ile Asn Asn Tyr Ala Arg Asn Gly Asp Thr Leu Leu Phe Phe
       1300               1305               1310

Phe Ser Tyr Glu Cys Phe Val Gly Asp Lys Met Ile Leu Lys Met Asp
       1315               1320               1325

Gly Gly Cys Ala Gly Phe Phe Thr Asp Glu Glu Leu Ala Asp Gly Lys
       1330               1335               1340

Gly Val Ile Arg Thr Glu Glu Ile Lys Ala Arg Ser Leu Val Gln
1345               1350               1355               1360

Lys Gln Arg Phe Asn Pro Leu Leu Asp Cys Pro Lys Thr Gln Phe Ser
            1365               1370               1375

Tyr Gly Asp Ile His Lys Leu Leu Thr Ala Asp Ile Glu Gly Cys Phe
            1380               1385               1390

Gly Pro Ser His Ser Gly Val His Gln Pro Ser Leu Cys Phe Ala Ser
            1395               1400               1405

Glu Lys Phe Leu Met Ile Glu Gln Val Ser Lys Val Asp Arg Thr Gly
       1410               1415               1420

Gly Thr Trp Gly Leu Gly Leu Ile Glu Gly His Lys Gln Leu Glu Ala
1425               1430               1435               1440

Asp His Trp Tyr Phe Pro Cys His Phe Lys Gly Asp Gln Val Met Ala
            1445               1450               1455

Gly Ser Leu Met Ala Glu Gly Cys Gly Gln Leu Leu Gln Phe Tyr Met
            1460               1465               1470

Leu His Leu Gly Met His Thr Gln Thr Lys Asn Gly Arg Phe Gln Pro
       1475               1480               1485

Leu Glu Asn Ala Ser Gln Gln Val Arg Cys Arg Gly Gln Val Leu Pro
       1490               1495               1500

Gln Ser Gly Val Leu Thr Tyr Arg Met Glu Val Thr Glu Ile Gly Phe
1505               1510               1515               1520

Ser Pro Arg Pro Tyr Ala Lys Ala Asn Ile Asp Ile Leu Leu Asn Gly
            1525               1530               1535

Lys Ala Val Val Asp Phe Gln Asn Leu Gly Val Met Ile Lys Glu Glu
            1540               1545               1550

Asp Glu Cys Thr Arg Tyr Pro Leu Leu Thr Glu Ser Thr Thr Ala Ser
       1555               1560               1565

Thr Ala Gln Val Asn Ala Gln Thr Ser Ala Lys Lys Val Tyr Lys Pro
       1570               1575               1580

Ala Ser Val Asn Ala Pro Leu Met Ala Gln Ile Pro Asp Leu Thr Lys
1585               1590               1595               1600

Glu Pro Asn Lys Gly Val Ile Pro Ile Ser His Val Glu Ala Pro Ile
            1605               1610               1615

Thr Pro Asp Tyr Pro Asn Arg Val Pro Asp Thr Val Pro Phe Thr Pro
            1620               1625               1630

Tyr His Met Phe Glu Phe Ala Thr Gly Asn Ile Glu Asn Cys Phe Gly
            1635               1640               1645
```

Pro Glu Phe Ser Ile Tyr Arg Gly Met Ile Pro Pro Arg Thr Pro Cys
    1650                1655                1660

Gly Asp Leu Gln Val Thr Thr Arg Val Ile Glu Val Asn Gly Lys Arg
1665                1670                1675                1680

Gly Asp Phe Lys Lys Pro Ser Ser Cys Ile Ala Glu Tyr Glu Val Pro
            1685                1690                1695

Ala Asp Ala Trp Tyr Phe Asp Lys Asn Ser His Gly Ala Val Met Pro
        1700                1705                1710

Tyr Ser Ile Leu Met Glu Ile Ser Leu Gln Pro Asn Gly Phe Ile Ser
    1715                1720                1725

Gly Tyr Met Gly Thr Thr Leu Gly Phe Pro Gly Leu Glu Leu Phe Phe
1730                1735                1740

Arg Asn Leu Asp Gly Ser Gly Glu Leu Leu Arg Glu Val Asp Leu Arg
1745                1750                1755                1760

Gly Lys Thr Ile Arg Asn Asp Ser Arg Leu Leu Ser Thr Val Met Ala
            1765                1770                1775

Gly Thr Asn Ile Ile Gln Ser Phe Ser Phe Glu Leu Ser Thr Asp Gly
        1780                1785                1790

Glu Pro Phe Tyr Arg Gly Thr Ala Val Phe Gly Tyr Phe Lys Gly Asp
    1795                1800                1805

Ala Leu Lys Asp Gln Leu Gly Leu Asp Asn Gly Lys Val Thr Gln Pro
1810                1815                1820

Trp His Val Ala Asn Gly Val Ala Ala Ser Thr Lys Val Asn Leu Leu
1825                1830                1835                1840

Asp Lys Ser Cys Arg His Phe Asn Ala Pro Ala Asn Gln Pro His Tyr
            1845                1850                1855

Arg Leu Ala Gly Gly Gln Leu Asn Phe Ile Asp Ser Val Glu Ile Val
        1860                1865                1870

Asp Asn Gly Gly Thr Glu Gly Leu Gly Tyr Leu Tyr Ala Glu Arg Thr
    1875                1880                1885

Ile Asp Pro Ser Asp Trp Phe Phe Gln Phe His Phe His Gln Asp Pro
1890                1895                1900

Val Met Pro Gly Ser Leu Gly Val Glu Ala Ile Ile Glu Thr Met Gln
1905                1910                1915                1920

Ala Tyr Ala Ile Ser Lys Asp Leu Gly Ala Asp Phe Lys Asn Pro Lys
            1925                1930                1935

Phe Gly Gln Ile Leu Ser Asn Ile Lys Trp Lys Tyr Arg Gly Gln Ile
        1940                1945                1950

Asn Pro Leu Asn Lys Gln Met Ser Met Asp Val Ser Ile Thr Ser Ile
    1955                1960                1965

Lys Asp Glu Asp Gly Lys Lys Val Ile Thr Gly Asn Ala Ser Leu Ser
    1970                1975                1980

Lys Asp Gly Leu Arg Ile Tyr Glu Val Phe Asp Ile Ala Ile Ser Ile
1985                1990                1995                2000

Glu Glu Ser Val

<210> SEQ ID NO 10
<211> LENGTH: 543
<212> TYPE: PRT
<213> ORGANISM: Shewanella putrefaciens

<400> SEQUENCE: 10

Met Asn Pro Thr Ala Thr Asn Glu Met Leu Ser Pro Trp Pro Trp Ala
    1               5                   10                  15

-continued

```
Val Thr Glu Ser Asn Ile Ser Phe Asp Val Gln Val Met Glu Gln Gln
         20                  25                  30

Leu Lys Asp Phe Ser Arg Ala Cys Tyr Val Val Asn His Ala Asp His
         35                  40                  45

Gly Phe Gly Ile Ala Gln Thr Ala Asp Ile Val Thr Glu Gln Ala Ala
         50                  55                  60

Asn Ser Thr Asp Leu Pro Val Ser Ala Phe Thr Pro Ala Leu Gly Thr
 65              70                  75                      80

Glu Ser Leu Gly Asp Asn Asn Phe Arg Arg Val His Gly Val Lys Tyr
                 85                  90                  95

Ala Tyr Tyr Ala Gly Ala Met Ala Asn Gly Ile Ser Ser Glu Glu Leu
             100                 105                 110

Val Ile Ala Leu Gly Gln Ala Gly Ile Leu Cys Gly Ser Phe Gly Ala
             115                 120                 125

Ala Gly Leu Ile Pro Ser Arg Val Glu Ala Ala Ile Asn Arg Ile Gln
             130                 135                 140

Ala Ala Leu Pro Asn Gly Pro Tyr Met Phe Asn Leu Ile His Ser Pro
145                 150                 155                 160

Ser Glu Pro Ala Leu Glu Arg Gly Ser Val Glu Leu Phe Leu Lys His
                 165                 170                 175

Lys Val Arg Thr Val Glu Ala Ser Ala Phe Leu Gly Leu Thr Pro Gln
                 180                 185                 190

Ile Val Tyr Tyr Arg Ala Ala Gly Leu Ser Arg Asp Ala Gln Gly Lys
             195                 200                 205

Val Val Val Gly Asn Lys Val Ile Ala Lys Val Ser Arg Thr Glu Val
             210                 215                 220

Ala Glu Lys Phe Met Met Pro Ala Pro Ala Lys Met Leu Gln Lys Leu
225                 230                 235                 240

Val Asp Asp Gly Ser Ile Thr Ala Glu Gln Met Glu Leu Ala Gln Leu
                 245                 250                 255

Val Pro Met Ala Asp Asp Ile Thr Ala Glu Ala Asp Ser Gly Gly His
                 260                 265                 270

Thr Asp Asn Arg Pro Leu Val Thr Leu Leu Pro Thr Ile Leu Ala Leu
         275                 280                 285

Lys Glu Glu Ile Gln Ala Lys Tyr Gln Tyr Asp Thr Pro Ile Arg Val
         290                 295                 300

Gly Cys Gly Gly Gly Val Gly Thr Pro Asp Ala Ala Leu Ala Thr Phe
305                 310                 315                 320

Asn Met Gly Ala Ala Tyr Ile Val Thr Gly Ser Ile Asn Gln Ala Cys
                 325                 330                 335

Val Glu Ala Gly Ala Ser Asp His Thr Arg Lys Leu Leu Ala Thr Thr
             340                 345                 350

Glu Met Ala Asp Val Thr Met Ala Pro Ala Ala Asp Met Phe Glu Met
             355                 360                 365

Gly Val Lys Leu Gln Val Val Lys Arg Gly Thr Leu Phe Pro Met Arg
             370                 375                 380

Ala Asn Lys Leu Tyr Glu Ile Tyr Thr Arg Tyr Asp Ser Ile Glu Ala
385                 390                 395                 400

Ile Pro Leu Asp Glu Arg Glu Lys Leu Glu Lys Gln Val Phe Arg Ser
                 405                 410                 415

Ser Leu Asp Glu Ile Trp Ala Gly Thr Val Ala His Phe Asn Glu Arg
             420                 425                 430
```

```
Asp Pro Lys Gln Ile Glu Arg Ala Glu Gly Asn Pro Lys Arg Lys Met
        435                 440                 445

Ala Leu Ile Phe Arg Trp Tyr Leu Gly Leu Ser Ser Arg Trp Ser Asn
        450                 455                 460

Ser Gly Glu Val Gly Arg Glu Met Asp Tyr Gln Ile Trp Ala Gly Pro
465                 470                 475                 480

Ala Leu Gly Ala Phe Asn Gln Trp Ala Lys Gly Ser Tyr Leu Asp Asn
                485                 490                 495

Tyr Gln Asp Arg Asn Ala Val Asp Leu Ala Lys His Leu Met Tyr Gly
            500                 505                 510

Ala Ala Tyr Leu Asn Arg Ile Asn Ser Leu Thr Ala Gln Gly Val Lys
        515                 520                 525

Val Pro Ala Gln Leu Leu Arg Trp Lys Pro Asn Gln Arg Met Ala
    530                 535                 540

<210> SEQ ID NO 11
<211> LENGTH: 499
<212> TYPE: PRT
<213> ORGANISM: Shewanella putrefaciens

<400> SEQUENCE: 11

Met Arg Lys Pro Leu Gln Thr Ile Asn Tyr Asp Tyr Ala Val Trp Asp
1               5                   10                  15

Arg Thr Tyr Ser Tyr Met Lys Ser Asn Ser Ala Ser Ala Lys Arg Tyr
            20                  25                  30

Tyr Glu Lys His Glu Tyr Pro Asp Asp Thr Phe Lys Ser Leu Lys Val
        35                  40                  45

Asp Gly Val Phe Ile Phe Asn Arg Thr Asn Gln Pro Val Phe Ser Lys
    50                  55                  60

Gly Phe Asn His Arg Asn Asp Ile Pro Leu Val Phe Glu Leu Thr Asp
65                  70                  75                  80

Phe Lys Gln His Pro Gln Asn Ile Ala Leu Ser Pro Gln Thr Lys Gln
                85                  90                  95

Ala His Pro Pro Ala Ser Lys Pro Leu Asp Ser Pro Asp Asp Val Pro
            100                 105                 110

Ser Thr His Gly Val Ile Ala Thr Arg Tyr Gly Pro Ala Ile Tyr Tyr
        115                 120                 125

Ser Ser Thr Ser Ile Leu Lys Ser Asp Arg Ser Gly Ser Gln Leu Gly
    130                 135                 140

Tyr Leu Val Phe Ile Arg Leu Ile Asp Glu Trp Phe Ile Ala Glu Leu
145                 150                 155                 160

Ser Gln Tyr Thr Ala Ala Gly Val Glu Ile Ala Met Ala Asp Ala Ala
                165                 170                 175

Asp Ala Gln Leu Ala Arg Leu Gly Ala Asn Thr Lys Leu Asn Lys Val
            180                 185                 190

Thr Ala Thr Ser Glu Arg Leu Ile Thr Asn Val Asp Gly Lys Pro Leu
        195                 200                 205

Leu Lys Leu Val Leu Tyr His Thr Asn Asn Gln Pro Pro Met Leu
    210                 215                 220

Asp Tyr Ser Ile Ile Ile Leu Leu Val Glu Met Ser Phe Leu Leu Ile
225                 230                 235                 240

Leu Ala Tyr Phe Leu Tyr Ser Tyr Phe Leu Val Arg Pro Val Arg Lys
                245                 250                 255

Leu Ala Ser Asp Ile Lys Lys Met Asp Lys Ser Arg Glu Ile Lys Lys
            260                 265                 270
```

```
Leu Arg Tyr His Tyr Pro Ile Thr Glu Leu Val Lys Val Ala Thr His
            275                 280                 285
Phe Asn Ala Leu Met Gly Thr Ile Gln Glu Gln Thr Lys Gln Leu Asn
290                 295                 300
Glu Gln Val Phe Ile Asp Lys Leu Thr Asn Ile Pro Asn Arg Arg Ala
305                 310                 315                 320
Phe Glu Gln Arg Leu Glu Thr Tyr Cys Gln Leu Leu Ala Arg Gln Gln
                325                 330                 335
Ile Gly Phe Thr Leu Ile Ile Ala Asp Val Asp His Phe Lys Glu Tyr
            340                 345                 350
Asn Asp Thr Leu Gly His Leu Ala Gly Asp Glu Ala Leu Ile Lys Val
            355                 360                 365
Ala Gln Thr Leu Ser Gln Gln Phe Tyr Arg Ala Glu Asp Ile Cys Ala
370                 375                 380
Arg Phe Gly Gly Glu Glu Phe Ile Met Leu Phe Arg Asp Ile Pro Asp
385                 390                 395                 400
Glu Pro Leu Gln Arg Lys Leu Asp Ala Met Leu His Ser Phe Ala Glu
                405                 410                 415
Leu Asn Leu Pro His Pro Asn Ser Ser Thr Ala Asn Tyr Val Thr Val
            420                 425                 430
Ser Leu Gly Val Cys Thr Val Ala Val Asp Asp Phe Glu Phe Lys
            435                 440                 445
Ser Glu Ser His Ile Ile Gly Ser Gln Ala Ala Leu Ile Ala Asp Lys
            450                 455                 460
Ala Leu Tyr His Ala Lys Ala Cys Gly Arg Asn Gln Ala Leu Ser Lys
465                 470                 475                 480
Thr Thr Ile Thr Val Asp Glu Ile Glu Gln Leu Glu Ala Asn Lys Ile
                485                 490                 495
Gly His Gln

<210> SEQ ID NO 12
<211> LENGTH: 40138
<212> TYPE: DNA
<213> ORGANISM: Vibrio marinus

<400> SEQUENCE: 12
aatagatcga ctcgcaaaag ttgcttaaga tagtgtcaat atagcttctt atttgtaaat      60
attgttttt  atgtgtaaac atgtttagtg tgtgtaaatg ctgttaatta tcctttggg     120
attgtaatag ctgatgttgc tggctaatga gtacttttag ttcggcaata tcttgcttta    180
aatcgctaac ttcagttttt aattcaccca cacttgttgt attttttaagg ctctcttccc   240
caccatcgac aaaccaggat gatatgaaac cggtaaacgt accaaagaga ccgacacctg    300
cagtcatgag taatgccgca atgatacgtc cgccagtggt gacggggtag tagtcaccgt    360
aaccaacagt cgttattgtc acaaatgacc accaaagtgc gtcgatgccg ttattgatgt    420
tactgcctac ttgatcctgt tctaacaata aataccgat  agcaccaaag gtgacaagga    480
tgaaggatat cgcagatacc agcgaaaagg tggctttaaa ccgatgttca aaaatcattt    540
ttaagataat ttttgatgag cgtatattct gaatagatct taatactcta gcgatacgaa    600
ttatgcgaat aaactgcagt tgctcgacca tcggaatact cgacagtagg tcaatccaac    660
cccatttcat aaactgaaat ttattctcag cttggtgaaa gcgaattaca aagtcagtga    720
aaaagaataa gcaaatcgta ttatctacgc tcgttaatat ttcagtgacg ttacttgaaa    780
```

```
aggtaaaaat aagttgcagt agtgatgata cgaccacatg aagtgataaa ataagcatga    840
aaatctgaaa tggatttaca tcactgttgt ttttggtgcc acttttaagg ttcgttttca    900
caatctgctg cctcggttca ttgattttgt taatataaac cttagtcagt agcaagacaa    960
aatatattta catcaatgtc atcgtattat tcaaccgcgc gtcgtgtatt cagaccaaga   1020
tcgttgtata tgttagtcat gtagcgatga gattatcatg cgacaggaga gaattatgtt   1080
tgttattatt ttttacgtac ctaaagttaa tgttgaagaa gtaaaacagg cgttatttaa   1140
cgtcggagct ggcaccatcg gtgattatga tagttgtgct tggcaatgtt tggggactgg   1200
gcagttccaa cctttacttg gtagccagcc acatattggt aagctaaatg aggttgaatt   1260
cgttgatgag tttagagtag aaatggtttg tcgagcagaa aatgtaaggg cagcaataaa   1320
tgcacttatt gctgcgcacc cttatgaaga acctgcttat catattctgc aaacattgaa   1380
tcttgatgag ttaccttaag ttagatgcac tgcacttaat tggttcgctg tgctaggtta   1440
gcaattagca attttgacca tgttagcgat agttttggca caagtgatcg atattaaact   1500
atccgattca gatcccattt ttactgctga attaggtttc attacacttg ttctagtggt   1560
ttttcccgac aggtgtaact ctgttacttg cgtaaggttg ataatctcta ccgcattggc   1620
aggagttaca cctgcaccag gcataatact aattctacca tctgcttggt taactaacgt   1680
ttggattaag gcgcagcctt ctagcgcttg agcttgttga ccagaggtta aaatacgctc   1740
acaaccagca gtgatcaagg tctccaaggc ttgttgtgga tcattacaca agtcgaaagc   1800
gcggtggaag gttacgccga gatcacgtga tgccaccatt aagcgtttta aagctggctc   1860
gtcaatatta ccatctgctg ttaacgcgcc aataacgacc ccttggacac cgagtaactt   1920
catgaatttg atgtcggaaa ccataatatc aacttcttgt tcgctatata caaaatcacc   1980
ggcgcgaggg cgaataatgg cataaatggg gatcgttgct agatcaatag acttttgtac   2040
aaaacctgcg ttggcggtca agccacctaa tgctaatgcc gagcacaact caatacgatc   2100
ggcgccagat gcttgagccg tcagcagtga ttctatatta tcgacacata cttctattgt   2160
cattgtcata tacttctctt taaaaagttt attaaaaata ataaagccag cataagtcgt   2220
tttatacaat atgaaagggg aaaaggcgac ttagctcgcc tagatcaatt attatggcag   2280
aatactgccg tattgtgatt agaaagacag ttttttaagc tcaatagccg ttatcgcgtt   2340
gttatctacc atcgtgtaac ttttctggcc tgggtgcttt attaacactg tttcagtggc   2400
tggattaggg tgaaatgatt cttttttcaa atctgttttt ttgtatttga acgtacctgt   2460
aatgtcttgc tgctcacgaa gacgtacaaa tattggttgc gcatagcttg gtagtgccgc   2520
attgacatgt tgatagaatt cagacgctga aaattcatga ataggcaat tcaaagtcag    2580
cgcgaccatg cctgctcggc catcgtgatg tgggagcttg acaccataag ccacactttg   2640
ctcaatttgc acaaaatcgt taacttgagc ttctacttgc gtcgtggcga cattttcacc   2700
tttccagcgg aatgtatcac ctaatctatc cacaaaggaa atatggcgat aaccttggta   2760
atgaacgaga tcgccggtat taaaataaca gtcaccgtct tttaatactg acttaaatag   2820
cttttattta ctttcgttgt catcggtata accatcaaat ggtgaacgtt tagttatctt   2880
tgttagcagt agccctgttt ctcccgtttt tactttggtc atttttccctt tcgcattata   2940
cacaggtttg tcattgtcaa tatcatattg tatgacggta aaagcaagtg gagtaacccc   3000
cgctgtatgc ggtaagttca gcgcattgga gaacacaaga ttacactcac tggcgccata   3060
gaattcatta atatgctcga tcccaaaacg ttgttggaaa tgatcccaaa tttcggggcg   3120
taatccatta cctatgattt tctttatatt atgctgtttg tctttattgc taggcggtac   3180
```

```
atttaataaa taacggcaga gctcgccgat gtaagtaaac gcagtggcat tatgagcacg    3240
aacttcatcc caaaagcgac ttgaactgaa tttttcagaa agtgcgaggg ttgctgcgct    3300
accaaacacg gcgcttaatg acactgtcag tgcattgtta tggtataggg ggagtgataa    3360
atacaataca tcatcagctg ttaagcgtaa tgatgccatc cccatgcctg ccatggattt    3420
aaaccaacgg tgatggctca ttcttgctgc ttttggcagt ccagttttc ccgaggtaaa    3480 gatataaaac gcgcaatgct taagctgtat ttgtgctgtt gattcagggt tcaatactga    3540
atatcctgcg actagtgtag atatgttttt ataaccatca ctcatgtctg gcgtttctaa    3600
agcgggtacg taaaagacat tctgttgtaa tgtcgatgac aaattggttt caatattatt    3660
aatggcggat gtgtatagtt catctgcgat gagtaatttg gtatcgacca cgctaagact    3720
atgttcgagg attgaatccc gttgtgtcgt atttatcata caagcaatcg cgccaagctt    3780
gacaactgcg agggcaataa tgatggtttc aggcctgtta tcgagcatga tggcgacttt    3840
atcattttta ccaatgccgt attcatgaag gaaatgggca tattgatttg cttgcttatt    3900
caatgaatcg taactataac gctggtcttt aaattgtatt gcgatcaagt cagagttatt    3960
gacagcttgc tgctctagta ataaaccaat agacataaaa cgttcgggct tgcttgttg    4020 taagtgccat aagcctttga tgattggctt tggggttttt aatagattga tggtacttt    4080 caggaattgt ttgccggtta taacagtcat aagctaattc tttttatcaa gaagaggggt    4140
tatgacacca aataaatggg tcacgcgttg gtttaatttg gttagactaa atgtgttgtt    4200
ttgctgtgat aatgcgacgt tcaaacaaac ttgagaaggt aaaaaaatag catttttaaa    4260
ttgaacatca atactaatgt gttgaatatc aatcaagttt tctaactgtg cgagcacgcg    4320
tgctttagca aacatgccat gtgctattgc tgttttaaac cccattagtt tcgctgggat    4380
aaaatgtaaa tggattggat ttgtgtcttt ggagatataa gcatatttat atacgtcaaa    4440
aggactaaat ttaaacaatg aaatcggctc gtaagcataa ttcgctggcg tatttactat    4500
tttctcaccg ctggaacgtt gagatcgttg gcacgttttt cgctgtttcg ttttctgtaa    4560
gaatgtcgat gtacactccc acgcaaattg tccatctaca aacacatcaa tatgagtatc    4620
aatgaaacgt cctgtatccg ttatgtactc cttaattaca cgacatgtgc tcgtcaatat    4680
cgcgtttaat gctatcggtt gatgttgtgt tatgcgattt cgataatgga ctagtcctaa    4740
tatagatatc ggaaattgtg ttgatgtcat gagtttcatc aataatggaa agatcatcac    4800
aaatggataa gtaaccggta catagtttgt gttattaaac ccacagcatt taatatattg    4860
ctttaaattt cgctgatcta ttttttgtcc actgatacta aattgctcag tacacacttg    4920
tgtcgaccaa gtgttcatca gtgttttaac aattgtattg accactgctt tcacatataa    4980
aagcgagata atcggttgct ttgttaacag tgtgatctgg ttagcgtgca ttgaaataat    5040
tcatataaga gtatgtagca tttatgttaa tattttgttt tggaagttga attggcgaat    5100
ccgtaatcgg tttatggcag ttcggtcaaa tacttcaggt aaactcgtta ctcataccat    5160
tgatagtgtt aaagtgattg actgaataaa gaatagagct aaaagtggaa aaattatgca    5220
agatgcgggt atgttattac gcattgctta tgaggcaatg aaagagttag aggttgatgt    5280
cattgaagta ctttctcgtt gtaacataag tgaagagta ctgaatgata aggatcttcg    5340
cacacctaat catgcacaaa cacattttg gcaagtatta aagacatat cacaagatcc    5400 taacatcggc atttcacttg gtgagagaat gccagtgttc acgggcagg tattacagta    5460 tctttttctc agtagtccta catttggtac tggctgggaa cgcgcaacaa aatactttcg    5520
```

-continued

```
attaatcagt gatgcggcga gtgtttctat caagatggaa ggctgtgaag cgcgattatc    5580
tgtgaactta gatggtttag cggaagatgc gaatcgtcat ttgaatgatt gcctagtgat    5640
cggtgcattt aaattttgtt tatatgtgac agaaggcgaa tttaaagtaa gcaaaatagc    5700
ctttgctcat gctcgcccga aagatattac tgcctatacc aatgtattta catgtccgat    5760
tgagtttgct gccgaagata attatattta tttcgatgct gatttactcg aacgtccttc    5820
ttcgcatgcg gagcctgagc tattcgcctt acacgatcag cttgcaagcc gtaaaatagc    5880
caagttagaa ctgcaagatt tagtggataa agtacgtaag gttattgcac aacaacttga    5940
gtctggtgtg gtgactttag aaagtatcgc cactgaactt gacatgaaac cacgtatgct    6000
aagagcgaag ttagctgaca ttgattataa ctttaatcaa atactcgctg attttcgttg    6060
cgagttatca aaaaaactgt tggcgaatac ggacgagtct attgatcaga ttgtctatct    6120
cactggtttt tctgaaccaa gtactttttta tcgtgccttt aagcgctggg ttaaaatgac    6180
gccaattgaa tatcgccgta gcaaactcgc ggttaggcat gctaatcaac acgagtccta    6240
aaaattcgct gcttagtgca tagtgcatag tgcatagtgc tagtaagcca agtacaaagc    6300
gttaaagtta agtacttgag cgaaccatca gacaccactt actagattaa gcacctatta    6360
atgattgacc acaaattctg atcgtattgc ctgtgatccc tgcagcttga ggttgcgcaa    6420
aaaaagctat cgcttcagca acatcaactg gcttaccacc ttgttttaat gaattcatac    6480
gacgaccagc ttcacgaact gtaaatggaa tcgctgctgt cattttttgtt tcaataaagc    6540 ctggtgcaac agcattaatg gtgatgtatt tgtctgcaag cggagtttgc attgcatcaa    6600
cataaccaat gactgcggcc ttagacgttg cataattagt ctgaccaaag ttacccgcaa    6660
tcccactcat cgaagacaca caaacaatgc ggccatagtc gttgagcaga tcatcattta    6720
gcagtcgctc attgattctt tccattgccg acaagttaat atccatcagt acatcccaat    6780
ggttatccgg catacgtgct agcgttttgt cttttgttac cccggcatta tggacgatga    6840
tatcaagcga ctgttctcgc acaaagtcag caatgatatt tggggcgtca gcagcggtaa    6900
tatcagcaac aatgctgcta cctttcaagc aatgagctac tttttcaagg tcctgttttta    6960 atgccggaat gtctaagcaa ataacatgtg cgccatcacg ggcgagtgtt tcagcaatag    7020
cagccccgat gccacgtgat gcaccagtga caagtgctgt cttccttgt aatggttttg    7080 ccgtgttact tgtttcgtta ataacttcgt taataacttc gttaataact tcgttaatag    7140
ccccattaat cgaaccgggt tttacgttaa taacctgtgc tgagatatag gctgattttg    7200
ctgaggttaa gaaacgtagc ggggcctcta ataattgctc actaccaggt tgtacataga    7260
taagttgaca ggtactacca ttcttgccta tttctttggc gacactgcga caaaacccttt    7320 ctaaagatct ttgtacagtc gcgtagctta catcgtcaag atgttcactc ggatgaccta    7380
acacgatcac tctgctgcat ggcgagagct gcttaattac aggttgaaaa aaacgatgta    7440
atgcacttaa ttgcttgctg ttcttaatgc ctgaggcgtc gaagataata ccgttgaagc    7500 gatctgttttt agcgatagca ttaaggctaa taggtgtcgc gactaaagac gtttgattaa    7560
attcaatatt aagatcggct aacgctgacg tgttattagg ataagaaatc gtgacttcag    7620 catcttttaaa tgtgttaaga atgggtttaa ttaatttgct gttgctggct cgccgatga    7680 gtaagttgcc agagatgaga tcggttccct gatcgtagcg tgttaacgta accggtcgtg    7740
gcagattaag cgctttaaat aaacctgatg tccacttgcc attagcgagt tttgcgtatg    7800
tatccgtcat tttctaatcc ttgttatagt gaacagtttg aatctcgaag atgtacatgt    7860
gttaaaaatt atctgatagc tatgacttat ctgccactac gtaataataa atagaccagt    7920
```

-continued

```
tcattacatc gttaatcgat atagtataac taaatactaa gtaaattata atgataagac      7980
tgttatcgta ctcggatcaa actctgatca gcaaataatc aaattagagt ttttatttta      8040
aacttgtatc aacaatgtta cattaatgta tcttacgtct aatgtgctac gggcatattt      8100
aagtcactaa attaaaggaa taaaccatga caggtcaaac aataagaaga gtagcaatta      8160
tcggcggtaa ccgtatcccg tttgcacgtt caaatacagc gtattcaaaa ctaagtaacc      8220
aagatatgct gacggaaact atccgtggct tggtggttaa atataaccta cgtggtgaac      8280
aactggggga agttgttgct ggtgcggtaa ttaagcattc tcgtgatttt aacttaacac      8340
gtgaagccgt gctaagtgca ggtcttgcac ctgaaacgcc ttgttatgac attcaacaag      8400
cttgtggtac tggtctagct gcagctatcc aagtagcaaa caaaattgcg cttggtcaaa      8460
tagaagcggg tattgctggt ggttctgata cgacatcaga tgcaccgatt gcagtcagtg      8520
aaggcatgcg tagtgtatta cttgagctta atcgagctaa aacgggtaag caacgtttga      8580
aagcactatc tcgtctacgt ctaaaacact ttgcgccact aacgcctgca aataaagagc      8640
cgcgtaccaa aatggcgatg ggcgatcatt gtcaagtaac agcgaaagag tggaatatct      8700
cacgtgaagc acaagatgca ttggcctgcg caagtcatca aaaattagct gcagcatatg      8760
aagaaggttt ctttgatacg ttagtttcac ctatggccgg cttaacgaaa gataacgtat      8820
tacgcgcaga tacaacagtt gagaaactgg ctaaattgaa accttgtttt gataaagtaa      8880
acggcactat gacggcgggt aacagtacta accttaccga tggagcatca gctgtattac      8940
ttgcaagtga agaatgggca gcggcacata acttaccagt acaagcttat ctaacatttg      9000
gtgaaacggc cgctatcgac ttcgttgata agaaagaagg tctgttaatg gcgcctgcat      9060
acgcagtgcc aaaaatgttg aagcgtgctg gccttacatt acaagacttc gattactatg      9120
aaatacatga agcatttgct gcgcagttat tagcaacgct agcagcttgg gaagacgaaa      9180
aattctgtaa agaaaaactg ggtctagatg ctgcgcttgg ttcaattgat atgaccaagt      9240
taaacgtgaa agggagtagc ttagccacgg gtcacccatt tgccgcaact ggtggtcgtg      9300
ttgtcgctac gctagcgcaa ttacttgatc agaaaggttc aggtcgtggt ttgatctcga      9360
tttgtgctgc tggtggtcaa ggtatcacgg caatttttaga gaaataaacg cactgttttat      9420 tatctattga ttaagctgtc ctgagatact ggatattttt aaataaaacg ccaatactgc      9480
agagtattgg cgttttttttg taataccaat tcctatataa cggtgcattt taaacactta      9540
atttccggca ttggtatcat aaaaaagcag caccgaagtg ctgcttgatt gtagattaac      9600
ctattaaaat agagaggcta gaattagtct tcgtatgctt cattatgtac gccagctgca      9660
cgacccgatg gatcagcatt gttttggaaa ctttcatccc aagctaatgc ttctacagtt      9720
gaacaagcaa cggatttacc aaacggtacg catttcgctg ctgaatcacc tgggaagtga      9780
tcttcaaaga tggcacgata gtagtaacct tctttcgtat ctggtgtgtt aattgggaac      9840
ttaaatgctg cacttgctaa catttgatca gttaccgctt cttcaacgtg tactttaagt      9900
tggtcaatcc aagaataacc aacaccatca gagaattgtt cttttttgacg ccatacaatt      9960 tcttcaggta gtaaatcttc aaatgcttct cgaatgatgt ttttctcaat gcggtcgccc     10020
gtgatcattt ttagttcagg gtttagacgc attgacgcat caacaaattc tttatctaag     10080
aaaggaacac gtgcttcgat gccccaagct gccatagatt tgtttgcacg taagcaatca     10140
aacatatgta atttattttac tttacgtacc gtctcttcat ggaattcttt cgcatttggc     10200
gctttgtgga agtacaagta accaccgaac agttcatcag caccttcacc agaaagcacc     10260
```

```
atcttaatcc ccatggcttt aattttacgt gccattaggt acatagggt tgatgcacga    10320 attgttgtta catcgtaggt ttcaatgtgg taaatcacgt cgcgtaaagc gtcgatacct    10380
tcttgcacag taaattcaat tgaatgatgg atagtaccta agtgatctgc cacttttgt     10440 gcagcggcta atctggaga accatttagg cctacagaga aagagtgtag ttgtggccac    10500
catgcttcgg ttttaccacc gtcttcaata cgacgttttg catactgttg ggtgattgct    10560
gaaataacag atgaatctaa cccgcctgat aataatacgc cgtaaggtac atcacacatt    10620
aattgacgtt taactgcatc ttccaaacct tgcttaacaa cgcttttatc accaccattt    10680
tgtgcaacgt tatcaaaatc tttccaatca cgttgataat aaggcgtgac tacaccatcc    10740
ttactccaca ggtaatgacc tgctgggaat tcttcaattt gagtacaaat tggcactagt    10800
gctttcattt cagaggcaac ataaaagtta ccgtgttcat catagcccgt ataagaggg    10860 atgataccga tatggtcacg gccaatcagg taagcgtcct ctgtttcgtc atataaagcg    10920
aaagcaaaaa taccatttag atcatctaaa aattgtgtgc ctttttcttt atatagcgca    10980
agtatcactt cgcaatctga ttctgttgg aattcaaagt ctacgttcag cgttttcttt     11040
aaatctttgt ggttataaat ttcaccatta acagcaagta cgtgtgtctt ttcttcatta    11100
tatagcggct gtgcaccatt atttacatcg acaatagcaa gacgttcatg aactaaaata    11160
gcattgtcac ttgtatagat acctgaccaa tctgggccgc ggtgacgtag taactttgat    11220
agttctagtg cttgttcgcg aagaggttta atgtctgatt tgatgtctag aattccgaat    11280
attgagcaca taactaattc cttctgggc tgcgtctgca gctaactttc taaatagtgt     11340
gtctaatttg ccacattgta gatttaatgc aaacattaat gataaaacat ttataaaaaa    11400
tgtaattcaa tgtggaatcg ataatttaat ggcttaaaag tgaagatcca ttaattgtga    11460
tggcgaggtg atagaccaat gtagaccta atgaataaag caggcacgat tgaatccatt     11520
caacgcaaag tggtactaac tattgtttta aacgttataa atagtgtttt aaaggttata    11580
agtaaataat ttaaaaacaa taataatcca catgcattaa atttatcatg ataaaccgct    11640
atatctcaat ggcaatttgg gataagtgta aaatatatgt aaaatgaatg agttgacttg    11700
ctttttttac actaagtgat gaaattaaag ctagatgtcg ttgttagcat tgattaataa    11760
cgtactaaaa tacgacatct agtatagaaa ttaaaaaac agttggtttt gatagcataa    11820
ctgcataaac taatcagctt attgtctgta atatttttgt aatttaaata ggtttaataa    11880
aattatatgt ctgataaata taaaccgtac gacctttcct ttaaaagac gttttgctg     11940 cctaagtttt ggcctgtgtg gttcggggtg tttgcaatat acttattagc ttttatgcca    12000
gtaaagccgc gtgataaatt tgctcgattc atagcgaaga aattgtttag tctaaaaatg    12060
atggcaaagc gtaaaaggt agcaaagatc aatttatcta tgtgcttccc tgaaatggat     12120
gatacggaac aagaccgtat aatcatggtc aatctagtta ctttttgtca aactatctta    12180
agttatgcag agccaagtgc gcgtagtcgt gcttataacc gtgaccgtat gatagtgcat    12240
ggtggcgaga atttatttcc gctacttgaa caaggtaagg cttgtatctt attagtgccg    12300
catagcttcg ctattgattt tgcaggttta cacattgctt cttatggcgc gccattttgt    12360
actatgttta acaattctga gaatgagttg ttcgattggc tgatgacacg tcaacgcgct    12420
atgtttggag gcactgttta tcaccgcaag gcagggctag gggctctagt taaatcactt    12480
aagagcggtg aaagctgtta ttacttacct gatgaagacc atggacctaa gcgtagtgta    12540
tttgcgcctt tatttgcgac tcaaaaagca actttacctg taatgggcaa gctagcagaa    12600
aaaacaaatg cactcgttgt tcctgtttat gcggcatata atgaatcact aggtaaattt    12660
```

```
gaaacctttta ttcgaccagc aatgcaaaac tttccatcag aaagcccaga acaagatgca   12720
gtgatgatga ataaagagat tgaagccttg attgaatgtg gtgttgatca atatatgtgg   12780
acacttagat tattgagaac acgtccggac ggtaaaaaaa tctactaata aagtttaata   12840
aacaccataa tcttcgttga atatggtgtt taccccctg aataccctct aaattaataa    12900
caaaaaaagc catttacgta acatctaatg atgatttagc ctgcacttgc tttgttttta   12960
gtcttaagag cctaataaac ttgatctagg tatagattct gtctttcttt acgtaacgcg   13020
atctattttt tttaaccgat agttgttata attagtttca tatgaaagag atatcgtttc   13080
agtaaaagct atttcgtttc aatagataat ttatttatag tcatattttc tgtaatgaca   13140
atcattttct catctagact atagataaga atacgaatta agtaagaaca ttaattttac   13200
aagaatataa aatatcccat cggagctata agaatgaaaa agactaaaat tgtttgtaca   13260
attggtccaa aaactgaatc agtagagaaa ctaacgagc ttgttaatgc aggcatgaac    13320
gttatgcgtt taaatttctc tcatggtaac tttgctgaac attcagtgcg tattcaaaat   13380
atccgtcaag taagtgaaaa cctgaataag aaaattgctg ttttactgga tactaaaggt   13440
ccagaaatcc gtacgattaa actagaaaac ggtgacgatg taatgttgac cgctggtcag   13500
tcattcacgt ttacaacaga cattaacgtg gtaggtaata aagactgtgt tgctgtaaca   13560
tatgctggtt ttgctaaaga ccttaatcct ggtgcaatca tccttgttga tgatggttta   13620
attgaaatgg aagttgttgc aacaactgac actgaagtta aatgtacagt attaaatact   13680
ggtgcacttg gtgaaaataa aggcgttaac ttacctaaca tcagtgtagg tctacctgca   13740
ttgtcagaaa aagataaagc tgatttagcg ttttggttgtg agcaagaagt tgattttgtt   13800
gctgcatcat ttattcgtaa ggctgatgat gtaagagaaa ttcgtgaaat cctatttaat   13860
aatggtggcg aaaacattca gattatctcg aaaattgaaa accaagaagg tgtagacaat   13920
ttcgatgaaa tcttagctga atcagacggt atcatggttg ctcgtggcga tctcggtgtt   13980
gagatcccag ttgaagaagt gatcatggca cagaagatga tgatcaaaaa atgtaataaa   14040
gcaggtaaag ttgtaattac tgcaacacaa atgcttgatt caatgatcag taacccacgt   14100
ccaacacgtg cagaagcggg cgatgttgcc aatgctgtgc ttgacggtac cgacgcggta   14160
atgctttctg gtgaaactgc gaaaggtaaa tacccagttg aagctgtgtc tatcatggca   14220
aacatctgtg aacgtactga taactcaatg tcttcggatt taggtgcgaa cattgttgct   14280
aaaagcatgc gcattacaga agctgtgtgt aaaggtgcgg tagaaacaac agaaaaattg   14340
tgtgctccac ttattgttgt tgcaactcgt ggcggtaaat cagcaaaatc tgttcgtaaa   14400
tacttcccga aagcaaatat tcttgctatc acaacaaatg aaaaagcagc gcaacagtta   14460
tgcctaacta aaggcgtaag cagctgcatc gttgagcaga ttgatagcac tgatgagttc   14520
taccgtaaag gtaagagct tgcattagca actggtttag ctaaagaagg cgatatcgtt   14580
gttatggtat caggtgcgtt agtaccatca ggtacaacga atacggcatc tgttcaccaa   14640
ctttaagttg ccatattgat attataaaaa agagagcgta tgctctcttt ttttatatct   14700
gtagtttata tgtctgtaca aaaaaatgat aaagagtaca taaactatta atatagcgta   14760
atatataatt attaacggtg atgaaagggt taaataaatg gatagtgcta aacataaaat   14820
tggcttagtc ctttctggcg gtggtgcgaa aggtattgct catcttggtg tattaaaata   14880
cctgttagag caagatataa gaccgaatgt aattgcgggt acaagtgctg gctctatggt   14940
tggtgcactt tattgctcag gacttgagat tgatgacatt ttacaattct tcatcgatgt   15000
```

```
aaaaccttt   tcttggaagt  ttacccgtgc  ccgtgctggc  tttatagacc  cggcaaaatt  15060
atatcctgaa  gtgctaaaat  atatcccgga  ggatagcttt  gagtaccttc  aacctgaatt  15120
gcgcattgtt  gccaccaaca  tgttactcgg  taaagagcat  atatttaaag  atggctccgt  15180
gattaatgcc  ttattagcat  cagccagcta  ccctttagtt  ttttctccga  tgatcattga  15240
cgatcaagtg  tattcagatg  gcggtattgt  taatcatttc  cccgtgagtg  tcattgaaga  15300
tgattgcgat  aaaataatcg  gcgtatacgt  gtcgcccatt  cgtcaggtcg  aagctgacga  15360
actctcgagt  ataaaagacg  tggtattacg  tgcgttcacg  ctgcagggta  gtggtgctga  15420
attagataaa  ctatcgcaat  gtgatgtgca  aatttatcca  gaagcgctat  tgaattacaa  15480
tacgtttgca  accgatgaaa  aatcattacg  ggagatctac  cagattggtt  atgatgctgc  15540
aaaagatcaa  catgacaacc  ttatggcatt  gaaagaaagt  atcaccacca  gcgaggttaa  15600
aaagaacgtc  tttagcaaat  ggtttggtga  taaacttgct  agcaacagcg  gcaaatagcg  15660
gcccacacgg  atttatacac  taggataatg  ggcgttaata  gcctcactgt  cgttgtgtgg  15720
tctctaattt  tagctaaatc  ttgtgttata  ctgacttcct  attaatcata  aacgatttat  15780
cacggtaaac  atgactcaaa  taaataaccc  gcttcacggc  atgacactcg  aaaaagtaat  15840
taacagtctc  gttgaacaat  atggctggga  tggtcttgga  tactacatca  acattcgttg  15900
ctttactgaa  aatccaagtg  ttaagtctag  tcttaaattt  ttacgtaaaa  cccttgggc   15960 acgtgataaa  gtagaagcgc  tatatatcaa  aatggtgact  gaaggctaac  tgtctccacg  16020
ctagcgaacc  gctgtttata  gttaatataa  gtactataag  cagggctcgt  taattcagta  16080
tgtaattaat  cctgaatacc  tccgcttatt  tcaacattgt  actctctaga  taacactctc  16140
aacattacac  cttcaacatc  acagcctcca  cataacatcc  gatgacatag  ccctgttatt  16200
tttcacattt  atctatatgc  tatatatttt  agccatttga  tcaattgagt  taatttctgc  16260
aatgacaaag  ataaccatc   atccagtaca  aatttattat  gaagataccg  accattctgg  16320
tgttgtttac  caccctaact  ttttaaaata  ctttgaacgt  gcacgtgagc  atgtgataaa  16380
tagtgactta  ctagcaacat  tgtggaatga  acgcggttta  ggttttgcgg  tgtataaagc  16440
caatatgact  tttcaggatg  gggtcgaatt  tgctgaagtg  tgtgatattc  gcacttcttt  16500
tgtcctagac  ggtaagtaca  aaacgatctg  gcgccaagaa  gtatggcgtc  cgaatgcgac  16560
tagggctgcc  gttatcggtg  atattgaaat  ggtgtgctta  gacaaacaaa  aacgtttaca  16620
gcccatccct  gatgatgtgt  tagctgcaat  ggttagtgaa  taaatggttc  atgcataaat  16680
agttaataca  tgattctggc  ccgtcacgtt  tacagataag  aggcatccga  tgcctccttc  16740
ctattaccaa  tactactgct  tatcccttc   taactatctt  tagcgtccat  aacacactga  16800
gcatttattc  tattaatcag  tgattgtgat  ttaattatct  tctatatatg  taatttaatg  16860
taattttcaa  tttatttta   gctacattaa  ggcttacgaa  tgtacgctaa  aatgagatgt  16920
cagactaatt  ttagcttatt  aatctgttag  ccgtttatat  tttataaaga  tgggatttaa  16980
cttaaatgca  attaattatg  gcgtaaatag  agtgaaaaca  tggctaatat  tcactaagtc  17040 ctgaattta   tataaagttt  aatctgttat  tttagcgttt  acctggtctt  atcagtgagg  17100
tttatagcca  ttattagtgg  gattgaagtg  atttttaaag  ctatgtatat  tattgcaaat  17160
ataaattgta  acaattaaga  ctttggacac  ttgagttcaa  tttcgaattg  attggcataa  17220
aatttaaaac  agctaaatct  acctcaatca  ttttagcaaa  tgtatgcagg  tagatttttt  17280 tcgccatta   agagtacact  tgtacgctag  gttttttgttt  agtgtgcaaa  tgaacgtttt  17340
gatgagcatt  gttttttagag  cacaaaatag  atccttacag  gagcaataac  gcaatggcta  17400
```

-continued

```
aaaagaacac cacatcgatt aagcacgcca aggatgtgtt aagtagtgat gatcaacagt   17460
taaattctcg cttgcaagaa tgtccgattg ccatcattgg tatggcatcg gtttttgcag   17520
atgctaaaaa cttggatcaa ttctgggata acatcgttga ctctgtggac gctattattg   17580
atgtgcctag cgatcgctgg aacattgacg accattactc ggctgataaa aaagcagctg   17640
acaagacata ctgcaaacgc ggtggtttca ttccagagct tgattttgat ccgatggagt   17700
ttggtttacc gccaaatatc ctcgagttaa ctgacatcgc tcaattgttg tcattaattg   17760
ttgctcgtga tgtattaagt gatgctggca ttggtagtga ttatgaccat gataaaattg   17820
gtatcacgct gggtgtcggt ggtggtcaga acaaatttc gccattaacg tcgcgcctac    17880
aaggcccggt attagaaaaa gtattaaaag cctcaggcat tgatgaagat gatcgcgcta   17940
tgatcatcga caaatttaaa aaagcctaca tcggctggga agagaactca ttcccaggca   18000
tgctaggtaa cgttattgct ggtcgtatcg ccaatcgttt tgattttggt ggtactaact   18060
gtgtggttga tgcggcatgc gctggctccc ttgcagctgt taaaatggcg atctcagact   18120
tacttgaata tcgttcagaa gtcatgatat cgggtggtgt atgttgtgat aactcgccat   18180
tcatgtatat gtcattctcg aaaacaccag catttaccac caatgatgat atccgtccgt   18240
ttgatgacga ttcaaaaggc atgctggttg gtgaaggtat tggcatgatg gcgtttaaac   18300
gtcttgaaga tgctgaacgt gacggcgaca aaatttattc tgtactgaaa ggtatcggta   18360
catcttcaga tggtcgtttc aaatctattt acgctccacg cccagatggc caagcaaaag   18420
cgctaaaacg tgcttatgaa gatgccggtt ttgcccctga acatgtggt ctaattgaag     18480 gccatggtac gggtaccaaa gcgggtgatg ccgcagaatt tgctggcttg accaaacact   18540
ttggcgccgc cagtgatgaa aagcaatata tcgccttagg ctcagttaaa tcgcaaattg   18600
gtcatactaa atctgcggct ggctctgcgg gtatgattaa ggcggcatta cgctgcatc    18660 ataaaatctt acctgcaacg atccatatcg ataaaccaag tgaagccttg gatatcaaaa   18720
acagcccgtt ataccttaaac agcgaaacgc gtccttggat gccacgtgaa gatggtattc   18780
cacgtcgtgc aggtatcagc tcatttggtt ttggcggcac caacttccat attattttag   18840
aagagtatcg cccaggtcac gatagcgcat atcgcttaaa ctcagtgagc caaactgtgt   18900
tgatctcggc aaacgaccaa caaggtattg ttgctgagtt aaataactgg cgtactaaac   18960
tggctgtcga tgctgatcat caagggtttg tatttaatga gttagtgaca acgtggccat   19020
taaaaccccc atccgttaac caagctcgtt taggttttgt tgcgcgtaat gcaaatgaag   19080
cgatcgcgat gattgatacg gcattgaaac aattcaatgc gaacgcagat aaaatgacat   19140
ggtcagtacc taccggggtt tactatcgtc aagccggtat tgatgcaaca ggtaaagtgg   19200
ttgcgctatt ctcagggcaa ggttcgcaat acgtgaacat gggtcgtgaa ttaacctgta   19260
acttcccaag catgatgcac agtgctgcgg cgatggataa agagttcagt gccgctggtt   19320
taggccagtt atctgcagtt actttcccta tccctgtta tacggatgcc gagcgtaagc     19380
tacaagaaga gcaattacgt ttaacgcaac atgcgcaacc agcgattggt agtttgagtg   19440
ttggtctgtt caaaacgttt aagcaagcag gttttaaagc tgattttgct gccggtcata   19500
gtttcggtga gttaaccgca ttatgggctg ccgatgtatt gagcgaaagc gattacatga   19560
tgttagcgcg tagtcgtggt caagcaatgg ctgcgccaga gcaacaagat tttgatgcag   19620
gtaagatggc cgctgttgtt ggtgatccaa agcaagtcgc tgtgatcatt gatacccttg   19680
atgatgtctc tattgctaac ttcaactcga ataaccaagt tgttattgct ggtactacgg   19740
```

```
agcaggttgc tgtagcggtt acaaccttag gtaatgctgg tttcaaagtt gtgccactgc   19800
cggtatctgc tgcgttccat acacctttag ttcgtcacgc gcaaaaacca tttgctaaag   19860
cggttgatag cgctaaattt aaagcgccaa gcattccagt gtttgctaat ggcacaggct   19920
tggtgcattc aagcaaaccg aatgacatta agaaaaacct gaaaaccac atgctggaat    19980 ctgttcattt caatcaagaa attgacaaca tctatgctga tggtggccgc gtatttatcg   20040
aatttggtcc aaagaatgta ttaactaaat tggttgaaaa cattctcact gaaaaatctg   20100
atgtgactgc tatcgcggtt aatgctaatc ctaaacaacc tgcggacgta caaatgcgcc   20160
aagctgcgct gcaaatggca gtgcttggtg tcgcattaga caatattgac ccgtacgacg   20220
ccgttaagcg tccacttgtt gcgccgaaag catcaccaat gttgatgaag ttatctgcag   20280
cgtcttatgt tagtccgaaa acgaagaaag cgtttgctga tgcattgact gatggctgga   20340
ctgttaagca agcgaaagct gtacctgctg ttgtgtcaca accacaagtg attgaaaaga   20400
tcgttgaagt tgaaaagata gttgaacgca ttgtcgaagt agagcgtatt gtcgaagtag   20460
aaaaaatcgt ctacgttaat gctgacggtt cgcttatatc gcaaaataat caagacgtta   20520
acagcgctgt tgttagcaac gtgactaata gctcagtgac tcatagcagt gatgctgacc   20580
ttgttgcctc tattgaacgc agtgttggtc aatttgttgc acaccaacag caattattaa   20640
atgtacatga acagtttatg caaggtccac aagactacgc gaaaacagtg cagaacgtac   20700
ttgctgcgca gacgagcaat gaattaccgg aaagtttaga ccgtacattg tctatgtata   20760
acgagttcca atcagaaacg ctacgtgtac atgaaacgta cctgaacaat cagacgagca   20820
acatgaacac catgcttact ggtgctgaag ctgatgtgct agcaaccca ataactcagg    20880 tagtgaatac agccgttgcc actagtcaca aggtagttgc tccagttatt gctaatacag   20940
tgacgaatgt tgtatctagt gtcagtaata acgcggcggt tgcagtgcaa actgtggcat   21000
tagcgcctac gcaagaaatc gctccaacag tcgctactac gccagcaccc gcattggttg   21060
ctatcgtggc tgaacctgtg attgttgcgc atgttgctac agaagttgca ccaattacac   21120
catcagttac accagttgtc gcaactcaag cggctatcga tgtagcaact attaacaaag   21180
taatgttaga agttgttgct gataaaaccg gttatccaac ggatatgctg gaactgagca   21240
tggacatgga agctgactta ggtatcgact caatcaaacg tgttgagata ttaggcgcag   21300
tacaggaatt gatccctgac ttacctgaac ttaatcctga agatcttgct gagctacgca   21360
cgcttggtga gattgtcgat tacatgaatt caaaagccca ggctgtagct cctacaacag   21420
tacctgtaac aagtgcacct gtttcgcctg catctgctgg tattgattta gcccacatcc   21480
aaaacgtaat gttagaagtg gttgcagaca aaaccggtta cccaacagac atgctagaac   21540
tgagcatgga tatggaagct gacttaggta ttgattcaat caagcgtgtg gaaatcttag   21600
gtgcagtaca ggagatcata actgatttac ctgagctaaa ccctgaagat cttgctgaat   21660
tacgcaccct aggtgaaatc gttagttaca tgcaaagcaa agcgccagtc gctgaaagtg   21720
cgccagtggc gacggctcct gtagcaacaa gctcagcacc gtctatcgat ttgaaccaca   21780
ttcaaacagt gatgatggat gtagttgcag ataagactgg ttatccaact gacatgctag   21840
aacttggcat ggacatggaa gctgatttag gtatcgattc aatcaaacgt gtggaaatat   21900
taggcgcagt gcaggagatc atcactgatt tacctgagct aaacccagaa gacctcgctg   21960
aattacgcac gctaggtgaa atcgttagtt acatgcaaag caaagcgcca gtcgctgaga   22020
gtgcgccagt agcgacggct tctgtagcaa caagctctgc accgtctatc gatttaaacc   22080
atatccaaac agtgatgatg gaagtggttg cagacaaaac cggttatcca gtagacatgt   22140
```

```
tagaacttgc tatggacatg gaagctgacc taggtatcga ttcaatcaag cgtgtagaaa    22200
ttttaggtgc ggtacaggaa atcattactg acttacctga gcttacccct gaagatcttg    22260
ctgaactacg tacattaggt gaaatcgtta gttacatgca aagcaaagcg cccgtagctg    22320
aagcgcctgc agtacctgtt gcagtagaaa gtgcacctac tagtgtaaca agctcagcac    22380
cgtctatcga tttagaccac atccaaaatg taatgatgga tgttgttgct gataagactg    22440
gttatcctgc caatatgctt gaattagcaa tggacatgga agccgacctt ggtattgatt    22500
caatcaagcg tgttgaaatt ctaggcgcgg tacaggagat cattactgat ttacctgaac    22560
taaacccaga agacttagct gaactacgta cgttagaaga aattgtaacc tacatgcaaa    22620
gcaaggcgag tggtgttact gtaaatgtag tggctagccc tgaaaataat gctgtatcag    22680
atgcatttat gcaaagcaat gtggcgacta tcacagcggc cgcagaacat aaggcggaat    22740
ttaaaccggc gccgagcgca accgttgcta tctctcgtct aagctctatc agtaaaataa    22800
gccaagattg taaaggtgct aacgccttaa tcgtagctga tggcactgat aatgctgtgt    22860
tacttgcaga ccacctattg caaactggct ggaatgtaac tgcattgcaa ccaacttggg    22920
tagctgtaac aacgacgaaa gcatttaata agtcagtgaa cctggtgact ttaaatggcg    22980
ttgatgaaac tgaaatcaac aacattatta ctgctaacgc acaattggat gcagttatct    23040
atctgcacgc aagtagcgaa attaatgcta tcgaataccc acaagcatct aagcaaggcc    23100
tgatgttagc cttcttatta gcgaaattga gtaaagtaac tcaagccgct aaagtgcgtg    23160
gcgcctttat gattgttact cagcagggtg gttcattagg ttttgatgat atcgattctg    23220
ctacaagtca tgatgtgaaa acagacctag tacaaagcgg cttaaacggt ttagttaaga    23280
cactgtctca cgagtgggat aacgtattct gtcgtgcggt tgatattgct tcgtcattaa    23340
cggctgaaca agttgcaagc cttgttagtg atgaactact tgatgctaac actgtattaa    23400
cagaagtggg ttatcaacaa gctggtaaag gccttgaacg tatcacgtta actggtgtgg    23460
ctactgacag ctatgcatta acagctggca ataacatcga tgctaactcg gtatttttag    23520
tgagtggtgg cgcaaaaggt gtaactgcac attgtgttgc tcgtatagct aaagaatatc    23580
agtctaagtt catcttattg ggacgttcaa cgttctcaag tgacgaaccg agctgggcaa    23640
gtggtattac tgatgaagcg gcgttaaaga aagcagcgat gcagtctttg attacagcag    23700
gtgataaacc aacacccgtt aagatcgtac agctaatcaa accaatccaa gctaatcgtg    23760
aaattgcgca aaccttgtct gcaattaccg ctgctggtgg ccaagctgaa tatgtttctg    23820
cagatgtaac taatgcagca agcgtacaaa tggcagtcgc tccagctatc gctaagttcg    23880
gtgcaatcac tggcatcatt catggcgcgg gtgtgttagc tgaccaattc attgagcaaa    23940
aaacactgag tgattttgag tctgtttaca gcactaaaat tgacggtttg ttatcgctac    24000
tatcagtcac tgaagcaagc aacatcaagc aattggtatt gttctcgtca gcggctggtt    24060
tctacggtaa ccccggccag tctgattact cgattgccaa tgagatctta aataaaaccg    24120
cataccgctt taaatcattg cacccacaag ctcaagtatt gagctttaac tggggtcctt    24180
gggacggtgg catggtaacg cctgagctta acgtatgtt tgaccaacgt ggtgtttaca    24240
ttattccact tgatgcaggt gcacagttat tgctgaatga actagccgct aatgataacc    24300
gttgtccaca aatcctcgtg ggtaatgact tatctaaaga tgctagctct gatcaaaagt    24360
ctgatgaaaa gagtactgct gtaaaaaagc cacaagttag tcgtttatca gatgctttag    24420
taactaaaag tatcaaagcg actaacagta gctctttatc aaacaagact agtgctttat    24480
```

```
cagacagtag tgcttttcag gttaacgaaa accactttt agctgaccac atgatcaaag    24540
gcaatcaggt attaccaacg gtatgcgcga ttgcttggat gagtgatgca gcaaaagcga    24600
cttatagtaa ccgagactgt gcattgaagt atgtcggttt cgaagactat aaattgttta    24660
aaggtgtggt tttgatggc aatgaggcgg cggattacca aatccaattg tcgcctgtga    24720
caagggcgtc agaacaggat tctgaagtcc gtattgccgc aaagatcttt agcctgaaaa    24780
gtgacggtaa acctgtgttt cattatgcag cgacaatatt gttagcaact cagccactta    24840
atgctgtgaa ggtagaactt ccgacattga cagaaagtgt tgatagcaac aataaagtaa    24900
ctgatgaagc acaagcgtta tacagcaatg gcaccttgtt ccacggtgaa agtctgcagg    24960
gcattaagca gatattaagt tgtgacgaca agggcctgct attggcttgt cagataaccg    25020
atgttgcaac agctaagcag ggatccttcc cgttagctga caacaatatc tttgccaatg    25080
atttggttta tcaggctatg ttggtctggg tgcgcaaaca atttggttta ggtagcttac    25140
cttcggtgac aacggcttgg actgtgtatc gtgaagtggt tgtagatgaa gtattttatc    25200
tgcaacttaa tgttgttgag catgatctat tgggttcacg cggcagtaaa gcccgttgtg    25260
atattcaatt gattgctgct gatatgcaat tacttgccga agtgaaatca gcgcaagtca    25320
gtgtcagtga cattttgaac gatatgtcat gatcgagtaa ataataacga taggcgtcat    25380
ggtgagcatg gcgtctgctt tcttcatttt ttaacattaa caatattaat agctaaacgc    25440
ggttgcttta aaccaagtaa acaagtgctt ttagctatta ctattccaaa caggatatta    25500
aagagaatat gacggaatta gctgttattg gtatggatgc taaatttagc ggacaagaca    25560
atattgaccg tgtggaacgc gctttctatg aaggtgctta tgtaggtaat gttagccgcg    25620
ttagtaccga atctaatgtt attagcaatg gcgaagaaca agttattact gccatgacag    25680
ttcttaactc tgtcagtcta ctagcgcaaa cgaatcagtt aaatatagct gatatcgcgg    25740
tgttgctgat tgctgatgta aaaagtgctg atgatcagct tgtagtccaa attgcatcag    25800
caattgaaaa acagtgtgcg agttgtgttg ttattgctga tttaggccaa gcattaaatc    25860
aagtagctga tttagttaat aaccaagact gtcctgtggc tgtaattggc atgaataact    25920
cggttaattt atctcgtcat gatcttgaat ctgtaactgc aacaatcagc tttgatgaaa    25980
ccttcaatgg ttataacaat gtagctgggt tcgcgagttt acttatcgct tcaactgcgt    26040
ttgccaatgc taagcaatgt tatatatacg ccaacattaa gggcttcgct caatcgggcg    26100
taaatgctca atttaacgtt ggaaacatta gcgatactgc aaagaccgca ttgcagcaag    26160
ctagcataac tgcagagcag gttggtttgt tagaagtgtc agcagtcgct gattcggcaa    26220
tcgcattgtc tgaaagccaa ggtttaatgt ctgcttatca tcatacgcaa actttgcata    26280
ctgcattaag cagtgcccgt agtgtgactg gtgaaggcgg gtgtttttca caggtcgcag    26340
gtttattgaa atgtgtaatt ggtttacatc aacgttatat tccggcgatt aaagattggc    26400
aacaaccgag tgacaatcaa atgtcacggt ggcggaattc accattctat atgcctgtag    26460
atgctcgacc ttggttccca catgctgatg gctctgcaca cattgccgct tatagttgtg    26520
tgactgctga cagctattgt catattcttt tacaagaaaa cgtcttacaa gaacttgttt    26580
tgaaagaaac agtcttgcaa gataatgact taactgaaag caagcttcag actcttgaac    26640
aaaacaatcc agtagctgat ctgcgcacta atggttactt tgcatcgagc gagttagcat    26700
taatcatagt acaaggtaat gacgaagcac aattacgctg tgaattagaa actattacag    26760
ggcagttaag tactactggc ataagtacta tcagtattaa acagatcgca gcagactgtt    26820
atgcccgtaa tgatactaac aaagcctata gcgcagtgct tattgccgag actgctgaag    26880
```

```
agttaagcaa agaaataacc ttggcgtttg ctggtatcgc tagcgtgttt aatgaagatg   26940
ctaaagaatg gaaaacccg aagggcagtt atttaccgc gcagcctgca aataaacagg    27000
ctgctaacag cacacagaat ggtgtcacct tcatgtaccc aggtattggt gctacatatg   27060
ttggtttagg gcgtgatcta tttcatctat tcccacagat ttatcagcct gtagcggctt   27120
tagccgatga cattggcgaa agtctaaaag atactttact taatccacgc agtattagtc   27180
gtcatagctt taaagaactc aagcagttgg atctggacct gcgcggtaac ttagccaata   27240
tcgctgaagc cggtgtgggt tttgcttgtg tgtttaccaa ggtatttgaa gaagtctttg   27300
ccgttaaagc tgactttgct acaggttata gcatgggtga agtaagcatg tatgcagcac   27360
taggctgctg gcagcaaccg ggattgatga gtgctcgcct tgcacaatcg aatacctta   27420 atcatcaact ttgcggcgag ttaagaacac tacgtcagca ttggggcatg gatgatgtag   27480
ctaacggtac gttcgagcag atctgggaaa cctataccat taaggcaacg attgaacagg   27540
tcgaaattgc ctctgcagat gaagatcgtg tgtattgcac cattatcaat acacctgata   27600
gcttgttgtt agccggttat ccagaagcct gtcagcgagt cattaagaat ttaggtgtgc   27660
gtgcaatggc attgaatatg gcgaacgcaa ttcacagcgc gccagcttat gccgaatacg   27720
atcatatggt tgagctatac catatggatg ttactccacg tattaatacc aagatgtatt   27780
caagctcatg ttatttaccg attccacaac gcagcaaagc gatttcccac agtattgcta   27840
aatgtttgtg tgatgtggtg gatttcccac gtttggttaa taccttacat gacaaaggtg   27900
cgcgggtatt cattgaaatg ggtccaggtc gttcgttatg tagctgggta gataagatct   27960
tagttaatgg cgatggcgat aataaaaagc aaagccaaca tgtatctgtt cctgtgaatg   28020
ccaaaggcac cagtgatgaa cttacttata ttcgtgcgat tgctaagtta attagtcatg   28080
gcgtgaattt gaatttagat agcttgttta acgggtcaat cctggttaaa gcaggccata   28140
tagcaaacac gaacaaatag tcaacatcga tatctagcgc tggtgagtta tacctcatta   28200
gttgaaatat ggatttaaag agagtaatta tggaaaatat tgcagtagta ggtattgcta   28260
atttgttccc gggctcacaa gcaccggatc aattttggca gcaattgctt gaacaacaag   28320
attgccgcag taaggcgacc gctgttcaaa tgggcgttga tcctgctaaa tataccgcca   28380
acaaaggtga cacagataaa ttttactgtg tgcacggcgg ttacatcagt gatttcaatt   28440
ttgatgcttc aggttatcaa ctcgataatg attatttagc cggtttagat gaccttaatc   28500
aatgggggct ttatgttacg aaacaagccc ttaccgatgc gggttattgg ggcagtactg   28560
cactagaaaa ctgtggtgtg attttaggta atttgtcatt cccaactaaa tcatctaatc   28620
agctgtttat gcctttgtat catcaagttg ttgataatgc cttaaaggcg gtattacatc   28680
ctgattttca attaacgcat tacacagcac cgaaaaaaac acatgctgac aatgcattag   28740
tagcaggtta tccagctgca ttgatcgcgc aagcggcggg tcttggtggt tcacattttg   28800
cactggatgc ggcttgtgct tcatcttgtt atagcgttaa gttagcgtgt gattacctgc   28860
atacgggtaa agccaacatg atgcttgctg gtgcggtatc tgcagcagat cctatgttcg   28920
taaatatggg tttctcgata ttccaagctt acccagctaa caatgtacat gccccgtttg   28980
accaaaattc acaaggtcta tttgccggtg aaggcgcggg catgatggta ttgaaacgtc   29040
aaagtgatgc agtacgtgat ggtgatcata tttacgccat tattaaaggc ggcgcattat   29100
cgaatgacgg taaaggcgag tttgtattaa gcccgaacac caagggccaa gtattagtat   29160
atgaacgtgc ttatgccgat gcagatgttg acccgagtac agttgactat attgaatgtc   29220
```

-continued

```
atgcaacggg cacacctaag ggtgacaatg ttgaattgcg ttcgatggaa accttttca    29280 gtcgcgtaaa taacaaacca ttactgggct cggttaaatc taaccttggt catttgttaa   29340
ctgccgctgg tatgcctggc atgaccaaag ctatgttagc gctaggtaaa ggtcttattc   29400
ctgcaacgat taacttaaag caaccactgc aatctaaaaa cggttacttt actggcgagc   29460
aaatgccaac gacgactgtg tcttggccaa caactccggg tgccaaggca gataaaccgc   29520
gtaccgcagg tgtgagcgta tttggttttg gtggcagcaa cgcccatttg gtattacaac   29580
agccaacgca aacactcgag actaatttta gtgttgctaa accacgtgag cctttggcta   29640
ttattggtat ggacagccat tttggtagtg ccagtaattt agcgcagttc aaaaccttat   29700
taaataataa tcaaaatacc ttccgtgaat taccagaaca acgctggaaa ggcatggaaa   29760
gtaacgctaa cgtcatgcag tcgttacaat tacgcaaagc gcctaaaggc agttacgttg   29820
aacagctaga tattgatttc ttgcgttta aagtaccgcc taatgaaaaa gattgcttga    29880
tcccgcaaca gttaatgatg atgcaagtgg cagacaatgc tgcgaaagac ggaggtctag   29940
ttgaaggtcg taatgttgcg gtattagtag cgatgggcat ggaactggaa ttacatcagt   30000
atcgtggtcg cgttaatcta accacccaaa ttgaagacag cttattacag caaggtatta   30060
acctgactgt tgagcaacgt gaagaactga ccaatattgc taaagacggt gttgcctcgg   30120
ctgcacagct aaatcagtat acgagtttca ttggtaatat tatggcgtca cgtatttcgg   30180
cgttatggga ttttttctggt cctgctatta ccgtatcggc tgaagaaaac tctgtttatc   30240
gttgtgttga attagctgaa aatctatttc aaaccagtga tgttgaagcc gttattattg   30300
ctgctgttga tttgtctggt tcaattgaaa acattacttt acgtcagcac tacggtccag   30360
ttaatgaaaa gggatctgta agtgaatgtg gtccggttaa tgaaagcagt tcagtaacca   30420
acaatattct tgatcagcaa caatggctgg tgggtgaagg cgcagcggct attgtcgtta   30480
aaccgtcatc gcaagtcact gctgagcaag tttatgcgcg tattgatgcg gtgagttttg   30540
cccctggtag caatgcgaaa gcaattacga ttgcagcgga taaagcatta acacttgctg   30600
gtatcagtgc tgctgatgta gctagtgttg aagcacatgc aagtggtttt agtgccgaaa   30660
ataatgctga aaaaccgcg ttaccgactt tatcccaag cgcaagtatc agttcggtga    30720
aagccaatat tggtcatacg tttaatgcct cgggtatggc gagtattatt aaaacggcgc   30780
tgctgttaga tcagaatacg agtcaagatc agaaaagcaa acatattgct attaacggtc   30840
taggtcgtga taacagctgc gcgcatctta tcttatcgag ttcagcgcaa gcgcatcaag   30900
ttgcaccagc gcctgtatct ggtatggcca agcaacgccc acagttagtt aaaaccatca   30960
aactcggtgg tcagttaatt agcaacgcga ttgttaacag tgcgagttca tctttacacg   31020
ctattaaagc gcagtttgcc ggtaagcact aaacaaagt taaccagcca gtgatgatgg   31080
ataacctgaa gccccaaggt attagcgctc atgcaaccaa tgagtatgtg gtgactggag   31140
ctgctaacac tcaagcttct aacattcaag catctcatgt tcaagcgtca agtcatgcac   31200
aagagatagc accaaaccaa gttcaaaata tgcaagctac agcagccgct gtaagttcac   31260
ccctttctca acatcaacac acagcgcagc ccgtagcggc accgagcgtt gttggagtga   31320
ctgtgaaaca taaagcaagt aaccaaattc atcagcaagc gtctacgcat aaagcatttt   31380
tagaaagtcg tttagctgca cagaaaaacc tatcgcaact tgttgaattg caaaccaagc   31440
tgtcaatcca aactggtagt gacaatacat ctaacaatac tgcgtcaaca agcaatacag   31500
tgctaacaaa tcctgtatca gcaacgccat taacacttgt gtctaatgcg cctgtagtag   31560
cgacaaacct aaccagtaca gaagcaaaag cgcaagcagc tgctacacaa gctggttttc   31620
```

```
agataaaagg acctgttggt tacaactatc caccgctgca gttaattgaa cgttataata    31680
aaccagaaaa cgtgatttac gatcaagctg atttggttga attcgctgaa ggtgatattg    31740
gtaaggtatt tggtgctgaa tacaatatta ttgatggcta ttcgcgtcgt gtacgtctgc    31800
caacctcaga ttacttgtta gtaacacgtg ttactgaact tgatgccaag gtgcatgaat    31860
acaagaaatc atacatgtgt actgaatatg atgtgcctgt tgatgcaccg ttcttaattg    31920
atggtcagat cccttggtct gttgccgtcg aatcaggcca gtgtgatttg atgttgattt    31980
catatatcgg tattgatttc caagcgaaag gcgaacgtgt ttaccgttta cttgattgtg    32040
aattaacttt ccttgaagag atggcttttg gtggcgatac tttacgttac gagatccaca    32100
ttgattcgta tgcacgtaac ggcgagcaat tattattctt cttccattac gattgttacg    32160 tagggataa gaaggtactt atcatgcgta atggttgtgc tggtttcttt actgacgaag    32220
aactttctga tggtaaaggc gttattcata acgacaaaga caaagctgag tttagcaatg    32280
ctgttaaatc atcattcacg ccgttattac aacataaccg tggtcaatac gattataacg    32340
acatgatgaa gttggttaat ggtgatgttg ccagttgttt tggtccgcaa tatgatcaag    32400
gtggccgtaa tccatcattg aaattctcgt ctgagaagtt cttgatgatt gaacgtatta    32460
ccaagataga cccaaccggt ggtcattggg actaggcct gttagaaggt cagaaagatt    32520
tagaccctga gcattggtat ttcccttgtc actttaaagg tgatcaagta atggctggtt    32580
cgttgatgtc ggaaggttgt ggccaaatgg cgatgttctt catgctgtct cttggtatgc    32640
ataccaatgt gaacaacgct cgtttccaac cactaccagg tgaatcacaa acggtacgtt    32700
gtcgtgggca agtactgcca cagcgcaata ccttaactta ccgtatggaa gttactgcga    32760
tgggtatgca tccacagcca ttcatgaaag ctaatattga tattttgctt gacggtaaag    32820
tggttgttga tttcaaaaac ttgagcgtga tgatcagcga acaagatgag cattcagatt    32880
accctgtaac actgccgagt aatgtggcgc ttaaagcgat tactgcacct gttgcgtcag    32940
tagcaccagc atcttcaccc gctaacagcg cggatctaga cgaacgtggt gttgaaccgt    33000
ttaagtttcc tgaacgtccg ttaatgcgtg ttgagtcaga cttgtctgca ccgaaaagca    33060
aaggtgtgac accgattaag cattttgaag cgcctgctgt tgctggtcat catagagtgc    33120
ctaaccaagc accgtttaca ccttggcata tgtttgagtt tgcgacgggt aatatttcta    33180
actgtttcgg tcctgatttt gatgtttatg aaggtcgtat tccacctcgt acaccttgtg    33240
gcgatttaca agttgttact caggttgtag aagtgcaggg cgaacgtctt gatcttaaaa    33300
atccatcaag ctgtgtagct gaatactatg taccggaaga cgcttggtac tttactaaaa    33360
acagccatga aaactggatg ccttattcat taatcatgga aattgcattg caaccaaatg    33420
gctttatttc tggttacatg ggcacgacgc ttaaataccc tgaaaaagat ctgttcttcc    33480
gtaaccttga tggtagcggc acgttattaa agcagattga tttacgcggc aagaccattg    33540
tgaataaatc agtcttggtt agtacggcta ttgctggtgg cgcgattatt caaagtttca    33600
cgtttgatat gtctgtagat ggcgagctat tttatactgg taaagctgta tttggttact    33660
ttagtggtga atcactgact aaccaactgg gcattgataa cggtaaaacg actaatgcgt    33720
ggtttgttga taacaataccc cccgcagcga atattgatgt gtttgattta actaatcagt    33780
cattggctct gtataaagcg cctgtggata aaccgcatta taaattggct ggtggtcaga    33840
tgaactttat cgatacagtg tcagtggttg aaggcggtgg taaagcgggc gtggcttatg    33900
tttatggcga acgtacgatt gatgctgatg attggttctt ccgttatcac ttccaccaag    33960
```

-continued

```
atccggtgat gccaggttca ttaggtgttg aagctattat tgagttgatg cagacctatg    34020
cgcttaaaaa tgatttgggt ggcaagtttg ctaacccacg tttcattgcg ccgatgacgc    34080
aagttgattg gaaataccgt gggcaaatta cgccgctgaa taaacagatg tcactggacg    34140
tgcatatcac tgagatcgtg aatgacgctg gtgaagtgcg aatcgttggt gatgcgaatc    34200
tgtctaaaga tggtctgcgt atttatgaag ttaaaaacat cgttttaagt attgttgaag    34260
cgtaaagggt caagtgtaac gtgcttaagc gccgcattgg ttaaagacgc tttgcacgcc    34320
gtgaatccgt ccatggaggc ttggggttgg catccatgcc aacaacagca agcttacttt    34380
aatcaatacg gcttggtgtc catttagacg cctcgaactt agtagttaat agacaaaata    34440
atttagctgt ggaatgaata tagtaagtaa tcattcggca gctacaaaaa aggaattaag    34500
aatgtcgagt ttaggtttta acaataacaa cgcaattaac tgggcttgga aagtagatcc    34560
agcgtcagtt catacacaag atgcagaaat taaagcagct ttaatggatc taactaaacc    34620
tctctatgtg gcgaataatt caggcgtaac tggtatagct aatcatacgt cagtagcagg    34680
tgcgatcagc aataacatcg atgttgatgt attggcgttt gcgcaaaagt taaacccaga    34740
agatctgggt gatgatgctt acaagaaaca gcacggcgtt aaatatgctt atcatggcgg    34800
tgcgatggca aatggtattg cctcggttga attggttgtt gcgttaggta aagcagggct    34860
gttatgttca tttggtgctg caggtctagt gcctgatgcg gttgaagatg caattcgtcg    34920
tattcaagct gaattaccaa atggccctta tgcggttaac ttgatccatg caccagcaga    34980
agaagcatta gagcgtggcg cggttgaacg tttcctaaaa cttggcgtca agacggtaga    35040
ggcttcagct taccttggtt taactgaaca cattgtttgg tatcgtgctg ctggtctaac    35100
taaaaacgca gatggcagtg ttaatatcgg taacaaggtt atcgctaaag tatcgcgtac    35160
cgaagttggt cgccgcttta tggaacctgc accgcaaaaa ttactggata agttattaga    35220
acaaaataag atcacccctg aacaagctgc tttagcgttg cttgtaccta tggctgatga    35280
tattactggg gaagcggatt ctggtggtca tacagataac cgtccgtttt taacattatt    35340
accgacgatt attggtctgc gtgatgaagt gcaagcgaag tataacttct ctcctgcatt    35400
acgtgttggt gctggtggtg gtatcggaac gcctgaagca gcactcgctg catttaacat    35460
gggcgcggct tatatcgttc tgggttctgt gaatcaggcg tgtgttgaag cgggtgcatc    35520
tgaatatact cgtaaactgt tatcgacagt tgaaatggct gatgtgacta tggcacctgc    35580
tgcagatatg tttgaaatgg gtgtgaagct gcaagtatta aaacgcggtt ctatgttcgc    35640
gatgcgtgcg aagaaactgt atgacttgta tgtggcttat gactcgattg aagatatccc    35700
agctgctgaa cgtgagaaga ttgaaaaaca aatcttccgt gcaaacctag acgagatttg    35760
ggatggcact atcgctttct ttactgaacg cgatccagaa atgctagccc gtgcaacgag    35820
tagtcctaaa cgtaaaatgg cacttatctt ccgttggtat cttggccttt cttcacgctg    35880
gtcaaacaca ggcgagaagg gacgtgaaat ggattatcag atttgggcag gcccaagttt    35940
aggtgcattc aacagctggg tgaaaggttc ttaccttgaa gactataccc gccgtggcgc    36000
tgtagatgtt gctttgcata tgcttaaagg tgctgcgtat ttacaacgtg taaaccagtt    36060
gaaattgcaa ggtgttagct taagtacaga attggcaagt tatcgtacga gtgattaatg    36120
ttacttgatg atatgtgaat taattaaagc gcctgagggc gctttttttg gtttttaact    36180
caggtgttgt aactcgaaat tgcccctttc aagttagatc gattactcac tcacaatatg    36240
ttgatatcgc acttgccata tacttgctca tccaaagccc tatattgata atggtgttaa    36300 tagtcttaa tatccgagtc tttcttcagc ataatactaa tatagagact cgaccaatgt    36360
```

```
taaacacaac aaagaatata ttcttgtgta ctgccttatt attaacgagt gcgagtacga   36420
cagctactac gctaaacaat tcgatatcag caattgaaca acgtatttct ggtcgtatcg   36480
gtgtggctgt tttagatacg caaaataaac aaacgtgggc ttacaatggt gatgcacatt   36540
ttccgatgat gagtacattc aaaaccctcg cttgcgcgaa aatgctaagt gaatcgacaa   36600
atggtaatct ggatcccagt actagctcat tgataaaggc tgaagaatta atcccttggt   36660
caccagtcac taaaacgttt gtgaataaca ctattacagt ggcgaaagcg tgtgaagcaa   36720
caatgctgac cagtgataat accgcggcta atattgtttt acagtatatc ggaggccctc   36780
aaggcgttac tgcattcttg cgagaaattg gtgatgaaga gagtcagtta gatcgtatag   36840
aacctgaatt gaatgaagct aaggtcggag acttgcgtga taccacgaca ccgaaagcca   36900
tagttaccac gctcaacaaa ctactacttg gtgatgttct acttgatttg gataaaaacc   36960
aacttaaaac atggatgcaa aataataaag tgtcagatcc tttactgcgt tctatattac   37020
cgcaaggctg gtttattgcc gaccgctcag gtgcgggtgg taatggttct cgaggtataa   37080
ctgctatgct ttggcactcc gagcgtcaac cgctaatcat cagtatttat ttaaccgaaa   37140
ctgagttagc aatggcaatg cgcaatgaga ttattgttga gatcggtaag ctgatattca   37200
aagaatacgc ggtgaaataa taagttatt ttttgataata ctttaacgag cgtagctatc   37260
gaagtgaggg cgtcaattag acaccttgc ttcccctaca aaatctaatg tgtattacct   37320
cggctagtac aattgcccta agttatttct gtccagcttt ggcttagtgc aattgcgtta   37380
gccaatgtga acaccaaggg actttgtcgt accataacta ccaagcgact ttgtcgtttt   37440 tatctttct tagacaaaca gaggttaaat gagtgacgcc ttccaaatca caggaatgaa   37500
tccgcatttc aataaaatct aacccgtacc aactccgtac aagttgatct ttagttgttt   37560
aaaatctata ataaattcaa ttacggaatt aatccgtaca actggaggtt ttatggctac   37620
tgcaagactt gatatccgtt tggatgaaga aatcaaagct aaggctgaga aagcatcagc   37680
tttactcggc ttaaaaagtt taaccgaata cgttgttcgc ttaatggacg aagattcaac   37740
taaagtagtt tctgagcatg agagtattac cgttgaagcg aatgtattcg accaatttat   37800
ggctgcttgt gatgaagcga aagccccaaa taaagcatta cttgaagccg ctgtatttac   37860
tcagaatggt gagtttaagt gagttattcc aaacgtttca aagaactgga taaatcaaaa   37920
catgacagag catcatttga ctgtggcgaa aaagagctaa atgattttat ccaaactcaa   37980
gcagccaaac atatgcaagc aggtattagc cgcactctgg ttttacctgc ttctgcgccg   38040
ttaccaaaca aaaatatcc aatttgctca ttttatagta tcgcgccaag ctcaattagc   38100
cgcgatacgt taccacaagc aatggctaaa aagttaccac gttatcctat ccctgttttt   38160
cttttggctc aacttgccgt ccataaagag tttcatggga gtgggttagg caaagttagc   38220
ttaattaaag cgttagagta cctttgggaa attaactctc acatgagagc ttacgccatc   38280
gttgttgatt gtttaactga acaagctgag tcattctacg ctaaatatgg tttcgacgtt   38340
ctctgcgaaa taaatggtcg agtaagaatg ttcatatcaa tgaaaacagt caatcagtta   38400
ttcacttaac agtaagagtt agtataacag ttgtatgaat taaatttatt atattcggta   38460
atctcattgc gatcacgcta gaagtgcgag cgggtcagac cgaggccaca atagcagccg   38520
ttacgtttag gggatgactt aaaaagataa ctactacgtc agtggcgatc ctagaggatt   38580
aaaggtttat gattcacaac atttatttat tgtgcttaat ttttctatc caatatgcgc   38640 aagctgtaaa tatcactgaa gtagacttt atgtcagtga tgatatccct aaagatgttg   38700
```

```
ccaaattaaa gataggtgaa tccataacga actccagcct tattctaagt aactcatcta     38760
ttccactctc gcgggagacg ggtaacatat attactcttc atcaattgct aacttgaact     38820
atgactcgat agaatttgtt atggctcaat tgatggccga agattccagc ctttacaaga     38880
tgctggtaaa tagcgatagg ttgtccgtgc tagtaatgac atcttcccag tccacagatc     38940
tctatggctc gacttactcg gcttattttc ctaatgttgc ggtcatcgat ttgaattgtg     39000
actcgctaac tttagaacat gagctcggcc atctatacgg agctgaacat gaagaaatat     39060
atgacgacta tgtcttctat gctgcgatat gtggagacta tacgactatc atgaactcta     39120
tgcagcctga aatgaaagaa aaacaaatga taaaggcata ttcattccct gaattaaaag     39180
tggatggctt gcagtgcgga aatgaaaata cgaataacaa aaaggttatt ttagacaata     39240
ttggtcggtt tagataggat tgggatatta ttctcattcg gctctactta gtgctgttat     39300
tatgagtgcc agtgcttcta tctacgatat tggtcttaac aagtatttat ctatagacgc     39360
taaggtgtta tgtatttaag ggatgttcaa gatgaaacta ggtgtaaacg atgtatagtt     39420
gtataacatt ttttcaacgg ttggaacgtt cgattctatc gggtaacaag accgcgacga     39480
tccgcgataa gtccgatagt cattacttag ttggtcagat gttagatgct tgtactcacg     39540
aagataatcg gaaaatgtgt caaatagaaa tactgagcat tgaatatgtg acgtttagtg     39600
aattaaaccg tgcgcacgcc aatgctgaag gtttaccgtt tttgtttatg cttaagtgga     39660
tagttcgaaa gatttatccg acttcaaatg atttattttt cataagtttc agagttgtaa     39720
ctatcgatat cttataagtc ttagtgcaca aaacagaact atttatagcg ctcaagaagg     39780
cgataatttg ataatgaatt atcgccttgt tactattaag agactttaaa tgactgagat     39840
ataagatatg acacggaaga acatattgat cacaggcgca agttcagggt tgggccgagg     39900
tatggccatc gaatttgcaa aatcaggtca taacttagca cttgtgcac gtagacttga      39960 taatttagtt gcactgaaag cagaactctt agccctcaat cctcacatcc aaatcgaaat     40020
aaaacctctt gatgtcaatg aacatgaaca agtcttcact gttttccatg aattcaaagc     40080
tgaatttggt acgcttgatc gtattattgt taatgctgga ttaggcaagg gtggatcc       40138

<210> SEQ ID NO 13
<211> LENGTH: 19227
<212> TYPE: DNA
<213> ORGANISM: Vibrio marinus

<400> SEQUENCE: 13
aaatgcaatt aattatggcg taaatagagt gaaaacatgg ctaatattca ctaagtcctg       60
aattttatat aaagtttaat ctgttatttt agcgtttacc tggtcttatc agtgaggttt      120
atagccatta ttagtgggat tgaagtgatt tttaaagcta tgtatattat tgcaaatata      180
aattgtaaca attaagactt tggacacttg agttcaattt cgaattgatt ggcataaaat      240
ttaaaacagc taaatctacc tcaatcattt tagcaaatgt atgcaggtag atttttttcg      300
ccatttaaga gtacacttgt acgctaggtt tttgtttagt gtgcaaatga acgttttgat      360
gagcattgtt tttagagcac aaaatagatc cttacaggag caataacgca atggctaaaa      420
agaacaccac atcgattaag cacgccaagg atgtgttaag tagtgatgat caacagttaa      480
attctcgctt gcaagaatgt ccgattgcca tcattggtat ggcatcggtt tttgcagatg      540
ctaaaaactt ggatcaattc tgggataaca tcgttgactc tgtggacgct attattgatg      600
tgcctagcga tcgctggaac attgacgacc attactcggc tgataaaaaa gcagctgaca      660
agacatactg caaacgcggt ggtttcattc cagagcttga ttttgatccg atggagtttg      720
```

-continued

```
gtttaccgcc aaatatcctc gagttaactg acatcgctca attgttgtca ttaattgttg    780
ctcgtgatgt attaagtgat gctggcattg gtagtgatta tgaccatgat aaaattggta    840
tcacgctggg tgtcggtggt ggtcagaaac aaatttcgcc attaacgtcg cgcctacaag    900
gcccggtatt agaaaagta ttaaaagcct caggcattga tgaagatgat cgcgctatga    960
tcatcgacaa atttaaaaaa gcctacatcg gctgggaaga gaactcattc ccaggcatgc   1020
taggtaacgt tattgctggt cgtatcgcca atcgttttga ttttggtggt actaactgtg   1080
tggttgatgc ggcatgcgct ggctcccttg cagctgttaa aatggcgatc tcagacttac   1140
ttgaatatcg ttcagaagtc atgatatcgg gtggtgtatg ttgtgataac tcgccattca   1200
tgtatatgtc attctcgaaa acaccagcat ttaccaccaa tgatgatatc cgtccgtttg   1260
atgacgattc aaaaggcatg ctggttggtg aaggtattgg catgatggcg tttaaacgtc   1320
ttgaagatgc tgaacgtgac ggcgacaaaa tttattctgt actgaaaggt atcggtacat   1380
cttcagatgg tcgtttcaaa tctatttacg ctccacgccc agatggccaa gcaaaagcgc   1440
taaaacgtgc ttatgaagat gccggttttg cccctgaaac atgtggtcta attgaaggcc   1500
atggtacggg taccaaagcg ggtgatgccg cagaatttgc tggcttgacc aaacactttg   1560
gcgccgccag tgatgaaaag caatatatcg ccttaggctc agttaaatcg caaattggtc   1620
atactaaatc tgcggctggc tctgcgggta tgattaaggc ggcattagcg ctgcatcata   1680
aaatcttacc tgcaacgatc catatcgata accaagtga agccttggat atcaaaaaca   1740
gcccgttata cctaaacagc gaaacgcgtc cttggatgcc acgtgaagat ggtattccac   1800
gtcgtgcagg tatcagctca tttggttttg gcggcaccaa cttccatatt attttagaag   1860
agtatcgccc aggtcacgat agcgcatatc gcttaaactc agtgagccaa actgtgttga   1920
tctcggcaaa cgaccaacaa ggtattgttg ctgagttaaa taactggcgt actaaactgg   1980
ctgtcgatgc tgatcatcaa gggtttgtat ttaatgagtt agtgacaacg tggccattaa   2040
aaacccccatc cgttaaccaa gctcgtttag gttttgttgc gcgtaatgca aatgaagcga   2100
tcgcgatgat tgatacggca ttgaaacaat tcaatgcgaa cgcagataaa atgacatggt   2160
cagtacctac cggggtttac tatcgtcaag ccggtattga tgcaacaggt aaagtggttg   2220
cgctattctc agggcaaggt tcgcaatacg tgaacatggg tcgtgaatta acctgtaact   2280
tcccaagcat gatgcacagt gctgcggcga tggataaaga gttcagtgcc gctggtttag   2340
gccagttatc tgcagttact ttccctatcc ctgtttatac ggatgccgag cgtaagctac   2400
aagaagagca attacgttta acgcaacatg cgcaaccagc gattggtagt ttgagtgttg   2460
gtctgttcaa aacgtttaag caagcaggtt ttaaagctga ttttgctgcc ggtcatagtt   2520
tcggtgagtt aaccgcatta tgggctgccg atgtattgag cgaaagcgat tacatgatgt   2580
tagcgcgtag tcgtggtcaa gcaatggctg cgccagagca acaagatttt gatgcaggta   2640
agatggccgc tgttgttggt gatccaaagc aagtcgctgt gatcattgat acccttgatg   2700
atgtctctat tgctaacttc aactcgaata accaagttgt tattgctggt actacggagc   2760
aggttgctgt agcggttaca accttaggta atgctggttt caagttgtgc cactgccgg   2820
tatctgctgc gttccataca ccttttagttc gtcacgcgca aaaccatttt gctaaagcgg   2880
ttgatagcgc taaatttaaa gcgccaagca ttccagtgtt tgctaatggc acaggcttgg   2940
tgcattcaag caaaccgaat gacattaaga aaaacctgaa aaaaccacatg ctggaatctg   3000
ttcatttcaa tcaagaaatt gacaacatct atgctgatgg tggccgcgta tttatcgaat   3060
```

```
ttggtccaaa gaatgtatta actaaattgg ttgaaaacat tctcactgaa aaatctgatg    3120
tgactgctat cgcggttaat gctaatccta acaacctgc ggacgtacaa atgcgccaag     3180
ctgcgctgca aatggcagtg cttggtgtcg cattagacaa tattgacccg tacgacgccg    3240
ttaagcgtcc acttgttgcg ccgaaagcat caccaatgtt gatgaagtta tctgcagcgt    3300
cttatgttag tccgaaaacg aagaaagcgt ttgctgatgc attgactgat ggctggactg    3360
ttaagcaagc gaaagctgta cctgctgttg tgtcacaacc acaagtgatt gaaaagatcg    3420
ttgaagttga aaagatagtt gaacgcattg tcgaagtaga gcgtattgtc gaagtagaaa    3480
aaatcgtcta cgttaatgct gacggttcgc ttatatcgca aaataatcaa gacgttaaca    3540
gcgctgttgt tagcaacgtg actaatagct cagtgactca tagcagtgat gctgaccttg    3600
ttgcctctat tgaacgcagt gttggtcaat tgttgcaca ccaacagcaa ttattaaatg      3660
tacatgaaca gtttatgcaa ggtccacaag actacgcgaa aacagtgcag aacgtacttg    3720
ctgcgcagac gagcaatgaa ttaccggaaa gtttagaccg tacattgtct atgtataacg    3780
agttccaatc agaaacgcta cgtgtacatg aaacgtacct gaacaatcag acgagcaaca    3840
tgaacaccat gcttactggt gctgaagctg atgtgctagc aaccccaata actcaggtag    3900
tgaatacagc cgttgccact agtcacaagg tagttgctcc agttattgct aatacagtga    3960
cgaatgttgt atctagtgtc agtaataacg cggcggttgc agtgcaaact gtggcattag    4020
cgcctacgca agaaatcgct ccaacagtcg ctactacgcc agcacccgca ttggttgcta    4080
tcgtggctga acctgtgatt gttgcgcatg ttgctacaga agttgcacca attacaccat    4140
cagttacacc agttgtcgca actcaagcgg ctatcgatgt agcaactatt aacaaagtaa    4200
tgttagaagt tgttgctgat aaaaccggtt atccaacgga tatgctggaa ctgagcatgg    4260
acatggaagc tgacttaggt atcgactcaa tcaaacgtgt tgagatatta ggcgcagtac    4320
aggaattgat ccctgactta cctgaactta atcctgaaga tcttgctgag ctacgcacgc    4380
ttggtgagat tgtcgattac atgaattcaa aagcccaggc tgtagctcct acaacagtac    4440
ctgtaacaag tgcacctgtt tcgcctgcat ctgctggtat tgatttagcc cacatccaaa    4500
acgtaatgtt agaagtggtt gcagacaaaa ccggttaccc aacagacatg ctagaactga    4560
gcatggatat ggaagctgac ttaggtattg attcaatcaa gcgtgtggaa atcttaggtg    4620
cagtacagga gatcataact gatttacctg agctaaaccc tgaagatctt gctgaattac    4680
gcaccctagg tgaaatcgtt agttacatgc aaagcaaagc gccagtcgct gaaagtgcgc    4740
cagtggcgac ggctcctgta gcaacaagct cagcaccgtc tatcgatttg aaccacattc    4800
aaacagtgat gatggatgta gttgcagata agactggtta tccaactgac atgctagaac    4860
ttggcatgga catggaagct gatttaggta tcgattcaat caaacgtgtg gaaatattag    4920
gcgcagtgca ggagatcatc actgatttac ctgagctaaa cccagaagac ctcgctgaat    4980
tacgcacgct aggtgaaatc gttagttaca tgcaaagcaa agcgccagtc gctgagagtg    5040
cgccagtagc gacggcttct gtagcaacaa gctctgcacc gtctatcgat ttaaaccata    5100
tccaaacagt gatgatggaa gtggttgcag acaaaaccgg ttatccagta gacatgttag    5160
aacttgctat ggacatggaa gctgacctag gtatcgattc aatcaagcgt gtagaaattt    5220
taggtgcggt acaggaaatc attactgact tacctgagct taaccctgaa gatcttgctg    5280
aactacgtac attaggtgaa atcgttagtt acatgcaaag caaagcgccc gtagctgaag    5340
cgcctgcagt aacctgttgca gtagaaagtg cacctactag tgtaacaagc tcagcaccgt    5400
ctatcgattt agaccacatc caaaatgtaa tgatggatgt tgttgctgat aagactggtt    5460
```

```
atcctgccaa tatgcttgaa ttagcaatgg acatggaagc cgaccttggt attgattcaa    5520
tcaagcgtgt tgaaattcta ggcgcggtac aggagatcat tactgattta cctgaactaa    5580
acccagaaga cttagctgaa ctacgtacgt tagaagaaat tgtaacctac atgcaaagca    5640
aggcgagtgg tgttactgta aatgtagtgg ctagccctga aaataatgct gtatcagatg    5700
catttatgca aagcaatgtg gcgactatca cagcggccgc agaacataag gcggaattta    5760
aaccggcgcc gagcgcaacc gttgctatct ctcgtctaag ctctatcagt aaaataagcc    5820
aagattgtaa aggtgctaac gccttaatcg tagctgatgg cactgataat gctgtgttac    5880
ttgcagacca cctattgcaa actggctgga atgtaactgc attgcaacca acttgggtag    5940
ctgtaacaac gacgaaagca tttaataagt cagtgaacct ggtgacttta aatggcgttg    6000
atgaaactga aatcaacaac attattactg ctaacgcaca attggatgca gttatctatc    6060
tgcacgcaag tagcgaaatt aatgctatcg aatacccaca agcatctaag caaggcctga    6120
tgttagcctt cttattagcg aaattgagta agtaactca agccgctaaa gtgcgtggcg    6180
cctttatgat tgttactcag cagggtggtt cattaggttt tgatgatatc gattctgcta    6240
caagtcatga tgtgaaaaca gacctagtac aaagcggctt aaacggttta gttaagacac    6300
tgtctcacga gtgggataac gtattctgtc gtgcggttga tattgcttcg tcattaacgg    6360
ctgaacaagt tgcaagcctt gttagtgatg aactacttga tgctaacact gtattaacag    6420
aagtgggtta tcaacaagct ggtaaaggcc ttgaacgtat cacgttaact ggtgtggcta    6480
ctgacagcta tgcattaaca gctggcaata acatcgatgc taactcggta ttttttagtga    6540 gtggtggcgc aaaaggtgta actgcacatt gtgttgctcg tatagctaaa gaatatcagt    6600
ctaagttcat cttattggga cgttcaacgt tctcaagtga cgaaccgagc tgggcaagtg    6660
gtattactga tgaagcggcg ttaaagaaag cagcgatgca gtctttgatt acagcaggtg    6720
ataaaccaac acccgttaag atcgtacagc taatcaaacc aatccaagct aatcgtgaaa    6780
ttgcgcaaac cttgtctgca attaccgctg ctggtggcca agctgaatat gtttctgcag    6840
atgtaactaa tgcagcaagc gtacaaatgg cagtcgctcc agctatcgct aagttcggtg    6900
caatcactgg catcattcat ggcgcgggtg tgttagctga ccaattcatt gagcaaaaaa    6960
cactgagtga ttttgagtct gtttacagca ctaaaattga cggtttgtta tcgctactat    7020
cagtcactga agcaagcaac atcaagcaat tggtattgtt ctcgtcagcg gctggttttct    7080 acggtaaccc cggccagtct gattactcga ttgccaatga gatcttaaat aaaaccgcat    7140
accgctttaa atcattgcac ccacaagctc aagtattgag ctttaactgg ggtccttggg    7200
acggtggcat ggtaacgcct gagcttaaac gtatgtttga ccaacgtggt gtttacatta    7260
ttccacttga tgcaggtgca cagttattgc tgaatgaact agccgctaat gataaccgtt    7320
gtccacaaat cctcgtgggt aatgacttat ctaaagatgc tagctctgat caaaagtctg    7380
atgaaaagag tactgctgta aaaaagccac aagttagtcg tttatcagat gctttagtaa    7440
ctaaaagtat caaagcgact aacagtagct ctttatcaaa caagactagt gctttatcag    7500
acagtagtgc ttttcaggtt aacgaaaacc acttttttagc tgaccacatg atcaaaggca    7560
atcaggtatt accaacggta tgcgcgattg cttggatgag tgatgcagca aaagcgactt    7620
atagtaaccg agactgtgca ttgaagtatg tcggtttcga agactataaa ttgtttaaag    7680
gtgtggtttt tgatggcaat gaggcggcgg attaccaaat ccaattgtcg cctgacaa    7740 gggcgtcaga acaggattct gaagtccgta ttgccgcaaa gatctttagc ctgaaaagtg    7800
```

```
acggtaaacc tgtgtttcat tatgcagcga caatattgtt agcaactcag ccacttaatg      7860
ctgtgaaggt agaacttccg acattgacag aaagtgttga tagcaacaat aaagtaactg      7920
atgaagcaca agcgttatac agcaatggca ccttgttcca cggtgaaagt ctgcagggca      7980
ttaagcagat attaagttgt gacgacaagg gcctgctatt ggcttgtcag ataaccgatg      8040
ttgcaacagc taagcaggga tccttcccgt tagctgacaa caatatcttt gccaatgatt      8100
tggtttatca ggctatgttg gtctgggtgc gcaaacaatt tggtttaggt agcttacctt      8160
cggtgacaac ggcttggact gtgtatcgtg aagtggttgt agatgaagta ttttatctgc      8220
aacttaatgt tgttgagcat gatctattgg gttcacgcgg cagtaaagcc cgttgtgata      8280
ttcaattgat tgctgctgat atgcaattac ttgccgaagt gaaatcagcg caagtcagtg      8340
tcagtgacat tttgaacgat atgtcatgat cgagtaaata ataacgatag gcgtcatggt      8400
gagcatggcg tctgctttct tcatttttta acattaacaa tattaatagc taaacgcggt      8460
tgctttaaac caagtaaaca agtgctttta gctattacta ttccaaacag gatattaaag      8520
agaatatgac ggaattagct gttattggta tggatgctaa atttagcgga caagacaata      8580
ttgaccgtgt ggaacgcgct ttctatgaag gtgcttatgt aggtaatgtt agccgcgtta      8640
gtaccgaatc taatgttatt agcaatggcg aagaacaagt tattactgcc atgacagttc      8700
ttaactctgt cagtctacta gcgcaaaacga atcagttaaa tatagctgat atcgcggtgt      8760
tgctgattgc tgatgtaaaa agtgctgatg atcagcttgt agtccaaatt gcatcagcaa      8820
ttgaaaaaca gtgtgcgagt tgtgttgtta ttgctgattt aggccaagca ttaaatcaag      8880
tagctgattt agttaataac caagactgtc ctgtggctgt aattggcatg aataactcgg      8940
ttaatttatc tcgtcatgat cttgaatctg taactgcaac aatcagcttt gatgaaacct      9000
tcaatggtta taacaatgta gctgggttcg cgagtttact tatcgcttca actgcgtttg      9060
ccaatgctaa gcaatgttat atatacgcca acattaaggg cttcgctcaa tcgggcgtaa      9120
atgctcaatt taacgttgga aacattagcg atactgcaaa gaccgcattg cagcaagcta      9180
gcataactgc agagcaggtt ggtttgttag aagtgtcagc agtcgctgat tcggcaatcg      9240
cattgtctga aagccaaggt ttaatgtctg cttatcatca tacgcaaaact ttgcatactg      9300 cattaagcag tgcccgtagt gtgactggtg aaggcgggtg ttttttcacag gtcgcaggtt      9360 tattgaaatg tgtaattggt ttacatcaac gttatattcc ggcgattaaa gattggcaac      9420
aaccgagtga caatcaaatg tcacggtggc ggaattcacc attctatatg cctgtagatg      9480
ctcgaccttg gttcccacat gctgatggct ctgcacacat tgccgcttat agttgtgtga      9540
ctgctgacag ctattgtcat attcttttac aagaaaacgt cttacaagaa cttgttttga      9600
aagaaacagt cttgcaagat aatgacttaa ctgaaagcaa gcttcagact cttgaacaaa      9660
acaatccagt agctgatctg cgcactaatg gttactttgc atcgagcgag ttagcattaa      9720
tcatagtaca aggtaatgac gaagcacaat tacgctgtga attagaaact attacagggc      9780
agttaagtac tactggcata agtactatca gtattaaaca gatcgcagca gactgttatg      9840
cccgtaatga tactaacaaa gcctatagcg cagtgcttat tgccgagact gctgaagagt      9900
taagcaaaga aataaccttg gcgtttgctg gtatcgctag cgtgtttaat gaagatgcta      9960
aagaatggaa aaccccgaag gcagttatt ttaccgcgca gcctgcaaat aaacaggctg     10020
ctaacagcac acagaatggt gtcaccttca tgtacccagg tattggtgct acatatgttg     10080
gtttagggcg tgatctattt catctattcc cacagattta tcagcctgta gcggctttag     10140
ccgatgacat tggcgaaagt ctaaaagata cttttacttaa tccacgcagt attagtcgtc     10200
```

```
atagctttaa agaactcaag cagttggatc tggacctgcg cggtaactta gccaatatcg    10260
ctgaagccgg tgtgggtttt gcttgtgtgt ttaccaaggt atttgaagaa gtctttgccg    10320
ttaaagctga ctttgctaca ggttatagca tgggtgaagt aagcatgtat gcagcactag    10380
gctgctggca gcaaccggga ttgatgagtg ctcgccttgc acaatcgaat acctttaatc    10440
atcaactttg cggcgagtta agaacactac gtcagcattg gggcatggat gatgtagcta    10500
acggtacgtt cgagcagatc tgggaaacct ataccattaa ggcaacgatt gaacaggtcg    10560
aaattgcctc tgcagatgaa gatcgtgtgt attgcaccat tatcaataca cctgatagct    10620
tgttgttagc cggttatcca gaagcctgtc agcgagtcat taagaattta ggtgtgcgtg    10680
caatggcatt gaatatggcg aacgcaattc acagcgcgcc agcttatgcc gaatacgatc    10740
atatggttga gctataccat atggatgtta ctccacgtat taataccaag atgtattcaa    10800
gctcatgtta tttaccgatt ccacaacgca gcaaagcgat ttcccacagt attgctaaat    10860
gtttgtgtga tgtggtggat ttcccacgtt tggttaatac cttacatgac aaaggtgcgc    10920
gggtattcat tgaaatgggt ccaggtcgtt cgttatgtag ctgggtagat aagatcttag    10980
ttaatggcga tggcgataat aaaaagcaaa gccaacatgt atctgttcct gtgaatgcca    11040
aaggcaccag tgatgaactt acttatattc gtgcgattgc taagttaatt agtcatggcg    11100
tgaatttgaa tttagatagc ttgtttaacg ggtcaatcct ggttaaagca ggccatatag    11160
caaacacgaa caaatagtca acatcgatat ctagcgctgg tgagttatac ctcattagtt    11220
gaaatatgga tttaaagaga gtaattatgg aaaatattgc agtagtaggt attgctaatt    11280
tgttcccggg ctcacaagca ccggatcaat tttggcagca attgcttgaa caacaagatt    11340
gccgcagtaa ggcgaccgct gttcaaatgg gcgttgatcc tgctaaatat accgccaaca    11400
aaggtgacac agataaattt tactgtgtgc acggcggtta catcagtgat ttcaattttg    11460
atgcttcagg ttatcaactc gataatgatt atttagccgg tttagatgac cttaatcaat    11520
gggggcttta tgttacgaaa caagccctta ccgatgcggg ttattgggc agtactgcac    11580 tagaaaactg tggtgtgatt ttaggtaatt tgtcattccc aactaaatca tctaatcagc    11640
tgtttatgcc tttgtatcat caagttgttg ataatgcctt aaaggcggta ttacatcctg    11700
attttcaatt aacgcattac acagcaccga aaaaaacaca tgctgacaat gcattagtag    11760
caggttatcc agctgcattg atcgcgcaag cggcgggtct tggtggttca cattttgcac    11820
tggatgcggc ttgtgcttca tcttgttata gcgttaagtt agcgtgtgat tacctgcata    11880
cgggtaaagc caacatgatg cttgctggtg cggtatctgc agcagatcct atgttcgtaa    11940
atatgggttt ctcgatattc caagcttacc cagctaacaa tgtacatgcc ccgtttgacc    12000
aaaattcaca aggtctattt gccggtgaag gcgcgggcat gatggtattg aaacgtcaaa    12060
gtgatgcagt acgtgatggt gatcatattt acgccattat taaaggcggc gcattatcga    12120
atgacggtaa aggcgagttt gtattaagcc cgaacaccaa gggccaagta ttagtatatg    12180
aacgtgctta tgccgatgca gatgttgacc cgagtacagt tgactatatt gaatgtcatg    12240
caacgggcac acctaagggt gacaatgttg aattgcgttc gatggaaacc tttttcagtc    12300
gcgtaaataa caaaccatta ctgggctcgg ttaaatctaa ccttggtcat tgttaactg     12360 ccgctggtat gcctggcatg accaaagcta tgttagcgct aggtaaaggt cttattcctg    12420
caacgattaa cttaaagcaa ccactgcaat ctaaaaacgg ttactttact ggcgagcaaa    12480
tgccaacgac gactgtgtct tggccaacaa ctccgggtgc caaggcagat aaaccgcgta    12540
```

-continued

```
ccgcaggtgt gagcgtattt ggttttggtg gcagcaacgc ccatttggta ttacaacagc    12600
caacgcaaac actcgagact aattttagtg ttgctaaacc acgtgagcct ttggctatta    12660
ttggtatgga cagccatttt ggtagtgcca gtaatttagc gcagttcaaa accttattaa    12720
ataataatca aaataccttc cgtgaattac cagaacaacg ctggaaaggc atggaaagta    12780
acgctaacgt catgcagtcg ttacaattac gcaaagcgcc taaaggcagt tacgttgaac    12840
agctagatat tgatttcttg cgttttaaag taccgcctaa tgaaaaagat tgcttgatcc    12900
cgcaacagtt aatgatgatg caagtggcag acaatgctgc gaaagacgga ggtctagttg    12960
aaggtcgtaa tgttgcggta ttagtagcga tgggcatgga actggaatta catcagtatc    13020
gtggtcgcgt taatctaacc acccaaattg aagacagctt attacagcaa ggtattaacc    13080
tgactgttga gcaacgtgaa gaactgacca atattgctaa agacggtgtt gcctcggctg    13140
cacagctaaa tcagtatacg agtttcattg gtaatattat ggcgtcacgt atttcggcgt    13200
tatgggattt ttctggtcct gctattaccg tatcggctga agaaaactct gtttatcgtt    13260
gtgttgaatt agctgaaaat ctatttcaaa ccagtgatgt tgaagccgtt attattgctg    13320
ctgttgattt gtctggttca attgaaaaca ttactttacg tcagcactac ggtccagtta    13380
atgaaaaggg atctgtaagt gaatgtggtc cggttaatga aagcagttca gtaaccaaca    13440
atattcttga tcagcaacaa tggctggtgg gtgaaggcgc agcggctatt gtcgttaaac    13500
cgtcatcgca agtcactgct gagcaagttt atgcgcgtat tgatgcggtg agttttgccc    13560
ctggtagcaa tgcgaaagca attacgattg cagcggataa agcattaaca cttgctggta    13620
tcagtgctgc tgatgtagct agtgttgaag cacatgcaag tggttttagt gccgaaaata    13680
atgctgaaaa aaccgcgtta ccgactttat acccaagcgc aagtatcagt tcggtgaaag    13740
ccaatattgg tcatacgttt aatgcctcgg gtatggcgag tattattaaa acggcgctgc    13800
tgttagatca gaatacgagt caagatcaga aaagcaaaca tattgctatt aacggtctag    13860
gtcgtgataa cagctgcgcg catcttatct tatcgagttc agcgcaagcg catcaagttg    13920
caccagcgcc tgtatctggt atggccaagc aacgcccaca gttagttaaa accatcaaac    13980
tcggtggtca gttaattagc aacgcgattg ttaacagtgc gagttcatct ttacacgcta    14040
ttaaagcgca gtttgccggt aagcacttaa acaaagttaa ccagccagtg atgatggata    14100
acctgaagcc ccaaggtatt agcgctcatg caaccaatga gtatgtggtg actggagctg    14160
ctaacactca agcttctaac attcaagcat ctcatgttca agcgtcaagt catgcacaag    14220
agatagcacc aaaccaagtt caaaatatgc aagctacagc agccgctgta agttcacccc    14280
tttctcaaca tcaacacaca gcgcagcccg tagcggcacc gagcgttgtt ggagtgactg    14340
tgaaacataa agcaagtaac caaattcatc agcaagcgtc tacgcataaa gcattttag    14400 aaagtcgttt agctgcacag aaaaacctat cgcaacttgt tgaattgcaa accaagctgt    14460
caatccaaac tggtagtgac aatacatcta acaatactgc gtcaacaagc aatacagtgc    14520
taacaaatcc tgtatcagca acgccattaa cacttgtgtc taatgcgcct gtagtagcga    14580
caaacctaac cagtacagaa gcaaaagcgc aagcagctgc tacacaagct ggttttcaga    14640
taaaaggacc tgttggttac aactatccac cgctgcagtt aattgaacgt tataataaac    14700
cagaaaacgt gatttacgat caagctgatt tggttgaatt cgctgaaggt gatattggta    14760
aggtatttgg tgctgaatac aatattattg atggctattc gcgtcgtgta cgtctgccaa    14820
cctcagatta cttgttagta acacgtgtta ctgaacttga tgccaaggtg catgaataca    14880
agaaatcata catgtgtact gaatatgatg tgcctgttga tgcaccgttc ttaattgatg    14940
```

```
gtcagatccc ttggtctgtt gccgtcgaat caggccagtg tgatttgatg ttgatttcat    15000
atatcggtat tgatttccaa gcgaaaggcg aacgtgttta ccgtttactt gattgtgaat    15060
taactttcct tgaagagatg gcttttggtg gcgatacttt acgttacgag atccacattg    15120
attcgtatgc acgtaacggc gagcaattat tattcttctt ccattacgat tgttacgtag    15180
gggataagaa ggtacttatc atgcgtaatg gttgtgctgg tttctttact gacgaagaac    15240
tttctgatgg taaaggcgtt attcataacg acaaagacaa agctgagttt agcaatgctg    15300
ttaaatcatc attcacgccg ttattacaac ataaccgtgg tcaatacgat tataacgaca    15360
tgatgaagtt ggttaatggt gatgttgcca gttgttttgg tccgcaatat gatcaaggtg    15420
gccgtaatcc atcattgaaa ttctcgtctg agaagttctt gatgattgaa cgtattacca    15480
agatagaccc aaccggtggt cattgggac taggcctgtt agaaggtcag aaagatttag    15540
accctgagca ttggtatttc ccttgtcact ttaaaggtga tcaagtaatg gctggttcgt    15600
tgatgtcgga aggttgtggc caaatggcga tgttcttcat gctgtctctt ggtatgcata    15660
ccaatgtgaa caacgctcgt ttccaaccac taccaggtga atcacaaacg gtacgttgtc    15720
gtgggcaagt actgccacag cgcaatacct taacttaccg tatggaagtt actgcgatgg    15780
gtatgcatcc acagccattc atgaaagcta atattgatat tttgcttgac ggtaaagtgg    15840
ttgttgattt caaaaacttg agcgtgatga tcagcgaaca agatgagcat tcagattacc    15900
ctgtaacact gccgagtaat gtggcgctta agcgattac tgcacctgtt gcgtcagtag    15960
caccagcatc ttcacccgct aacagcgcgg atctagacga acgtggtgtt gaaccgttta    16020
agtttcctga acgtccgtta atgcgtgttg agtcagactt gtctgcaccg aaaagcaaag    16080
gtgtgacacc gattaagcat tttgaagcgc ctgctgttgc tggtcatcat agagtgccta    16140
accaagcacc gtttacacct tggcatatgt ttgagtttgc gacgggtaat atttctaact    16200
gtttcggtcc tgattttgat gtttatgaag gtcgtattcc acctcgtaca ccttgtggcg    16260
atttacaagt tgttactcag gttgtagaag tgcagggcga acgtcttgat cttaaaaatc    16320
catcaagctg tgtagctgaa tactatgtac cggaagacgc ttggtacttt actaaaaaca    16380
gccatgaaaa ctggatgcct tattcattaa tcatggaaat tgcattgcaa ccaaatggct    16440
ttatttctgg ttacatgggc acgacgctta aatacctga aaaagatctg ttcttccgta    16500
accttgatgg tagcggcacg ttattaaagc agattgattt acgcggcaag accattgtga    16560
ataaatcagt cttggttagt acggctattg ctggtggcgc gattattcaa agtttcacgt    16620
ttgatatgtc tgtagatggc gagctatttt atactggtaa agctgtattt ggttactta    16680 gtggtgaatc actgactaac caactgggca ttgataacgg taaaacgact aatgcgtggt    16740
ttgttgataa caatacccc gcagcgaata ttgatgtgtt tgatttaact aatcagtcat    16800
tggctctgta taaagcgcct gtggataaac cgcattataa attggctggt ggtcagatga    16860
actttatcga tacagtgtca gtggttgaag gcggtggtaa agcgggcgtg gcttatgttt    16920
atggcgaacg tacgattgat gctgatgatt ggttcttccg ttatcacttc caccaagatc    16980
cggtgatgcc aggttcatta ggtgttgaag ctattattga gttgatgcag acctatgcgc    17040
ttaaaaatga tttgggtggc aagtttgcta acccacgttt cattgcgccg atgacgcaag    17100
ttgattggaa ataccgtggg caaattacgc cgctgaataa acagatgtca ctggacgtgc    17160
atatcactga gatcgtgaat gacgctggtg aagtgcgaat cgttggtgat gcgaatctgt    17220
ctaaagatgg tctgcgtatt tatgaagtta aaacatcgt tttaagtatt gttgaagcgt    17280
```

```
aaagggtcaa gtgtaacgtg cttaagcgcc gcattggtta aagacgcttt gcacgccgtg      17340
aatccgtcca tggaggcttg gggttggcat ccatgccaac aacagcaagc ttactttaat      17400
caatacggct tggtgtccat ttagacgcct cgaacttagt agttaataga caaataatt       17460 tagctgtgga atgaatatag taagtaatca ttcggcagct acaaaaaagg aattaagaat      17520
gtcgagttta ggttttaaca ataacaacgc aattaactgg gcttggaaag tagatccagc      17580
gtcagttcat acacaagatg cagaaattaa agcagcttta atggatctaa ctaaacctct      17640
ctatgtggcg aataattcag gcgtaactgg tatagctaat catacgtcag tagcaggtgc      17700
gatcagcaat aacatcgatg ttgatgtatt ggcgtttgcg caaaagttaa acccagaaga     17760
tctgggtgat gatgcttaca agaaacagca cggcgttaaa tatgcttatc atggcggtgc      17820
gatggcaaat ggtattgcct cggttgaatt ggttgttgcg ttaggtaaag cagggctgtt      17880
atgttcattt ggtgctgcag gtctagtgcc tgatgcggtt gaagatgcaa ttcgtcgtat      17940
tcaagctgaa ttaccaaatg gcccttatgc ggttaacttg atccatgcac cagcagaaga     18000
agcattagag cgtggcgcgg ttgaacgttt cctaaaactt ggcgtcaaga cggtagaggc      18060
ttcagcttac cttggtttaa ctgaacacat tgtttggtat cgtgctgctg gtctaactaa      18120
aaacgcagat ggcagtgtta atatcggtaa caaggttatc gctaaagtat cgcgtaccga     18180
agttggtcgc cgctttatgg aacctgcacc gcaaaaatta ctggataagt tattagaaca     18240
aaataagatc acccctgaac aagctgcttt agcgttgctt gtacctatgg ctgatgatat     18300
tactggggaa gcggattctg gtggtcatac agataaccgt ccgttttaa cattattacc      18360 gacgattatt ggtctgcgtg atgaagtgca agcgaagtat aacttctctc ctgcattacg      18420
tgttggtgct ggtggtggta tcggaacgcc tgaagcagca ctcgctgcat taacatggg      18480 cgcggcttat atcgttctgg gttctgtgaa tcaggcgtgt gttgaagcgg gtgcatctga     18540
atatactcgt aaactgttat cgacagttga aatggctgat gtgactatgg cacctgctgc     18600
agatatgttt gaaatgggtg tgaagctgca agtattaaaa cgcggttcta tgttcgcgat     18660
gcgtgcgaag aaactgtatg acttgtatgt ggcttatgac tcgattgaag atatcccagc     18720
tgctgaacgt gagaagattg aaaaacaaat cttccgtgca aacctagacg agatttggga    18780
tggcactatc gctttcttta ctgaacgcga tccagaaatg ctagcccgtg caacgagtag    18840
tcctaaacgt aaatggcac ttatcttccg ttggtatctt ggcctttctt cacgctggtc     18900
aaacacaggc gagaaggggac gtgaaatgga ttatcagatt tgggcaggcc caagtttagg    18960
tgcattcaac agctgggtga aaggttctta ccttgaagac tatacccgcc gtggcgctgt    19020
agatgttgct ttgcatatgc ttaaaggtgc tgcgtattta caacgtgtaa accagttgaa    19080
attgcaaggt gttagcttaa gtacagaatt ggcaagttat cgtacgagtg attaatgtta    19140
cttgatgata tgtgaattaa ttaaagcgcc tgagggcgct ttttttggtt tttaactcag    19200
gtgttgtaac tcgaaattgc ccctttc                                         19227

<210> SEQ ID NO 14
<211> LENGTH: 217
<212> TYPE: DNA
<213> ORGANISM: Shewanella putrefaciens

<400> SEQUENCE: 14
attggtaaaa ataggggtta tgtttgttgc tttaaagagt gtcctgaaaa attgctaact         60
tctcgattga tttccttata cttctgtccg ttaacaatac aagagtgcga taaccagact        120
acagagttgg ttaagtcatg gctgcctgaa gatgagttaa ttaaggttaa tcgctacatt        180
```

```
aaacaagaag ctaaaactca aggtttaatg gtaagag                                217
```

<210> SEQ ID NO 15
<211> LENGTH: 72
<212> TYPE: PRT
<213> ORGANISM: Shewanella putrefaciens

<400> SEQUENCE: 15

```
Ile Gly Lys Asn Arg Gly Tyr Val Cys Cys Phe Lys Glu Cys Pro Glu
 1               5                  10                  15

Lys Leu Leu Thr Ser Arg Leu Ile Ser Leu Tyr Phe Cys Pro Leu Thr
             20                  25                  30

Ile Gln Glu Cys Asp Asn Gln Thr Thr Glu Leu Val Lys Ser Trp Leu
         35                  40                  45

Pro Glu Asp Glu Leu Ile Lys Val Asn Arg Tyr Ile Lys Gln Glu Ala
     50                  55                  60

Lys Thr Gln Gly Leu Met Val Arg
 65                  70
```

<210> SEQ ID NO 16
<211> LENGTH: 885
<212> TYPE: DNA
<213> ORGANISM: Shewanella putrefaciens

<400> SEQUENCE: 16

```
agcgaaatgc ttatcaagaa attccaagat caatacatca ctgggaagaa aattcattcc    60
ctggttcact gggtaacgtt atttccggcc gtattgctaa ccgcttcgac cttggtggca   120
tgaactgtgt cgttgatgca gcatgtgcag gccctcttgc tgcattgcgt atggcattaa   180
gcgagcttgt tgaaggccgc agcgaaatga tgattacagg tggtgtgtgt accgataact   240
caccaaccat gtacatgagc ttctctaaaa caccggcatt cacgacaaac gaaacaattc   300
aaccattcga tattgactcg aaaggtatga tgattggtga aggtatcggt atgattgcgc   360
ttaaacgtct tgaagacgca gagcgtgatg gcgaccgtat ctattccgtg attaaaggtg   420
ttgggtgcat cttcagacgg taatttatta agagtantta tgcgcntcgt cctgaaggtc   480
aggctaaggc acttaaacgt gcttacgacg atgcaggttt cgcaccgcac acacttggct   540
tacttgaagc ccacggcaca ggcacagcag caggtgatgt ggcagaattc agtggtctta   600
actctgtatt cagtgaaggc aatgacgaaa agcaacacat cgcattaggt tcagtgaaat   660
cacagattgg tcacactaaa tcaacagcgg gtactgcggg tctaatcaaa gcgtctttag   720
cactgcacca taagtactg ccgccaacaa tcaatgtaac cagccctaac cctaaactga   780
atattgaaga ctcgcctttc tacctcaata cacagacgcg tccatggatg caacgtgtcg   840
atggtacacc gcgtcgtgct ggtattagct catttggttt tggtg               885
```

<210> SEQ ID NO 17
<211> LENGTH: 409
<212> TYPE: DNA
<213> ORGANISM: Shewanella putrefaciens

<400> SEQUENCE: 17

```
ccaagctaaa gcacttaacc gtgcttatga agatgccggt tttgcccctg aaacatgtgg    60
tctaattgaa ggccatggta cgggtaccaa agcgggtgat gccgcagaat tgctggctt   120
gaccaaacac tttggcgccg ccagtgatga aaagcaatat atcgccttag ctcagttaa   180
atcgcaaatt ggtcatacta atctgcggc tggctctgcg ggtatgatta aggcggcatt   240
```

```
agcgctgcat cataaaatct tacctgcaac gatccatatc gataaaccaa gtgaagcctt      300
ggatatcaaa aacagcccgt tatacctaaa cagcgaaacg cgtccttgga tgccacgtga      360
agatggtatt ccacgtcgtg caggtattag ctcatttggt tttggtggc                  409

<210> SEQ ID NO 18
<211> LENGTH: 81
<212> TYPE: DNA
<213> ORGANISM: Artificial Sequence
<220> FEATURE:
<223> OTHER INFORMATION: Description of Artificial Sequence: SYNTHETIC

<400> SEQUENCE: 18
ccaagctaaa gcacttaacc gtgcctatga tgatgccggt tttgcccctg aaacatgtgg       60
tctaattgaa ggccatggta c                                                81

<210> SEQ ID NO 19
<211> LENGTH: 81
<212> TYPE: DNA
<213> ORGANISM: Artificial Sequence
<220> FEATURE:
<223> OTHER INFORMATION: Description of Artificial Sequence: SYNTHETIC

<400> SEQUENCE: 19
ccaagctaaa gcacttaacc gtgcttatga agatgccggt tttgcccctg aaacatgtgg       60
tctaattgaa ggccatggta c                                                81

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: SYNTHETIC

<400> SEQUENCE: 20
agaacgcaaa gttgccgcac tgtttggtcg ccaaggttca caa                        43

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: SYNTHETIC

<400> SEQUENCE: 21
caaagcgggt gatgccgcac tgtttggtcg cttgacctaa cac                        43

<210> SEQ ID NO 22
<211> LENGTH: 55
<212> TYPE: DNA
<213> ORGANISM: Artificial Sequence
<220> FEATURE:
<223> OTHER INFORMATION: Description of Artificial Sequence: SYNTHETIC

<400> SEQUENCE: 22
cattgcgcta ggttcagtta aatcacaaat tggtcatact aaatcaactg caggt           55

<210> SEQ ID NO 23
<211> LENGTH: 55
<212> TYPE: DNA
<213> ORGANISM: Artificial Sequence
<220> FEATURE:
<223> OTHER INFORMATION: Description of Artificial Sequence: SYNTHETIC
```

```
<400> SEQUENCE: 23
tatcgcctta ggctcagtta aatcgcaaat tggtcatact aaatctgcgg ctggc          55

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 24
cggcttcgat tttggcggca tgaacggtg                                       29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 25
cgcgtatgat taaggcggca ttagcgctg                                       29

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: SYNTHETIC

<400> SEQUENCE: 26
gcactgctgc aagcatgaac gcgtcgtt                                        28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: SYNTHETIC

<400> SEQUENCE: 27
gctctgcggc tatcattaac gcggcatt                                        28

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 28
tccctggtgc taaccatatc agcaaacca                                       29

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 29
tacctgcaac gatccatatc gataaacca                                       29

<210> SEQ ID NO 30
<211> LENGTH: 98
```

```
<212> TYPE: DNA
<213> ORGANISM: Artificial Sequence
<220> FEATURE:
<223> OTHER INFORMATION: Description of Artificial Sequence: SYNTHETIC

<400> SEQUENCE: 30
ctcacctttg tatctaaaca ctgagacttc gtccatggtt accacgtgtt gatggtacgc      60
cgcgccgcgc gggtattagc tcatttggtt ttggtggc                             98

<210> SEQ ID NO 31
<211> LENGTH: 98
<212> TYPE: DNA
<213> ORGANISM: Artificial Sequence
<220> FEATURE:
<223> OTHER INFORMATION: Description of Artificial Sequence: SYNTHETIC

<400> SEQUENCE: 31
cagcccgtta tacctaaaca gcgaaacggc gtccttggat gccacgtgaa gatggtattc      60
cacgtcgtgc aggtattagc tcatttggtt ttggtggc                             98

<210> SEQ ID NO 32
<211> LENGTH: 4
<212> TYPE: PRT
<213> ORGANISM: Shewanella putrefaciens

<400> SEQUENCE: 32

Asp Xaa Ala Cys
  1

<210> SEQ ID NO 33
<211> LENGTH: 4
<212> TYPE: PRT
<213> ORGANISM: Shewanella putrefaciens

<400> SEQUENCE: 33

Gly Phe Gly Gly
  1

<210> SEQ ID NO 34
<211> LENGTH: 5
<212> TYPE: PRT
<213> ORGANISM: Shewanella putrefaciens

<400> SEQUENCE: 34

Gly His Ser Xaa Gly
  1               5

<210> SEQ ID NO 35
<211> LENGTH: 6
<212> TYPE: PRT
<213> ORGANISM: Shewanella putrefaciens

<400> SEQUENCE: 35

Leu Gly Xaa Asp Ser Leu
  1               5

<210> SEQ ID NO 36
<211> LENGTH: 6
<212> TYPE: PRT
<213> ORGANISM: Shewanella putrefaciens

<400> SEQUENCE: 36

Leu Gly Xaa Asp Ser Ile
  1               5
```

```
<210> SEQ ID NO 37
<211> LENGTH: 6
<212> TYPE: PRT
<213> ORGANISM: Shewanella putrefaciens

<400> SEQUENCE: 37

Gly Xaa Gly Xaa Xaa Gly
 1               5

<210> SEQ ID NO 38
<211> LENGTH: 6
<212> TYPE: PRT
<213> ORGANISM: Shewanella putrefaciens

<400> SEQUENCE: 38

Gly Xaa Gly Xaa Xaa Ala
 1               5

<210> SEQ ID NO 39
<211> LENGTH: 6
<212> TYPE: PRT
<213> ORGANISM: 'Axial Seamount' polynoid polychaete

<400> SEQUENCE: 39

Gly Xaa Gly Xaa Xaa Pro
 1               5

<210> SEQ ID NO 40
<211> LENGTH: 5
<212> TYPE: PRT
<213> ORGANISM: Shewanella putrefaciens

<400> SEQUENCE: 40

Gly Xaa Ser Xaa Gly
 1               5

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: synthetic

<400> SEQUENCE: 41
cuacuacuac uaccaagcta aagcacttaa ccgtg                              35

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: synthetic

<400> SEQUENCE: 42
cuacuacuac uaacagcgaa atgcttatca ag                                 32

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: synthetic

<400> SEQUENCE: 43
```
cuacuacuac uagcgaccaa aaccaaauga gcuaauac      38

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence: synthetic

<400> SEQUENCE: 44
aagcccgggc tt      12

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 45
gtacaagccc gggcttagct      20

<210> SEQ ID NO 46
<211> LENGTH: 56
<212> TYPE: DNA
<213> ORGANISM: Artificial Sequence
<220> FEATURE:
<223> OTHER INFORMATION: Description of Artificial Sequence: synthetic

<400> SEQUENCE: 46
cgcgatttaa atggcgcgcc ctgcaggcgg ccgcctgcag ggcgcgccat ttaaat      56

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence: synthetic

<400> SEQUENCE: 47
ctgcagctcg agacaatgtt gatttcctta tacttctgtc c      41

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 48
ggatccagat ctctagctag tcttagctga agctcga      37

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 49
tctagactcg agacaatgag ccagacctct aaacctaca      39

<210> SEQ ID NO 50
<211> LENGTH: 37
<212> TYPE: DNA
<213> ORGANISM: Artificial Sequence

```
<220> FEATURE:
<223> OTHER INFORMATION: Description of Artificial Sequence: synthetic

<400> SEQUENCE: 50
cccgggctcg agctaattcg cctcactgtc gtttgct                                      37

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 51
gaattcctcg agacaatgcc gctgcgcatc gcacttatc                                    39

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 52
ggtaccagat ctttagactt ccccttgaag taaatgg                                      37

<210> SEQ ID NO 53
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 53
gaattcgtcg acacaatgtc attaccagac aatgcttct                                    39

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence: synthetic

<400> SEQUENCE: 54
tctagagtcg acttatacag attcttcgat gctgatag                                     38

<210> SEQ ID NO 55
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 55
gaattcgtcg acacaatgaa tcctacagca actaacgaa                                    39

<210> SEQ ID NO 56
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 56
tctagaggat ccttaggcca ttctttggtt tggcttc                                      37
```

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 57
tctagagtcg acacaatggc ggaattagct gttattggt                                    39

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: synthetic

<400> SEQUENCE: 58
gtcgacggat ccctatttgt tcgtgtttgc tatatg                                       36

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence: synthetic

<400> SEQUENCE: 59
gtcgacggat ccacaatgaa tatagtaagt aatcattcgg ca                                42

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 60
gtcgacctcg agttaatcac tcgtacgata acttgcc                                      37

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 61
cccgggtcga cacaatggct aaaaagaaca ccacatcga                                    39

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: synthetic

<400> SEQUENCE: 62
cccgggtcga ctcatgacat atcgttcaaa atgtcactga                                   40

<210> SEQ ID NO 63
<211> LENGTH: 44
<212> TYPE: DNA
<213> ORGANISM: Artificial Sequence
<220> FEATURE:
<223> OTHER INFORMATION: Description of Artificial Sequence: synthetic -continued

```
<400> SEQUENCE: 63
tcgacatgga aaatattgca gtagtaggta ttgctaattt gttc                    44

<210> SEQ ID NO 64
<211> LENGTH: 44
<212> TYPE: DNA
<213> ORGANISM: Artificial Sequence
<220> FEATURE:
<223> OTHER INFORMATION: Description of Artificial Sequence: synthetic

<400> SEQUENCE: 64
ccgggaacaa attagcaata cctactactg caatattttc catg                    44

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: synthetic

<400> SEQUENCE: 65
tcagatgaac tttatcgata c                                             21

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: synthetic

<400> SEQUENCE: 66
tcatgagacg tcgtcgactt acgcttcaac aatact                             36
```

PRODUCTION OF POLYUNSATURATED FATTY ACIDS BY EXPRESSION OF POLYKETIDE-LIKE SYNTHESIS GENES IN PLANTS

CROSS-REFERENCE TO RELATED APPLICATION

This application is a continuation-in-part of provisional application U.S. Ser. No. 60/048,650 filed Jun. 4, 1997, which is incorporated herein by reference.

INTRODUCTION

1. Field of the Invention

This invention relates to modulating levels of enzymes and/or enzyme components capable of modifying long chain poly-unsaturated fatty acids (PUFAs) in a host cell, and constructs and methods for producing PUFAs in a host cell. The invention is exemplified by production of eicosapentenoic acid (EPA) using genes derived from *Shewanella putrefaciens* and *Vibrio marinus*.

2. Background

Two main families of poly-unsaturated fatty acids (PUFAs) are the ω3 fatty acids, exemplified by eicosapentenoic acid, and the ω6 fatty acids, exemplified by arachidonic acid. PUFAs are important components of the plasma membrane of the cell, where they can be found in such forms as phospholipids, and also can be found in triglycerides. PUFAs also serve as precursors to other molecules of importance in human beings and animals, including the prostacyclins, leukotrienes and prostaglandins. Long chain PUFAs of importance include docosahexenoic acid (DHA) and eicosapentenoic acid (EPA), which are found primarily in different types of fish oil, gamma-linolenic acid (GLA), which is found in the seeds of a number of plants, including evening primrose (*Oenothera biennis*), borage (*Borago officinalis*) and black currants (*Ribes nigrum*), stearidonic acid (SDA), which is found in marine oils and plant seeds, and arachidonic acid (ARA), which along with GLA is found in filamentous fungi. ARA can be purified from animal tissues including liver and adrenal gland. Several genera of marine bacteria are known which synthesize either EPA or DHA. DHA is present in human milk along with ARA.

PUFAs are necessary for proper development, particularly in the developing infant brain, and for tissue formation and repair. As an example, DHA, is an important constituent of many human cell membranes, in particular nervous cells (gray matter), muscle cells, and spermatozoa and believed to affect the development of brain functions in general and to be essential for the development of eyesight. EPA and DHA have a number of nutritional and pharmacological uses. As an example adults affected by diabetes (especially non insulin-dependent) show deficiencies and imbalances in their levels of DHA which are believed to contribute to later coronary conditions. Therefore a diet balanced in DHA may be beneficial to diabetics.

For DHA, a number of sources exist for commercial production including a variety of marine organisms, oils obtained from cold water marine fish, and egg yolk fractions. The purification of DHA from fish sources is relatively expensive due to technical difficulties, making DHA expensive and in short supply. In algae such as Amphidinium and Schyzochytrium and marine fungi such as Thraustochytrium DHA may represent up to 48% of the fatty acid content of the cell. A few bacteria also are reported to produce DHA. These are generally deep sea bacteria such as *Vibrio marinus*. For ARA, microorganisms including the genera Mortierella, Entomophthora, Phytium and Porphyridium can be used for commercial production. Commercial sources of SDA include the genera Trichodesma and Echium. Commercial sources of GLA include evening primrose, black currants and borage. However, there are several disadvantages associated with commercial production of PUFAs from natural sources. Natural sources of PUFA, such as animals and plants, tend to have highly heterogeneous oil compositions. The oils obtained from these sources can require extensive purification to separate out one or more desired PUFA or to produce an oil which is enriched in one or more desired PUFA.

Natural sources also are subject to uncontrollable fluctuations in availability. Fish stocks may undergo natural variation or may be depleted by overfishing. Animal oils, and particularly fish oils, can accumulate environmental pollutants. Weather and disease can cause fluctuation in yields from both fish and plant sources. Cropland available for production of alternate oil-producing crops is subject to competition from the steady expansion of human populations and the associated increased need for food production on the remaining arable land. Crops which do produce PUFAs, such as borage, have not been adapted to commercial growth and may not perform well in monoculture. Growth of such crops is thus not economically competitive where more profitable and better established crops can be grown. Large-scale fermentation of organisms such as Shewanella also is expensive. Natural animal tissues contain low amounts of ARA and are difficult to process. Microorganisms such as Porphyridium and Shewanella are difficult to cultivate on a commercial scale.

Dietary supplements and pharmaceutical formulations containing PUFAs can retain the disadvantages of the PUFA source. Supplements such as fish oil capsules can contain low levels of the particular desired component and thus require large dosages. High dosages result in ingestion of high levels of undesired components, including contaminants. Care must be taken in providing fatty acid supplements, as overaddition may result in suppression of endogenous biosynthetic pathways and lead to competition with other necessary fatty acids in various lipid fractions in vivo, leading to undesirable results. For example, Eskimos having a diet high in ω3 fatty acids have an increased tendency to bleed (U.S. Pat. No. 4,874,603). Fish oils have unpleasant tastes and odors, which may be impossible to economically separate from the desired product, such as a food supplements. Unpleasant tastes and odors of the supplements can make such regimens involving the supplement undesirable and may inhibit compliance by the patient.

A number of enzymes have been identified as being involved in PUFA biosynthesis. Linoleic acid (LA, 18:2 Δ9, 12) is produced from oleic acid (18:1 Δ9) by a Δ12-desaturase. GLA (18:3 Δ6, 9, 12) is produced from linoleic acid (LA, 18:2 Δ9, 12) by a Δ6-desaturase. ARA (20:4 Δ5, 8, 11, 14) is produced from DGLA (20:3 Δ8, 11, 14), catalyzed by a Δ5-desaturase. Eicosapentenoic acid (EPA) is a 20 carbon, omega 3 fatty acid containing 5 double bonds (Δ5, 8, 11, 14, 17), all in the cis configuration. EPA, and the related DHA (Δ4, 7, 10, 13, 16, 19, C22:6) are produced from oleic acid by a series of elongation and desaturation reactions. Additionally, an elongase (or elongases) is required to extend the 18 carbon PUFAs out to 20 and 22 carbon chain lengths. However, animals cannot convert oleic acid (18:1 Δ9) into linoleic acid (18:2 Δ9, 12). Likewise, μ-linolenic acid (ALA, 18:3 Δ9, 12, 15) cannot be synthesized by mammals. Other eukaryotes, including fungi and plants, have enzymes which desaturate at positions Δ12 and Δ15. The major poly-unsaturated fatty acids of animals therefore are either derived from diet and/or from desaturation and elongation of linoleic acid (18:2 Δ9, 12) or μ-linolenic acid (18:3 Δ9, 12, 15).

Poly-unsaturated fatty acids are considered to be useful for nutritional, pharmaceutical, industrial, and other purposes. An expansive supply of poly-unsaturated fatty acids from natural sources and from chemical synthesis are not sufficient for commercial needs. Because a number of separate desaturase and elongase enzymes are required for fatty acid synthesis from linoleic acid (LA, 18:2 Δ9, 12), common in most plant species, to the more saturated and longer chain PUFAs, engineering plant host cells for the expression of EPA and DHA may require expression of five or six separate enzyme activities to achieve expression, at least for EPA and DHA, and for production of quantities of such PUFAs additional engineering efforts may be required, for instance the down regulation of enzymes competing for substrate, engineering of higher enzyme activities such as by mutagenesis or targeting of enzymes to plastid organelles. Therefore it is of interest to obtain genetic material involved in PUFA biosynthesis from species that naturally produce these fatty acids and to express the isolated material alone or in combination in a heterologous system which can be manipulated to allow production of commercial quantities of PUFAs.

Relevant Literature

Several genera of marine bacteria have been identified which synthesize either EPA or DHA (DeLong and Yayanos, *Applied and Environmental Microbiology* (1986) 51: 730–737). Researchers of the Sagami Chemical Research Institute have reported EPA production in *E. coli* which have been transformed with a gene cluster from the marine bacterium, *Shewanella putrefaciens*. A minimum of 5 open reading frames (ORFs) are required for fatty acid synthesis of EPA in *E. coli*. To date, extensive characterization of the functions of the proteins encoded by these genes has not been reported (Yazawa (1996) *Lipids* 31, S-297; WO 93/23545; WO 96/21735).

The protein sequence of open reading frame (ORF) 3 as published by Yazawa, U.S. Pat. No. 5,683,898 is not a functional protein. Yazawa defines the protein as initiating at the methionine codon at nucleotides 9016–9014 of the Shewanella PKS-like cluster (Genbank accession U73935) and ending at the stop codon at nucleotides 8185–8183 of the Shewanella PKS-like cluster. However, when this ORF is expressed under control of a heterologous promoter in an *E. coli* strain containing the entire PKS-like cluster except ORF 3, the recombinant cells do not produce EPA.

Polyketides are secondary metabolites the synthesis of which involves a set of enzymatic reactions analogous to those of fatty acid synthesis (see reviews: Hopwood and Sherman, *Annu. Rev. Genet.* (1990) 24: 37–66, and Katz and Donadio, in *Annual Review of Microbiology* (1993) 47: 875–912). It has been proposed to use polyketide synthases to produce novel antibiotics (Hutchinson and Fujii, *Annual Review of Microbiology* (1995) 49:201–238).

SUMMARY OF THE INVENTION

Novel compositions and methods are provided for preparation of long chain poly-unsaturated fatty acids (PUFAs) using polyketide-like synthesis (PKS-like) genes in plants and plant cells. In contrast to the known and proposed methods for production of PUFAs by means of fatty acid synthesis genes, by the invention constructs and methods are provided for producing PUFAs by utilizing genes of a PKS-like system. The methods involve growing a host cell of interest transformed with an expression cassette functional in the host cell, the expression cassette comprising a transcriptional and translational initiation regulatory region, joined in reading frame 5' to a DNA sequence to a gene or component of a PKS-like system capable of modulating the production of PUFAs (PKS-like gene). An alteration in the PUFA profile of host cells is achieved by expression following introduction of a complete PKS-like system responsible for a PUFA biosynthesis into host cells. The invention finds use for example in the large scale production of DHA and EPA and for modification of the fatty acid profile of host cells and edible plant tissues and/or plant parts.

BRIEF DESCRIPTION OF THE DRAWINGS

FIG. 1A shows the organization of the genes; those ORFs essential for EPA production in *E. coli* are numbered. FIG. 1B shows the designations given to subclones.

FIGS. 2A–2F provides the Shewanella PKS-like domain structure, motifs and 'Blast' matches of ORF 6 (FIG. 2A), ORF 7 (FIG. 2B), ORF 8 (FIG. 2C), ORF 9 (FIG. 2D) and ORF 3 (FIG. 2E). FIG. 2F shows the structure of the region of the Anabeana chromosome that is related to domains present in Shewanella EPA ORFs.

FIG. 4A shows the DNA sequence (SEQ ID NO:1) for the PKS-like cluster found in Shewanella, containing ORF's 3–9. FIG. 4B shows the amino acid sequence (SEQ ID NO:2) of ORF 2, which is coded by nucleotides 6121–8103 of the sequence shown in FIG. 4A. FIG. 4C shows the amino acid sequence (SEQ ID NO:3) of the published, inactive ORF3, translated from the strand complementary to that shown in FIG. 4A, nucleotides 9016–8186. FIG. 4D shows the nucleotide sequence 8186–9157 (SEQ ID NO:4); its complementary strand codes for ORF 3 active in EPA synthesis. FIGS. 4E–J show the amino acid sequences (SEQ ID NOS:5–10) corresponding to ORF's 4–9, which are encoded by nucleotides 9681–12590, 13040–13903, 13906–22173, 22203–24515, 24518–30529 and 30730–32358, respectively, of FIG. 4A. FIG. 4K shows the amino acid sequence (SEQ ID NO:11) corresponding to nucleotides 32834–34327.

FIG. 5 shows the sequence (SEQ ID NO:12) for the PKS-like cluster in an approximately 40 kb DNA fragment of *Vibrio marinus*, containing ORFs 6, 7, 8 and 9. The start and last condons for each ORF are as follows: ORF 6:17394, 25352; ORF 7: 25509, 28160; ORF 8: 28209, 34265; ORF 9: 34454, 36118.

FIG. 6 shows the sequence (SEQ ID NO:13) for an approximately 19 kb portion of the PKS-like cluster of FIG. 5 which contains the ORFs 6, 7, 8 and 9. The start and last condons for each ORF are as follows: ORF6: 411, 8369; ORF 7:8526, 11177; ORF 8:11226, 17282; ORF9: 17471, 19135.

FIG. 7B is the *Vibrio marinus* operon sequence.

FIG. 16 is a table of PUFA values from the ORF 8 complementation experiment, the chromatogram of which is shown in FIG. 15.

FIG. 24 shows the translated DNA sequence (SEQ ID NO:14) upstream of the published ORF 3 and the corresponding amino acids for which they code (SEQ ID NO: 15).

Figure 1A:
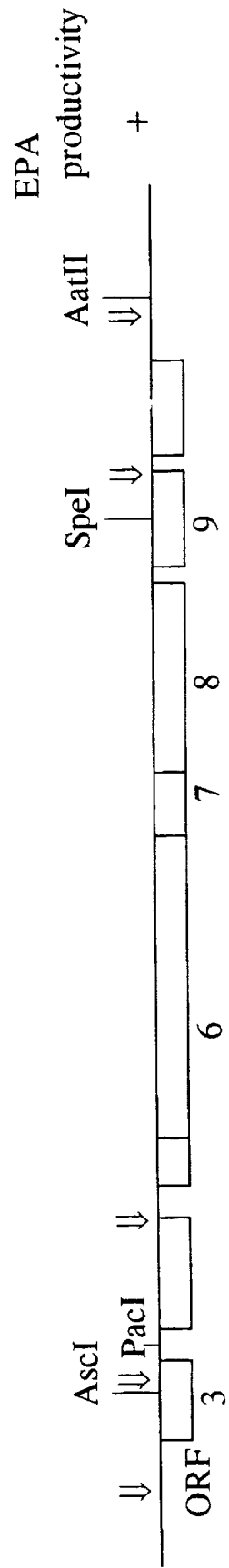
FIGS. 1A–1B provides designations for the ORFs of the EPA gene cluster of Shewanella.

The ATG start codon at position 9016 is the start codon for the protein described by Yazawa et al (1996) supra. The other arrows depict TTG or ATT codons that can also serve as start codons in bacteria. When ORF 3 is started from the published ATG codon at 9016, the protein is not functional in making EPA. When ORF 3 is initiated at the TTG codon at position 9157, the protein is capable of facilitating EPA synthesis.

FIG. 25 shows the PCR product (SEQ ID NO:16) for SS9 Photobacter using primers in Example 1.

FIG. 26 shows probe sequences (SEQ ID NOS:17–31) resulting from PCR with primers presented in Example 1.

DESCRIPTION OF THE PREFERRED EMBODIMENTS

In accordance with the subject invention, novel DNA sequences, DNA constructs and methods are provided, which include some or all of the polyketide-like synthesis (PKS-like) pathway genes from Shewanella, Vibrio or other microorganisms, for modifying the poly-unsaturated long chain fatty acid content of host cells, particularly host plant cells. The present invention demonstrates that EPA synthesis genes in *Shewanella putrefaciens* constitute a polyketide-like synthesis pathway. Functions are ascribed to the Shewanella and Vibrio genes and methods are provided for the production of EPA and DHA in host cells. The method includes the step of transforming cells with an expression cassette comprising a DNA encoding a polypeptide capable of increasing the amount of one or more PUFA in the host cell. Desirably, integration constructs are prepared which provide for integration of the expression cassette into the genome of a host cell. Host cells are manipulated to express a sense or antisense DNA encoding a polypeptide(s) that has PKS-like gene activity. By "PKS-like gene" is intended a polypeptide which is responsible for any one or more of the functions of a PKS-like activity of interest. By "polypeptide" is meant any chain of amino acids, regardless of length or post-translational modification, for example, glycosylation or phosphorylation. Depending upon the nature of the host cell, the substrate(s) for the expressed enzyme may be produced by the host cell or may be exogenously supplied. Of particular interest is the selective control of PUFA production in plant tissues and/or plant parts such as leaves, roots, fruits and seeds. The invention can be used to synthesize EPA, DHA, and other related PUFAs in host cells.

There are many advantages to transgenic production of PUFAs. As an example, in transgenic *E. coli* as in Shewanella, EPA accumulates in the phospholipid fraction, specifically in the sn-2 position. It may be possible to produce a structured lipid in a desired host cell which differs substantially from that produced in either Shewanella or *E.* coli. Additionally transgenic production of PUFAs in particular host cells offers several advantages over purification from natural sources such as fish or plants. In transgenic plants, by utilizing a PKS-like system, fatty acid synthesis of PUFAs is achieved in the cytoplasm by a system which produces the PUFAs through de novo production of the fatty acids utilizing malonyl Co-A and acetyl Co-A as substrates. In this fashion, potential problems, such as those associated with substrate competition and diversion of normal products of fatty acid synthesis in a host to PUFA production, are avoided.

Production of fatty acids from recombinant plants provides the ability to alter the naturally occurring plant fatty acid profile by providing new synthetic pathways in the host or by suppressing undesired pathways, thereby increasing levels of desired PUFAs, or conjugated forms thereof, and decreasing levels of undesired PUFAs. Production of fatty acids in transgenic plants also offers the advantage that expression of PKS-like genes in particular tissues and/or plant parts means that greatly increased levels of desired PUFAs in those tissues and/or parts can be achieved, making recovery from those tissues more economical. Expression in a plant tissue and/or plant part presents certain efficiencies, particularly where the tissue or part is one which is easily harvested, such as seed, leaves, fruits, flowers, roots, etc. For example, the desired PUFAs can be expressed in seed; methods of isolating seed oils are well established. In addition to providing a source for purification of desired PUFAs, seed oil components can be manipulated through expression of PKS-like genes, either alone or in combination with other genes such as elongases, to provide seed oils having a particular PUFA profile in concentrated form. The concentrated seed oils then can be added to animal milks and/or synthetic or semisynthetic milks to serve as infant formulas where human nursing is impossible or undesired, or in cases of malnourishment or disease in both adults and infants.

Transgenic microbial production of fatty acids offers the advantages that many microbes are known with greatly simplified oil compositions as compared with those of higher organisms, making purification of desired components easier. Microbial production is not subject to fluctuations caused by external variables such as weather and food supply. Microbially produced oil is substantially free of contamination by environmental pollutants. Additionally, microbes can provide PUFAs in particular forms which may have specific uses. For example, Spirulina can provide PUFAs predominantly at the first and third positions of triglycerides; digestion by pancreatic lipases preferentially releases fatty acids from these positions. Following human or animal ingestion of triglycerides derived from Spirulina, the PUFAs are released by pancreatic lipases as free fatty acids and thus are directly available, for example, for infant brain development. Additionally, microbial oil production can be manipulated by controlling culture conditions, notably by providing particular substrates for microbially expressed enzymes, or by addition of compounds which suppress undesired biochemical pathways. In addition to these advantages, production of fatty acids from recombinant microbes provides the ability to alter the naturally occurring microbial fatty acid profile by providing new synthetic pathways in the host or by suppressing undesired pathways, thereby increasing levels of desired PUFAs, or conjugated forms thereof, and decreasing levels of undesired PUFAs.

Production of fatty acids in animals also presents several advantages. Expression of desaturase genes in animals can produce greatly increased levels of desired PUFAs in animal tissues, making recovery from those tissues more economical. For example, where the desired PUFAs are expressed in the breast milk of animals, methods of isolating PUFAs from animal milk are well established. In addition to providing a source for purification of desired PUFAs, animal breast milk can be manipulated through expression of desaturase genes, either alone or in combination with other human genes, to provide animal milks with a PUFA composition substantially similar to human breast milk during the different stages of infant development. Humanized animal milks could serve as infant formulas where human nursing is impossible or undesired, or in the cases of malnourishment or disease.

DNAs encoding desired PKS-like genes can be identified in a variety of ways. In one method, a source of a desired PKS-like gene, for example genomic libraries from a Shewanella or Vibrio spp., is screened with detectable enzymatically- or chemically-synthesized probes. Sources of ORFs having PKS-like genes are those organisms which produce a desired PUFA, including DHA-producing or EPA-producing deep sea bacteria growing preferentially under high pressure or at relatively low temperature. Microorgansims such as Shewanella which produce EPA or DHA also can be used as a source of PKS-like genes. The probes can be made from DNA, RNA, or non-naturally occurring nucleotides, or mixtures thereof. Probes can be enzymatically synthesized from DNAs of known PKS-like genes for normal or reduced-stringency hybridization methods. For discussions of nucleic acid probe design and annealing conditions, see, for example, Sambrook et al, *Molecular Cloning: A Laboratory Manual* ($2^{nd}$ ed.), Vols. 1–3, Cold Spring Harbor Laboratory, (1989) or *Current Protocols in Molecular Biology*, F. Ausubel et al, ed., Greene Publishing and Wiley-Interscience, New York (1987), each of which is incorporated herein by reference. Techniques for manipulation of nucleic acids encoding PUFA enzymes such as subcloning nucleic acid sequences encoding polypeptides into expression vectors, labelling probes, DNA hybridization, and the like are described generally in Sambrook, supra.

Oligonucleotide probes also can be used to screen sources and can be based on sequences of known PKS-like genes, including sequences conserved among known PKS-like genes, or on peptide sequences obtained from a desired purified protein. Oligonucleotide probes based on amino acid sequences can be degenerate to encompass the degeneracy of the genetic code, or can be biased in favor of the preferred codons of the source organism. Alternatively, a desired protein can be entirely sequenced and total synthesis of a DNA encoding that polypeptide performed.

Once the desired DNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA can also be employed.

For the most part, some or all of the coding sequences for the polypeptides having PKS-like gene activity are from a natural source. In some situations, however, it is desirable to modify all or a portion of the codons, for example, to enhance expression, by employing host preferred codons. Host preferred codons can be determined from the codons of highest frequency in the proteins expressed in the largest amount in a particular host species of interest. Thus, the coding sequence for a polypeptide having PKS-like gene activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable to the desired host cell. Methods for synthesizing sequences and bringing sequences together are well established in the literature. In vitro mutagenesis and selection, site-directed mutagenesis, or other means can be employed to obtain mutations of naturally occurring PKS-like genes to produce a polypeptide having PKS-like gene activity in vivo with more desirable physical and kinetic parameters for function in the host cell, such as a longer half-life or a higher rate of production of a desired polyunsaturated fatty acid.

Of particular interest are the *Shewanella putrefaciens* ORFs and the corresponding ORFs of *Vibrio marinus*. The *Shewanella putrefaciens* PKS-like genes can be expressed in transgenic plants to effect biosynthesis of EPA. Other DNAs which are substantially identical in sequence to the *Shewanella putrefaciens* PKS-like genes, or which encode polypeptides which are substantially similar to PKS-like genes of *Shewanella putrefaciens* can be used, such as those identified from *Vibrio marinus*. By substantially identical in sequence is intended an amino acid sequence or nucleic acid sequence exhibiting in order of increasing preference at least 60%, 80%, 90% or 95% homology to the DNA sequence of the *Shewanella putrefaciens* PKS-like genes or nucleic acid sequences encoding the amino acid sequences for such genes. For polypeptides, the length of comparison sequences generally is at least 16 amino acids, preferably at least 20 amino acids, and most preferably 35 amino acids. For nucleic acids, the length of comparison sequences generally is at least 50 nucleotides, preferably at least 60 nucleotides, and more preferably at least 75 nucleotides, and most preferably, 110 nucleotides.

Homology typically is measured using sequence analysis software, for example, the Sequence Analysis software package of the Genetics Computer Group, University of Wisconsin Biotechnology Center, 1710 University Avenue, Madison, Wis. 53705, MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). BLAST (National Center for Biotechnology Information (WCBI) www.ncbi.nlm.gov; FASTA (Pearson and Lipman, *Science* (1985) 227:1435–1446). Such software matches similar sequences by assigning degrees of homology to various substitutions, deletions, and other modifications. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* (1982) 157: 105–132), or on the basis of the ability to assume similar polypeptide secondary structure (Chou and Fasman, *Adv. Enzymol.* (1978) 47: 45–148, 1978). A related protein to the probing sequence is identified when $p \geq 0.01$, preferably $p \geq 10^{-7}$ or $10^{-8}$.

Encompassed by the present invention are related PKS-like genes from the same or other organisms. Such related PKS-like genes include variants of the disclosed PKS-like ORFs that occur naturally within the same or different species of Shewanella, as well as homologues of the disclosed PKS-like genes from other species and evolutionarily related proteins having analogous function and activity. Also included are PKS-like genes which, although not substantially identical to the *Shewanella putrefaciens* PKS-like genes, operate in a similar fashion to produce PUFAs as part of a PKS-like system. Related PKS-like genes can be identified by their ability to function substantially the same as the disclosed PKS-like genes; that is, they can be substituted for corresponding ORFs of Shewanella or Vibrio and still effectively produce EPA or DHA. Related PKS-like genes also can be identified by screening sequence databases for sequences homologous to the disclosed PKS-like genes, by hybridization of a probe based on the disclosed PKS-like genes to a library constructed from the source organism, or by RT-PCR using mRNA from the source organism and primers based on the disclosed PKS-like gene. Thus, the phrase "PKS-like genes" refers not only to the nucleotide sequences disclosed herein, but also to other nucleic acids that are allelic or species variants of these nucleotide sequences. It is also understood that these terms include nonnatural mutations introduced by deliberate mutation using recombinant technology such as single site mutation or by excising short sections of DNA open reading frames coding for PUFA enzymes or by substituting new codons or adding new codons. Such minor alterations substantially maintain the immunoidentity of the original expression product and/or its biological activity. The biological properties of the altered PUFA enzymes can be determined by expressing the enzymes in an appropriate cell line and by determining the ability of the enzymes to synthesize PUFAs. Particular enzyme modifications considered minor would include substitution of amino acids of similar chemical properties, e.g., glutamic acid for aspartic acid or glutamine for asparagine.

When utilizing a PUFA PKS-like system from another organism, the regions of a PKS-like gene polypeptide important for PKS-like gene activity can be determined through routine mutagenesis, expression of the resulting mutant polypeptides and determination of their activities. The coding region for the mutants can include deletions, insertions and point mutations, or combinations thereof. A typical functional analysis begins with deletion mutagenesis to determine the N- and C-terminal limits of the protein necessary for function, and then internal deletions, insertions or point mutants are made in the open ready frame to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a PKS-like gene polypeptide important for activity. A mutated construct is expressed, and the ability of the resulting altered protein to function as a PKS-like gene is assayed. Such structure-function analysis can determine which regions may be deleted, which regions tolerate insertions, and which point mutations allow the mutant protein to function in substantially the same way as the native PKS-like gene. All such mutant proteins and nucleotide sequences encoding them are within the scope of the present invention. EPA is produced in Shewanella as the product of a PKS-like system, such that the EPA genes encode components of this system. In Vibrio, DHA is produced by a similar system. The enzymes which synthesize these fatty acids are encoded by a cluster of genes which are distinct from the fatty acid synthesis genes encoding the enzymes involved in synthesis of the C16 and C18 fatty acids typically found in bacteria and in plants. As the Shewanella EPA genes represent a PKS-like gene cluster, EPA production is, at least to some extent, independent of the typical bacterial type II FAS system. Thus, production of EPA in the cytoplasm of plant cells can be achieved by expression of the PKS-like pathway genes in plant cells under the control of appropriate plant regulatory signals.

EPA production in $E.$ $coli$ transformed with the Shewanella EPA genes proceeds during anaerobic growth, indicating that $O_2$-dependent desaturase reactions are not involved. Analyses of the proteins encoded by the ORFs essential for EPA production reveals the presence of domain structures characteristic of PKS-like systems. FIG. 2A shows a summary of the domains, motifs, and also key homologies detected by "BLAST" data bank searches. Because EPA is different from many of the other substances produced by PKS-like pathways, i.e., it contains 5, cis double bonds, spaced at 3 carbon intervals along the molecule, a PKS-like system for synthesis of EPA is not expected.

Figure 2F:
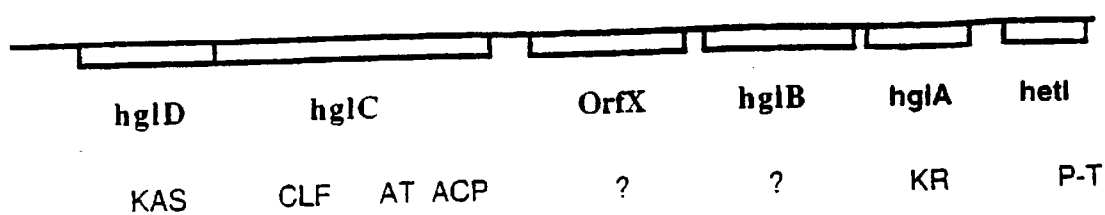

Further, BLAST searches using the domains present in the Shewanella EPA ORFs reveal that several are related to proteins encoded by a PKS-like gene cluster found in Anabeana. The structure of that region of the Anabeana chromosome is shown in FIG. 2F. The Anabeana PKS-like genes have been linked to the synthesis of a long-chain (C26), hydroxy-fatty acid found in a glycolipid layer of heterocysts. The EPA protein domains with homology to the Anabeana proteins are indicated in FIG. 2F.

ORF 6 of Shewanella contains a KAS domain which includes an active site motif (DXAC*), SEQ ID NO:32 as well as a "GFGG", SEQ ID NO:33 motif which is present at the end of many Type II KAS proteins (see FIG. 2A). Extended motifs are present but not shown here. Next is a malonyl-CoA:ACP acyl transferase (AT) domain. Sequences near the active site motif (GHS*XG), SEQ ID NO:34 suggest it transfers malonate rather than methylmalonate, i.e., it resembles the acetate-like ATs. Following a linker region, there is a cluster of 6 repeating domains, each ~100 amino acids in length, which are homologous to PKS-like ACP sequences. Each contains a pantetheine binding site motif (LGXDS*(L/I)), SEQ ID NOS:35 and 36. The presence of 6 such ACP domains has not been observed previously in fatty acid synthases (FAS) or PKS-like systems. Near the end of the protein is a region which shows homology to β-keto-ACP reductases (KR). It contains a pyridine nucleotide binding site motif "GXGXX (G/A/P)", SEQ ID NOS:37, 38 and 39.

The Shewanella ORF 8 begins with a KAS domain, including active site and ending motifs (FIG. 2C). The best match in the data banks is with the Anabeana HglD. There is also a domain which has sequence homology to the N-terminal one half of the Anabeana HglC. This region also shows weak homology to KAS proteins although it lacks the active site and ending motifs. It has the characteristics of the so-called chain length factors (CLF) of Type II PKS-like systems. ORF 8 appears to direct the production of EPA versus DHA by the PKS-like system. ORF 8 also has two domains with homology to β-hydroxyacyl-ACP dehydrases (DH). The best match for both domains is with $E.$ $coli$ FabA, a bi-functional enzyme which carries out both the dehydrase reaction and an isomerization (trans to cis) of the resulting double bond. The first DH domain contains both the active site histidine (H) and an adjacent cysteine (C) implicated in FabA catalysis. The second DH domain has the active site H but lacks the adjacent C (FIG. 2C). Blast searches with the second DH domain also show matches to FabZ, a second $E.$ $coli$ DH, which does not possess isomerase activity.

The N-terminal half of ORF 7 (FIG. 2B) has no significant matches in the data banks. The best match of the C-terminal half is with a C-terminal portion of the Anabeana HglC. This domain contains an acyl-transferase (AT) motif (GXSXG), SEQ ID NO:40. Comparison of the extended active site sequences, based on the crystal structure of the $E.$ $coli$ malonyl-CoA:ACP AT, reveals that ORF 7 lacks two residues essential for exclusion of water from the active site ($E.$ $coli$ nomenclature; Q11 and R117). These data suggest that ORF 7 may function as a thioesterase.

Figure 3:
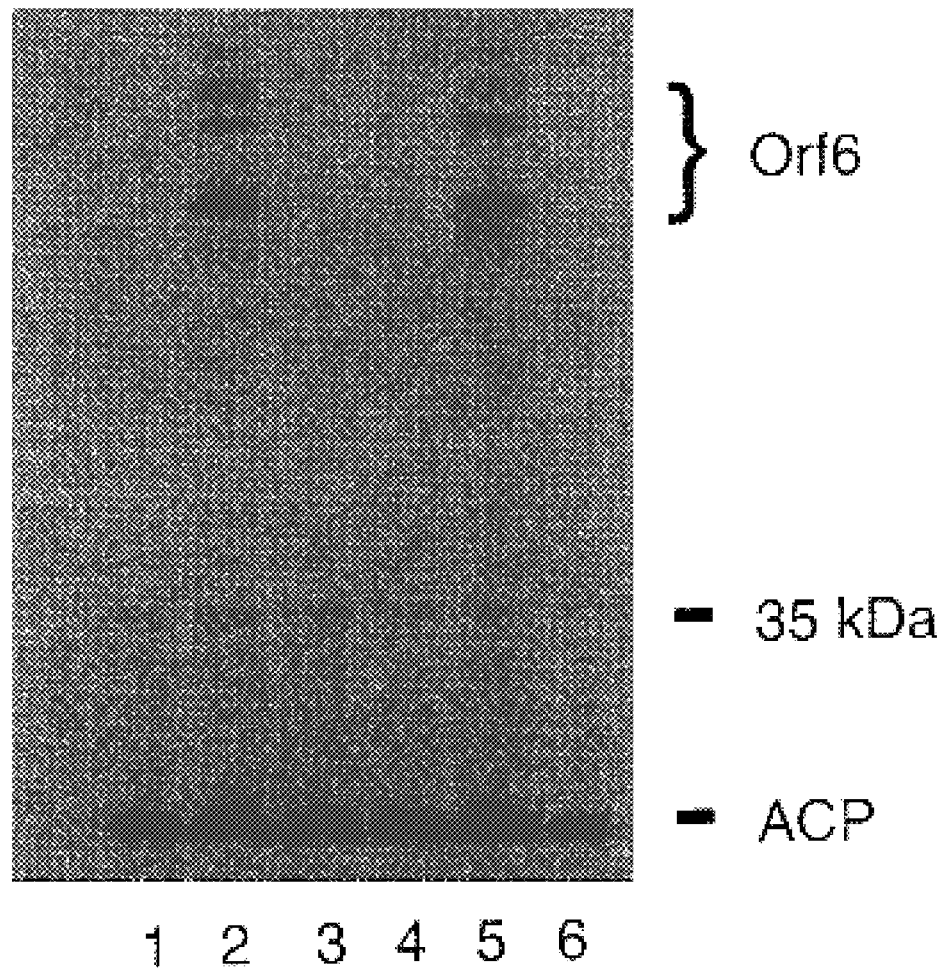
FIG. 3 shows results for pantethenylation—ORF 3 in *E. coli* strain SJ16. The image shows [$C^{14}$] β-Alanine labelled proteins from *E. coli* (strain SJ16) cells transformed with the listed plasmids. Lane 1 represents pUC19, lane 2 represents pPA-NEB (Δ ORF 3), lane 3 represents pAA-Neb (EPA+), lane 4 represents ORF 6 subclone, lane 5 represents ORF 6+ORF 3 subclones, and lane 6 represents ORF 3 subclone. ACP and an unknown (but previously observed) 35 kD protein were labelled in all of the samples. The high molecular mass proteins detected in lanes 2 and 5 are full-length (largest band) and truncated products of the Shewanella ORF-6 gene (confirmed by Western analysis). *E. Coli* strain SJ16 is conditionally blocked in β-alanine synthesis.

ORF 9 (FIG. 2D) is homologous to an ORF of unknown function in the Anabeana Hgl cluster. It also exhibits a very weak homology to NIFA, a regulatory protein in nitrogen fixing bacteria. A regulatory role for the ORF 9 protein has not been excluded. ORF 3 (FIG. 2E) is homologous to the Anabeana HetI as well as EntD from $E.$ $coli$ and Sfp of Bacillus. Recently, a new enzyme family of phosphopantetheinyl transferases has been identified that includes HetI, EntD and Sfp (Lamblot R H, et al. (1996) A new enzyme superfamily—the phosphopantetheinyl transferases. $Chemistry$ $&$ $Biology$, Vol 3, #11, 923–936). The data of FIG. 3 demonstrates that the presence of ORF 3 is required for addition of β-alanine (i.e. pantetheine) to the ORF 6 protein. Thus, ORF 3 encodes the phosphopantetheinyl transferase specific for the ORF 6 ACP domains. (See, Haydock S F et al. (1995) Divergent sequence motifs correlated with the substrate specificity of (methyl)malonyl-CoA:acyl carrier protein transacylase domains in modular polyketide synthases, $FEBS$ $Lett.$, 374, 246–248). Malonate is the source of the carbons utilized in the extension reactions of EPA synthesis. Additionally, malonyl-CoA rather than malonyl-ACP is the AT substrate, i.e., the AT region of ORF 6 uses malonyl Co-A.

Once the DNA sequences encoding the PKS-like genes of an organism responsible for PUFA production have been obtained, they are placed in a vector capable of replication in a host cell, or propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells. A PUFA synthesis enzyme or a homologous protein can be expressed in a variety of recombinantly engineered cells. Numerous expression systems are available for expression of DNA encoding a PUFA enzyme. The expression of natural or synthetic nucleic acids encoding PUFA enzyme is typically achieved by operably linking the DNA to a promoter (which is either constitutive or inducible) within an expression vector. By expression vector is meant a DNA molecule, linear or circular, that comprises a segment encoding a PUFA enzyme, operably linked to additional segments that provide for its transcription. Such additional segments include promoter and terminator sequences. An expression vector also may include one or more origins of replication, one or more selectable markers, an enhancer, a polyadenylation signal, etc. Expression vectors generally are derived from plasmid or viral DNA, and can contain elements of both. The term "operably linked" indicates that the segments are arranged so that they function in concert for their intended purposes, for example, transcription initiates in the promoter and proceeds through the coding segment to the terminator. See Sambrook et al, supra.

The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell. In vitro expression can be accomplished, for example, by placing the coding region for the desaturase polypeptide in an expression vector designed for in vitro use and adding rabbit reticulocyte lysate and cofactors; labeled amino acids can be incorporated if desired. Such in vitro expression vectors may provide some or all of the expression signals necessary in the system used. These methods are well known in the art and the components of the system are commercially available. The reaction mixture can then be assayed directly for PKS-like enzymes for example by determining their activity, or the synthesized enzyme can be purified and then assayed.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a nucleic acid construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus. To achieve expression in a host cell, the transformed DNA is operably associated with transcriptional and translational initiation and termination regulatory regions that are functional in the host cell.

Transcriptional and translational initiation and termination regions are derived from a variety of nonexclusive sources, including the DNA to be expressed, genes known or suspected to be capable of expression in the desired system, expression vectors, chemical synthesis The termination region can be derived from the 3' region of the gene from which the initiation region was obtained or from a different gene. A large number of termination regions are known to and have been found to be satisfactory in a variety of hosts from the same and different genera and species. The termination region usually is selected more as a matter of convenience rather than because of any particular property. When expressing more than one PKS-like ORF in the same cell, appropriate regulatory regions and expression methods should be used. Introduced genes can be propagated in the host cell through use of replicating vectors or by integration into the host genome. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced genes are expressed at the necessary levels to provide for synthesis of the desired products.

A variety of procaryotic expression systems can be used to express PUFA enzyme. Expression vectors can be constructed which contain a promoter to direct transcription, a ribosome binding site, and a transcriptional terminator. Examples of regulatory regions suitable for this purpose in *E. coli* are the promoter and operator region of the *E. coli* tryptophan biosynthetic pathway as described by Yanofsky (1984) *J. Bacteriol.*, 158:1018–1024 and the leftward promoter of phage lambda (Pλ) as described by Herskowitz and Hagen, (1980) *Ann. Rev. Genet.*, 14:399–445. The inclusion of selection markers in DNA vectors transformed in *E. coli* is also useful. Examples of such markers include genes specifying resistance to ampicillin, tetracycline, or chloramphenicol. Vectors used for expressing foreign genes in bacterial hosts generally will contain a selectable marker, such as a gene for antibiotic resistance, and a promoter which functions in the host cell. Plasmids useful for transforming bacteria include pBR322 (Bolivar, et al, (1977) *Gene* 2:95–113), the pUC plasmids (Messing, (1983) *Meth. Enzymol.* 101:20–77, Vieira and Messing, (1982) *Gene* 19:259–268), pCQV2 (Queen, ibid.), and derivatives thereof. Plasmids may contain both viral and bacterial elements. Methods for the recovery of the proteins in biologically active form are discussed in U.S. Pat. Nos. 4,966,963 and 4,999,422, which are incorporated herein by reference. See Sambrook, et al for a description of other prokaryotic expression systems.

For expression in eukaryotes, host cells for use in practicing the present invention include mammalian, avian, plant, insect, and fungal cells. As an example, for plants, the choice of a promoter will depend in part upon whether constitutive or inducible expression is desired and whether it is desirable to produce the PUFAs at a particular stage of plant development and/or in a particular tissue. Considerations for choosing a specific tissue and/or developmental stage for expression of the ORFs may depend on competing substrates or the ability of the host cell to tolerate expression of a particular PUFA. Expression can be targeted to a particular location within a host plant such as seed, leaves, fruits, flowers, and roots, by using specific regulatory sequences, such as those described in U.S. Pat. No. 5,463,174, U.S. Pat. No. 4,943,674, U.S. Pat. No. 5,106,739, U.S. Pat. No. 5,175,095, U.S. Pat. No. 5,420,034, U.S. Pat. No. 5,188,958, and U.S. Pat. No. 5,589,379. Where the host cell is a yeast, transcription and translational regions functional in yeast cells are provided, particularly from the host species. The transcriptional initiation regulatory regions can be obtained, for example from genes in the glycolytic pathway, such as alcohol dehydrogenase, glyceraldehyde-3-phosphate dehydrogenase (GPD), phosphoglucoisomerase, phosphoglycerate kinase, etc. or regulatable genes such as acid phosphatase, lactase, metallothionein, glucoamylase, etc. Any one of a number of regulatory sequences can be used in a particular situation, depending upon whether constitutive or induced transcription is desired, the particular efficiency of the promoter in conjunction with the open-reading frame of interest, the ability to join a strong promoter with a control region from a different promoter which allows for inducible transcription, ease of construction, and the like. Of particular interest are promoters which are activated in the presence of galactose. Galactose-inducible promoters (GAL1, GAL7, and GAL10) have been extensively utilized for high level and regulated expression of protein in yeast (Lue et al, (1987) *Mol. Cell. Biol.* 7:3446; Johnston, (1987) *Microbiol. Rev.* 51:458). Transcription from the GAL promoters is activated by the GAL4 protein, which binds to the promoter region and activates transcription when galactose is present. In the absence of galactose, the antagonist GAL80 binds to GAL4 and prevents GAL4 from activating transcription. Addition of galactose prevents GAL80 from inhibiting activation by GAL4. Preferably, the termination region is derived from a yeast gene, particularly Saccharomyces, Schizosaccharomyces, Candida or Kluyveromyces. The 3' regions of two mammalian genes, γ interferon and α2 interferon, are also known to function in yeast.

Nucleotide sequences surrounding the translational initiation codon ATG have been found to affect expression in yeast cells. If the desired polypeptide is poorly expressed in yeast, the nucleotide sequences of exogenous genes can be modified to include an efficient yeast translation initiation sequence to obtain optimal gene expression. For expression in Saccharomyces, this can be done by site-directed mutagenesis of an inefficiently expressed gene by fusing it in-frame to an endogenous Saccharomyces gene, preferably a highly expressed gene, such as the lactase gene.

As an alternative to expressing the PKS-like genes in the plant cell cytoplasm, is to target the enzymes to the chloroplast. One method to target proteins to the chloroplast entails use of leader peptides attached to the N-termini of the proteins. Commonly used leader peptides are derived from the small subunit of plant ribulose bis phosphate carboxylase. Leader sequences from other chloroplast proteins may also be used. Another method for targeting proteins to the chloroplast is to transform the chloroplast genome (Stable transformation of chloroplasts of *Chlamydomonas reinhardtii* (1 green alga) using bombardment of recipient cells with high-velocity tungsten microprojectiles coated with foreign DNA has been described. See, for example, Blowers et al *Plant Cell* (1989) 1:123–132 and Debuchy et al *EMBO J* (1989) 8:2803–2809. The transformation technique, using tungsten microprojectiles, is described by Kline et al, *Nature* (London) (1987) 327:70–73). The most common method of transforming chloroplasts involves using biolistic techniques, but other techniques developed for the purpose may also be used. (Methods for targeting foreign gene products into chloroplasts (Shrier et al *EMBO J.* (1985) 4:25–32) or mitochnodria (Boutry et al, supra) have been described. See also Tomai et al *Gen. Biol. Chem.* (1988) 263:15104–15109 and U.S. Pat. No. 4,940,835 for the use of transit peptides for translocating nuclear gene products into the chloroplast.

Methods for directing the transport of proteins to the chloroplast are reviewed in Kenauf *TIBTECH* (1987) 5:40–47.

For producing PUFAs in avian species and cells, gene transfer can be performed by introducing a nucleic acid sequence encoding a PUFA enzyme into the cells following procedures known in the art. If a transgenic animal is desired, pluripotent stem cells of embryos can be provided with a vector carrying a PUFA enzyme encoding transgene and developed into adult animal (U.S. Pat. No. 5,162,215; Ono et al. (1996) *Comparative Biochemistry and Physiology* A 113(3):287–292; WO 9612793; WO 9606160). In most cases, the transgene is modified to express high levels of the PKS-like enzymes in order to increase production of PUFAs. The transgenes can be modified, for example, by providing transcriptional and/or translational regulatory regions that function in avian cells, such as promoters which direct expression in particular tissues and egg parts such as yolk. The gene regulatory regions can be obtained from a variety of sources, including chicken anemia or avian leukosis viruses or avian genes such as a chicken ovalbumin gene.

Production of PUFAs in insect cells can be conducted using baculovirus expression vectors harboring PKS-like transgenes. Baculovirus expression vectors are available from several commercial sources such as Clonetech. Methods for producing hybrid and transgenic strains of algae, such as marine algae, which contain and express a desaturase transgene also are provided. For example, transgenic marine algae can be prepared as described in U.S. Pat. No. 5,426,040. As with the other expression systems described above, the timing, extent of expression and activity of the desaturase transgene can be regulated by fitting the polypeptide coding sequence with the appropriate transcriptional and translational regulatory regions selected for a particular use. Of particular interest are promoter regions which can be induced under preselected growth conditions. For example, introduction of temperature sensitive and/or metabolite responsive mutations into the desaturase transgene coding sequences, its regulatory regions, and/or the genome of cells into which the transgene is introduced can be used for this purpose.

The transformed host cell is grown under appropriate conditions adapted for a desired end result. For host cells grown in culture, the conditions are typically optimized to produce the greatest or most economical yield of PUFAs, which relates to the selected desaturase activity. Media conditions which may be optimized include: carbon source, nitrogen source, addition of substrate, final concentration of added substrate, form of substrate added, aerobic or anaerobic growth, growth temperature, inducing agent, induction temperature, growth phase at induction, growth phase at harvest, pH, density, and maintenance of selection. Microorganisms such as yeast, for example, are preferably grown using selected media of interest, which include yeast peptone broth (YPD) and minimal media (contains amino acids, yeast nitrogen base, and ammonium sulfate, and lacks a component for selection, for example uracil). Desirably, substrates to be added are first dissolved in ethanol. Where necessary, expression of the polypeptide of interest may be induced, for example by including or adding galactose to induce expression from a GAL promoter.

When increased expression of the PKS-like gene polypeptide in a host cell which expresses PUFA from a PKS-like system is desired, several methods can be employed. Additional genes encoding the PKS-like gene polypeptide can be introduced into the host organism. Expression from the native PKS-like gene locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (see U.S. Pat. No. 4,910,141 and U.S. Pat. No. 5,500,365). Thus, the subject host will have at least have one copy of the expression construct and may have two or more, depending upon whether the gene is integrated into the genome, amplified, or is present on an extrachromosomal element having multiple copy numbers. Where the subject host is a yeast, four principal types of yeast plasmid vectors can be used: Yeast Integrating plasmids (YIps), Yeast Replicating plasmids (YRps), Yeast Centromere plasmids (YCps), and Yeast Episomal plasmids (YEps). YIps lack a yeast replication origin and must be propagated as integrated elements in the yeast genome. YRps have a chromosomally derived autonomously replicating sequence and are propagated as medium copy number (20 to 40), autonomously replicating, unstably segregating plasmids. YCps have both a replication origin and a centromere sequence and propagate as low copy number (10–20), autonomously replicating, stably segregating plasmids. YEps have an origin of replication from the yeast 2 μm plasmid and are propagated as high copy number, autonomously replicating, irregularly segregating plasmids. The presence of the plasmids in yeast can be ensured by maintaining selection for a marker on the plasmid. Of particular interest are the yeast vectors pYES2 (a YEp plasmid available from Invitrogen, confers uracil prototrophy and a GAL1 galactose-inducible promoter for expression), and pYX424 (a YEp plasmid having a constitutive TP1 promoter and conferring leucine prototrophy; (Alber and Kawasaki (1982). *J. Mol. & Appl. Genetics* 1: 419).

Figure 1B:
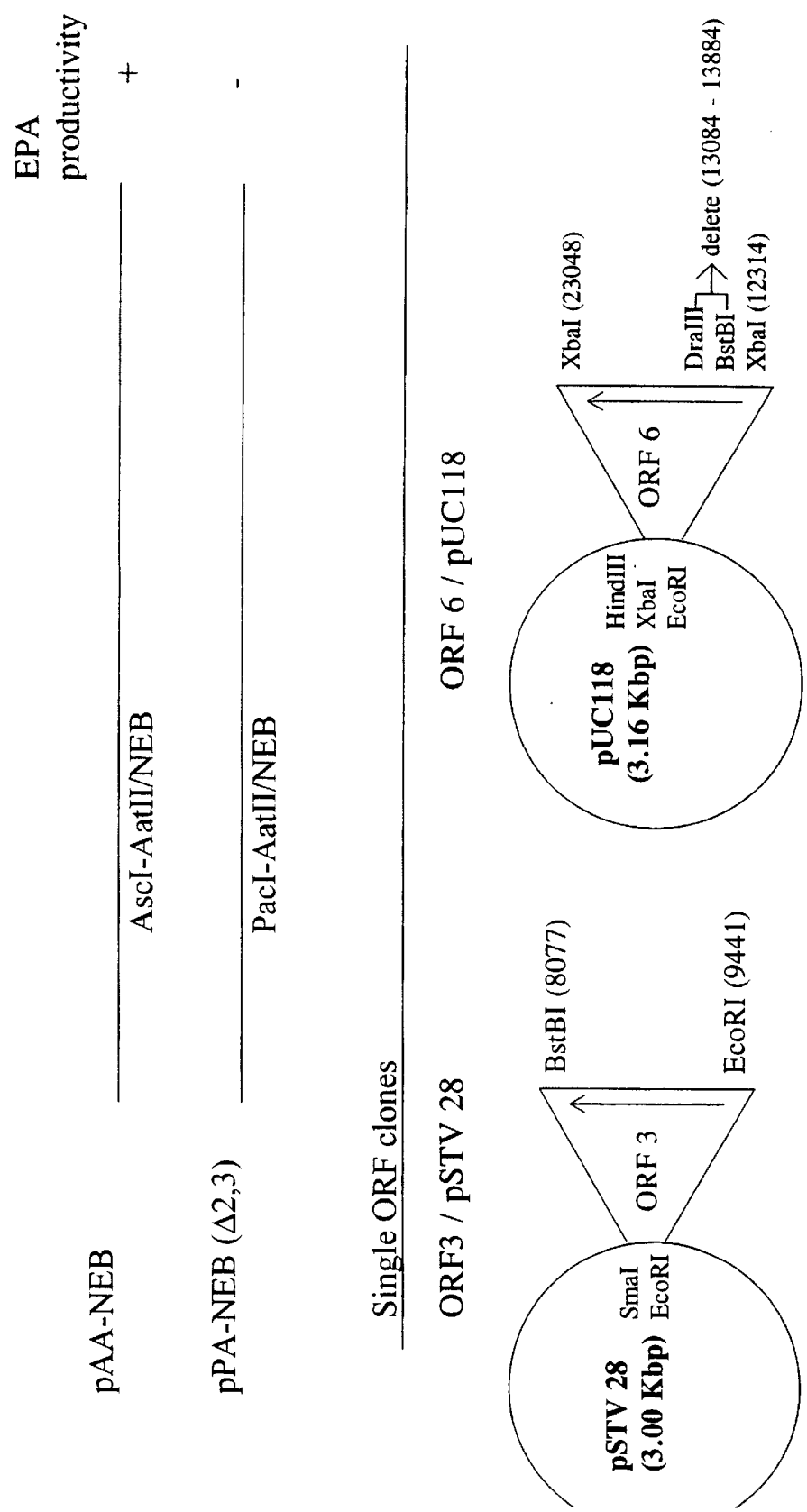

The choice of a host cell is influenced in part by the desired PUFA profile of the transgenic cell, and the native profile of the host cell. Even where the host cell expresses PKS-like gene activity for one PUFA, expression of PKS-like genes of another PKS-like system can provide for production of a novel PUFA not produced by the host cell. In particular instances where expression of PKS-like gene activity is coupled with expression of an ORF 8 PKS-like gene of an organism which produces a different PUFA, it can be desirable that the host cell naturally have, or be mutated to have, low PKS-like gene activity for ORF 8. As an example, for production of EPA, the DNA sequence used encodes the polypeptide having PKS-like gene activity of an organism which produces EPA, while for production of DHA, the DNA sequences used are those from an organism which produces DHA. For use in a host cell which already expresses PKS-like gene activity it can be necessary to utilize an expression cassette which provides for overexpression of the desired PKS-like genes alone or with a construct to downregulate the activity of an existing ORF of the existing PKS-like system, such as by antisense or co-suppression. Similarly, a combination of ORFs derived from separate organisms which produce the same or different PUFAs using PKS-like systems may be used. For instance, the ORF 8 of Vibrio directs the expression of DHA in a host cell, even when ORFs 3, 6, 7 and 9 are from Shewanella, which produce EPA when coupled to ORF 8 of Shewanella. Therefore, for production of eicosapentanoic acid (EPA), the expression cassettes used generally include one or more cassettes which include ORFs 3, 6, 7, 8 and 9 from a PUFA-producing organism such as the marine bacterium *Shewanella putrefaciens* (for EPA production) or *Vibrio marinus* (for DHA production). ORF 8 can be used for induction of DHA production, and ORF 8 of Vibrio can be used in conjunction with ORFs 3, 6, 7 and 9 of Shewanella to produce DHA. The organization and numbering scheme of the ORFs identified in the Shewanella gene cluster are shown in FIG. 1A. Maps of several subclones referred to in this study are shown in FIG. 1B. For expression of a PKS-like gene polypeptide, transcriptional and translational initiation and termination regions functional in the host cell are operably linked to the DNA encoding the PKS-like gene polypeptide.

Constructs comprising the PKS-like ORFs of interest can be introduced into a host cell by any of a variety of standard techniques, depending in part upon the type of host cell. These techniques include transfection, infection, bolistic impact, electroporation, microinjection, scraping, or any other method which introduces the gene of interest into the host cell (see U.S. Pat. No. 4,743,548, U.S. Pat. No. 4,795,855, U.S. Pat. No. 5,068,193, U.S. Pat. No. 5,188,958, U.S. Pat. No. 5,463,174, U.S. Pat. No. 5,565,346 and U.S. Pat. No. 5,565,347). Methods of transformation which are used include lithium acetate transformation (*Methods in Enzymology*, (1991) 194:186–187). For convenience, a host cell which has been manipulated by any method to take up a DNA sequence or construct will be referred to as "transformed" or "recombinant" herein. The subject host will have at least have one copy of the expression construct and may have two or more, depending upon whether the gene is integrated into the genome, amplified, or is present on an extrachromosomal element having multiple copy numbers.

For production of PUFAs, depending upon the host cell, the several polypeptides produced by pEPA, ORFs 3, 6, 7, 8 and 9, are introduced as individual expression constructs or can be combined into two or more cassettes which are introduced individually or co-transformed into a host cell. A standard transformation protocol is used. For plants, where less than all PKS-like genes required for PUFA synthesis have been inserted into a single plant, plants containing a complementing gene or genes can be crossed to obtain plants containing a full complement of PKS-like genes to synthesize a desired PUFA.

The PKS-like-mediated production of PUFAs can be performed in either prokaryotic or eukaryotic host cells. The cells can be cultured or formed as part or all of a host organism including an animal. Viruses and bacteriophage also can be used with appropriate cells in the production of PUFAs, particularly for gene transfer, cellular targeting and selection. Any type of plant cell can be used for host cells, including dicotyledonous plants, monocotyledonous plants, and cereals. Of particular interest are crop plants such as Brassica, Arabidopsis, soybean, corn, and the like. Prokaryotic cells of interest include Eschericia, Baccillus, Lactobaccillus, cyanobacteria and the like. Eukaryotic cells include plant cells, mammalian cells such as those of lactating animals, avian cells such as of chickens, and other cells amenable to genetic manipulation including insect, fungal, and algae cells. Examples of host animals include mice, rats, rabbits, chickens, quail, turkeys, cattle, sheep, pigs, goats, yaks, etc., which are amenable to genetic manipulation and cloning for rapid expansion of a transgene expressing population. For animals, PKS-like transgenes can be adapted for expression in target organelles, tissues and body fluids through modification of the gene regulatory regions. Of particular interest is the production of PUFAs in the breast milk of the host animal.

Examples of host microorganisms include *Saccharomyces cerevisiae, Saccharomyces carlsbergensis*, or other yeast such as *Candida, Kluyveromyces* or other fungi, for example, filamentous fungi such as Aspergillus, Neurospora, Penicillium, etc. Desirable characteristics of a host microorganism are, for example, that it is genetically well characterized, can be used for high level expression of the product using ultra-high density fermentation, and is on the GRAS (generally recognized as safe) list since the proposed end product is intended for ingestion by humans. Of particular interest is use of a yeast, more particularly baker's yeast (*S. cerevisiae*), as a cell host in the subject invention. Strains of particular interest are SC334 (Mat α pep4-3 prb1-1122 ura3-52 leu2-3, 112 reg1-501 gal1; (Hovland et al (1989) Gene 83:57–64); BJ1995 (Yeast Genetic Stock Centre, 1021 Donner Laboratory, Berkeley, Calif. 94720), INVSC1 (Mat α hiw3Δ1 leu2 trp1-289 ura3-52 (Invitrogen, 1600 Faraday Ave., Carlsbad, Calif. 92008) and INVSC2 (Mat α his3Δ200 ura3-167; (Invitrogen). Bacterial cells also may be used as hosts. This includes *E. coli*, which can be useful in fermentation processes. Alternatively, a host such as a Lactobacillus species can be used as a host for introducing the products of the PKS-like pathway into a product such as yogurt.

The transformed host cell can be identified by selection for a marker contained on the introduced construct. Alternatively, a separate marker construct can be introduced with the desired construct, as many transformation techniques introduce multiple DNA molecules into host cells. Typically, transformed hosts are selected for their ability to grow on selective media. Selective media can incorporate an antibiotic or lack a factor necessary for growth of the untransformed host, such as a nutrient or growth factor. An introduced marker gene therefor may confer antibiotic resistance, or encode an essential growth factor or enzyme, and permit growth on selective media when expressed in the transformed host cell. Desirably, resistance to kanamycin and the amino glycoside G418 are of particular interest (see U.S. Pat. No. 5,034,322). For yeast transformants, any marker that functions in yeast can be used, such as the ability to grow on media lacking uracil, lencine, lysine or tryptophan.

Selection of a transformed host also can occur when the expressed marker protein can be detected, either directly or indirectly. The marker protein can be expressed alone or as a fusion to another protein. The marker protein can be one which is detected by its enzymatic activity; for example β-galactosidase can convert the substrate X-gal to a colored product, and luciferase can convert luciferin to a light-emitting product. The marker protein can be one which is detected by its light-producing or modifying characteristics; for example, the green fluorescent protein of *Aequorea victoria* fluoresces when illuminated with blue light. Antibodies can be used to detect the marker protein or a molecular tag on, for example, a protein of interest. Cells expressing the marker protein or tag can be selected, for example, visually, or by techniques such as FACS or panning using antibodies.

The PUFAs produced using the subject methods and compositions are found in the host plant tissue and/or plant part as free fatty acids and/or in conjugated forms such as acylglycerols, phospholipids, sulfolipids or glycolipids, and can be extracted from the host cell through a variety of means well-known in the art. Such means include extraction with organic solvents, sonication, supercritical fluid extraction using for example carbon dioxide, and physical means such as presses, or combinations thereof. Of particular interest is extraction with methanol and chloroform. Where appropriate, the aqueous layer can be acidified to protonate negatively charged moieties and thereby increase partitioning of desired products into the organic layer. After extraction, the organic solvents can be removed by evaporation under a stream of nitrogen. When isolated in conjugated forms, the products are enzymatically or chemically cleaved to release the free fatty acid or a less complex conjugate of interest, and are then subjected to further manipulations to produce a desired end product. Desirably, conjugated forms of fatty acids are cleaved with potassium hydroxide.

If further purification is necessary, standard methods can be employed. Such methods include extraction, treatment with urea, fractional crystallization, HPLC, fractional distillation, silica gel chromatography, high speed centrifugation or distillation, or combinations of these techniques. Protection of reactive groups, such as the acid or alkenyl groups, can be done at any step through known techniques, for example alkylation or iodination. Methods used include methylation of the fatty acids to produce methyl esters. Similarly, protecting groups can be removed at any step. Desirably, purification of fractions containing DHA and EPA is accomplished by treatment with urea and/or fractional distillation.

The uses of the subject invention are several. Probes based on the DNAs of the present invention find use in methods for isolating related molecules or in methods to detect organisms expressing PKS-like genes. When used as probes, the DNAs or oligonucleotides need to be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practicable to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labelling methods can be found in U.S. Pat. No. 5,011,770. Alternatively, the binding of target molecules can be directly detected by measuring the change in heat of solution on binding of a probe to a target via isothermal titration calorimetry, or by coating the probe or target on a surface and detecting the change in scattering of light from the surface produced by binding of a target or a probe, respectively, is done with the BIAcore system.

PUFAs produced by recombinant means find applications in a wide variety of areas. Supplementation of humans or animals with PUFAs in various forms can result in increased levels not only of the added PUFAs, but of their metabolic progeny as well. Complex regulatory mechanisms can make it desirable to combine various PUFAs, or to add different conjugates of PUFAs, in order to prevent, control or overcome such mechanisms to achieve the desired levels of specific PUFAs in an individual. In the present case, expression of PKS-like gene genes, or antisense PKS-like gene transcripts, can alter the levels of specific PUFAs, or derivatives thereof, found in plant parts and/or plant tissues. The PKS-like gene polypeptide coding region is expressed either by itself or with other genes, in order to produce tissues and/or plant parts containing higher proportions of desired PUFAs or containing a PUFA composition which more closely resembles that of human breast milk (Prieto et al., PCT publication WO 95/24494) than does the unmodified tissues and/or plant parts.

PUFAs, or derivatives thereof, made by the disclosed method can be used as dietary supplements for patients undergoing intravenous feeding or for preventing or treating malnutrition. For dietary supplementation, the purified PUFAs, or derivatives thereof, can be incorporated into cooking oils, fats or margarines formulated so that in normal use the recipient receives a desired amount of PUFA. The PUFAs also can be incorporated into infant formulas, nutritional supplements or other food products, and find use as anti-inflammatory or cholesterol lowering agents.

Particular fatty acids such as EPA can be used to alter the composition of infant formulas to better replicate the PUFA composition of human breast milk. The predominant triglyceride in human milk is reported to be 1,3-di-oleoyl-2-palmitoyl, with 2-palmitoyl glycerides reported as better absorbed than 2-oleoyl or 2-lineoyl glycerides (see U.S. Pat. No. 4,876,107). Typically, human breast milk has a fatty acid profile comprising from about 0.15% to about 0.36% as DHA, from about 0.03% to about 0.13% as EPA, from about 0.30% to about 0.88% as ARA, from about 0.22% to about 0.67% as DGLA, and from about 0.27% to about 1.04% as GLA. A preferred ratio of GLA:DGLA:ARA in infant formulas is from about 1:1:4 to about 1:1:1, respectively. Amounts of oils providing these ratios of PUFA can be determined without undue experimentation by one of skill in the art. PUFAs, or host cells containing them, also can be used as animal food supplements to alter an animal's tissue or milk fatty acid composition to one more desirable for human or animal consumption.

For pharmaceutical use (human or veterinary), the compositions generally are administered orally but can be administered by any route by which they may be successfully absorbed, e.g., parenterally (i.e. subcutaneously, intramuscularly or intravenously), rectally or vaginally or topically, for example, as a skin ointment or lotion. Where available, gelatin capsules are the preferred form of oral administration. Dietary supplementation as set forth above also can provide an oral route of administration. The unsaturated acids of the present invention can be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, described in PCT publication WO 96/33155. Preferred esters are the ethyl esters.

The PUFAs of the present invention can be administered alone or in combination with a pharmaceutically acceptable carrier or excipient. As solid salts, the PUFAs can also be administered in tablet form. For intravenous administration, the PUFAs or derivatives thereof can be incorporated into commercial formulations such as Intralipids. Where desired, the individual components of formulations can be individually provided in kit form, for single or multiple use. A typical dosage of a particular fatty acid is from 0.1 mg to 20 g, or even 100 g daily, and is preferably from 10 mg to 1, 2, 5 or 10 g daily as required, or molar equivalent amounts of derivative forms thereof. Parenteral nutrition compositions comprising from about 2 to about 30 weight percent fatty acids calculated as triglycerides are encompassed by the present invention. Other vitamins, and particularly fat-soluble vitamins such as vitamin A, D, E and L-carnitine optionally can be included. Where desired, a preservative such as a tocopherol can be added, typically at about 0.1% by weight.

The following examples are presented by way of illustration, not of limitation.

EXAMPLES

Example 1

The Identity of ORFs Derived from *Vibrio marinus*

Using polymerase chain reaction (PCR) with primers based on ORF 6 of Shewanella (Sp ORF 6) sequences (FW 5' primers CUACUACUACUACCAAGCT AAAGCACTTAACCGTG, SEQ ID NO:41 and CUACUACUACUAACAGCGAAATGCTTATCAAG, SEQ ID NO:42 for Vibrio and SS9 respectively and 3' BW primers: CAUCAUCAUCAUGCGACC AAAACCAAATGAGCTAATAC, SEQ ID NO:42 for both Vibrio and SS9) and genomic DNAs templates from Vibrio and a borophyllic photobacter producing EPA (provided by Dr. Bartlett, UC San Diego), resulted in PCR products of ca.400 bases for *Vibrio marinus* (Vibrio) and ca.900 bases for SS9 presenting more than 75% homology with corresponding fragments of Sp ORF 6 (see FIG. 25) as determined by direct counting of homologous amino acids.

A Vibrio cosmid library was then prepared and using the Vibrio ORF 6 PCR product as a probe (see FIG. 26); clones containing at least ORF 6 were selected by colony hybridization.

Figure 7A:
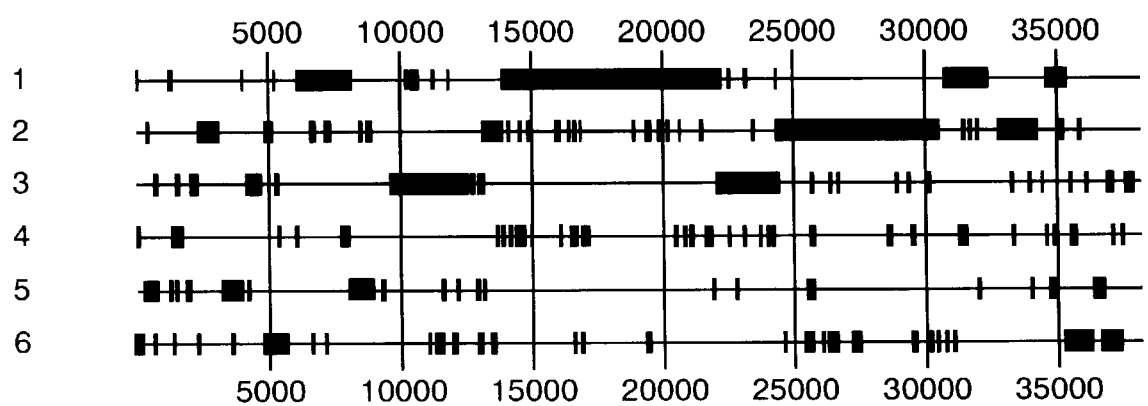
FIGS. 7A–7B shows a comparison of the PKS-like gene clusters of *Shewanella putrefaciens* and *Vibrio marinus*.
Figure 7B:
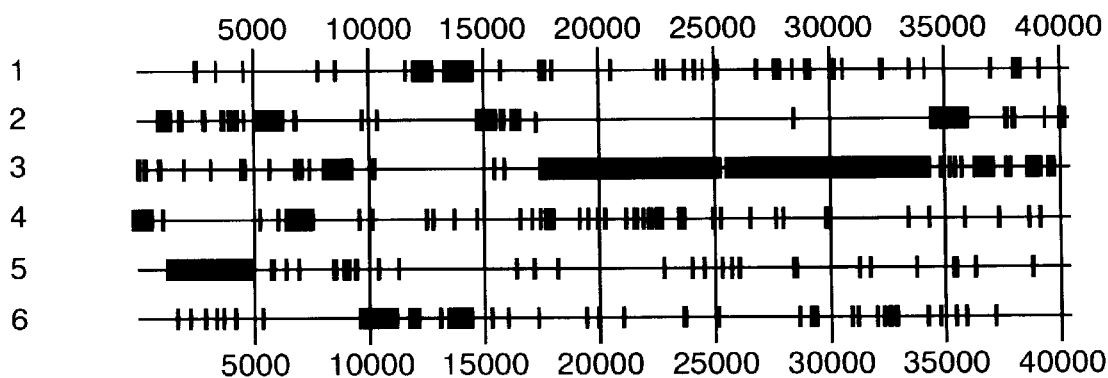

Through additional sequences of the selected cosmids such as cosmid #9 and cosmid #21, a Vibrio cluster (FIG. 5) with ORFs homologous to, and organized in the same sequential order (ORFs 6–9) as ORFs 6–9 of Shewanella, was obtained (FIG. 7). The Vibrio ORFs from this sequence are found at 17394 to 36115 and comprehend ORFs 6–9.

TABLE

| Vibrio operon figures | |
|---|---|
| 17394 to 25349 | length = 7956 nt |
| 25509 to 28157 | length = 2649 nt |
| 28209 to 34262 | length = 6054 nt |
| 34454 to 36115 | length = 1662 nt |

The ORF designations for the Shewanella genes are based on those disclosed in FIG. 4, and differ from those published for the Shewanella cluster (Yazawa et al, U.S. Pat. No. 5,683,898). For instance, ORF 3 of FIG. 4 is read in the opposite direction from the other ORFs and is not disclosed in Yazawa et al U.S. Pat. No. 5,683,898 (See FIG. 24) for comparison with Yazawa et al U.S. Pat. No. 5,683,898.

Sequences homologous to ORF 3, were not found in the proximity of ORF 6 (17000 bases upstream of ORF 6) or of ORF 9 (ca.4000 bases downstream of ORF 9). Motifs characteristic of phosphopantetheinyl transferases (Lambalot et al (1996) *Current Biology* 3:923–936) were absent from the Vibrio sequences screened for these motifs. In addition, there was no match to Sp ORF 3 derived probes in genomic digests of Vibrio and of SC2A Shewanella (another bacterium provided by the University of San Diego and also capable of producing EPA). Although ORF 3 may exist in Vibrio, its DNA may not be homologous to that of Sp ORF 3 and/or could be located in portions of the genome that were not sequenced.

Figure 8:
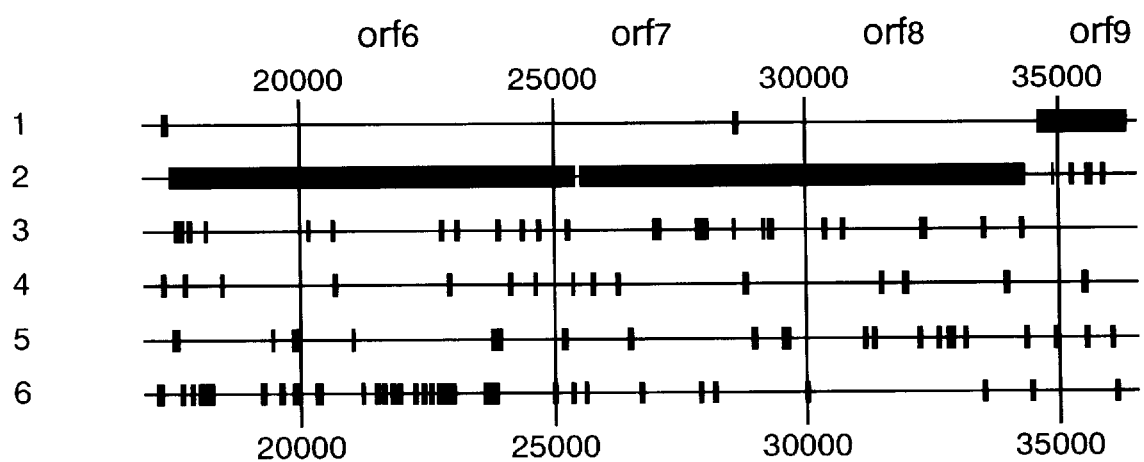
FIG. 8 is an expanded view of the PKS-like gene cluster portion of *Vibrio marinus* shown in FIG. 7B showing that ORFs 6, 7 and 8 are in reading frame 2, while ORF 9 is in reading frame 3.
Figure 9:
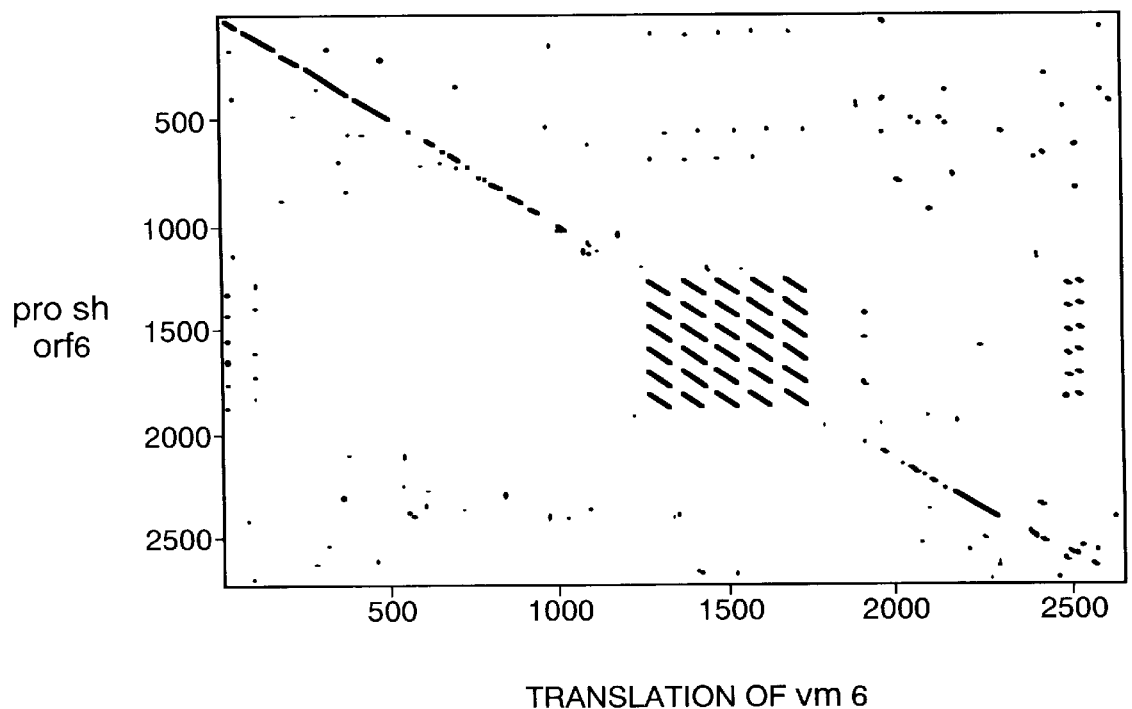
FIG. 9 demonstrates sequence homology of ORF 6 of *Shewanella putrefaciens* and *Vibrio marinus*. The Shewanella ORF 6 is depicted on the vertical axis, and the Vibrio ORF 6 is depicted on the horizontal axis. Lines indicate regions of the proteins that have a 60% identity. The repeated lines in the middle correspond to the multiple ACP domains found in ORF 6.
Figure 10:
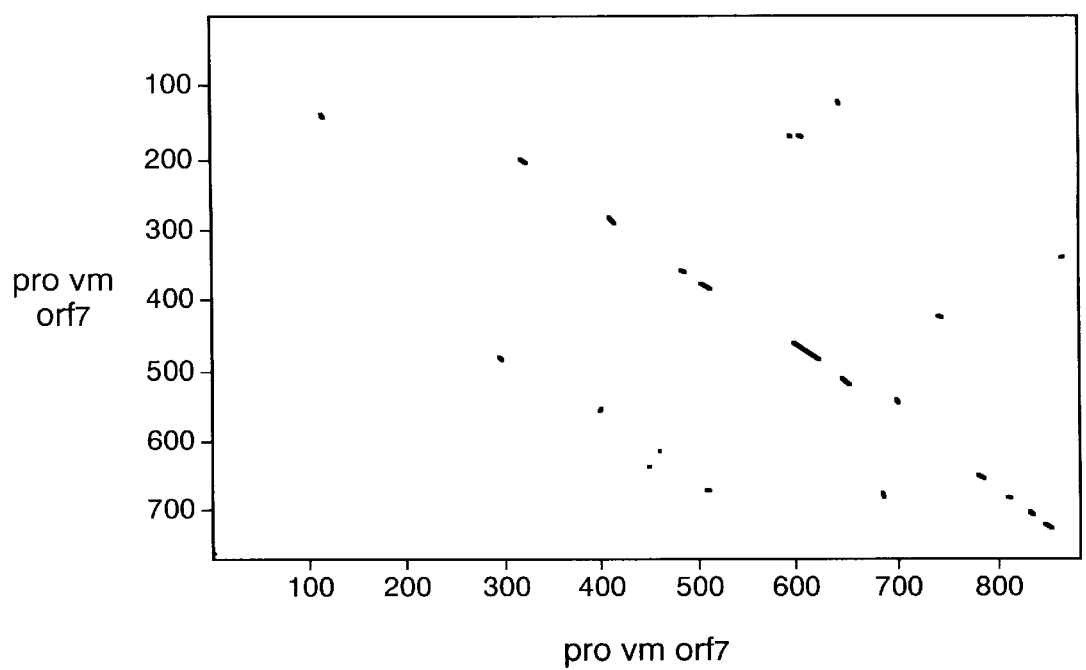
FIG. 10 demonstrates sequence homology of ORF 7 of *Shewanella putrefaciens* and *Vibrio marinus*. The Shewanella ORF 7 is depicted on the vertical axis, and the Vibrio ORF 7 is depicted on the horizontal axis. Lines indicate regions of the proteins that have a 60% identity.
Figure 11:
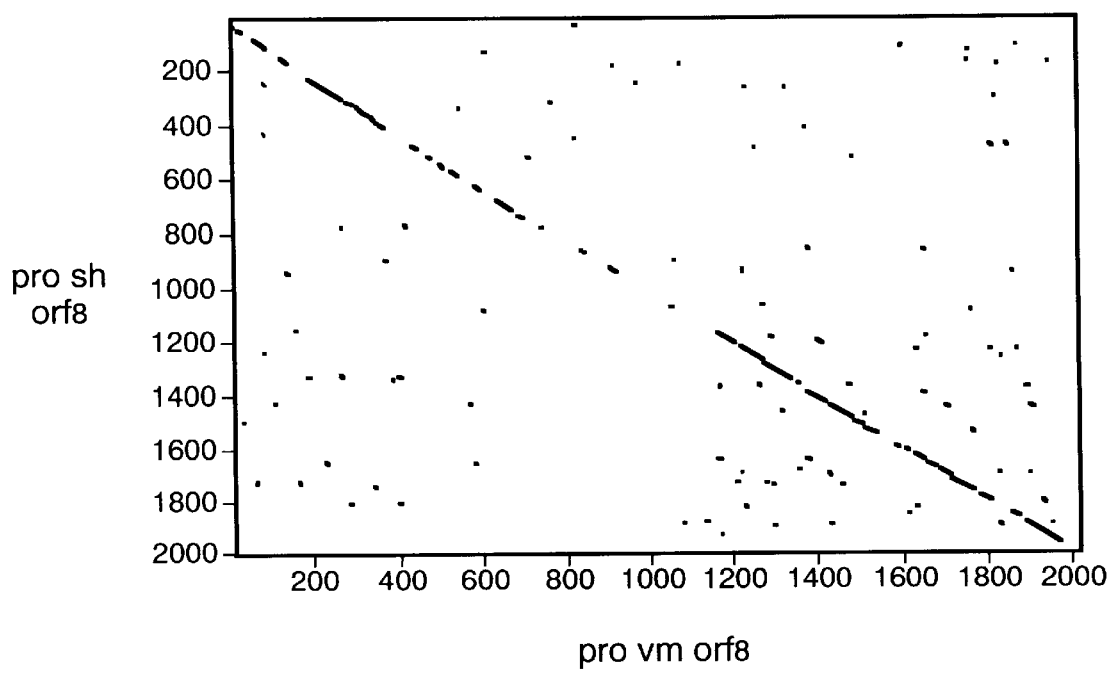
FIG. 11 demonstrates sequence homology of ORF 8 of *Shewanella putrefaciens* and *Vibrio marinus*. The Shewanella ORF 8 is depicted on the vertical axis, and the Vibro. ORF 8 is depicted on the horizontal axis. Lines indicate regions of the proteins that have a 60% identity.
Figure 12:
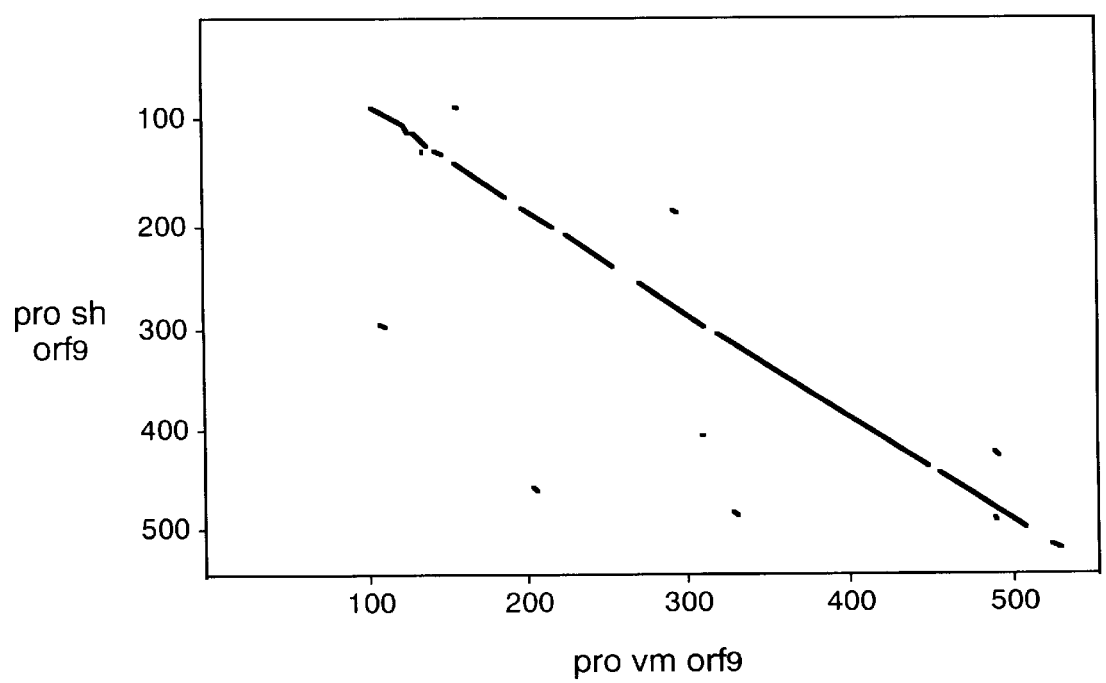
FIG. 12 demonstrates sequence homology of ORF 9 of *Shewanella putrefaciens* and *Vibrio marinus*. The Shewanella ORF 9 is depicted on the vertical axis, and the Vibrio ORF 9 is depicted on the horizontal axis. Lines indicate regions of the proteins that have a 60% identity.

FIG. 6 provides the sequence of an approximately 19 kb Vibrio clone comprising ORFs 6–9. FIGS. 7 and 8 compare the gene cluster organizations of the PKS-like systems of *Vibrio marinus* and *Shewanella putrefaciens*. FIGS. 9 through 12 show the levels of sequence homology between the corresponding ORFs 6, 7, 8 and 9, respectively.

Example 2

ORF 8 Directs DHA Production

As described in example 1, DNA homologous to Sp ORF 6 was found in an unrelated species, SS9 Photobacter, which also is capable of producing EPA. Additionally, ORFs homologous to Sp ORF 6–9 were found in the DHA producing *Vbrio marinus* (Vibrio). From these ORFs a series of experiments was designed in which deletions in each of Sp ORFs 6–9 that suppressed EPA synthesis in *E. coli* (Yazawa (1996) supra) were complemented by the corresponding homologous genes from Vibrio.

Figure 13:
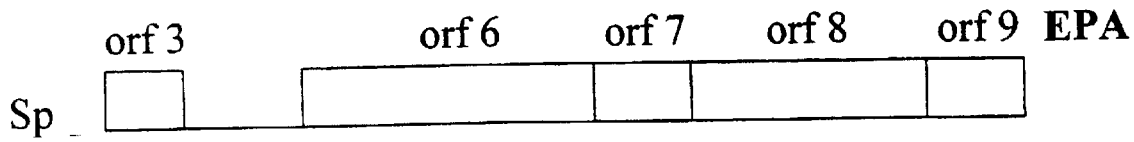
FIG. 13 is a depiction of various complementation experiments, and resulting PUFA production. On the right, is shown the longest PUFA made in the *E. coli* strain containing the Vibrio and Shewanella genes depicted on the left. The hollow boxes indicate ORFs from Shewanella. The solid boxes indicate ORFs from Vibrio.
Figure 13:
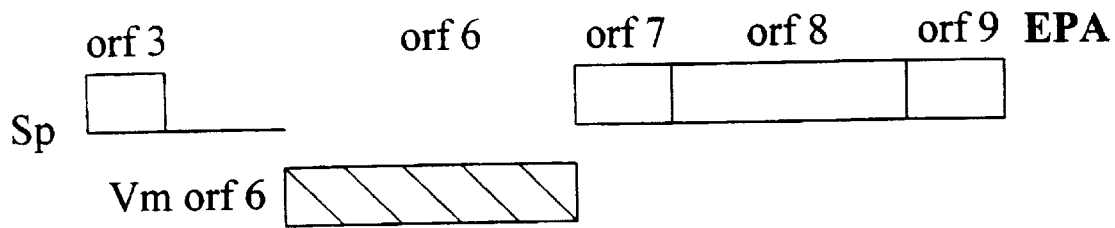
Figure 13:
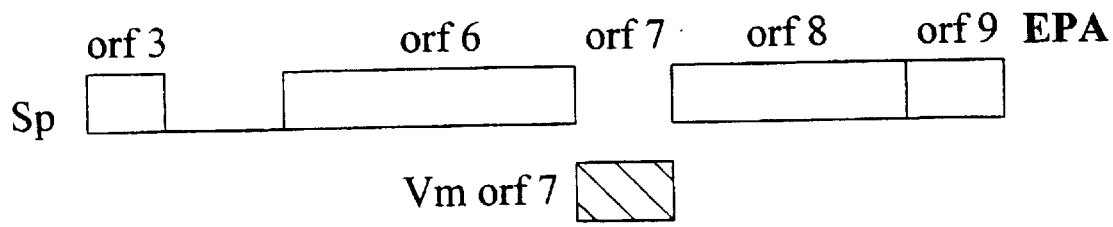
Figure 13:
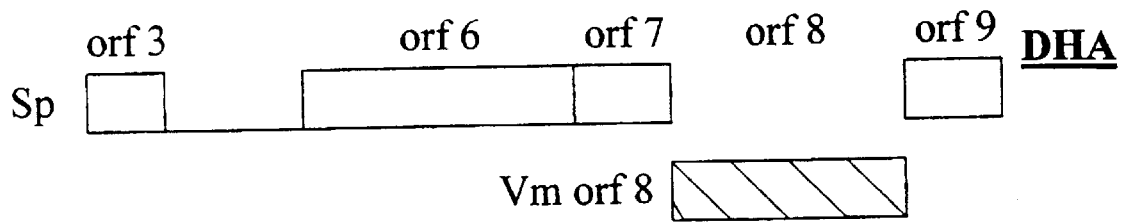

The Sp EPA cluster was used to determine if any of the Vibrio ORFs 6–9 was responsible for the production of DHA. Deletion mutants provided for each of the Sp ORFs are EPA and DHA null. Each deletion was then complemented by the corresponding Vibrio ORF expressed behind a lac promoter (FIG. 13).

Figure 14:
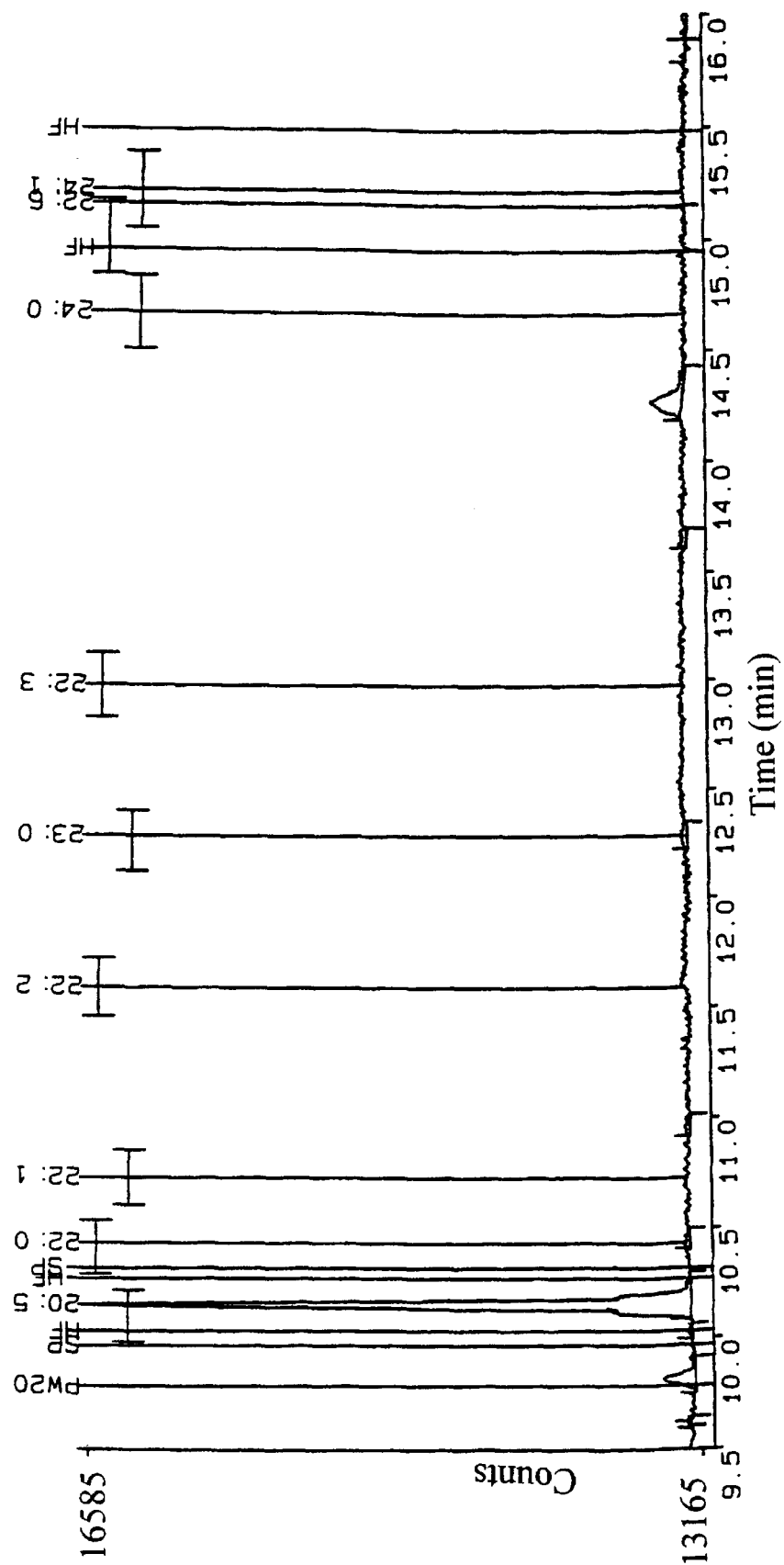
FIG. 14 is a chromatogram showing fatty acid production from complementation of pEPAD8 from Shewanella (deletion ORF 8) with ORF 8 from Shewanella, in *E. coli* Fad E-. The chromatogram presents an EPA (20:5) peak.
Figure 15:
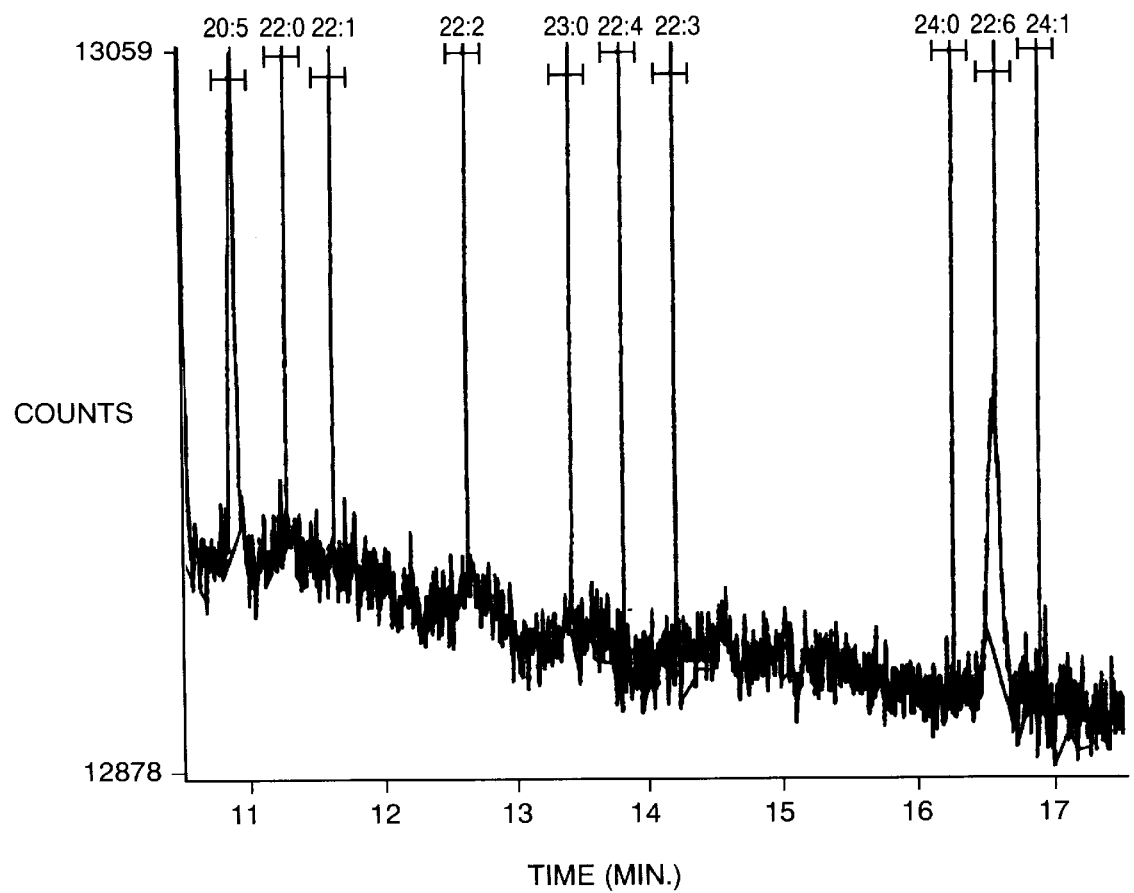
FIG. 15 is a chromatogram showing fatty acid production from complementation of pEPAD8 from Shewanella (deletion ORF 8) with ORF 8 from *Vibrio marinus*, in *E. coli* Fad E-. The chromatograph presents EPA (20:5) and DHA (22:6) peaks.

The complementation of a Sp ORF 6 deletion by a Vibrio ORF 6 reestablished the production of EPA. Similar results were obtained by complementing the Sp ORF 7 and ORF 9 deletions. By contrast, the complementation of a Sp ORF 8 deletion resulted in the production of C22:6. Vibrio ORF 8 therefore appears to be a key element in the synthesis of DHA. FIGS. 14 and 15 show chromatograms of fatty acid profiles from the respective complementations of Sp del ORF 6 with Vibrio ORF 6 (EPA and no DHA) and Sp del ORF 8 with Vibrio ORF 8 (DHA). FIG. 16 shows the fatty acid percentages for the ORF 8 complementation, again demonstrating that ORF 8 is responsible for DHA production.

These data show that polyketide-like synthesis genes with related or similar ORFs can be combined and expressed in a heterologous system and used to produce a distinct PUFA species in the host system, and that ORF 8 has a role in determining the ultimate chain length. The Vibrio ORFs 6, 7, 8, and 9 reestablish EPA synthesis. In the case of Vibrio ORF 8, DHA is also present (ca. 0.7%) along with EPA (ca. 0.6%) indicating that this gene plays a significant role in directing synthesis of DHA vs EPA for these systems.

Example 3

Requirements for Production of DHA

To determine how Vibrio ORFs of the cluster ORF 6–9 are used in combination with Vibrio ORF 8, some combinations of Vibrio ORF 8 with some or all of the other Vibrio ORFS 6–9 cluster were created to explain the synthesis of DHA.

Vibrio ORFs 6–9 were complemented with Sp ORF 3. The results of this complementation are presented in FIGS. 16*b* and 16*c*. The significant amounts of DHA measured (greater than about 9%) and the absence of EPA suggest that no ORFs other than those of Vibrio ORFs 6–9 are required for DHA synthesis when combined with Sp ORF 3. This suggests that Sp ORF 3 plays a general function in the synthesis of bacterial PUFAs.

With respect to the DHA vs EPA production, it may be necessary to combine Vibrio ORF 8 with other Vibrio ORFs of the 6–9 cluster in order to specifically produce DHA. The roles of Vibrio ORF 9 and each of the combinations of Vibrio ORFs (6,8), (7, 8), (8, 9), etc in the synthesis of DHA are being studied.

Example 4

Plant Expression Constructs

A cloning vector with very few restriction sites was designed to facilitate the cloning of large fragments and their subsequent manipulation. An adapter was assembled by annealing oligonucleotides with the sequences AAGCCCGGGCTT, SEQ ID NO:44 and GTACAAGCCCGGGCTTAGCT, SEQ ID NO:45. This adapter was ligated to the vector pBluescript II SK+ (Stratagene) after digestion of the vector with the restriction endonucleases Asp718 and SstI. The resulting vector, pCGN7769 had a single SrfI (and embedded SmaI) cloning site for the cloning of blunt ended DNA fragments.

Figure 17:
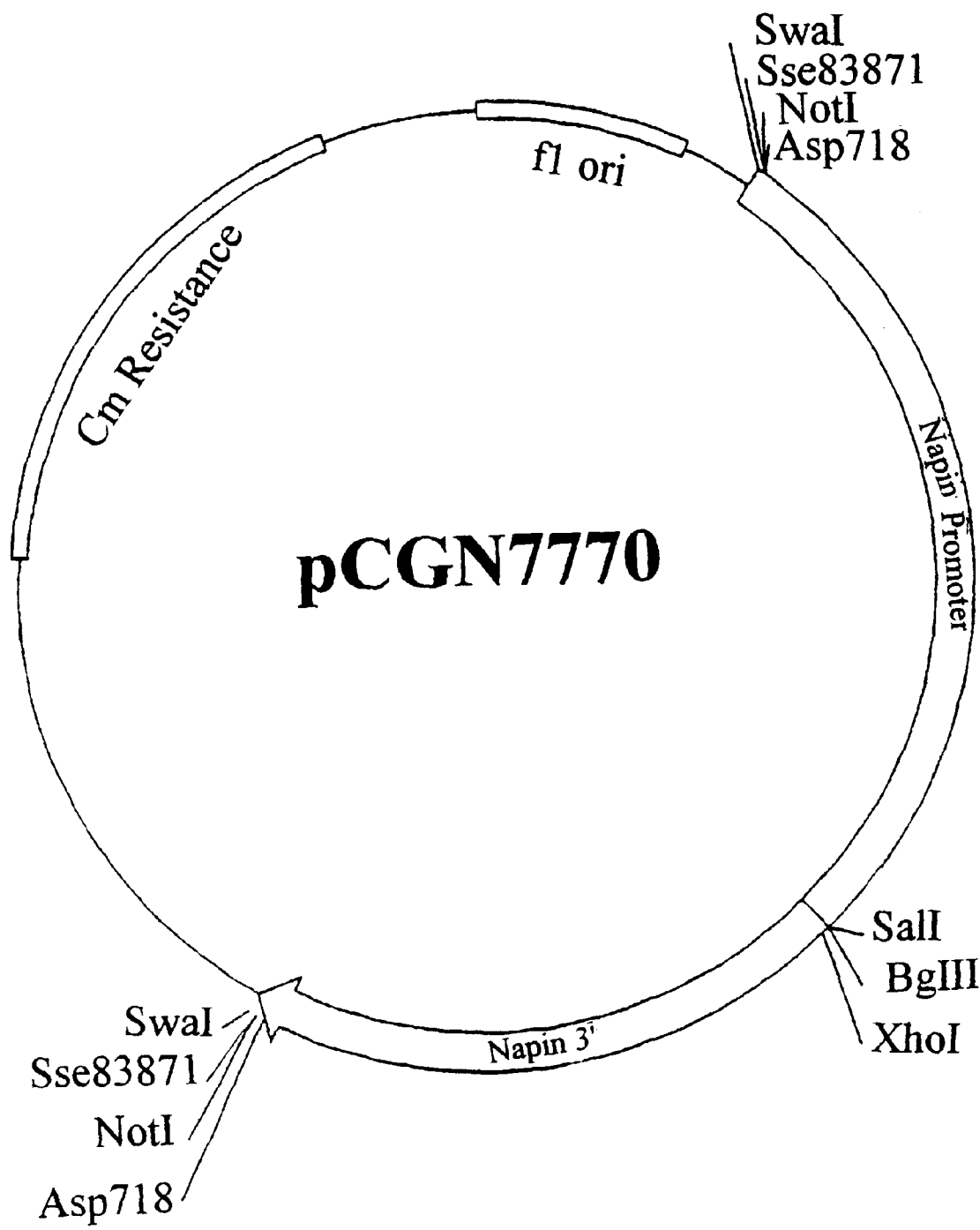
FIG. 17 is a plasmid map showing the elements of pCGN7770.

A plasmid containing the napin cassette from pCGN3223, (U.S. Pat. No. 5,639,790) was modified to make it more useful for cloning large DNA fragments containing multiple restriction sites, and to allow the cloning of multiple napin fusion genes into plant binary transformation vectors. An adapter comprised of the self annealed oligonucleotide of sequence CGCGATTTAAATGGCGCGCCCTGCAG-GCGGCCGCCTGCAGGGCGC GCCATTTAAAT, SEQ ID NO:46 was ligated into the vector pBC SK+ (Stratagene) after digestion of the vector with the restriction endonuclease BssHII to construct vector pCGN7765. Plamids pCGN3223 and pCGN7765 were digested with NotI and ligated together. The resultant vector, pCGN7770 (FIG. 17), contains the pCGN7765 backbone and the napin seed specific expression cassette from pCGN3223.

Shewanella Constructs

Genes encoding the Shewanella proteins were mutagenized to introduce suitable cloning sites 5' and 3' ORFs using PCR. The template for the PCR reactions was DNA of the cosmid pEPA (Yazawa et al, supra). PCR reactions were performed using Pfu DNA polymerase according to the manufacturers' protocols. The PCR products were cloned into SrfI digested pCGN7769. The primers CTGCAGCTCGAGACAATGTTGATT TCCTTATACTTCTGTCC, SEQ ID NO:47 and GGATC-CAGATCTCTAGCTAGTCTTAGCTGAAGC TCGA, SEQ ID NO:48 were used to amplify ORF 3, and to generate plasmid pCGN8520. The primers TCTAGACTCGAGA-CAATGAGCCAGACCTCTAAACCTACA, SEQ ID NO:49 and CCCGGGCTC GAGCTAATTCGCCTCACTGTCGTTTGCT, SEQ ID NO:50 were used to amplify ORF 6, and generate plasmid pCGN7776. The primers GAATTCCTCGAGACAATGC-CGCTGCGCATCG CACTTATC, SEQ ID NO:51 and GGTACCAGATCTTTAGACTTCCCCTTGAAGTAA ATGG, SEQ ID NO:52 were used to amplify ORF 7, and generate plasmid pCGN7771. The primers GAATTCGTCG ACACAATGTCATTACCAGACAATGCTTCT, SEQ ID NO:53 and TCTAGAGTCGACTTATAC AGATTCTTCGATGCTGATAG, SEQ ID NO:54 were used to amplify ORF 8, and generate plasmid pCGN7775. The primers GAATTCGTCGACACAATGAATCCTACAG-CAA CTAACGAA, SEQ ID NO:55 and TCTAGAGGATC-CTTAGGCCATTCTTTGGTTTGG CTTC, SEQ ID NO:56 were used to amplify ORF 9, and generate plasmid pCGN7773.

The integrity of the PCR products was verified by DNA sequencing of the inserts of pCGN7771, PCGN8520, and pCGN7773. ORF 6 and ORF 8 were quite large in size. In order to avoid sequencing the entire clones, the center portions of the ORFs were replaced with restriction fragments of pEPA. The 6.6 kilobase PacI/BamHI fragment of pEPA containing the central portion of ORF 6 was ligated into PacI/BamHI digested pCGN7776 to yield pCGN7776B4. The 4.4 kilobase BamHI/BglII fragment of pEPA containing the central portion of ORF 8 was ligated into BamHII/BglII digested pCGN7775 to yield pCGN7775A. The regions flanking the pEPA fragment and the cloning junctions were verified by DNA sequencing.

Plasmid pCGN7771 was cut with XhoI and BglII and ligated to pCGN7770 after digestion with SalI and BglII. The resultant napin/ORF 7 gene fusion plasmid was designated pCGN7783. Plasmid pCGN8520 was cut with XhoI and BglII and ligated to pCGN7770 after digestion with SalI and BglII. The resultant napin/ORF 3 gene fusion plasmid was designated pCGN8528. Plasmid pCGN7773 was cut with SalI and BamHI and ligated to pCGN7770 after digestion with SalI and BglII. The resultant napin/ORF 9 gene fusion plasmid was designated pCGN7785. Plasmid pCGN7775A was cut with SalI and ligated to pCGN7770 after digestion with SalI. The resultant napin/ORF 8 gene fusion plasmid was designated pCGN7782. Plasmid pCGN7776B4 was cut with XhoI and ligated to pCGN7770 after digestion with SalI. The resultant napin/ORF 6 gene fusion plasmid was designated pCGN7786B4.

Figure 18:
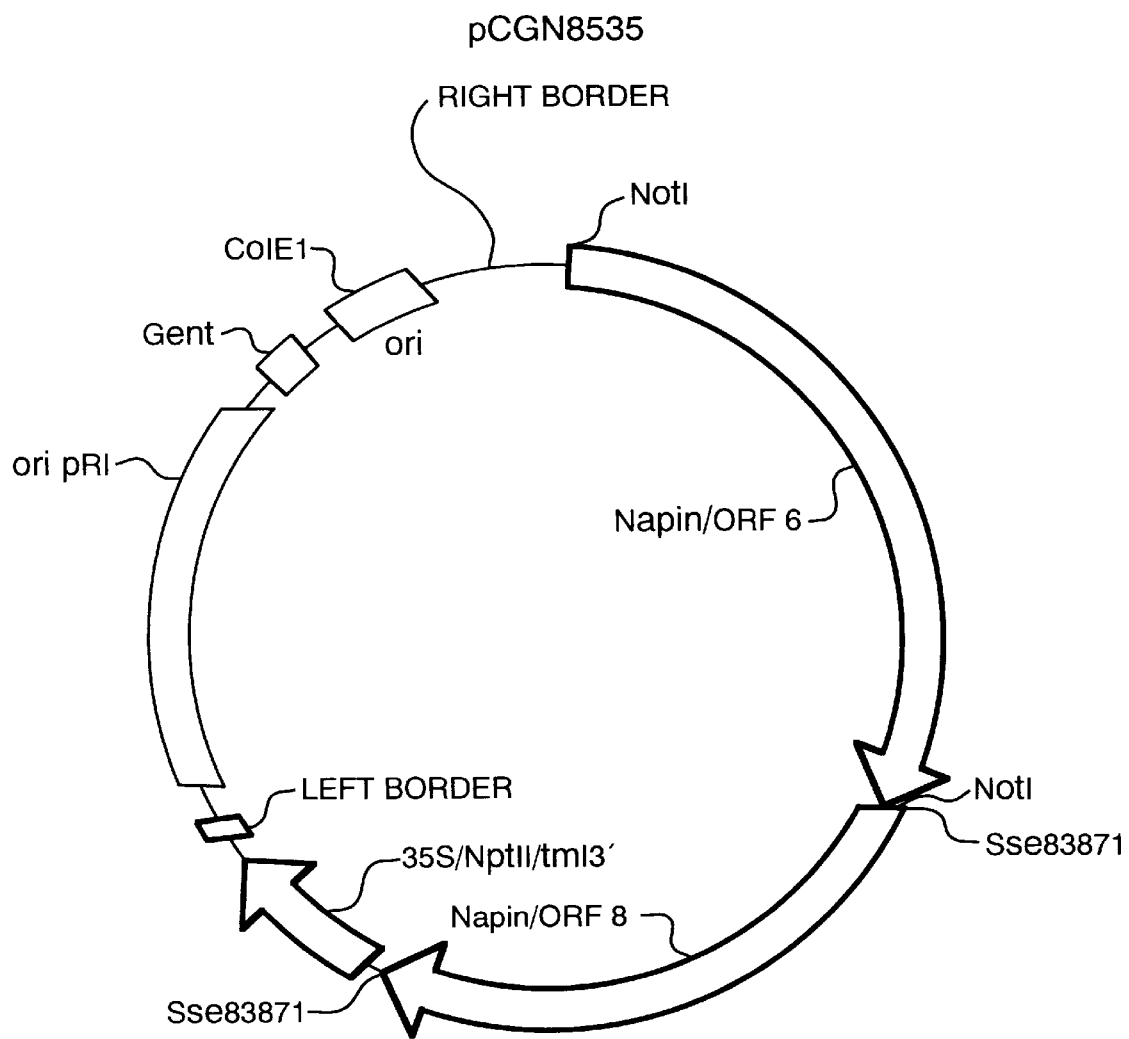
FIG. 18 is a plasmid map showing the elements of pCGN8535.

A binary vector for plant transformation, pCGN5139, was constructed from pCGN1558 (McBride and Summerfelt (1990) *Plant Molecular Biology*, 14:269–276). The polylinker of pCGN1558 was replaced as a HindIII/Asp718 fragment with a polylinker containing unique restriction endonuclease sites, AscI, PacI, XbaI, SwaI, BamHI, and NotI. The Asp718 and HindIII restriction endonuclease sites are retained in pCGN5139. PCGN5139 was digested with NotI and ligated with NotI digested pCGN7786B4. The resultant binary vector containing the napin/ORF 6 gene fusion was designated pCGN8533. Plasmid pCGN8533 was digested with Sse8387I and ligated with Sse8387I digested pCGN7782. The resultant binary vector containing the napin/ORF 6 gene fusion and the napin/ORF 8 gene fusion was designated pCGN8535 (FIG. 18).

Figure 19:
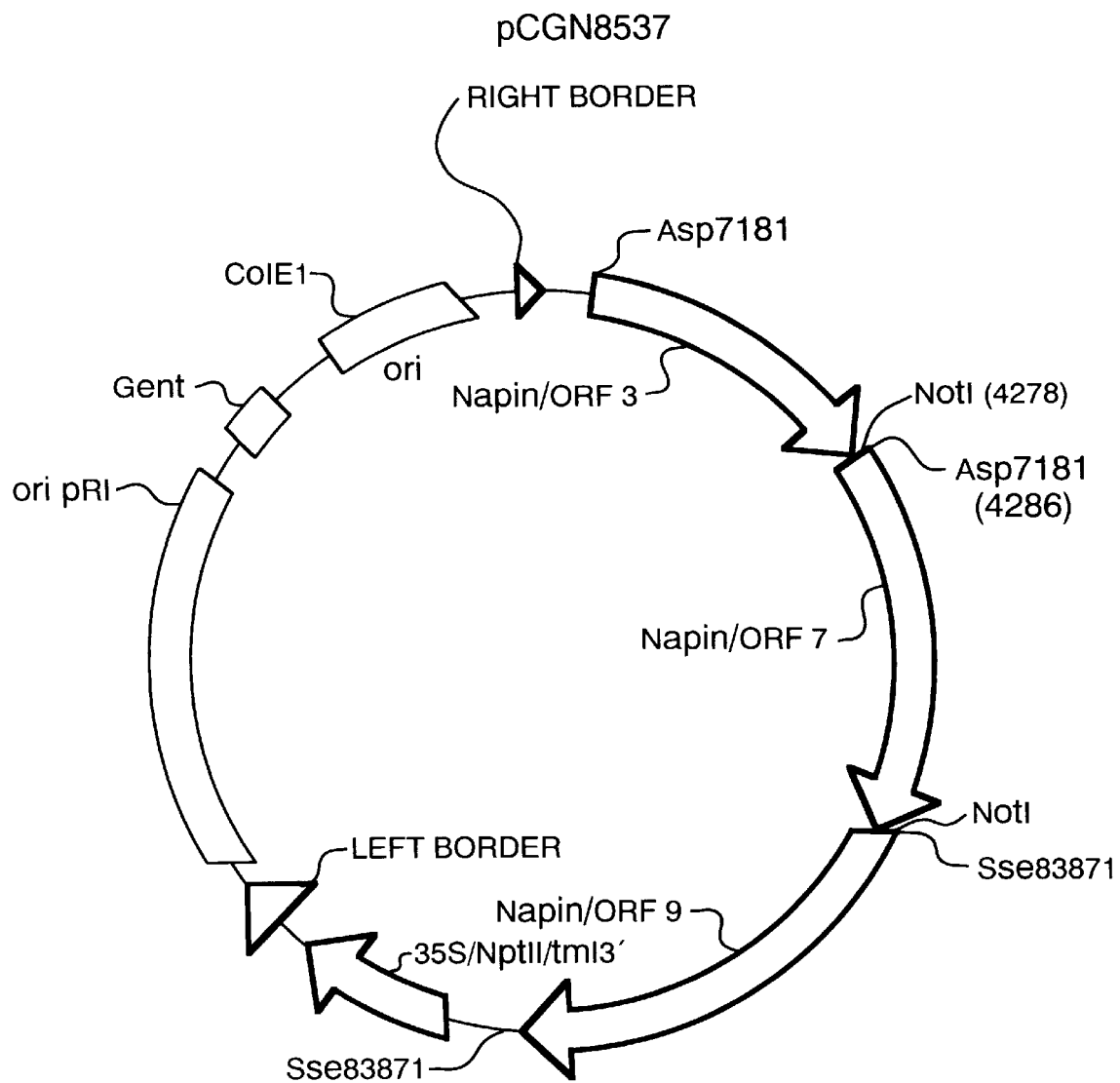
FIG. 19 is a plasmid map showing the elements of pCGN8537.
Figure 20:
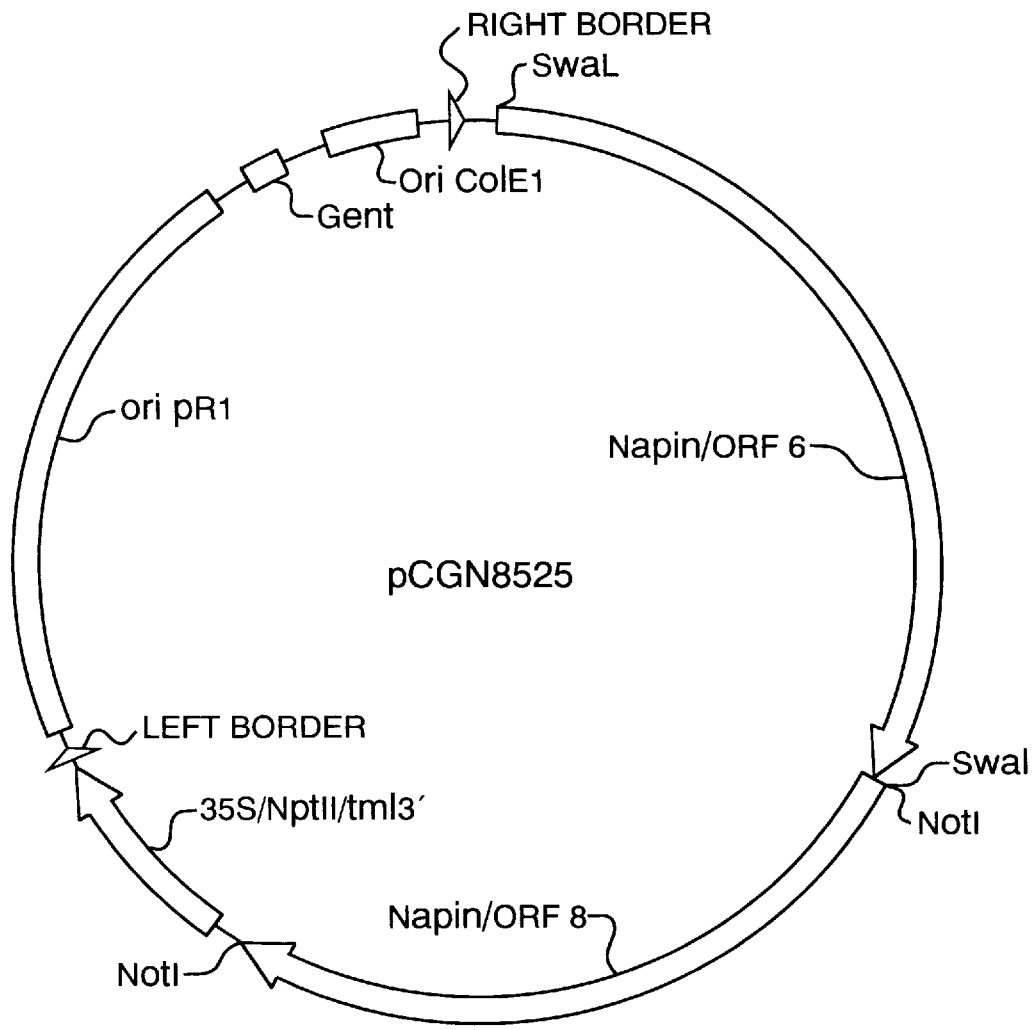
FIG. 20 is a plasmid map showing the elements of pCGN8525.
Figure 21:
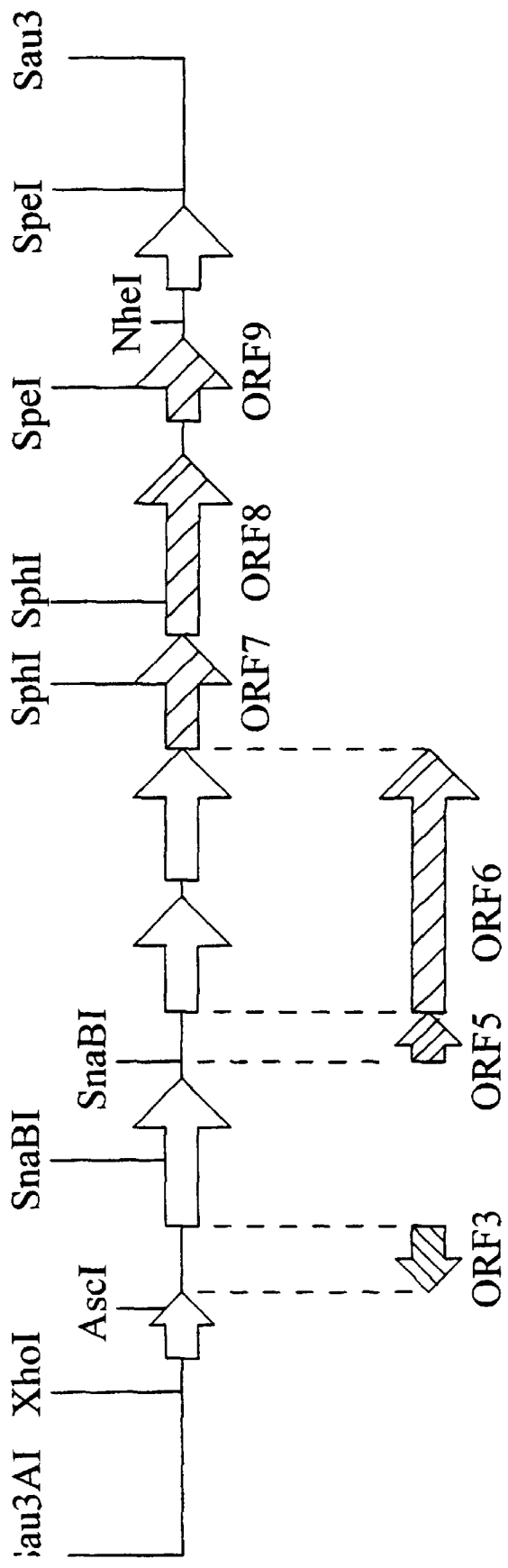
FIG. 21 is a comparison of the Shewanella ORFs as defined by Yazawa and those disclosed in FIG. 4. When a protein starting at the leucine (TTG) codon at nucleotides 9157–9155 and ending at the stop codon at nucleotides 8185–8183 is expressed under control of a heterologous promoter in an *E. coli* strain containing the entire PKS-like cluster except ORF 3, the recombinant cells do produce EPA. Thus, the published protein sequence is likely to be wrong, and the coding sequence for the protein may start at the TTG codon at nucleotides 9157–9155 or the TTG codon at nucleotides 9172–9170. This information is critical to the expression of a functional PKS-like cluster heterologous system.

The plant binary transformation vector, pCGN5139, was digested with Asp718 and ligated with Asp718 digested pCGN8528. The resultant binary vector containing the napin/ORF 3 gene fusion was designated pCGN8532. Plasmid pCGN8532 was digested with NotI and ligated with NotI digested pCGN7783. The resultant binary vector containing the napin/ORF 3 gene fusion and the napin/ORF 7 gene fusion was designated pCGN8534. Plasmid pCGN8534 was digested with Sse8387I and ligated with Sse8387I digested pCGN7785. The resultant binary vector containing the napin/ORF 3 gene fusion, the napin/ORF 7 gene fusion and the napin/ORF 9 gene fusion was designated pCGN8537 (FIG. 19).

Vibrio Constructs

The Vibrio ORFs for plant expression were all obtained using Vibrio cosmid #9 as a starting molecule. Vibrio cosmid #9 was one of the cosmids isolated from the Vibrio cosmid library using the Vibrio ORF 6 PCR product described in Example 1.

A gene encoding Vibrio ORF 7 (FIG. 6) was mutagenized to introduce a SalI site upstream of the open reading frame and BamHI site downstream of the open reading frame using the PCR primers: TCTAGAGTCGACACAATGGCGGAATTAGCTG TTATTGGT, SEQ ID NO:57 and GTCGACGGATCCCTATTTGTTCGTGTTTGCTATATG, SEQ ID NO:58. A gene encoding Vibrio ORF 9 (FIG. 6) was mutagenized to introduce a BamHI site upstream of the open reading frame and an XhoHI site downstream of the open reading frame using the PCR primers: GTCGACGGATC-CACAATGAATATAGTAAGTAATC ATTCGGCA, SEQ ID NO:59 and GTCGACCTCGAGTTAATCACTCGTAC-GATAACTT GCC, SEQ ID NO:60. The restriction sites were introduced using PCR, and the integrity of the mutagenized plasmids was verified by DNA sequence. The Vibrio ORF 7 gene was cloned as a SalI-BamHI fragment into the napin cassette of Sal-BglI digested pCGN7770 (FIG. 17) to yield pCGN8539. The Vibrio ORF 9 gene was cloned as a SalI-BamHI fragment into the napin cassette of Sal-BalI digested pCGN7770 (FIG. 17) to yield pCGN8543.

Genes encoding the Vibrio ORF 6 and ORF 8 were mutagenized to introduce SalI sites flanking the open reading frames. The SalI sites flanking ORF 6 were introduced using PCR. The primers used were: CCCGGGTCGACA-CAATGGCTAAAAAGAACA CCACATCGA, SEQ ID NO:61 and CCCGGGTCGACTCATG ACATATCGTTCAAAATGTCACTGA, SEQ ID NO:62. The central 7.3 kb BamHI-XhoI fragment of the PCR product was replaced with the corresponding fragment from Vibrio cosmid #9. The mutagenized ORF 6 were cloned into the SalI site of the napin cassette of pCGN7770 to yield plasmid pCGN8554.

The mutagenesis of ORF 8 used a different strategy. A BamHI fragment containing ORF 8 was subcloned into plasmid pHC79 to yield cosmid #9". A SalI site upstream of the coding region was introduced on and adapter comprised of the oligonucleotides TCGACATGGAAAATATTGCAG-TAGTAGGTATTGCTAATTT GTTC SEQ ID NO:63 and CCGGGAACAAATTAGCAATACCTACTACTGCAATA TTTTCCATG, SEQ ID NO:64. The adapter was ligated to cosmid #9" after digestion with SalI and XmaI. A SalI site was introduced downstream of the stop codon by using PCR for mutagenesis. A DNA fragment containing the stop codon was generated using cosmid #9" as a template with the primers TCAGATGAACTTTATCGATAC, SEQ ID NO:65 and TCATGAGACGTCGTCGACTTA CGCTTCAACAATACT, SEQ ID NO:66. The PCR product was digested with the restriction endonucleases ClaI and AatII and was cloned into the cosmid 9" derivative digested with the same enzymes to yield plasmid 8P3. The SalI fragment from 8P3 was cloned into SalI digested pCGN7770 to yield pCGN8515.

Figure 23:
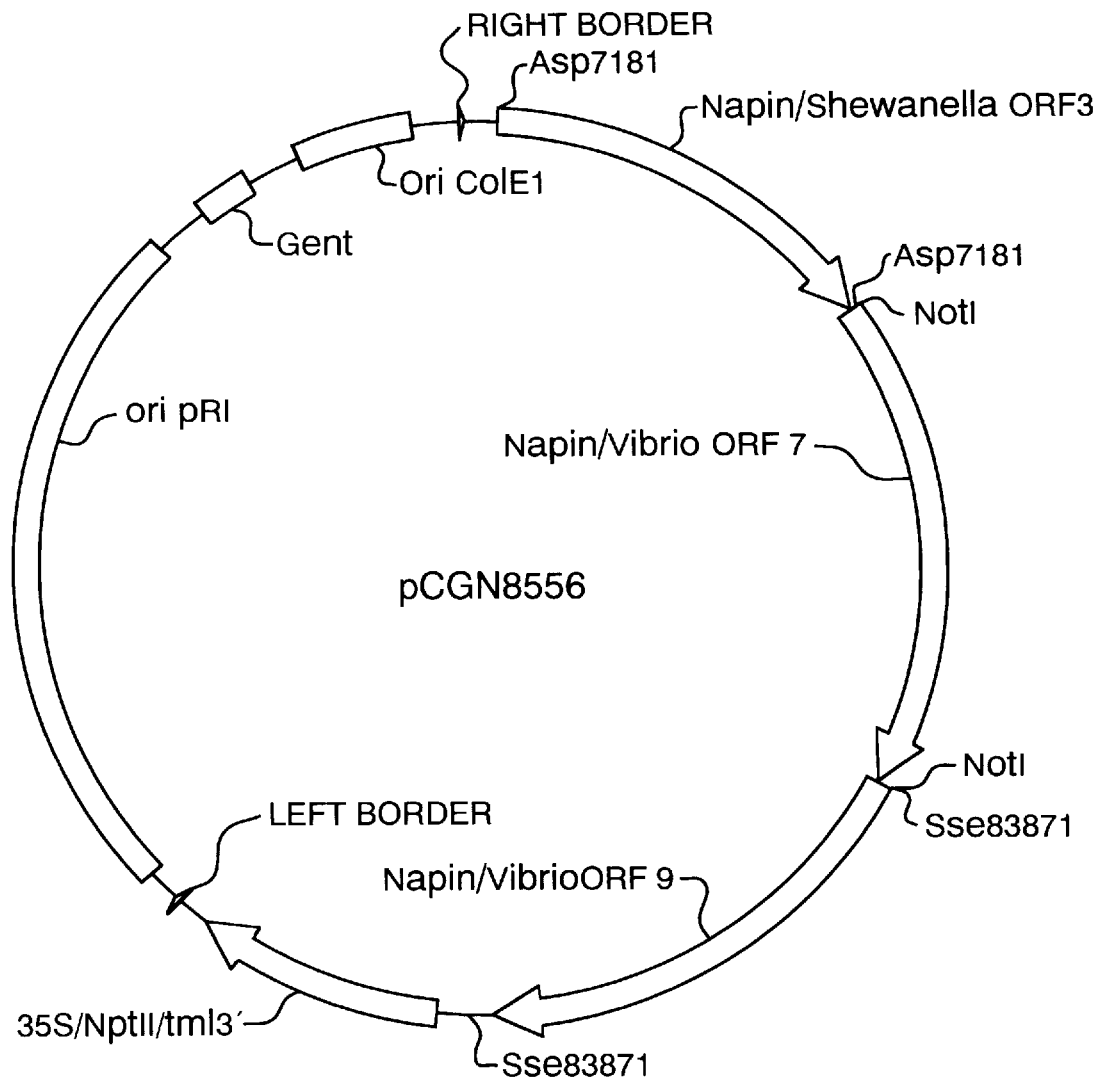
FIG. 23 is plasmid map showing the elements of pCGN8556.

PCGN8532, a binary plant transformation vector that contains a Shewannella ORF 3 under control of the napin promoter was digested with NotI, and a NotI fragment of pCGN8539 containing a napin Vibrio ORF 7 gene fusion was inserted to yield pCGN8552. Plasmid pCGN8556 (FIG. 23), which contains Shewannella ORF 3, and Vibrio ORFs 7 and 9 under control of the napin promoter was constructed by cloning the Sse8357 fragment from pCGN8543 into Sse8387 digested pCGN8552.

Figure 22:
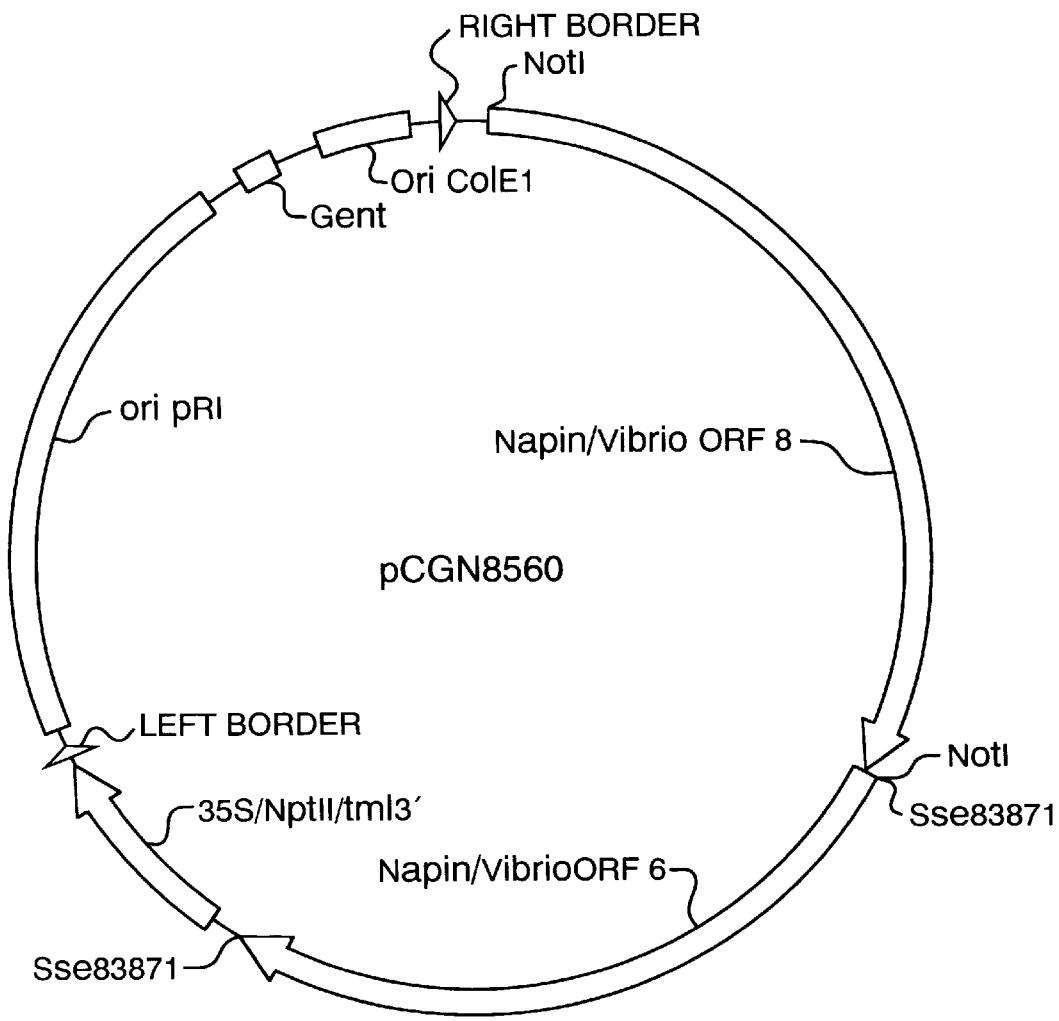
FIG. 22 is a plasmid map showing the elements of pCGN8560.

The NotI digested napin/ORF 8 gene from plasmid pCGN8515 was cloned into a NotI digested plant binary transformation vector pCGN5139 to yield pCGN8548. The Sse8387 digested napin/ORF 6 gene from pCGN8554 was subsequently cloned into the Sse8387 site of pCGN8566. The resultant binary vector containing the napin/ORF 6 gene fusion and napin/ORF 8 gene fusion was designated pCGN8560 (FIG. 22).

Example 5

Plant Transformation and PUFA Production

EPA Production

The Shewanella constructs pCGN8535 and pCGN8537 can be transformed into the same or separate plants. If separate plants are used, the transgenic plants can be crossed resulting in heterozygous seed which contains both constructs.

pCGN8535 and pCGN8537 are separately transformed into Brassica napus. Plants are selected on media containing kanamycin and transformation by full length inserts of the constructs is verified by Southern analysis. Immature seeds also can be tested for protein expression of the enzyme encoded by ORFs 3, 6, 7, 8, or 9 using western analysis, in which case, the best expressing pCGNE8535 and pCGN8537 T₁ transformed plants are chosen and are grown out for further experimentation and crossing. Alternatively, the T₁ transformed plants showing insertion by Southern are crossed to one another producing T₂ seed which has both insertions. In this seed, half seeds may be analyzed directly from expression of EPA in the fatty acid fraction. Remaining half-seed of events with the best EPA production are grown out and developed through conventional breeding techniques to provide Brassica lines for production of EPA.

Plasmids pCGN7792 and pCGN7795 also are simultaneously introduced into Brassica napus host cells. A standard transformation protocol is used (see for example U.S. Pat. No. 5,463,174 and U.S. Pat. No. 5,750,871, however Agrobacteria containing both plasmids are mixed together and incubated with Brassica cotyledons during the cocultivation step. Many of the resultant plants are transformed with both plasmids.

DHA Production

A plant is transformed for production of DHA by introducing pCGN8556 and pCGN8560, either into separate plants or simultaneously into the same plants as described for EPA production.

Alternatively, the Shewanella ORFs can be used in a concerted fashion with ORFs 6 and 8 of Vibrio, such as by transforming with a plant the constructs pCGN8560 and pCGN7795, allowing expression of the corresponding ORFs in a plant cell. This combination provides a PKS-like gene arrangement comprising ORFs 3, 7 and 9 of Shewanella, with an ORF 6 derived from Vibrio and also an OFR 8 derived from Vibrio. As described above, ORF 8 is the PKS-like gene which controls the identity of the final PUFA product. Thus, the resulting transformed plants produce DHA in plant oil.

Example 6

Transgenic Plants Containing the Shewanella PUFA Genes

Brassica Plants

Fifty-two plants cotransformed with plasmids pCGN8535 and pCGN8537 were analyzed using PCR to determine if the Shewanella ORFs were present in the transgenic plants. Forty-one plants contained plasmid pCGN8537, and thirty-five plants contained pCGN8535. 11 of the plants contained all five ORFs required for the synthesis of EPA. Several plants contained genes from both of the binary plasmids but appeared to be missing at least one of the ORFs. Analysis is currently being performed on approximately twenty additional plants.

Twenty-three plants transformed with pCGN8535 alone were analyzed using PCR to determine if the Shewanella ORFs were present in the transgenic plants. Thirteen of these plants contained both Shewanella ORF 6 and Shewanella ORF 8. Six of the plants contained only one ORF.

Nineteen plants transformed with pCGN8537 were alone analyzed using PCR to determine if the Shewanella ORFs were present in the transgenic plants. Eighteen of the plants contained Shewanella ORF 3, Shewanella ORF 7, and Shewanella ORF 9. One plant contained Shewanella ORFs 3 and 7.

Arabidopsis

More than 40 transgenic Arabidopsis plants cotransformed with plasmids pCGN8535 and pCGN8537 are growing in our growth chambers. PCR analysis to determine which of the ORFs are present in the plants is currently underway.

By the present invention PKS-like genes from various organisms can now be used to transform plant cells and modify the fatty acid compositions of plant cell membranes or plant seed oils through the biosynthesis of PUFAs in the transformed plant cells. Due to the nature of the PKS-like systems, fatty acid end-products produced in the plant cells can be selected or designed to contain a number of specific chemical structures. For example, the fatty acids can comprise the following variants: Variations in the numbers of keto or hydroxyl groups at various positions along the carbon chain; variations in the numbers and types (cis or trans) of double bonds; variations in the numbers and types of branches off of the linear carbon chain (methyl, ethyl, or longer branched moieties); and variations in saturated carbons. In addition, the particular length of the end-product fatty acid can be controlled by the particular PKS-like genes utilized.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated nucleic acid comprising:

a *Vibrio marinus* nucleotide sequence selected from the group consisting of the ORF 6, ORF 7, ORF 8 and ORF 9, wherein the start and last codons for ORF 6 are 411 and 8269, for ORF 7 are 8526 and 11177, for ORF 8 are 11226 and 17282 and for ORF 9 are 17471 and 19135 as encoded by SEQ ID NO:13 and as shown in FIG. 6.

2. An isolated nucleic acid comprising:

a nucleotide sequence which encodes a polypeptide of a polyketide-like synthesis system, wherein said system produces a docosahexanoic acid when expressed in a host cell, and wherein said nucleotide sequence is a *Vibrio marinus* ORF 8, wherein the start and last codons for ORF 8 are 11226 and 17282 as encoded by SEQ ID NO:13 and as shown in FIG. 6.

3. An isolated nucleic acid comprising:

a nucleotide sequence which is substantially identical to a sequence of at least 50 nucleotides of a *Vibrio marinus* nucleotide sequence selected from the group consisting of ORF 6, ORF 7, ORF 8 and ORF 9, wherein the start and last codons for ORF 6 are 411 and 8269, for ORF 7 are 8526 and 11177, for ORF 8 are 11226 and 17282 and for ORF 9 are 17471 and 19135 as encoded by SEQ ID NO:13 and as shown in FIG. 6.

* * * * *